US008481050B2

(12) United States Patent
Choo et al.

(10) Patent No.: US 8,481,050 B2
(45) Date of Patent: Jul. 9, 2013

(54) TISSUE CULTURE SYSTEM FOR PRODUCTION OF HEPATITIS C VIRUS

(75) Inventors: Qui-Lim Choo, El Cerrito, CA (US); Jang Han, Lafayette, CA (US); Michael Houghton, Danville, CA (US); Taewoo Kwon, Oakland, CA (US); Hyun Chul Song, Eunpyung-gu (SG); Yifei Zhu, Fremont, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 477 days.

(21) Appl. No.: 12/310,309

(22) PCT Filed: Aug. 22, 2007
(Under 37 CFR 1.47)

(86) PCT No.: PCT/US2007/018591
§ 371 (c)(1),
(2), (4) Date: Feb. 1, 2011

(87) PCT Pub. No.: WO2008/024413
PCT Pub. Date: Feb. 28, 2008

(65) Prior Publication Data
US 2010/0227311 A1    Sep. 9, 2010

Related U.S. Application Data

(60) Provisional application No. 60/839,608, filed on Aug. 22, 2006.

(51) Int. Cl.
*A61K 48/00* (2006.01)
*A61K 50/00* (2006.01)

(52) U.S. Cl.
USPC .................................. 424/205.1; 424/228.1

(58) Field of Classification Search
None
See application file for complete search history.

(56) References Cited

U.S. PATENT DOCUMENTS 6,921,634 B2 *   7/2005   Lemon et al. ..................... 435/3
7,288,369 B2 *  10/2007   Lemon et al. ..................... 435/5

OTHER PUBLICATIONS

Jopling Catherine L., et al., "Modulation of Hepatitis C Virus RNA Abundance by a Liver-Specific MicroRNA", Science 309, pp. 1577-1581 (2005).
Schaller, Torsten, et al., "Analysis of Hepatitis C Virus Superinfection Exclusion by Using Novel Fluorochrome Gene-Tagged Viral Genomes", Journal of Virology, May 2007 vol. 81, pp. 4591-4603.
Zhang, Yingjia, et al , "Novel Chimeric Genotype 1b/2a Hepatitis C Virus Suitable for High-Throughput Screening", Antimicrobial Agents and Chemotherapy, Feb. 2008, vol. 52, No. 2 pp. 666-674..
Supplementary European Search Report, EP 07837218, mailed Oct. 22, 2010.
Baker, et al., "Protein Expression Using Cotranslational Fusion And Cleavage Of Ubiquiutin," *J Biol Chem* 269(41):25381-25386 (1994).
Bartenschlager, et al., "Replication Of Hepatitis C Virus," *J Gen Virol* 81:1631-1648 (2000).
Blight, et al., "Highly Permissive Cell Lines For Subgenomic And Genomic Hepatitis C Virus RNA Replication," *J Virol* 76:13001-13014 (2002).
Brass, et al., "Molecular Virology Of Hepatitis C Virus (HCV): 2006 Update," *Int J Med Sci* 3(2):29-34 (2006).
Cai, et al., "Robust Production Of Infectious Hepatitis C Virus (HCV) From Stably HCV cDNA-Transfected Human Hepatoma Cells," *J Virol* 79(22):13963-13973 (2005).
Cao, et al., "Identification Of An RNA Silencing Suppressor From A Plant Double-Stranded RNA Virus," *J Virol* 79(20):13018-13027 (2005).
De Felipe, "Skipping The Co-Expression Problem: The New 2A 'Chysel' Technology," *Genet Vaccines Ther* 2(13):1-6 (2004).
Delgadillo, et al., "Human Influenza Virus NS1 Protein Enhances Viral Pathogenicity And Acts As An RNA Silencing Suppressor In Plants," *J Gen Virol* 85:993-999 (2004).
Ferko, et al., "Immunogenicity And Protection Efficacy Of Replicant-Deficient Influenza A Viruses With Altered NS1 Genes," *J Virol* 78(23):13037-13045 (2004).
Hatada, et al., "Mutant Influenza Viruses With A Defective NS1 Protein Cannot Block The Activation Of PKR In Infected Cells," *J Virol* 73(3):2425-2433 (1999).
Ikeda, et al., "Selectable Subgenomic And Genome-Length Dicistronic Rnas Derived From An Infectious Molecular Clone Of The HCV-N Strain Of Hepatitis C Virus Replicate Efficiently In Cultured Huh7 Cells," *J Virol* 76:2997-3006 (2002).
Kanazawa, et al., "Regulation Of Hepatitis C Virus Replication By Interferon Regulatory Factor 1," *J Virol* 78(18):9713-9720 (2004).
Li, et al., "Interferon Antagonist Proteins Of Influenza And Vaccina Viruses Are Suppressors Of RNA Silencing," PNAS 101(5):1350-1355 (2004).
Lindenbach, et al., "Complete Replication Of Hepatitis C Virus In Cell Culture," *Science* 309:623-626 (2005).
Lohmann, et al., "Replication Of Subgenomic Hepatitis C Virus Rnas In A Hepatoma Cell Line," *Science* 285:110-113 (1999).
Mattion, et al., "Foot-And-Mouth Disease Virus 2A Protease Mediates Cleavage In Attenuated Sabin 3 Poliovirus Vectors Engineered For Delivery Of Foreign Antigens," *J Virol* 70(11):8124-8127 (1996).
Pietschmann, et al., "Persistent and Transient Replication Of Full-Length Hepatitis C Virus Genomes In Cell Culture," *J Virol* 76:4008-4021 (2002).
Pietschmann, et al., Construction And Characterization Of Infectious Intragenotypic And Intergenotypic Hepatits C Virus Chimeras, *PNAS* 103(19):7408-7413 (2006).
Pileri, et al., "Binding Of Hepatitis C Virus To CD81," *Science* 282:938-941 (1998).

(Continued)

*Primary Examiner* — Bao Li
(74) *Attorney, Agent, or Firm* — Roberta L. Robins; Kenneth M. Goldman

(57)    ABSTRACT

A tissue culture system for production of infectious hepatitis C virus is described. In particular, the invention provides recombinant monocistronic and bicistronic genomic constructs for production of virus, including constructs for production of wild-type HCV type 2a strain JFH1 and constructs for production of chimeric viruses comprising HCV proteins from strain JFH1 and a second HCV isolate. Constructs of the invention also include a reporter gene to facilitate measurement of RNA replication and viral infectivity in cultures. The cell culture system may also include various factors that improve viral replication or infectivity. In addition, a neutralization assay using HCV grown in cell culture is described.

48 Claims, 21 Drawing Sheets

OTHER PUBLICATIONS

Rouille, et al., "Subcellular Localization Of Hepatitis C Virus Structural Proteins In A Cell Culture System That Efficiently Replicates The Virus," *J Virol* 80(6):2832-2841 (2006).

Tscherne, et al., "Time- And Temperature-Dependant Activation Of Hepatitis C Virus For Low-pH-Triggerd Entry," *J Virol* 80(4):1734-1741 (2006).

Varnavski, et al., "Stable High-Level Expression Of Heterologous Genes In Vitro And In Vivo By Noncytopathic DNA-Based Kunjin Virus Replicon Vectors," *J Virol* 74(9):4394-4403 (2000).

Wakita, et al., "Production Of Infectious Hepatitis C Virus In Tissue Culture From A Cloned Viral Genome," *Nat Med* 11:791-796, 905 (2005).

Zhang, et al., "Expression Of Hepatitis C Virus Hypervariable Region 1 And Its Clinical Significance," *World J Gastroenterol* 9(5):1003-1007 (2003).

Zhong, et al., Robust Hepatitis C Virus Infection In Vitro, *PNAS* 102(26):9294-9299 (2005).

\* cited by examiner

Figure 17: Chimeric JFH-1 carrying E1E2 of types 1a, 1b, and 3a

US 8,481,050 B2

TISSUE CULTURE SYSTEM FOR PRODUCTION OF HEPATITIS C VIRUS

CROSS-REFERENCE TO RELATED APPLICATION

This application is a §371 filing from PCT/US2007/018591, filed Aug. 22, 2007, and claims the benefit under 35 U.S.C. §119(e)(1) of U.S. Provisional Application No. 60/839,608, filed Aug. 22, 2006, which applications are incorporated herein by reference in their entireties and from which applications priority is claimed pursuant to the provisions of 35 U.S.C. §§119/120.

TECHNICAL FIELD

The invention relates to a tissue culture system for production of infectious hepatitis C virus.

BACKGROUND

Hepatitis C virus (HCV) was identified over a decade ago and is now known to be the leading cause of non-A and non-B viral hepatitis (Choo et al., *Science* (1989) 244:359-362; Armstrong et al., *Hepatology* (2000) 31:777). HCV infects approximately 3% of the world population, an estimated 200 million people (Cohen, J., *Science* (1999) 285:26). About 30,000 newly acquired HCV infections occur in the United States annually. Additionally, there is a large incidence of HCV infection in developing countries. Although the immune response is capable of clearing HCV infection, the majority of infections become chronic. Most acute infections remain asymptomatic and liver disease usually occurs only after years of chronic infection.

The viral genomic sequence of HCV is known, as are methods for obtaining the sequence. See, e.g., International Publication Nos. WO 89/04669; WO 90/11089; and WO 90/14436. HCV has a 9.5 kb positive-sense, single-stranded RNA genome and is a member of the Flaviridae family of viruses. At least six distinct, but related genotypes of HCV, based on phylogenetic analyses, have been identified (Simmonds et al., *J. Gen. Virol.* (1993) 74:2391-2399). The virus encodes a single polyprotein having about 3000 amino acid residues (Choo et al., *Science* (1989) 244:359-362; Choo et al., *Proc. Natl. Acad. Sci. USA* (1991) 88:2451-2455; Han et al., *Proc. Natl. Acad. Sci. USA* (1991) 88:1711-1715).

In particular, several proteins are encoded by the HCV genome. The order and nomenclature of the cleavage products of the HCV polyprotein is as follows: $NH_2$—C-E1-E2-p7-NS2-NS3-NS4a-NS4b-NS5a-NS5b-COOH. Another protein (F) has also been identified and results from translational frame-shifting within the C gene. Branch et al., *Semin. Liver Dis.* (2005) 25:105-117. Initial cleavage of the polyprotein is catalyzed by host proteases which liberate three structural proteins, the N-terminal nucleocapsid protein (termed core) and two envelope glycoproteins, gpE1 (also known as E) and gpE2 (also known as E2/NS1), as well as nonstructural (NS) proteins that encode the viral enzymes and other activities. The NS regions are termed NS2, NS3, NS4 and NS5. NS2 is an integral membrane protein with proteolytic activity and, in combination with NS3, cleaves the NS2-NS3 junction. The NS3 protease, along with its NS4a cofactor, serves to process the remaining polyprotein. In these reactions, NS3 liberates an NS3 cofactor (NS4a), two proteins (NS4b and NS5a), and an RNA-dependent RNA polymerase (NS5b). Completion of polyprotein maturation is initiated by autocatalytic cleavage at the NS3-NS4a junction, catalyzed by the NS3 serine protease.

Development of anti-viral drugs and vaccines against HCV infection has been hindered by the lack of a suitable animal model or cell culture system for HCV replication. HCV has been found to grow poorly in cell culture, and the use of subgenomic replicons, which replicate more efficiently in cultured cells, has failed to produce infectious viral particles (Bartenschlager et al. (2000) J. Gen. Virol. 81:1631-1648; Lohmann et al. (1999) Science 285:110-113; Ikeda et al. (2002) J. Virol. 76:2997-3006; Pietschmann et al. (2002) J. Virol. 76:4008-4021). Furthermore, existing replication systems have been found to be inadequate for testing some antiviral strategies. Replication systems based on self-replicating subgenomic replicons that only express nonstructural viral proteins do not emulate all steps of the HCV virus life cycle that may be targeted for antiviral intervention. Cell lines that are stably transfected with HCV precursors, but that are incapable of HCV RNA replication, cannot be used to screen for antiviral drugs that block viral RNA replication. Recently, Pietschmann et al. demonstrated that infectious virus could be produced from a bicistronic artificial HCV genomic construct in cell culture utilizing a chimeric construct comprising on one cistron, sequences from HCV type 2a strain JFH1 and sequences from a second HCV strain, and on a separate cistron, a reporter gene for monitoring transcription and infection (PNAS (2006) 103:7408-7413).

There remains a need, however, for improved tissue culture systems for production of HCV and for development of a tissue culture system that can cost-effectively and efficiently produce infectious HCV particles that can be used in testing antiviral therapeutics.

SUMMARY OF THE INVENTION

The present invention is based on the development of a reliable cell culture system for production of infectious HCV particles. In particular, the invention provides methods of growing wild-type and chimeric HCV viruses in cells that are capable of being infected with HCV, such as hepatocytes or other liver derived primary cells or tumors cell lines. The methods utilize recombinant monocistronic and bicistronic genomic constructs for production of virus, including constructs for production of the wild-type HCV type 2a strain JFH1 and constructs for production of chimeric viruses comprising NS3 to NS5b and a C-terminal portion of NS2 from strain JFH1, and core to p7 and an N-terminal portion of NS2 from a second HCV isolate (e.g., type 1a H77C, type 1b Con1, or type 3a NZ1 or 452). Constructs of the invention may also include a reporter gene to facilitate measurement of RNA replication and viral infectivity in cultures. The cell culture system may also include various factors that improve viral replication or infectivity, such as an RNA silencing suppressor (e.g., an influenza virus NS1 polypeptide) to inhibit host defense pathways or CD81 to facilitate viral entry into host cells. In addition, a neutralization assay using HCV grown in cell culture is described and neutralization titers measured by this assay have been found to correlate well with actual protection from HCV infection in vaccinated animals.

Thus, the subject invention is represented by, but not limited to, the following embodiments:

In one aspect, the invention includes a recombinant HCV bicistronic genomic construct comprising a first cistron comprising a coding sequence for an N-terminal fragment of the JFH1 core protein comprising at least the first 12 residues and up to the first 18 residues of the JFH1 core protein, including any number of residues in between, such as residues 1-12, 1-13, 1-14, 1-15, 1-16, 1-17, or 1-18 of the JFH1 core protein, wherein the coding sequence for the N-terminal fragment of the JFH1 core protein is linked to and translated in frame with a reporter gene to generate a single polypeptide fusion product. The reporter gene is followed by an internal ribosomal entry site (IRES) for translation of a second cistron. The second cistron comprises a coding sequence for an HCV polyprotein comprising open reading frames for core, E1, E2, p7, NS2, NS3, NS4a, NS4b, NS5a, and NS5b regions, wherein the C-terminal portion of NS2, and the NS3, NS4a, NS4b, NS5a, and NS5b regions of the HCV polyprotein are derived from JFH1 and the core, E1, E2, and p7 regions, and the N-terminal portion of NS2 are derived from a second HCV isolate. The second isolate may be the same or a different subtype than JFH1. Preferably, the second isolate is a different subtype than JFH1. The non-JFH1 strain or isolate can be of HCV type 1a, 1b, 2a, 2b, 3a, 3b, 4, 5, or 6. In certain embodiments, the non-JFH1 strain or isolate is H77C, Con1, NZ1, or 452. The construct also contains a 5' HCV untranslated region, or a functional portion thereof, and a 3' HCV untranslated region, or a functional portion thereof, flanking the two cistrons. Exemplary HCV bicistronic genomic constructs comprise a nucleotide sequence selected from the group consisting of SEQ ID NOS:2-5.

In certain embodiments, the HCV NS2 gene is a chimeric gene, encoding an amino portion of NS2 from the same HCV strain or isolate as encoding the E1, E2, and P7 proteins and a carboxy portion of NS2 from JFH1. Suitable junction sites between the amino and carboxy portions of the NS2 gene are described in Pietschmann et al. (Proc. Natl. Acad. Sci. U.S.A. (2006) 103:7408-7413; herein incorporated by reference). In certain embodiments, the junction between the amino and carboxy portions of NS2 occurs at a residue selected from the group consisting of 871-877.

In certain embodiments, the recombinant HCV bicistronic genomic construct comprises a reporter gene encoding a firefly luciferase, *Renilla* luciferase, or, green fluorescent protein.

In one embodiment, the recombinant HCV bicistronic genomic construct comprises an encephalomyocarditis virus (EMCV) IRES.

In another aspect, the invention includes a recombinant HCV monocistronic genomic construct comprising coding sequences for core, E1, E2, p7, NS2, NS3, NS4a, NS4b, NS5a, and NS5b regions of an HCV polyprotein. In certain embodiments, the recombinant HCV monocistronic genomic construct encodes a chimeric HCV polyprotein, wherein the C-terminal portion of NS2, and the NS3, NS4a, NS4b, NS5a, and NS5b regions of the HCV polyprotein are derived from JFH1 and the core, E1, E2, and p7 regions, and the N-terminal portion of NS2 are derived from a second HCV isolate. The second isolate may be the same or a different subtype than JFH1. Preferably, the second isolate is a different subtype than JFH1. The non-JFH1 strain or isolate can be of HCV type 1a, 1b, 2a, 2b, 3a, 3b, 4, 5, or 6. In certain embodiments, the non-JFH1 strain or isolate is H77C, Con1, NZ1, or 452. The construct also contains a 5' HCV untranslated region, or a functional portion thereof, and a 3' HCV untranslated region, or a functional portion thereof, on opposite ends of the construct.

In some embodiments, the HCV NS2 gene is a chimeric gene, encoding an amino portion of NS2 from the same HCV strain or type as encoding the E1, E2, and P7 proteins and a carboxy portion of NS2 from the JFH1 type. Suitable junction sites between the amino and carboxy portions of the NS2 gene are described in Pietschmann et al. (supra). In certain embodiments, the junction between the amino and carboxy portions of NS2 occurs at a residue selected from the group consisting of 871-877.

In certain embodiments, the recombinant HCV monocistronic genomic construct comprises a coding sequence for an N-terminal fragment of the JFH1 core protein linked to a reporter gene, wherein the N-terminal fragment of the JFH1 core protein comprises at least the first 12 residues and up to the first 18 residues of the JFH1 core protein, including any number of residues in between, such as residues 1-12, 1-13, 1-14, 1-15, 1-16, 1-17, or 1-18 of the JFH1 core protein, wherein the coding sequence for the N-terminal fragment of the JFH1 core protein is linked to and translated in frame with the reporter gene. In certain embodiments, the reporter gene encodes a firefly luciferase, *Renilla* luciferase, or, green fluorescent protein. The recombinant HCV monocistronic genomic construct may also comprise a coding sequence for a cleavage site that allows separation of the expressed reporter gene product from the HCV polyprotein. In one embodiment, the recombinant HCV monocistronic genomic construct comprises a coding sequence for an FMDV 2A protease following the reporter gene. Additionally, the recombinant HCV monocistronic construct may further comprise a coding sequence for a ubiquitin protease cleavage site.

In certain embodiments, the invention includes a recombinant HCV monocistronic genomic construct comprising in 5' to 3' order:
  a) an HCV 5' untranslated region, or a functional portion thereof;
  b) a polynucleotide comprising a coding sequence for an N-terminal fragment of the JFH1 core protein, wherein said fragment comprises at least the first 12 residues and up to the first 18 residues of the JFH1 core protein, wherein the coding sequence for the N-terminal fragment of the JFH1 core protein is linked to a reporter gene;
  c) a coding sequence for a foot-and-mouth disease virus (FMDV) 2A protease;
  d) a coding sequence for a ubiquitin protease cleavage site;
  e) a polynucleotide encoding an HCV polyprotein comprising core, E1, E2, and p7 regions from an HCV strain or isolate other than JFH1, a chimeric NS2 region comprising an N-terminal portion of NS2 from an HCV strain or isolate other than JFH1 and a C-terminal portion of NS2 from JFH1, and NS3, NS4a, NS4b, NS5a, and NS5b regions from JFH1; and
  f) an HCV 3' untranslated region, or a functional portion thereof.

Exemplary recombinant HCV monocistronic genomic constructs comprise a polynucleotide selected from the group consisting of
  a) a polynucleotide comprising the contiguous sequence from nucleotide 7 to nucleotide 10953 of SEQ ID NO:8;
  b) a polynucleotide comprising the contiguous sequence from nucleotide 7 to nucleotide 10953 of SEQ ID NO:9;
  c) a polynucleotide comprising the contiguous sequence from nucleotide 7 to nucleotide 10971 of SEQ ID NO:10;
  d) a polynucleotide comprising the contiguous sequence from nucleotide 35 to nucleotide 9723 of SEQ ID NO:16
  e) a polynucleotide complementary to a polynucleotide of a)-d); and
  f) an RNA equivalent of a)-e).

In another aspect, the invention includes a vector comprising any of the bicistronic or monocistronic recombinant HCV genomic constructs described herein. In certain embodiments, the vector comprises a bicistronic construct comprising a nucleotide sequence selected from the group consisting of SEQ ID NOS:2-5. In other embodiments, the vector comprises a monocistronic construct comprising a nucleotide sequence selected from the group consisting of SEQ ID NOS: 6-10 and SEQ ID NO:16. In certain embodiments, the vector further comprises a promoter operably linked to the genomic construct that is capable of generating an RNA transcript from a DNA template. In one embodiment, the promoter is a T7 promoter.

In another aspect, the invention includes an HCV genomic RNA transcript comprising any of the bicistronic or monocistronic recombinant HCV genomic constructs described herein, wherein transfection of a suitable host cell with the HCV genomic RNA transcript is capable of producing infectious HCV particles.

In another aspect, the invention includes a tissue culture system for production of infectious HCV particles comprising a cell capable of supporting HCV replication transfected with a recombinant HCV genomic RNA transcript of the invention.

In certain embodiments, the tissue culture system comprises a cell capable of supporting HCV replication derived from human tissue. In certain embodiments, the tissue culture system comprises a hepatocellular carcinoma cell. In certain embodiments, the tissue culture system comprises a cell capable of supporting HCV replication from a cell line selected from the group consisting of Huh7, Huh7.5, Siena 8, and T7-11. In certain embodiments, the cell capable of supporting HCV replication is interferon-cured. In one preferred embodiment, the cell capable of supporting HCV replication is a hepatocyte or a hepatocyte-derived cell.

In certain embodiments, the tissue culture system further comprises a polynucleotide encoding a double stranded RNA binding protein that acts as an interferon antagonist or RNA silencing suppressor. The double stranded RNA binding protein can be an influenza virus NS1 protein. In certain embodiments, the NS1 polypeptide comprises the amino acid sequence of SEQ ID NO 15 or a functional fragment thereof that increases the yield of viral particles. In certain embodiments, the polynucleotide encoding the RNA silencing suppressor comprises a nucleotide sequence selected from the group consisting of SEQ ID NOS:11-14.

In certain embodiments, the tissue culture system further comprises a polynucleotide encoding a CD81 polypeptide to facilitate viral entry into host cells.

In certain embodiments, replication of the HCV genomic RNA transcript is maintained in the tissue culture system for at least 10 days after the genomic RNA transcript is introduced into a cell capable of supporting HCV replication. In certain embodiments, replication of the HCV genomic RNA transcript is maintained in the tissue culture system for at least 20 days after the genomic RNA transcript is introduced into a cell capable of supporting HCV replication. In certain embodiments, replication of the HCV genomic RNA transcript is maintained in the tissue culture system for at least 30 days after the genomic RNA transcript is introduced into a cell capable of supporting HCV replication. In some preferred embodiments, the cell capable of supporting HCV replication is a hepatocyte or hepatocyte-derived cell.

In certain embodiments, infectivity of virus produced from the HCV genomic construct is maintained in the tissue culture system for at least 9 days after the genomic RNA transcript is introduced into a cell capable of supporting HCV infection. In certain embodiments, infectivity of virus produced from the HCV genomic RNA transcript is maintained in the tissue culture system for at least 15 days after the genomic RNA transcript is introduced into a cell capable of supporting HCV infection.

In another aspect, the invention includes a method for producing infectious HCV particles in tissue culture, comprising transfecting a cell capable of supporting HCV infection with a recombinant HCV genomic RNA transcript of the invention and growing the cell in culture media under conditions suitable for replication of the HCV genomic RNA and secretion of infectious viral particles into the culture media.

In certain embodiments, the method further comprises the step of, prior to the transfection with the HCV genomic transcript, transfecting the cell capable of supporting HCV replication with a polynucleotide encoding an RNA silencing suppressor. The RNA silencing suppressor can be an influenza virus NS1 protein. In certain embodiments, the cell is transfected with a polynucleotide encoding an NS1 polypeptide comprising the amino acid sequence of SEQ ID NO 15 or a functional fragment thereof that increases the yield of viral particles. In certain embodiments, the polynucleotide encoding the RNA silencing suppressor comprises a nucleotide sequence selected from the group consisting of SEQ ID NOS: 11-14.

In certain embodiments, the cell capable of supporting HCV replication is derived from human tissue. In certain embodiments, the cell capable of supporting HCV replication is a hepatocellular carcinoma cell. In some embodiments, the cell is a hepatocyte cell. In certain embodiments, the hepatocyte cell is from a cell line selected from the group consisting of Huh7, Huh7.5, Huh7C, Siena 8, and T7-11. In certain embodiments, the hepatocyte cell is interferon-cured.

In another aspect, the invention includes a chimeric hepatitis C virus produced in a tissue culture system by any of the methods described herein, wherein the recombinant HCV genomic construct comprises a genomic sequence selected from the group of genomic sequences in SEQ ID NOS:3-5, SEQ ID NOS:8-10 and 16, the sequences of which include genomic HCV constructs and plasmid sequences.

In another aspect, the invention includes a kit comprising a cell capable of supporting HCV replication and any of the recombinant HCV genomic constructs described herein (i.e., RNA transcripts for infection and/or DNA vectors for production of viral RNA by in vitro transcription). In certain embodiments, the kit comprises a cell that is transfected with the recombinant HCV genomic construct. The kit may further comprise a polynucleotide encoding an RNA silencing suppressor. In certain embodiments, the kit comprises a cell that is transfected with the polynucleotide encoding the RNA silencing suppressor. In certain embodiments, the polynucleotide encodes an NS1 polypeptide comprising the amino acid sequence of SEQ ID NO 15 or a functional fragment thereof that increases the yield of viral particles. In certain embodiments, the polynucleotide encoding the RNA silencing suppressor comprises a nucleotide sequence selected from the group consisting of SEQ ID NOS:11-14.

In certain embodiments, the cell capable of supporting HCV infection is a hepatocyte cell and in yet further embodiments, the hepatocyte is derived from human tissue. In certain embodiments, the hepatocyte cell is a hepatocellular carcinoma cell. In certain embodiments, the hepatocyte cell is from a cell line selected from the group consisting of Huh7, Huh7.5, Huh7C, Siena 8, and T7-11. In certain embodiments, the hepatocyte cell is interferon-cured.

In another aspect, the invention includes a method of identifying a compound having anti-HCV activity, the method comprising:

a) treating an HCV tissue culture system described herein with a compound;
b) comparing at least one of HCV replication, expression of an HCV protein, or viral infectivity in said culture system treated with said compound to said tissue culture system not treated with said compound, wherein a reduction in the level of HCV replication, expression of HCV proteins, or viral infectivity in the tissue culture system treated with said compound is indicative of a compound with anti-HCV activity.

In one embodiment, the compound having anti-HCV activity can be a compound that inhibits HCV infectivity. In one embodiment, the compound that inhibits HCV infectivity is an antibody which in some embodiments can be a neutralizing antibody.

In another embodiment, the compound having anti-HCV activity can be a compound that inhibits HCV replication.

These and other embodiments of the subject invention will readily occur to those of skill in the art in view of the disclosure herein.

BRIEF DESCRIPTION OF THE SEQUENCES

Figure 1:
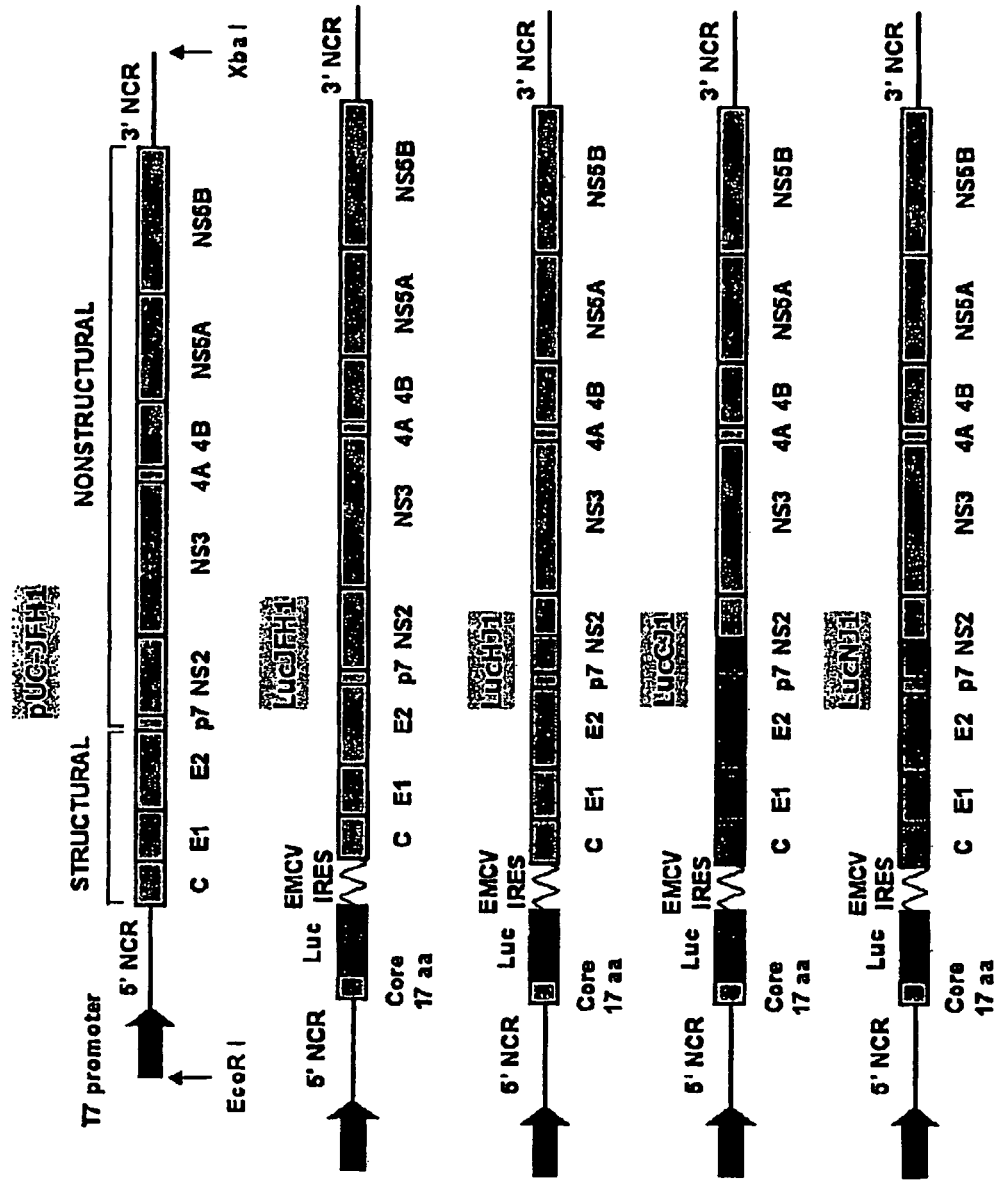
FIG. 1 depicts a schematic representation of recombinant wild-type and chimeric JFH1 genomic bicistronic constructs. Bicistronic constructs included a first cistron encoding the first 17 amino acids of the JFH1 core protein linked to a luciferase (Luc) reporter gene for monitoring RNA replication, an encephalomyocarditis virus (EMCV) internal ribosomal entry site (IRES), and a second cistron encoding a wild-type or chimeric JFH1 polyprotein. Chimeric constructs contained NS3 to NS5b coding regions from HCV type 2a strain JFH1, core to p7 coding regions from a different HCV isolate (construct LucHJ1: core to p7 region from HCV type 1a strain H77C, construct LucCJ1: core to p7 region from HCV type 1b strain Con1, and construct LucNJ1: core to p7 region from HCV type 3a strain NZ1), and a chimeric NS2 coding region with an intergenotypic junction at residue 871 of NS2 for the LucCJ1 and LucHJ1 constructs and at residue 877 of NS2 for the LucNJ1 construct.

SEQ ID NO:1 is the sequence of a pUC-18 derived plasmid containing the JFH1 genome.

SEQ ID NO:2 is the sequence of a pUC derived plasmid containing the JFH1 genome further comprising a luciferase gene.

SEQ ID NO:3 is the sequence of a pUC derived plasmid containing the JFH1/H77C chimeric genome further comprising the luciferase gene in a bicistronic configuration.

SEQ ID NO:4 is the sequence of a pUC derived plasmid containing the JFH1/Con1 chimeric genome further comprising the luciferase gene in a bicistronic configuration SEQ ID NO:5 is the sequence of a pUC derived plasmid containing the JFH1/NZ1 chimeric genome further comprising the luciferase gene in a bicistronic configuration SEQ ID NO:6 is the sequence of a pUC derived plasmid containing the JFH1 genome further comprising the luciferase gene in a monocistronic configuration SEQ ID NO:7 is the sequence of a pUC derived plasmid containing the JFH1 genome further comprising the green fluorescent protein gene in a monocistronic configuration SEQ ID NO:8 is the sequence of a pUC derived plasmid containing the JFH1/H77C chimeric genomic construct further comprising the luciferase gene in a monocistronic configuration. The chimeric HCV genomic construct comprises from about nucleotide 7 to about nucleotide 10953 of SEQ ID NO:8

SEQ ID NO:9 is the sequence of a pUC derived plasmid containing the JFH1/Con1 chimeric genome further comprising the luciferase gene in a monocistronic configuration. The chimeric HCV genomic construct comprises from about nucleotide 7 to about nucleotide 10953 of SEQ ID NO:9

SEQ ID NO:10 is the sequence of a pUC derived plasmid containing the JFH1/NZ1 chimeric genome further comprising the luciferase gene in a monocistronic configuration. The chimeric HCV genomic construct comprises from about nucleotide 7 to about nucleotide 10971 of SEQ ID NO:10.

SEQ ID NO:11 is the sequence of the influenza NS1 gene inserted into a pCMV plasmid.

SEQ ID NO:12 is the sequence of a portion of the influenza NS1 gene inserted into a pCMV plasmid.

SEQ ID NO:13 is the sequence of a portion of the influenza NS1 gene inserted into a pCMV plasmid.

SEQ ID NO:14 is the sequence of the influenza NS1 gene inserted into a pCMV plasmid wherein an internal portion of the ns1 gene is deleted.

SEQ ID NO:15 is the amino acid sequence of NS1 from influenza.

SEQ ID NO:16 is the sequence of a pUC derived plasmid containing the JFH1/452 chimeric genome further comprising the luciferase gene in a monocistronic configuration. The chimeric HCV genomic construct comprises from about nucleotide 35 to about nucleotide 9723 of SEQ ID NO:16.

DETAILED DESCRIPTION OF THE INVENTION

The practice of the present invention will employ, unless otherwise indicated, conventional methods of virology, chemistry, biochemistry, recombinant DNA techniques and immunology, within the skill of the art. Such techniques are explained fully in the literature. See, e.g., *Fundamental Virology*, 3rd Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Cotowick and N. Kaplan eds., Academic Press, Inc.).

All publications, patents and patent applications cited herein, whether supra or infra, are hereby incorporated by reference in their entireties.

The following amino acid abbreviations are used throughout the text:

Alanine: Ala (A) Arginine: Arg (R)
Asparagine: Asn (N) Aspartic acid: Asp (D)
Cysteine: Cys (C) Glutamine: Gln (O)
Glutamic acid: Glu (E) Glycine: Gly (G)
Histidine: His (H) Isoleucine: Ile (I)
Leucine: Leu (L) Lysine: Lys (K)
Methionine: Met (M) Phenylalanine: Phe (F)
Proline: Pro (P) Serine: Ser (S)
Threonine: Thr (T) Tryptophan: Trp (W)
Tyrosine: Tyr (Y) Valine: Val (V)

1. DEFINITIONS

In describing the present invention, the following terms will be employed, and are intended to be defined as indicated below.

It must be noted that, as used in this specification and the appended claims, the singular forms "a", "an" and "the" include plural references unless the content clearly dictates otherwise. Thus, for example, reference to "an HCV genomic RNA transcript" includes a mixture of two or more such transcripts, and the like. Similarly, transfection of a cell with an HCV genomic RNA transcript is meant to include the situation where a plurality of cells are transfected with a plurality of genomic RNA transcripts.

The term "hepatitis C virus" (HCV) refers to an agent causative of Non-A, Non-B Hepatitis (NANBH). The nucleic acid sequence and putative amino acid sequence of HCV is described in U.S. Pat. Nos. 5,856,437 and 5,350,671. The disease caused by HCV is called hepatitis C, formerly called NANBH. The term HCV, as used herein, denotes a viral species of which pathenogenic strains cause NANBH, as well as attenuated strains or defective interfering particles derived therefrom.

HCV is a member of the viral family flaviviridae. The morphology and composition of Flavivirus particles are known, and are discussed in Reed et al., Curr. Stud. Hematol. Blood Transfus. (1998), 62:1-37; HEPATITIS C VIRUSES IN FIELDS VIROLOGY (B. N. Fields, D. M. Knipe, P. M. Howley, eds.) (3d ed. 1996). It has recently been found that portions of the HCV genome are also homologous to pestiviruses. Generally, with respect to morphology, Flaviviruses contain a central nucleocapsid surrounded by a lipid bilayer. Virions are spherical and have a diameter of about 40-50 nm. Their cores are about 25-30 nm in diameter. Along the outer surface of the virion envelope are projections that are about 5-10 nm long with terminal knobs about 2 nm in diameter.

The HCV genome is comprised of RNA. It is known that RNA containing viruses have relatively high rates of spontaneous mutation. Therefore, there can be multiple strains, which can be virulent or avirulent, within the HCV class or species. The ORF of HCV, including the translation spans of the core, non-structural, and envelope proteins, is shown in U.S. Pat. Nos. 5,856,437 and 5,350,671.

The term "HCV genomic construct" refers to a nucleic acid, either RNA or DNA, comprising an entire HCV genome, including coding sequences for all of the structural and nonstructural proteins of HCV. A DNA vector comprising an HCV genomic construct can be used for production of HCV RNA by in vitro transcription. An RNA transcript comprising an HCV genomic construct can be used to transfect cells to produce infectious HCV viral particles.

The term "HCV genomic RNA transcript" refers to an RNA transcript comprising an HCV genomic construct that is capable of replicating and producing infectious HCV viral particles when present in a cell. HCV genomic RNA transcripts as described herein are introduced into hepatocyte cells according to the present invention. The cells can additionally contain additional viral replicons and or plasmids containing or expressing additional nucleic acids, genes or proteins. One or more other additional genes and/or regulatory regions can also optionally be present and expressed in a cell transfected with an HCV genomic RNA transcript. Additional genes or proteins can be provided on the HCV genomic RNA transcript or can be stably or transiently transfected into the host cell genome using various techniques well known in the art. An additional gene or protein can be used e.g., as a marker for cell survival. Furthermore, an additional gene or protein may provide an accessory function that enhances or enables HCV replication, expression and/or virus or virus like particle production (e.g., NS1, CD81).

As used herein, the term "additional gene" is meant to encompass a gene or other nucleic acid that expresses a protein or provides a regulatory function in the cell. The additional gene can be heterologous to HCV and the host cell or may be from HCV or the host cell genome. Thus, as used herein, the term can mean a host cell gene that is already present in the host cell genome, but is provided as an additional gene either as an episomal element or integrated into a site on the host cell genome distinct from (and in addition to) its normal location.

It should be understood that the terms "genomic construct", "HCV genomic RNA transcript", and "genetic element" encompass the sense strand of the viral RNA or any complementary sequence (e.g. a cDNA reverse transcript or complementary RNA) that can be converted into the sense strand (the viral genomic RNA) and can be translated into the viral proteins required for replication. The cDNA genomic constructs can comprise double stranded DNA as well known in the art. Those of skill in the art will understand that alternate constructs may be used depending upon the desired goal, e.g. cloning part or all of a viral genome, expressing an RNA viral transcript from a double strand cDNA template and generating a viral product.

It should be further understood that the description of the exemplary genomic constructs is referred to in terms of sequences comprising "about" with reference to precise borders, since the borders of the genomic sequences or other inserts can readily be modified or altered without departing from the spirit of the invention. Thus, an HCV genomic construct can comprise sequences of additional nucleotides, depending upon the well known artifacts of cloning using selected restriction enzyme sites.

A "neutralizing antibody" as used herein is meant to refer to an antibody that prevents or reduces the ability of HCV to infect host cells. The term antibody is meant to include the singular and plural and can also refer to a monoclonal or polyclonal antibody preparation, single chain antibodies, antibody Fab and F(ab)$_2$ fragments and chimeric and humanized antibodies as known in the art.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

"Recombinant host cells", "host cells," "cells", "cell lines," "cell cultures", and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of coding sequence can be determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

"Operably linked" refers to an arrangement of elements wherein the components so described are configured so as to perform their usual function. Thus, a given promoter operably linked to a coding sequence is capable of effecting the expression of the coding sequence when the proper enzymes are present. Expression is meant to include the transcription any one or more of transcription of an of mRNA or viral RNA from a DNA or RNA template and can further include translation of a protein from an mRNA template The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells. The term refers to both stable and transient uptake of the genetic material, and includes uptake of peptide- or antibody-linked DNAs.

The terms "effective amount" or "pharmaceutically effective amount" of a composition or agent, as provided herein, refer to a nontoxic but sufficient amount of the composition to provide the desired response, such as suppression of HCV RNA replication, expression, and/or viral infectivity, and optionally, a corresponding therapeutic effect. An appropriate "effective" amount in any individual case may be determined by one of ordinary skill in the art using routine experimentation.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

2. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

A. HCV Tissue Culture System

The present invention provides a tissue culture system for production of infectious HCV viral particles. The tissue culture system includes hepatocyte cells containing a recombinant HCV genomic RNA transcript comprising a reporter gene. The cells are transfected with an HCV genomic RNA transcript that supports the expression of viral and non-viral proteins including a reporter gene (e.g., a firefly luciferase, *Renilla* luciferase, or green fluorescent protein gene), linked to the replication and or expression of the HCV genome. After introducing the HCV genomic RNA transcript into hepatocyte cells, the reporter gene allows HCV RNA replication, expression, or viral particle production to be measured. According to various embodiments, human-derived cells that are adapted for growth and/or stability of the HCV genomic RNA transcript may be used. The HCV tissue culture system may be used to produce virus (e.g., for immunogenic compositions such as vaccines) or to evaluate potential activity of HCV anti-viral compounds, including determination of the presence or absence of neutralizing antibody.

Reporter gene activity can be measured at various steps in order to monitor various viral activities. For example, cells are transfected with a genomic RNA transcript comprising a reporter gene, then grown, and lysed. The amount of reporter activity in cell lysates is assayed and provides a measure of the level of viral replication occurring inside the transfected cell population.

Alternatively or in addition to the above assay, a first population of naïve cells capable of supporting HCV may be transfected, grown for a time period, and then the supernatant containing secreted virus particles is harvested. The supernatant is then used to infect a second population of naïve cells which support HCV replication. The infected naïve cells are then grown and lysed and reporter activity is measured. This measurement will be an indication of the infectivity of the virus used to infect the first cell population.

Some advantages of the tissue culture system are the following: it does not require the use of animal models; the recombinant HCV genomic RNA transcripts replicate efficiently in cultured cells and produce infectious viral particles; and all steps of the HCV virus life cycle that may be targeted for antiviral intervention are reproduced. The tissue culture system thus provides a convenient and cost-effective means for producing virus and screening and detecting potential anti-HCV therapeutic agents.

The cells used in the HCV tissue culture system may be any cells capable of replicating an HCV genomic RNA transcript and producing infectious virus, but are preferably immortalized human-derived cells, and in one embodiment are human hepatoma Huh7 cells or Huh7 derived cells. In some embodiments, the derived cells have been grown with a sub-genomic replicon, treated with interferon alpha to cure the cells of the replicon, and then Selected for an increased resistance to interferon alpha.

The HCV genomic constructs of the invention express the full HCV genome as a polyprotein, which includes the HCV structural proteins core, E1, and E2, and the HCV non-structural proteins p7, NS2, NS3, NS4a, NS4b, NS5a, and NS5b. In certain embodiments, a reporter gene is contained within the HCV genomic construct and is replicated when the construct is replicated. The presence of a reporter gene allows reporter activity to be measured for monitoring RNA replication and viral infectivity in the tissue culture system. In certain embodiments the reporter is firefly luciferase, *Renilla* luciferase, or green fluorescent protein.

The reporter gene may be co-expressed with the genes encoding the HCV proteins, either as a mono-cistronic, bicistronic or tricistronic RNA. In the bi-cistronic configuration, one or more genes within the genomic construct is under the translational control of a separate genetic element that does not regulate expression of the other genes also present in the construct. An additional gene or genes may be expressed (1) with the HCV protein(s), (2) with the reporter gene or (3) under the control of yet another separate translational control element contained in the genomic construct (i.e., the "tricistronic" configuration). Furthermore, the HCV proteins can be expressed together as an HCV polyprotein or may be under the expression of separate genetic elements as described above for the reporter gene and any additional gene(s). Alternatively, replication can be detected without protein expression of the reporter gene, for example, by assaying for the relative presence or absence of a nucleic acid that encodes reporter specific nucleic acid sequences.

In one preferred embodiment, the invention provides a monocistronic genomic HCV replicon having a luciferase gene encoded at the 5' region of the HCV polyprotein, and with a cleavage site between the HCV polyprotein and the reporter gene.

Genetic elements that regulate translation of genes are well known to the skilled artisan and include, e.g., an internal ribosome entry site (IRES). Suitable IRES sequences are known from poliovirus, encephalo-myocarditis virus (EMCV), and from HCV itself. In certain embodiments, the HCV genomic construct comprises an internal ribosome entry site (IRES). FIG. 1 shows exemplary bicistronic genomic constructs (described also in SEQ ID NOS:1-5) comprising an EMCV IRES. These bicistronic genomic constructs comprise a luciferase reporter gene (Luc) and wild-type JFH1 or chimeric virus genomes, as described in Example 2. The EMCV sequence is upstream of and drives expression of the HCV polyprotein. The EMCV IRES directs translation of the core to NS5B region that is flanked at the 3' end by the 3' non-coding region (NCR).

Figure 2:
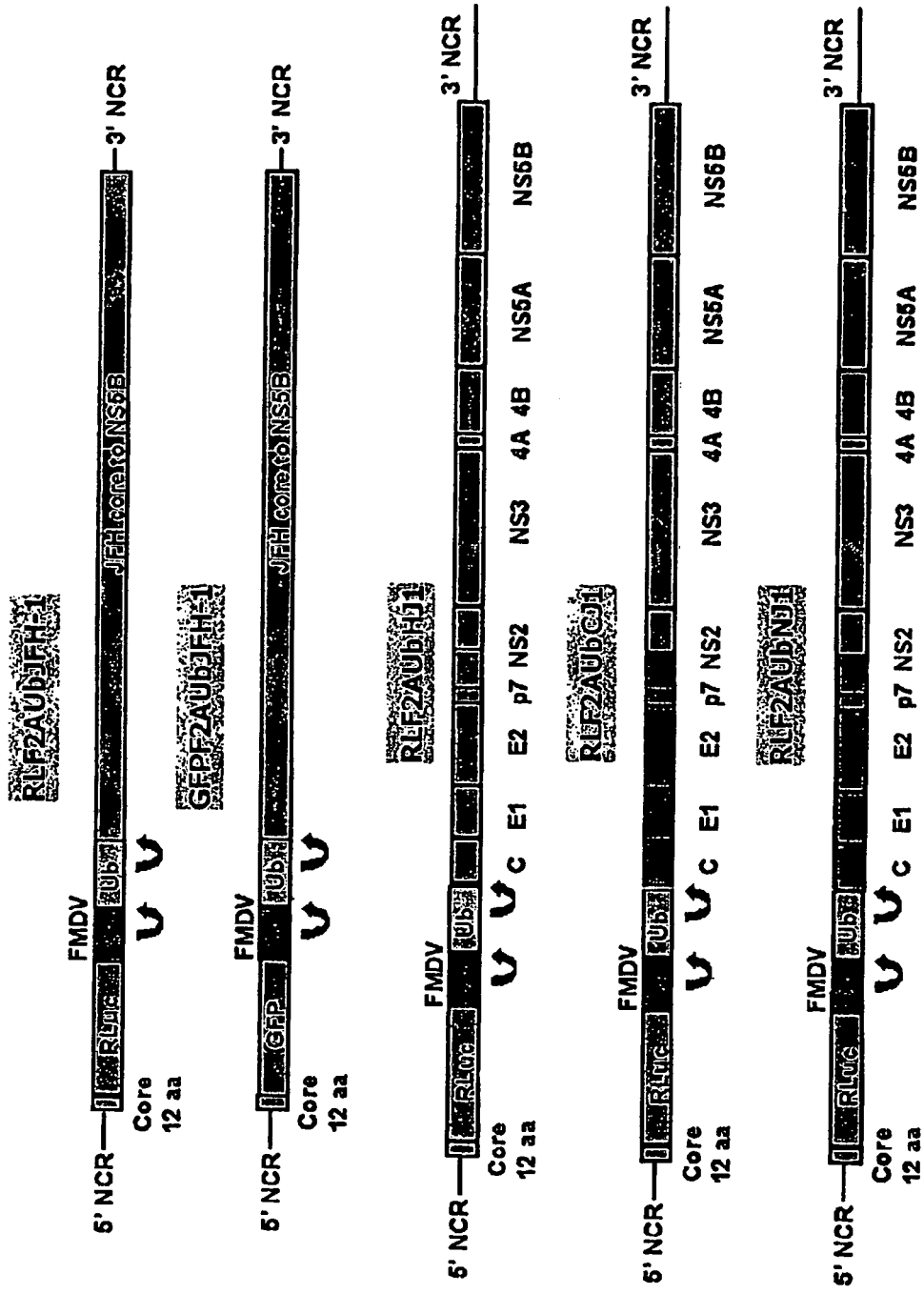
FIG. 2 depicts a schematic representation of recombinant wild-type and chimeric JFH1 monocistronic constructs. Monocistronic constructs included a region encoding the first 12 amino acids of the JFH1 core protein linked to a green fluorescent protein (GFP) or a *Renilla* luciferase (RLuc) reporter gene for monitoring RNA replication, a coding sequence for a foot-and-mouth disease virus (FMDV) 2A protease, a coding sequence for a ubiquitin protease cleavage site, and a wild-type or chimeric JFH1 polyprotein coding region. Chimeric constructs contained NS3 to NS5b coding regions from HCV type 2a strain JFH1, core to p7 coding regions from a different HCV isolate (RLF2AUbHJ1 construct: core to p7 region from HCV type 1a strain H77C, RLF2AUbCJ1 construct: core to p7 region from HCV type 1b strain Con1, and RLF2AUbNJ1 construct: core to p7 region from HCV type 3a strain NZ1), and a chimeric NS2 coding region with an intergenotypic junction at residue 871 of NS2 for the RLF2AubCJ1 and RLF2AUbHJ1 constructs and at residue 877 of NS2 for the RLF2AUbNJ1 construct.
Figure 17:
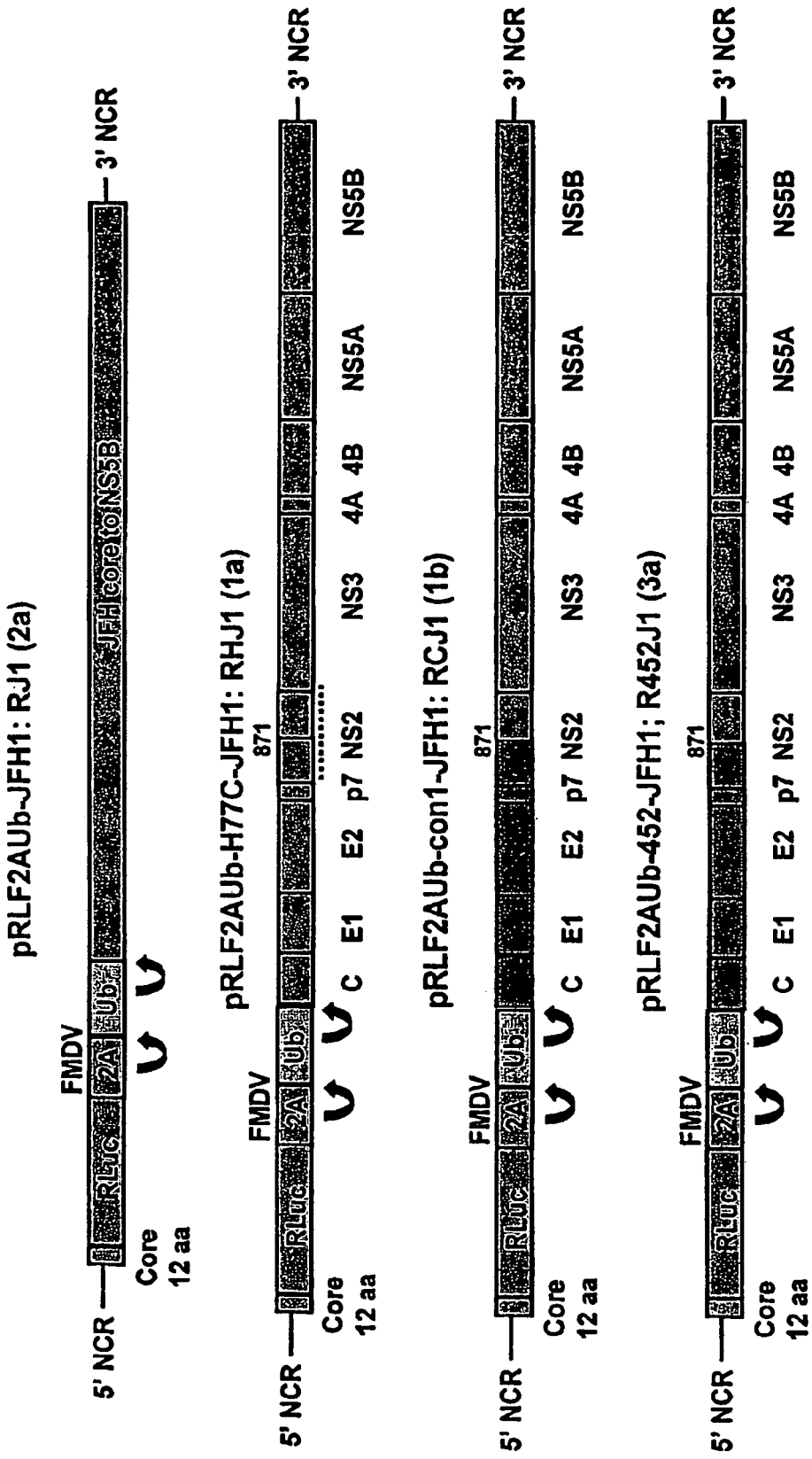
FIG. 17 depicts a schematic representation of recombinant wild-type and chimeric JFH1 monocistronic constructs, including RLF2AUbJFH1 (RJI): core to NS5b from HCV type 2a strain JFH1, RLF2AUbHJ1 (RHJ1): core to p7 region and N-terminal portion of NS2 from HCV type 1a strain H77C, RLF2AUbCJ1 (RCJ1) construct: core to p7 region and N-terminal portion of NS2 from HCV type 1b strain Con1, and RLF2AUb452JFH1 (R45211) construct: core to p7 region and N-terminal portion of NS2 from HCV type 3a strain 452, and a chimeric NS2 coding region with an intergenotypic junction at residue 871 in the RHJ1, RCJ1, and R452J1 constructs.

When the reporter gene contained in the HCV genomic construct is provided in the monocistronic configuration, it is expressed as part of the polyprotein produced by the genomic construct. The reporter gene can be cleaved from the polyprotein by providing cleavage recognition sites at both boundaries of the reporter gene product (or at one boundary if the reporter gene product is at the amino or carboxyl terminus of the polyprotein). The cleavage sites are recognized by a protease that specifically cleaves at the sites (e.g., the HCV protease). Alternatively, a CHYSEL sequence (cis-acting hydrolase element), such as the foot-and-mouth disease virus (FMDV) 2A sequence can be used to release the reporter gene product from the HCV polyprotein (Felipe (2004) Genetic Vaccines and Therapy 2:13). In another alternative, the reporter gene can be constructed without cleavage site(s) and can thus be expressed as a fusion protein fused to one of the HCV proteins. In a genomic construct, when the reporter gene is expressed as part of a fusion protein, the reporter gene can be linked to a coding sequence for a structural protein (i.e., core or envelope), or fragment thereof. In one embodiment, a coding sequence for an N-terminal fragment of the JFH1 core protein comprising at least the first 12 residues and up to the first 18 residues of the JFH1 core protein, including any number of residues in between, such as residues 1-12, 1-13, 1-14, 1-15, 1-16, 1-17, or 1-18 of the JFH1 core protein, is linked to the reporter gene. It is not necessary that the reporter gene always must express a protein. In some embodiments, the reporter can be detected by detecting the relative presence or absence of a nucleic acid sequence specific for the reporter.

FIGS. 2 and 17 show exemplary monocistronic genomic constructs comprising wild-type JFH1 or chimeric viral genomes and *Renilla* luciferase (RLuc) or green fluorescent protein (GFP) reporter genes (see Example 3 and SEQ ID NOS:6-10 and 16). These constructs, in addition, comprise downstream of the reporter gene a sequence encoding an FMDV 2A protease followed by a sequence encoding a ubiquitin (Ub) protease cleavage site, which together permit production of the HCV polyprotein with its natural N-terminus free of extraneous amino acids. The expressed FMDV2a protease undergoes self-cleavage at the penultimate amino acid at its C-terminus, thereby separating the reporter gene product from the HCV polyprotein, but leaving the one C-terminal FMDV2a amino acid linked to the remaining polyprotein fusion. Cleavage of the ubiquitin cleavage site at its C-terminus by host endogenous ubiquitin-specific proteases releases the HCV polyprotein product with its precise native N-terminus.

In some embodiments, the genomic construct expresses a selectable marker. The selectable marker allows for the selection of cells harboring the genomic construct. In some embodiments neomycin phosphotransferase gene (Neo) for selection with G418 is used. Examples of other markers based on drug resistance include aad, ble, dhfr, hpt, nptII, aphII, gat, and pac. Other markers may allow selection using antibiotics, such as Puromycin, Zeocin or Hygromycin, but one of skill in the art will understand that any marker gene known in the art that allows for selection of cells harboring the genomic construct may be used. In full length genomic constructs a neo gene is usually not present.

In certain embodiments, the genomic construct may have one or more cell-adaptive mutations. These mutations can enhance or allow HCV replication in cells that are either non-permissive or otherwise not efficient for HCV production. In one embodiment, wherein Huh7 cells are used, the genomic construct can have the following cell-adaptive mutations: E1202G, T12801 in the NS3 region and K1846T in NS4B region (Nicole Krieger, Volker Lohmann, and Ralf Bartenschlager, Enhancement of hepatitis C virus RNA replication by cell culture-adaptive mutations. 2001, Journal of Virology, 75(10): 4614-4624; Volker Lohmann, Sandra Hoffmann, Ulrike Herian, Francois Penin, and Ralf Bartenschlager, Viral and cellular determinants of hepatitis C virus RNA replication in cell culture. 2003, Journal of Virology, 77(5):3007-3019). Such cell-adaptive mutations are not necessarily required, however, as some cells can support HCV replication without having been adapted in cell culture (e.g., HCV-N or JFH-1). The tissue culture system of the invention can support replication of HCV genomic RNA transcripts with or without these mutations.

HCV genomic constructs may be derived from various viral strains and genotypes. The HCV genome can be a chimera of any types (e.g. 1, 2, 3, 4, 5, 6) or subtypes of HCV (e.g. 1a, 1b, 1c, 1d, 1e, 1f, 1g, 1 h, 1i, 1j, 1k, 1l, 1m, 2a, 2b, 2c, 2d, 2e, 2f, 2g, 2h, 2i, 2k, 2l, 2m, 3a, 3b, 3c, 3d, 3e, 3f, 3g, 3h, 3i, 3k, 4a, 4c, 4d, 4e, 4f, 4g, 4h, 4k, 4l, 4m, 4n, 4o, 4p, 4q, 4r, 4s, 4t, 5a, 6a, 6b, 6d, 6f, 6g, 6h, 6i, 6j, 6k, 6l, 6m, 6n). This nomenclature is the current standard, as set out by the NIAID Hepatitis C Virus (HCV) Sequence Database [hcv.lanl.govi-content/hcv-db/classification/genotable.hind] in which previous genotypes 7-9 have been reclassified as subtypes of type 6 (Simmonds et al. (1996) *J. Gen. Viral.* 77:3013-3024). Thus the new classification includes previous classifications I, II, III, IV, V, VI, 4α, 4β, 7a, 7b, 7c/NGII/VII, 7d, NGI, 8a, 8b, 9a, 9b, 9c, 10a/1133 and 11a.

For example, the complete sequences for several HCV-1 isolates are reported. See, e.g., NCBI accession nos. AB016785, AB049087, AB049088, AB049089, AB049090, AB049091, AB049092, AB049093, AB049094, AB049095, AB049096, AB049097, AB049098, AB049099, AB0490100, AB0490101, AB080299, AB 119282, AB154177, AB154178, AB154179, AB154180, AB154181, AB154182, AB154183, AB154184, AB154185, AB154186, AB154187, AB154188, AB154189, AB154190, AB154191, AB154192, AB154193, AB154194, AB154195, AB154196, AB154197, AB154198, AB 154199, AB 154200, AB 154201, AB 154202, AB 154203, AB 154204, AB 154205, AB154206, AB19133, AF009606, AF011751, AF011752, AF 011753, AF054247, AF054248, AF054249, AF054250, AF139594, AF165045, AF165046, AF165047, AF165048, AF165049, AF165050, AF165051, AF165052, AF165053, AF165054, AF165055, AF165056, AF165057, AF165058, AF165059, AF165060, AF165061, AF165062, AF165063, AF165064, AF176573, AF207752, AF207753, AF207754, AF207755, AF207756, AF207757, AF207758, AF207759, AF207760, AF207761, AF207762, AF207763, AF207764, AF207765, AF207766, AF207767, AF207768, AF207769, AF207770, AF207771, AF207772, AF207773, AF207774, AF208024, AF271632, AF290978, AF313916, AF333324, AF356827, AF483269, AF511948, AF511949, AF511950, AJ000009, AJ132996, AJ132997, AJ238799, AJ238800, AJ278830, AY045702, AY051292, AY460204, AY587016, D10934, D11168, D11355, D13558, D14484, D14853, D30613, D45172, D50480, D50481, D50482, D50483, D50484, D50485, D63857, D85516, D89815, D89872, D90208, L02836, M58335, M62321, M67463, M84754, M96362, NC_004102, S62220, U01214, U16362, U45476, U89019, X61596.

Similarly, the complete sequences for several HCV-2 isolates are reported. See, e.g., NCBI accession nos. AB030907, AB031663, AB047639, AB047640, AB047641, AB047642, AB047643, AB047644, AB047645, AF169002, AF169003, AF169004, AF169005, AF177036, AF238481, AF238482, AF238483, AF238484, AF238485, AF238486, AY232730, AY232731, AY232732, AY232733, AY232734, AY232735, AY232736, AY232737, AY232738, AY232739, AY232740, AY232741, AY232742, AY232743, AY232744, AY232745, AY232746, AY232747, AY232748, AY232749, AY587845, AY746460, D00944, D10988, D50409. One suitable HCV strain for use with the invention is the genotype 2a strain JFH1 (Kato et al. (2003) J. Med. Virol. 64:334-339).

The complete sequences for several HCV-3 isolates are also reported. See, e.g., NCBI accession nos. AF046866, D17763, D28917, D49374, D63821, X76918. The complete sequences for HCV-4 isolates are also known. See, e.g., NCBI accession no. Y11604. The complete sequences for several HCV-5 isolates are known. See, e.g., NCBI accession nos. AF064490 and Y13184. The complete sequences for several HCV-6 isolates are also known. See, e.g., NCBI accession nos. AY859526, AY878650, D63822, D84262, D84263, D84264, D84265, Y12083.

Additional sequences are as follows. Isolate HCV J1.1 is described in Kubo et al. (1989) *Japan. Nucl. Acids Res.* 17:10367-10372; Takeuchi et al. (1990) *Gene* 91:287-291; Takeuchi et al. (1990) J. Gen. Virol. 71:3027-3033; and Takeuchi et al. (1990) *Nucl. Acids Res.* 18:4626. The complete coding sequences of two independent isolates, HCV-J and BK, are described by Kato et al., (1990) *Proc. Natl. Acad. Sci. USA* 87:9524-9528 and Takamizawa et al., (1991) *J. Virol.* 65:1105-1113, respectively. HCV-1 isolates are described by Choo et al. (1990) *Brit. Med. Bull.* 46:423-441; Choo et al. (1991) *Proc. Natl. Acad. Sci. USA* 88:2451-2455 and Han et al. (1991) *Proc. Natl. Acad. Sci. USA* 88:1711-1715. HCV isolates HC-J1 and HC-J4 are described in Okamoto et al. (1991) *Japan J. Exp. Med.* 60:167-177. HCV isolates HCT 18, HCT 23, Th, HCT 27, EC1 and EC10 are described in Weiner et al. (1991) *Virol.* 180:842-848. HCV isolates Pt-1, HCV-K1 and HCV-K2 are described in Enomoto et al. (1990) *Biochem. Biophys. Res. Commun.* 170: 1021-1025. HCV isolates A, C, D & E are described in Tsukiyama-Kohara et al. (1991) *Virus Genes* 5:243-254.

In certain embodiments, the HCV genomic construct is chimeric comprising sequences derived from more than one viral strain or genotype. Such chimeric constructs encode a chimeric HCV polyprotein. In one embodiment, the chimeric polyprotein comprises a C-terminal portion of NS2, and the NS3, NS4a, NS4b, NS5a, and NS5b regions from JFH1 and the core, E1, E2, and p7 regions, and the N-terminal portion of NS2 from a second HCV isolate. The second isolate may be the same or a different subtype than JFH1. Preferably, the second isolate is a different subtype than JFH1. In certain embodiments, the non-JFH1 strain or isolate is of HCV type 1a, 1b, 2a, 2b, 3a, 3b, 4, 5, or 6. In certain embodiments, the non-JFH1 strain or isolate is H77C, Con1, NZ1, or 452.

In certain embodiments, the HCV NS2 gene is a chimeric gene, encoding an amino portion of NS2 from the same HCV strain or isolate as encoding the E1, E2, and P7 proteins and a carboxy portion of NS2 from JFH1. Suitable junction sites between the amino and carboxy portions of the NS2 gene are described in Pietschmann et al. (Proc. Natl. Acad. Sci. U.S.A. (2006) 103:7408-7413; herein incorporated by reference). In certain embodiments, the junction between the amino and carboxy portions of NS2 occurs at a residue selected from the group consisting of 871-877.

Exemplary bicistronic and monocistronic chimeric constructs are depicted in FIGS. 1, 2, and 17. Representative recombinant HCV monocistronic genomic constructs comprise a polynucleotide selected from the group consisting of: a polynucleotide comprising the contiguous sequence from nucleotide 7 to nucleotide 10953 of SEQ ID NO:8; a polynucleotide comprising the contiguous sequence from nucleotide 7 to nucleotide 10953 of SEQ ID NO:9; a polynucleotide comprising the contiguous sequence from nucleotide 7 to nucleotide 10971 of SEQ ID NO:10; a polynucleotide comprising the contiguous sequence from nucleotide 35 to nucleotide 9723 of SEQ ID NO:16; or RNA equivalents thereof. An HCV genomic RNA transcript comprising any of these bicistronic or monocistronic recombinant HCV genomic constructs can be used for transfection of a suitable host cell to produce infectious HCV particles.

RNA from an HCV genome can be used to make a complementary DNA copy. A DNA copy can be made by reverse transcription (RT). Alternatively, a DNA copy, or fragment thereof, can be made entirely or in part by synthetic means. Once a DNA copy of the RNA genome is available, it can be converted to double stranded DNA and can then be cloned into a vector (e.g. a plasmid), and the plasmid can be used to make DNA templates from which viral RNA can be transcribed. As an alternative, the DNA may be used to generate viral RNA without using a vector, in which case a suitable promoter for a DNA-dependent RNA polymerase will be introduced upstream of the start of the viral genome. Suitable promoters include the T7, T3 and SP6 promoters, which are used in in vitro transcription ('IVT') reactions. DNA copies of the virus can optionally be amplified e.g. using the polymerase chain reaction (PCR).

As an alternative, viral transcripts can be made from an RNA template using an RNA-dependent RNA polymerase, such as Qβ replicase. The transcription mediated amplification ('TMA') reaction may be used to amplify RNA.

Plasmids containing HCV sequences may be constructed by any method well-known in the art. See, e.g., Sambrook, Fritsch, and Maniatis, Molecular cloning a laboratory manual ($2^{nd}$ Edition) 1989 Cold Spring Harbor Laboratory Press; Joseph Sambrook, David W. Russell, Joe Sambrook, Molecular Cloning: a Laboratory Manual, ed. Cold Spring Harbor Laboratory Press, 2000 or PCR Applications, 1999, ed. M. Innis, D. Gelfand and J. Sninsky, Academic Press. The replicon LucJFH1 shown in FIGS. 12 and 13 may be constructed by replacing the Age1-NotI fragment from pJFH1 with the Age1-Not1 fragment from Luc-JFH1. Except for the chimeric constructs containing a part of JFH1 and part of various other HCV serotype structural protein genes, the genomic constructs of the invention were synthesized artificially utilizing (phosphodiester synthesis and cloned into pUC plasmids as described in the Figures and accompanying text.

The fragment of DNA that contained the coding sequences for the FMDV 2A protease and the ubiquitin protease cleavage site was generated by artificial synthesis as part of the pLucJFH1 monocistronic plasmid.

It will readily be appreciated by one of ordinary skill in the art that various alternative cloning strategies can be employed to construct the genomic viral constructs of the invention without departing from the scope of the invention.

Restriction enzyme sites were utilized to clone various chimeric HCV genomes into pUC plasmid vectors. Following successful generation of recombinant viral genomic constructs, restriction enzyme sites were utilized to generate genomic constructs. Sequences were confirmed following cloning using standard sequencing techniques.

A wide variety of methods can be used to deliver the expression constructs to cells. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, liposomes, peptoid delivery, or microinjection. See, e.g., Sambrook et al., supra, for a discussion of techniques for transforming cells of interest; and Feigner, P. L., *Advanced Drug Delivery Reviews* (1990) 5:163-187, for a review of delivery systems useful for gene transfer. Methods of delivering DNA using electroporation are described in, e.g., U.S. Pat. Nos. 6,132,419; 6,451, 002, 6,418,341, 6,233,483, U.S. Patent Publication No. 2002/0146831; and International Publication No. WO/0045823, all of which are incorporated herein by reference in their entireties.

Reporter Genes

The inclusion of reporter genes in the recombinant genomic constructs of the present invention allows anti-HCV activity of compounds to be monitored in the tissue culture system in real-time. In addition, it is desirable that anti-HCV activity be repeatedly quantitated rather than at a single time point, and the presence of a reporter gene facilitates such observations.

Preferably, the reporter gene is easily assayed. For example, the reporter gene may give a detectable signal, such as a visible signal. The reporter gene may encode a protein which gives a visible signal itself, or which catalyses a reaction, which gives a visible, change, e.g., a fluorescent protein or an enzyme. The reporter gene may encode an enzyme such as a beta-galactosidase or a peroxidase, both of which are commonly used with colored substrates and/or products. The reporter gene may encode a fluorescent protein, such as green fluorescent protein (GFP) or a fluorescent derivative thereof such as yellow fluorescent protein (YFP), red fluorescent protein (RFP), or cyan fluorescent protein (CFP). The reporter gene may encode a luminescent protein, such as firefly or *Renilla* luciferase. The reporter gene may drive DNA replication in the cell or may encode a drug resistance marker. The reporter gene may encode an antigen that can be detected with an antibody that specifically binds the antigen. In addition, reporter genes that encode for secreted proteins that are measurable in media may be used. Examples of such reporter genes are genes encoding for secreted alkaline phosphatase or human growth hormone. The reporter gene may also be a unique nucleic acid sequence that can be detected utilizing nucleic acid hybridization and/or amplification techniques. The above list is exemplary and is not meant to be limiting to sources for the reporter gene, many more which can readily be envisioned by the person of ordinary skill in the art.

Reporter genes that may find use in this invention include, e.g., antigens that have a known antibody for detection (e.g., human growth hormone and antibody to human growth hormone) and enzymes that have an activity that can be detected in vitro or in vivo (e.g., alkaline phosphatase, the luciferases, green fluorescent protein and the like). Additionally, as indicated above, detection of the presence of nucleic acid encoding the reporter can also be monitored to determine replication, expression or particle production.

Thus, as defined herein, detection of reporter gene "activity" includes the detection of the physical presence or chemical activity of the product of the reporter gene and also includes detection of all or part of a nucleic acid sequence that is specific for the reporter gene. The reporter signal can be detected in vivo in cell cultures or quantitated in vitro from cell lysates.

Cell Lines

Any cell line capable of supporting replication of the HCV genomic RNA transcripts may be used. Besides the Huh7 cell line, the human cancer cell line HeLa, murine hepatoma Hepa1-6, HEK293 human hepatoma cell lines HepG2 And IMY-N9 (a cell line derived from fusing human hepatocytes and HepG2 cells) are also known to support HCV replicon replication. Therefore, any of these tumor cell lines, or any other cell line that supports the replication of an HCV genomic RNA transcript may be used in the tissue culture system. In some embodiments, the cell line is derived from human cells, preferably from human hepatoma cell line Huh7.

One cell line for use with the invention is derived from a hepatocellular carcinoma, namely the human hepatoma cell line known as 'Huh7' (Nakabayashi et al. (1982) *Cancer Res* 42:3858-63). A useful Huh7-derived cell line is '21-5', which supports a full length HCV replicon (Pietschmann et al. (2002) *J Virol* 76:4008-21). Other suitable cell lines are Huh-7.5 and Huh-7.8, which are sub-lines of Huh-7 that can support complete HCV replication in cell culture (Blight et al. (2002) *J. Virol*. 76:13001-14; WO2004/044182), with Huh-7.5 being preferred. Cells derived by passaging of Huh7 cells (and their derivatives) can also be used, as well as cells derived by treating Huh7 cells with α-interferon and/or γ-interferon. As described in WO2004/044182, cell lines permissive for HCV can be prepared by a process comprising (a) culturing cells infected with HCV; (b) curing the cells of HCV; and (c) identifying a sub-line of the cured cells that is permissive for HCV replication.

The use of human-derived cells for HCV replication is desirable in order to provide a more accurate model of HCV replication and response to treatment in humans. It should be noted that in some embodiments, the cells are tumor cells. Tumor cells (e.g., Huh-7, HeLa, etc.) may be more easily passaged in culture. However, the invention is not limited to tumor cells but may be practiced with any cell or cell line that supports the replication of an HCV genomic RNA transcript.

According to various embodiments, the cell line may be adapted for increased growth rate in culture or increased HCV replication or expression (for example, as measured by a bioluminescent luciferase signal where a luciferase reporter is used). Cell lines that have been adapted for increased growth rate and/or adapted for stability of the HCV genomic RNA transcript in culture may be referred to herein as adapted cell lines.

In some embodiments, cells stably harboring HCV genomic RNA transcripts may be isolated by performing a luciferase (or other reporter) assay on the cells and then expanding the cells expressing the highest luciferase (or other reporter) signal.

In embodiments wherein adaptation for growth kinetics is performed first, the cells adapted for growth kinetics may not contain the HCV genomic RNA transcript (e.g., the cells may have been "cured" of the RNA transcript during passaging or the adapted cells may be derived from cells not harboring the RNA transcript). In these cases, the cells may be transfected with the HCV genomic RNA transcript prior to performing the luciferase (or other reporter) assay.

It should be noted that while adaptation for growth and/or stability may be desirable for some studies and cell lines, the invention may also be practiced with directly derived (non-adapted) cell lines, for example, Huh7 cells transfected with an HCV genomic RNA transcript.

Media

Any media capable of supporting cell growth and replication of the HCV genomic RNA transcripts may be used. In general, the methods described in Lidenbach et al. (*Science* (2005) 309:623-626; herein incorporated by reference) were utilized for cell culture.

Other Factors

In addition, the tissue culture system may also include various other factors that improve viral replication or infectivity. For example, the tissue culture system may further comprise a polynucleotide encoding a double stranded RNA binding protein that acts as an interferon antagonist or RNA silencing suppressor. Viral titers can be improved by blocking host antiviral defense mechanisms that interfere with viral replication. One trigger of host defense mechanisms is viral double-stranded RNA, which is produced as an intermediate during viral replication. Double stranded RNA induces host interferon and RNA silencing antiviral responses. Suppressors of interferon and RNA silencing responses are produced by certain viruses. For example, the NS1 protein of influenza virus is a double stranded RNA binding protein that blocks activation of host interferon-induced dsRNA-dependent protein kinase PKR and RNA interference (RNAi). NS1 is required for efficient influenza virus replication and also improves HCV infectivity.

Thus, in certain embodiments, cells are transfected with a polynucleotide encoding an RNA silencing suppressor prior to transfection with HCV genomic RNA. A polynucleotide encoding NS1 from any influenza strain, or a fragment thereof that suppresses RNA silencing, can be used in the practice of the invention. The full-length NS1 protein contains a dsRNA binding domain, which inhibits PKR and RNAi, and an effector domain, which functions in inhibiting pre-mRNA splicing and nuclear export of mRNA. A representative NS1 gene comprises the sequence of SEQ ID NO:15. The dsRNA binding domain and the effector domain reside at amino acid residues 1-82 and 138-147, respectively.

In addition, the NS1 protein comprises two nuclear localization signals (NLS1 and NLS2), a cleavage and polyadenylation specificity factor (CPSF) binding site, and a polyadenylation binding protein II (PABII) binding site.

In certain embodiments, a polynucleotide encoding an NS1 polypeptide comprising the amino acid sequence of SEQ ID NO 15 or a functional fragment thereof that increases the yield of viral particles is used in the practice of the invention. In certain embodiments, the polynucleotide encoding an NS1 polypeptide comprises a nucleotide sequence selected from the group consisting of SEQ ID NOS:11-14.

In addition, the tissue culture system may include a polynucleotide encoding a CD81 polypeptide. Increasing the expression of the CD81 receptor on the surface of cells facilitates viral entry into cells (Pileri et al. (1998) Science 282: 938-941; herein incorporated by reference). Cells can be transfected with a CD81 expression plasmid prior to transfection with HCV RNA to improve infectivity.

B. Applications

The HCV tissue culture system can be used to monitor replication, expression, or infectivity of HCV by detecting reporter gene activity from HCV genomic RNA transcripts. The HCV tissue culture system also provides a means for monitoring one or more essential steps in the life cycle of HCV by detecting or monitoring reporter gene activity present in HCV virus produced from cells containing the recombinant HCV genomic RNA transcript. The virus life cycle includes the steps required for a virus to enter into a cell, produce virus particles and exit the cell in order to infect other cells. These steps include binding to the cell surface, interacting with receptors on the surface which facilitate cell entry, uncoating the virus particle to release the viral genome, replication and expression of the viral genome, particle maturation including packaging the viral genome into a particle, egress through the cell and finally exiting the cell and the release of viral progeny. (See Fields Virology (1996) Chapter 10: Virus-Host Interactions D. Knipe).

In another aspect, the tissue culture system provides a model of HCV growth that may be used for evaluation and identification of inhibitors of HCV replication and infection, for pharmacokinetic (PK) and pharmacodynamic (PD), toxicity studies and rapid screening of anti-viral HCV candidate compounds.

In another aspect, the invention provides a method of identifying a compound having anti-HCV activity, i.e. a compound that reduces or inhibits the level of HCV replication, expression of HCV proteins, and/or viral infectivity. A compound can directly regulate replication by interfering with replication of the HCV genomic RNA transcript in the host cell or can indirectly regulate replication by interfering with expression of HCV proteins that are necessary for HCV replication in the host cell. Alternatively, as discussed below, the HCV tissue culture system provides a method of identifying compounds that have no effect on replication or expression per se, but instead reduce or inhibit virus particle formation.

Replication of an HCV genomic RNA transcript and/or viral infectivity titers can be measured by detecting reporter gene activity in cell cultures. In one embodiment, cells containing an HCV genomic RNA transcript further comprising a reporter gene, are contacted with one or more test compounds. The reporter gene is only replicated if the HCV genomic RNA transcript is replicated. As discussed herein, depending on the embodiment, expression of the reporter gene protein does not have to, but may optionally be linked to expression of the HCV polyprotein. Activity of the reporter gene contained within the HCV genomic RNA transcript in cells exposed to one or more test compounds is compared to activity of the reporter gene contained within the HCV genomic RNA transcript in cells that are not contacted with a test compound. A compound that reduces RNA replication, expression, and/or viral infectivity is a compound that may have use as a medicament for the regulation of HCV replication, expression, and/or infectivity in a human.

The HCV tissue culture system may be used to evaluate potential HCV antiviral compounds. In one embodiment, the hepatocyte cells, transfected with recombinant HCV genomic RNA transcripts, are treated with a compound known to reduce or prevent HCV replication and or particle formation and then the cells are treated with a second candidate compound to determine whether the second candidate compound has an additive or synergistic effect with the known compound in reducing or preventing HCV infection. The tissue culture system may also be used to measure replication, expression, and infectivity of HCV in culture as described herein.

Screening for Anti-Viral Compounds

The tissue culture system described herein can be used to identify compounds that have antiviral effects, for example, reduce replication, expression, or production of HCV in culture. In addition, combinations of compounds can be tested for synergistic or additive effects.

An "antiviral agent" or "antiviral compound" as used herein refers to an agent that is effective in reducing or inhibiting the formation and/or replication of a virus in a mammal. Antiviral agents as used herein are meant to include agents that act specifically on virus biology to reduce or inhibit viral replication. Antiviral agents can include agents targeted at interfering with one or more virus functions, including, but not limited to viral or host required enzymatic activity, viral binding, viral entry, viral packaging and viral infectivity. This group of compounds can include small molecules and antibodies and other biologics.

In the case of anti HCV agents, any antiviral agent that inhibits the replication or particle formation of HCV infectious virus is considered an antiviral agent and an anti-HCV virus agent. This includes agents that interfere with either host or viral mechanisms necessary for the formation and/or replication of a virus in a mammal. Anti-HCV virus agents include, for example, ribavirin, amantadine, VX-497 (merimepodib, Vertex Pharmaceuticals), VX-498 (Vertex Pharmaceuticals), Levovirin, Viramidine, Ceplene (maxamine), XTL-001 and XTL-002 (XTL Biopharmaceuticals), MN283-Valopictitabine, Idenix). Antiviral agents can also include nucleic acids (e.g., siRNA and antisense RNA) or small molecules that may interfere with one or more enzymatic activities necessary for viral replication and packaging such as protease, helicase and polymerase functions. Anti-HCV virus agents can also include nucleic acids (e.g., siRNA and antisense RNA) or small molecules that may interfere with one or more enzymatic activities necessary for HCV replication and packaging such as protease, helicase and polymerase functions. Such nucleic acids can be provided in the form of anti-sense molecules, double stranded duplex DNA, siRNA and the like. Antiviral agents can include immunomodulatory compounds, either as non-specific or specific modulators of the immune system. Anti HCV agents can also include vaccines such as therapeutic and prophylactic vaccines against HCV and antibodies or small molecules which interfere with HCV receptor binding.

Candidate Compounds

Typical candidate compounds for use in all the screening methods of the invention include, but are not restricted to, peptides, peptoids, proteins, lipids, metals, small organic molecules, RNA aptamers, antibiotics and other known pharmaceuticals, polyamines, antibodies or antibody derivatives (e.g., antigen-binding fragments, single chain antibodies including scFvs, etc.), and combinations or derivatives thereof. Small organic molecules have a molecular weight of about more than 50 and less than about 2,500 daltons, and most preferably between about 300 and about 800 daltons. Candidate compounds may be derived from large libraries of synthetic or natural compounds. For instance, synthetic compound libraries are commercially available from MayBridge Chemical Co. (Revillet, Cornwall, UK) or Aldrich (Milwaukee, Wis.). Alternatively, libraries of natural compounds in the form of bacterial, fungal, plant and animal extracts may be used. Additionally, candidate compounds may be synthetically produced using combinatorial chemistry either as individual compounds or as mixtures. Compounds can include antibodies or fragments of antibodies that retain the antibody antigen binding capacity.

Pharmacological Studies

The tissue culture system of the present invention may be used for pharmacokinetic, pharmacodynamic and toxicology studies of potential anti-viral compounds and protocols. The tissue culture system may also be used to monitor the course of HCV replication and also to determine the drug mechanism of action.

The tissue culture system may be used to identify and evaluate compounds or protocols that inhibit HCV replication. The tissue culture system may also be used to identify anti-viral compounds that may inhibit other steps in the viral life cycle (e.g., compounds that inhibit virus packaging or egress from the cell).

The tissue culture system is treated with a candidate compound or using a candidate protocol. Alternatively, the tissue culture system is treated with a combination of compounds already known or determined to be effective immunomodulators against HCV, such as, e.g., interferon-α. Anti-viral activity may be quantified and compared with a control or untreated tissue culture system, or quantified and used to determine the relative rankings of multiple candidates. The schedule of administration may be determined individually for each candidate compound. The schedule may be chosen to maintain an effective amount of test compound over a period of several days.

Anti-viral activity may be measured in several ways. A first method is using one or more of the reporter genes mentioned above (e.g. a luciferase assay technique). Reporter gene activity, or the amount of the reporter protein should correlate with the amount of HCV replicon replication. In addition to measuring the level of reporter protein, the efficacy of the candidate compound or protocol may be determined by measuring the level of HCV RNA or the level of viral proteins. Dose and/or time-dependent response curves (e.g., $EC_{50}$, $IC_{50}$) may be determined for candidate compounds and protocols.

In some embodiments, a second reporter gene may be stably or transiently transfected into the cell to allow the viability of cells to be assessed. If a test compound kills target cells then expression of the first reporter will not be seen, but because of cell death rather than because of any antiviral activity. Thus the second reporter acts as a marker for viability of cells containing the HCV genomic RNA transcript.

One suitable second reporter is a *Renilla* luciferase gene. Another method to determine this is to quantitate the gene copy number of an HCV gene on the HCV genomic RNA transcript, and a human gene contained in the hepatocyte cells (e.g., Huh7 or Huh7.5). Thus, by comparing the ratio of HCV gene copy number to human gene copy number in cells, it can be determined if treatment with an HCV inhibitor is inhibiting replication of the HCV genomic RNA transcript (HCV gene to human gene copy number ratio decreases) or if the compound is inhibiting human cell growth or inducing cell death in cells harboring the HCV genomic RNA transcript (HCV to human gene copy number ratio stays relatively constant). HCV gene and human gene copy number in cells is quantitated at day zero for the baseline and again at a later time or times.

Kits

The above-described tissue culture system, including the recombinant HCV genomic constructs, hepatocyte cells, and transfection reagents, can be provided in kits, with suitable instructions and other necessary reagents, in order to produce HCV virus as described above. The kit will normally contain in separate containers the combination of recombinant HCV genomic constructs (e.g., RNA transcripts for infection and/or DNA vectors for production of viral RNA by in vitro transcription) and hepatocyte cells (either already transfected or separate). Instructions (e.g., written, tape, VCR, CD-ROM, DVD, etc.) for growing the virus in tissue culture usually will be included in the kit. The kit can also contain other packaged reagents and materials (i.e., transfection reagents, polynucleotides encoding RNA silencing suppressors and/or CD81, antiviral compounds, buffers, media, and the like). Wild-type JFH1 and chimeric viruses, such as those described above, can be grown in culture using these kits.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

General Materials and Methods

Cells
Huh-7

Human hepatoma cell line Huh-7 (Cancer Res 42:3858-63) was maintained in Dulbecco's modified Eagle medium (DMEM) (Invitrogen, Carlsbad, Calif.) containing high glucose, 10% fetal bovine serum, L-glutamine, and non-essential amino acids, at 37° C. in 5% $CO_2$. Unless otherwise indicated, all cell culture in presence of HCV was performed as described and referenced herein.

Huh7C

Interferon-cured Huh7 (Huh7C) cells were prepared by treating Huh7 cells containing a subgenomic replicon with interferon-α at a concentration of 100 U/ml of culture for 14 days, as described previously by Kanazawa et al. (J. Virol. (2004) 78:9713-9720). Briefly, cured Huh7 cells, from which the replicon had been eliminated, were established by treating Huh7/Rep-Neo cells with 100 U of IFN-α/ml for 14 days. Clearance of replicon RNA was confirmed by reverse transcription-PCR (RT-PCR) and by the loss of resistance to G418.

T7-11

Five million Huh7 derived cells containing a subgenomic replicon in 0.2 ml of Hank's Balanced Salt Solution (HBSS) were implanted subcutaneously in female C.B17 SCID mice, which were irradiated (3 Gy) before cell implantation. A tumor emitting strong bioluminescence was excised 27 days later and the bioluminescent portion of the tumor was cultured in vitro in the presence of 0.5 mg/ml G418. Luciferase expression of G418-resistant colonies was evaluated using the Xenogen IVIS™ imaging system (Xenogen Corporation, Alameda, Calif.) and one colony with high expression was expanded and cured of the subgenomic replicon to create the cell line T7-11.

Siena 8

Huh 5.2 cells carrying a subgenomic replicon (Lohmann et al. (1999) Science 285(5424):110-113) were treated with interferon alpha at 100 IU/ml for 3 weeks to cure HCV RNA and individual colony was isolated to create Siena 8 cells. Cells were maintained in the same condition described for Huh 7 cells above.

RNA Preparation

RNA transcripts were prepared using the MEGASCRIPT kit (Ambion, Austin, Tex.). RNA was extracted and purified using TRIZOL reagent following manufacturer's instructions (Invitrogen, Carlsbad, Calif.).

RNA Transfection

Subconfluent cells were trypsinized and washed once with complete DMEM and once with serum-free DMEM-F12 medium. Cell pellets were resuspended in serum-free DMEM-F12 medium at a density of 10 cells/ml. To 200 ml of the cell suspensions in an electroporation cuvette (0.2-cm gap; BTX, San Diego, Calif.) 1 to 10 mg of in vitro-transcribed RNA was added. The cells were immediately electroporated with an ECM 630 apparatus (BTX) set to 200 V and 1,000 mF. After electroporation the cell suspension was kept for 5 minutes at room temperature and then diluted into DMEM supplemented with 10% fetal bovine serum and non-essential amino acids and seeded into a 10-cm diameter petri dish.

Example 2

Recombinant JFH1 Genomic Bicistronic Constructs

Several wild-type and chimeric JFH1 genomic constructs were prepared (see FIG. 1). A recombinant wild-type JFH1 genomic construct contained within a pUC18 plasmid as shown in the sequence of SEQ ID NO:1 was prepared as described previously (Wakita et al. (2005) Nature Medicine 11:791-796; herein incorporated by reference in its entirety). This construct includes open reading frames for HCV proteins core, E1, E2, p7, NS2, NS3, NS4A, NS4b, NS5a, and NS5b, flanked by 5' and 3' untranslated regions, and a T7 promoter.

In addition, a bicistronic wild-type JFH1 genomic construct (LucJFH1) comprising the sequence of SEQ ID NO:2 was generated that included a first cistron encoding the first 17 amino acids of the JFH1 core protein linked to a luciferase reporter gene for monitoring viral infection and RNA replication. This bicistronic construct also included an encephalomyocarditis virus (EMCV) internal ribosomal entry site (IRES) for expression of the second cistron, which encoded the wild-type JFH1 polyprotein.

A number of bicistronic chimeric constructs were also prepared encoding chimeric HCV polyproteins comprising sequences derived from JFH1 and a second HCV isolate. All bicistronic constructs contained a first cistron encoding the first 17 amino acids of the JFH1 core protein linked to a luciferase reporter gene, an EMCV IRES, and a second cistron, encoding a chimeric polyprotein comprising NS3 to NS5b regions from strain JFH1 and core to p7 regions from a second HCV isolate, linked by a chimeric NS2 region with an intergenotypic junction at residue 871 (LucCJ1 and LucHJ1) or 877 (LucNJ1) of NS2. Chimeric constructs included: (a) LucHJ1, contained in the sequence of SEQ ID NO:3, containing sequences from HCV type 2a strain JFH1 and type 1a strain (HJ1 fragment from the H77 isolate); (b) LucCJ1, contained in the sequence of SEQ ID NO:4, containing sequences from HCV type 2a strain JFH1 and type 1b strain (CJ1 fragment from the Con1 isolate); and (c) LucNJ1, contained in the sequence of SEQ ID NO:5, containing sequences from HCV type 2a strain JFH1 and type 1b strain (NJ1 fragment from the HNZ1 isolate).

Example 3

Recombinant JFH1 Genomic Monocistronic Constructs

Several monocistronic wild-type and chimeric JFH1 genomic constructs were also prepared (see FIG. 2). Monocistronic constructs included a region encoding the first 12 amino acids of the JFH1 core protein linked to a green fluorescent protein (GFP) or a *Renilla* luciferase (RLuc) reporter gene, a coding sequence for a foot-and-mouth disease virus (FMDV) 2A protease, a coding sequence for a ubiquitin protease cleavage site, and a wild-type JFH1 or chimeric polyprotein coding region. In some of these chimeric constructs, the polyprotein coding region comprised NS3 to NS5b sequences derived from strain JFH1 and core to p7 sequences derived from a second HCV isolate, linked by a chimeric NS2 coding region with an intergenotypic junction at residue 871 (RLF2AUba1 and RLF2AUbHJ1) or 877 (RLF2AUbNJ1) of NS2. Monocistronic constructs included plasmids encoding chimeric DNA constructs of the invention as follows: (a) RLF2AubJFH-1, as in SEQ ID NO:6, containing the wild-type JFH1 genome and an RLuc reporter gene; (b) GFPF2AUbJFH-1, comprising the sequence of SEQ ID NO:7, containing the wild-type JFH1 genome and a Green Fluorescent Protein (GFP) reporter gene and pUC plasmid sequences; (c) RLF2AUbHJ1, comprising the sequence of SEQ ID NO:8, containing sequences from HCV type 2a strain JFH1 and type 1a strain HJ1 and an RLuc reporter gene and pUC plasmid sequences, wherein the genomic construct includes from about nucleotide 7 to about nucleotide 10953 of SEQ ID NO:8; (d) RLF2AUbCJ1, comprising the sequence of SEQ ID NO:9, containing sequences from HCV type 2a strain JFH1 and type 1b strain Cu1 and an RLuc reporter gene and plasmid sequences, wherein the genomic construct includes from about nucleotide 7 to about nucleotide 10953 of SEQ ID NO:9; and (e) RLF2AUbNJ1, comprising the sequence of SEQ 1:13 NO:10, containing sequences from HCV type 2a strain JFH1 and type 1b strain NJ1 and an RLuc reporter gene and plasmid sequences, wherein the genomic construct includes from about nucleotide 7 to about nucleotide 10971 of SEQ ID NO:10.

Pietschmann et al. have demonstrated that bicistronic chimeric constructs containing an NS2 fusion protein with an intergenotypic junction between the first and second putative transmembrane domains of the NS2 protein yielded productive virus particles (Proc. Natl. Acad. Sci. U.S.A. (2006) 103:7408-7413).

Figure 12:
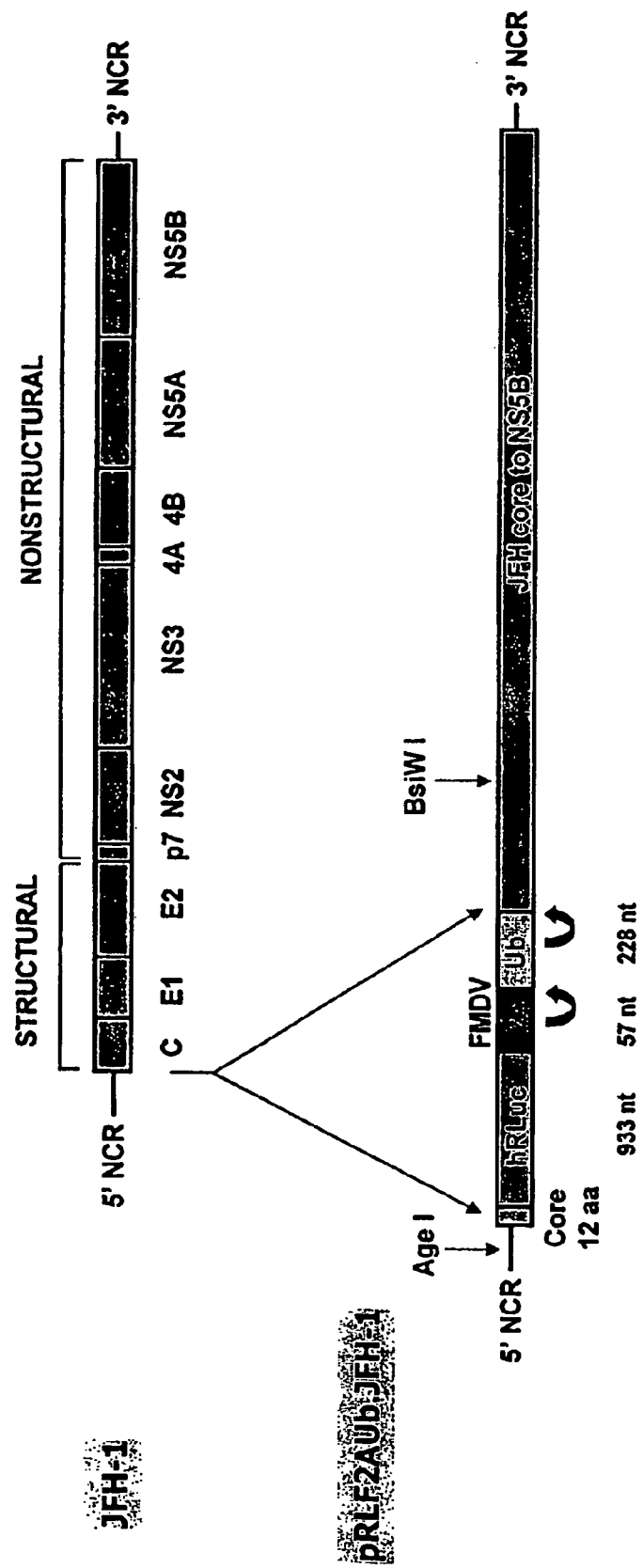
FIG. 12 shows a schematic representation of the genetic organization of the JFH1 viral genome, including the restriction enzyme digest sites used to make the genomic constructs of the invention.
Figure 13:
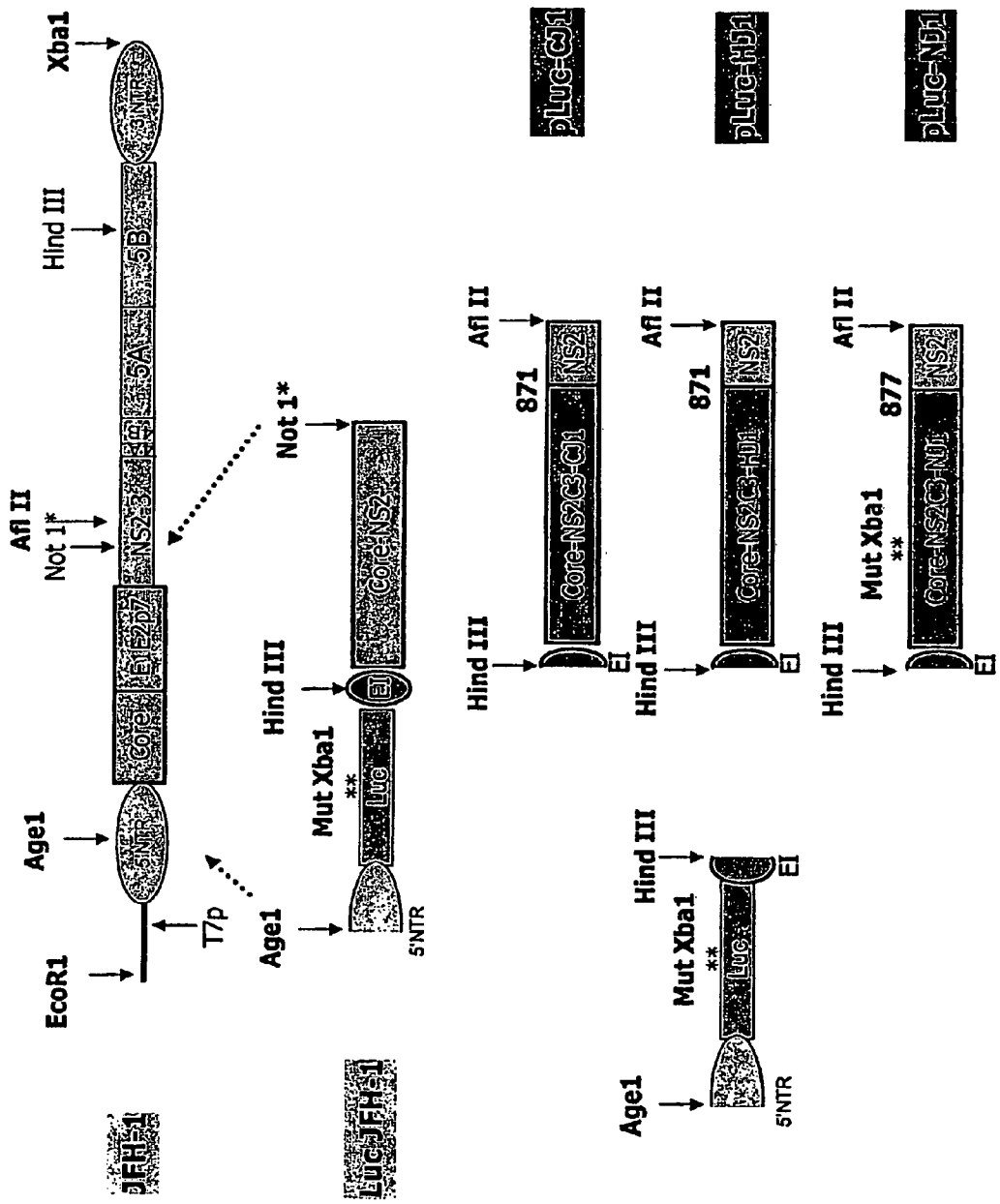
FIG. 13 shows a schematic representation of how the chimeric HCV genomic constructs were produced, including the restriction enzyme sites used to replace portions of the JFH1 genome with that of a second HCV isolate.

FIGS. 12 and 13, show the restriction enzyme sites that were utilized to make the described recombinant HCV genomic constructs. In particular, FIG. 12 shows JFH-1 and Luc JFH-1, two recombinant HCV genomes that were synthesized using phosphodiester synthesis. The HCV genomic constructs were cloned into the EcoRI/XbaI restriction enzyme sites of the plasmid PUC 18. Cloning was performed in *E. coli* as described in the figures and accompanying text.

Referring now to FIG. 13, the JFH-1 strain and the compatible restriction enzyme fragments from each HCV genome and the HCV genome containing the luciferase gene are shown. Compatible fragments were cloned into pUC vectors and transformed into E. coli. As indicated above, the full length JFH1 and JFH1 having reporter gene genomic constructs were synthesized in vitro and cloned into the EcoRI/Xba1 site of pUC18. The chimeric constructs were cloned using conventional restriction enzyme digestion, ligation and transformation of E. coli utilizing the restrictions sites depicted in FIGS. 1-3, 12, and 13. In each of the genomic constructs shown, the genomic construct is bordered by EcoR1 and Xba1 sites. Any other internal Eco R1 or Xba1 sites can be removed without altering the expression of any corresponding products.

Example 4

Renilla Luciferase Assay

Replication of viral RNA produced from recombinant genomic RNA transcripts can be measured by using a Renilla luciferase (RLuc) assay (see, e.g., Srikantha et al. (1996) J. Bacteriol. 178:121-129; Liu et al. (1999) Gene 237:153-159; Haan et al. (2004) J. Virol. 78:6048-6054; Kiel et al. (2003) J. Biol. Chem. 278:5659-5668; herein incorporated by reference). Luminescence is measured at 480 nm with a luminometer. Light emission is integrated over 10-30 seconds. RLuc assays were used to measure intracellular HCV RNA in cell lysates and infectious viral titers in culture media. RLuc activity was measured using cell lysates to measure the level of HCV replication in cells. To measure the titer of infectious virus titer present in the culture supernatant, conditioned media from the transfected or infected cells were inoculated into naïve Huh7 cells and RLuc activity from the infected cells was measured.

Example 5

Comparison of RNA Replication Efficiencies of Monocistronic and Bicistronic Recombinant Wild-Type JFH1 Genomic RNA Transcripts RNA replication efficiencies of monocistronic and bicistronic wild-type JFH1 genomic RNA transcripts were compared. RLF2AUbJFH-1 and LucJFH1 genomic RNA transcripts were introduced into separate cultures of Huh7 cells by electroporation. RNA levels were measured for 33 days after electroporation by quantitating luminescence from luciferase reporters.

Figure 3:
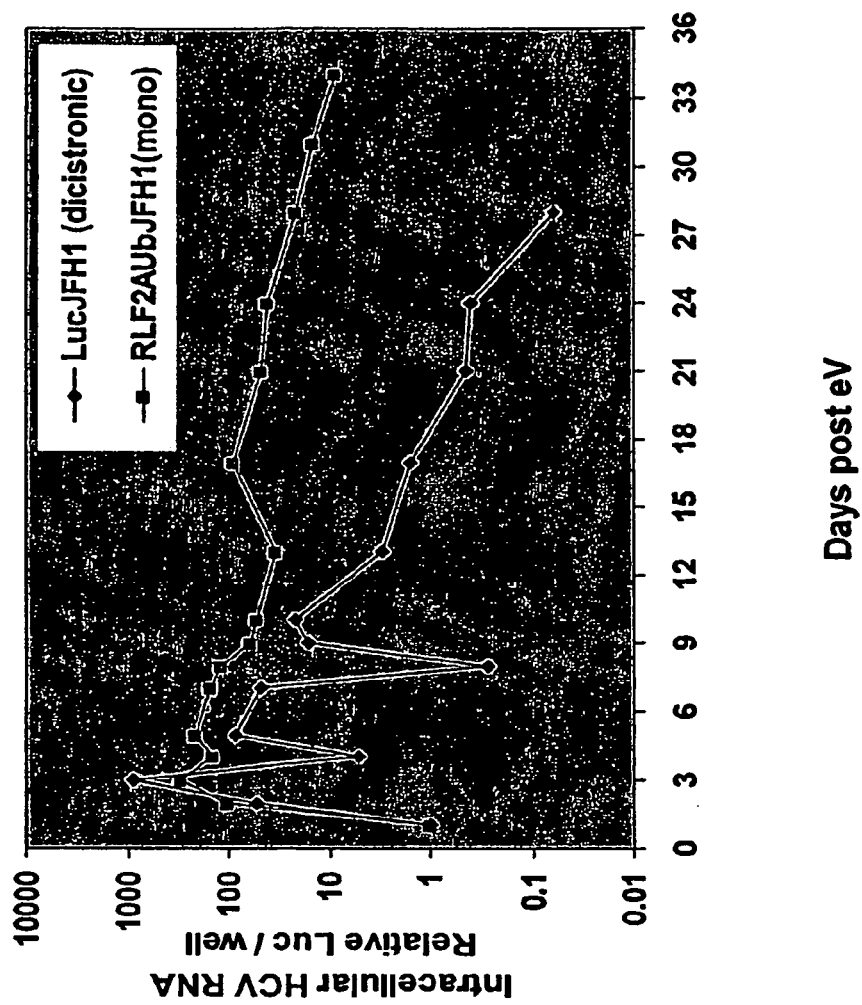
FIG. 3 compares the replication efficiencies of monocistronic RLF2AUbJFH-1 and bicistronic LucJFH1 wild-type JFH1 genomic constructs in Huh7 cells. Intracellular RNA levels were measured based on luciferase luminescence as a function of time after electroporation (eV) of the Huh7 cells.

FIG. 3 shows that the replication efficiency of the monocistronic RLF2AUbJFH-1 RNA transcript was superior to the bicistronic LucJFH1 RNA transcript. Although the replication of the bicistronic RNA transcript was comparable to the monocistronic RNA transcript initially, replication declined after 9 days, whereas the monocistronic RNA transcript maintained replication at higher levels for 33 days.

Example 6

Infectivity and RNA Replication Efficiencies of HCV Viruses Produced by the Monocistronic Recombinant Genomic RNA Transcripts Monocistronic HCV genomic constructs were evaluated for their ability to produce infectious viral particles and to replicate viral RNA in Huh7 cells. The infectivity of virus produced by recombinant genomic RNA transcripts in transfected Huh7 cells was determined by inoculating naïve Huh7 cells with virus released into the supernatants of cultures of transfected cells. Infectious viral titers and RNA replication levels were determined by RLuc assays as described in Example 4.

A. Recombinant Wild-Type JFH1 Genomic Monocistronic Construct

Figure 4:
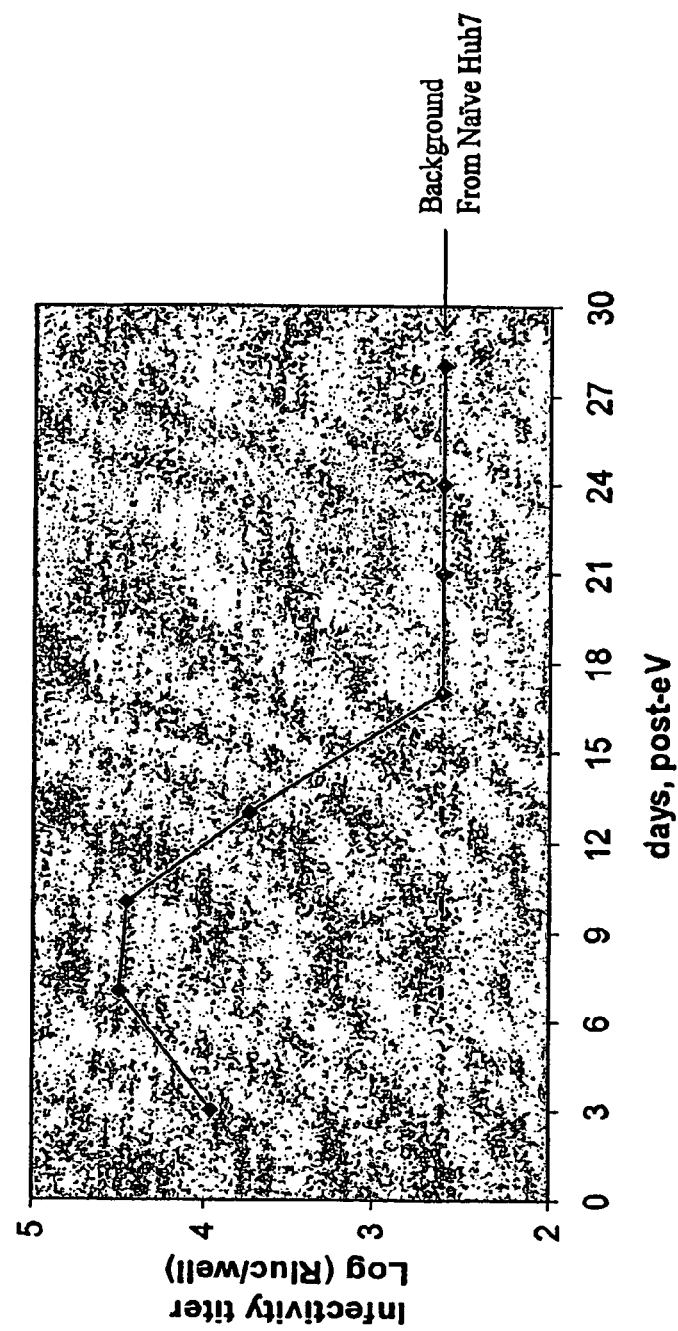
FIG. 4 shows the JFH1 infectivity titer in Huh7 cells transfected with the monocistronic RLF2AUbJFH-1 construct as a function of time after electroporation.

The recombinant wild-type JFH1 genomic monocistronic RLF2AUbJFH-1 RNA transcript was introduced into Huh7 cells by electroporation. Virus present in the culture supernatant after electroporation was then used to infect $5 \times 10^4$ naïve Huh7 cells, and infectious viral titers were measured by RLuc assay for 28 days after electroporation. As shown in FIG. 4, the RLF2AUbJFH-1 RNA transcript produced viral particles that were secreted from Huh7 cells and infectious in naïve Huh7 cells.

Figure 5:
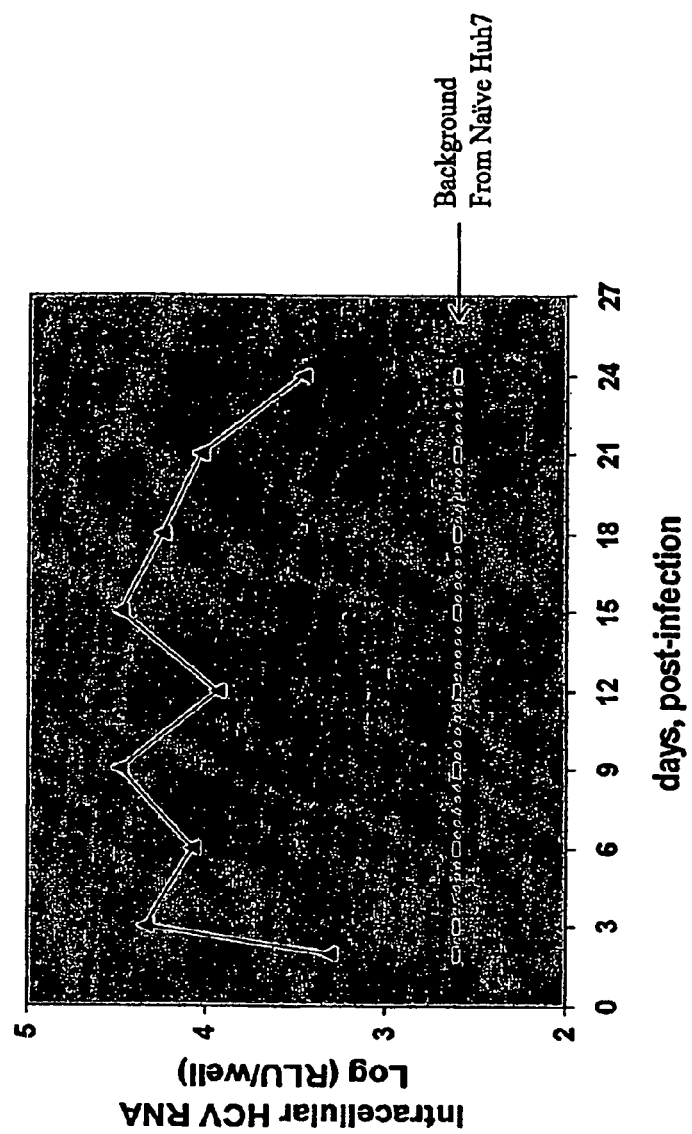
FIG. 5 shows the level of RNA replication of the monocistronic RLF2AUbJFH-1 construct in Huh7 cells as a function of time after infection with recombinant virus. Naive Huh7 cells were inoculated with virus from the culture supernatant of cells transfected with the RLF2AUbJFH-1 construct, as described in Example 6. Intracellular JFH1 RNA was measured by RLuc assay for 24 days after infection of Huh7 cells.

The level of RNA replication of RLF2AUbJFH-1 was also measured in Huh7 cells as a function of time after infection with recombinant virus. Naïve Huh7 cells ($5 \times 10^4$) were inoculated with virus from the culture supernatant of transfected cells 10 days after electroporation. Intracellular JFH1 RNA was measured by RLuc assay for 24 days after infection of Huh7 cells. As shown in FIG. 5, RNA was detectable by day 2 and persisted for 24 days.

B. Recombinant Chimeric Genomic Monocistronic Constructs

Figure 6:
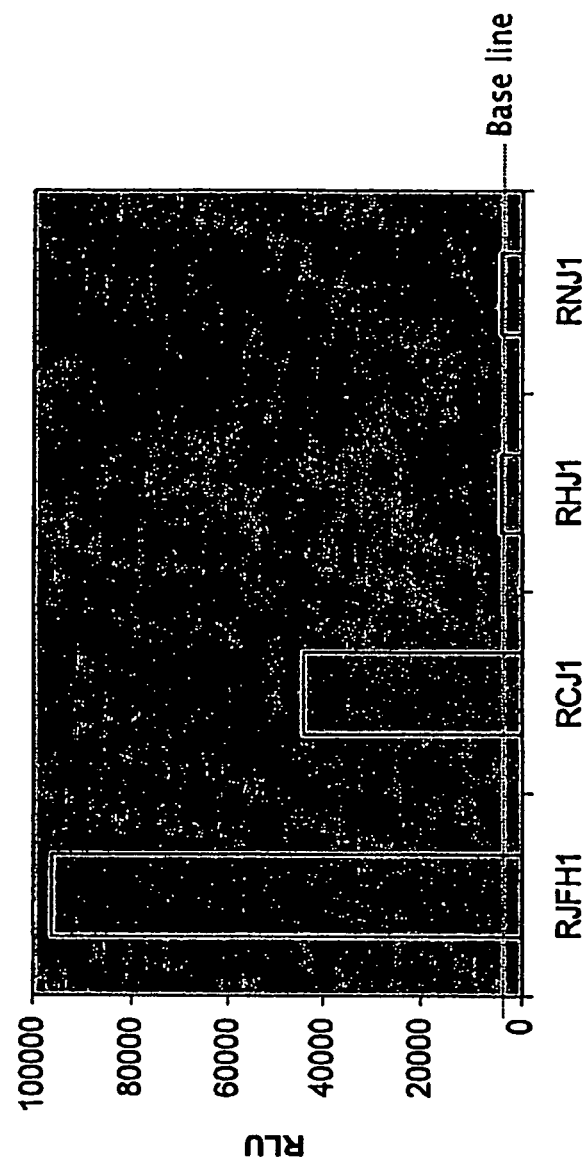
FIG. 6 compares the infectivity of wild-type JFH1 virus produced by the monocistronic construct RLF2AUbJFH-1 and chimeric viruses produced by the monocistronic constructs RLF2AUbHJ1, RLF2AUbCJ1, and RLF2AUbNJ1.

The infectivity of wild-type JFH1 virus, produced by the monocistronic construct RLF2AUbJFH-1, and chimeric viruses, produced by the monocistronic constructs RLF2AUbHJ1, RLF2AUbCJ1, and RLF2AUbNJ1, were compared. Cultures of naïve Huh7 cells were separately inoculated with each virus from culture supernatants of transfected cells after electroporation with genomic RNA transcripts. Viral titers were measured by RLuc assay. FIG. 6 shows that the recombinant wild-type JFH1 virus produced from the monocistronic RLF2AUbJFH-1 RNA transcript and the chimeric virus produced from the RLF2AUbCJ1 RNA transcript produced infectious virus in Huh7 cells.

RNA replication efficiencies of the wild-type JFH1 and chimeric genomic monocistronic constructs were also compared. RLF2AUbJFH-1, RLF2AUbHJ1, RLF2AUbCJ1, and RLF2AUbNJ1 RNA transcripts were introduced into separate cultures of Huh7 cells by electroporation. Cultures of the Huh7 cells were split three days and twelve days after electroporation, and RNA levels were measured by RLuc assay for 21 days after electroporation. A replication incompetent JFH-1 mutant (JFH1/GND mutant previously described by Wakita et al., supra) was used as a negative control for comparison.

Figure 7:
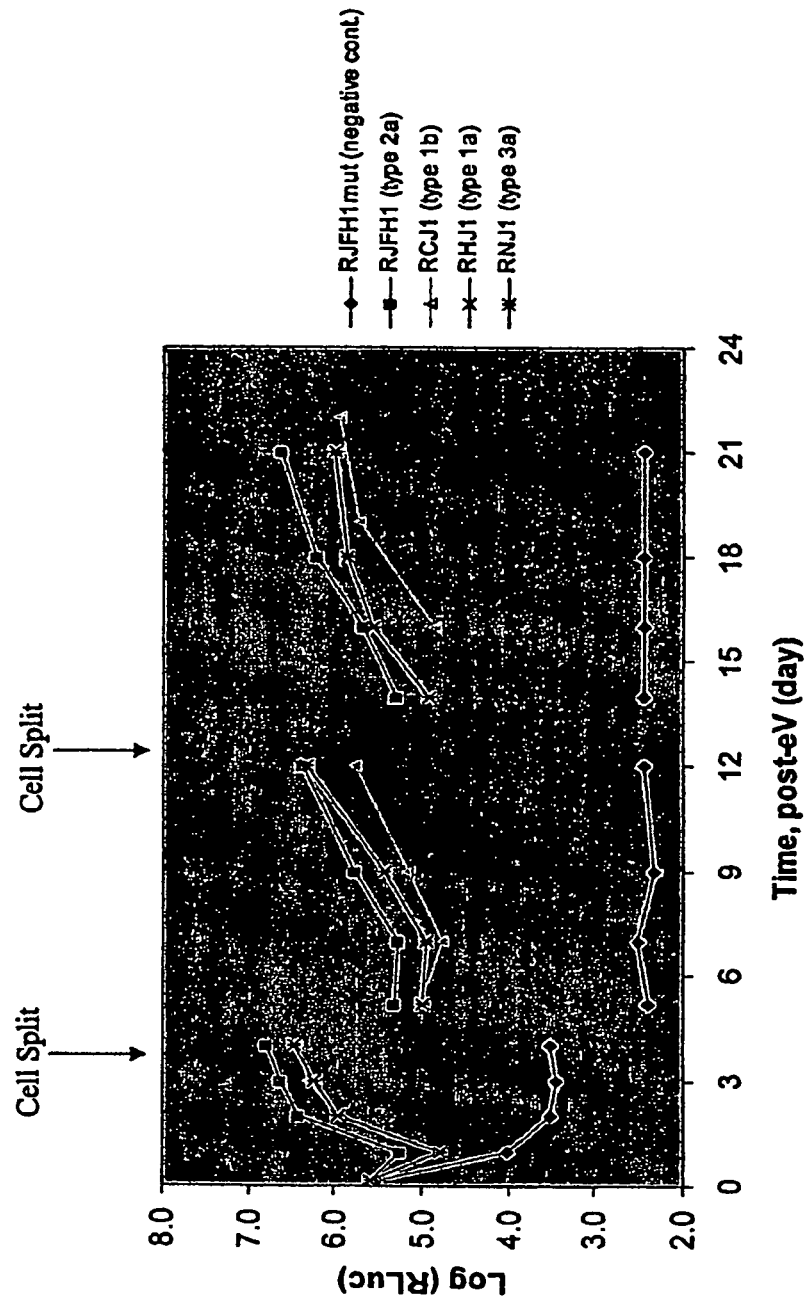
FIG. 7 compares the RNA replication efficiencies of the RLF2AUbJFH-1, RLF2AUbHJ1, RLF2AUbCJ1, and RLF2AUbNJ1 monocistronic constructs in Huh7 cells.

As shown in FIG. 7, all of the recombinant constructs replicated in Huh7 cells and continued to replicate after culture dilutions. The replication efficiencies of the chimeric RLF2AUbCJ1 and RLF2AUbNJ1 constructs were nearly as high as the wild-type RLF2AUbJFH-1 construct. The chimeric RLF2AUbHJ1 construct, however, showed significantly lower replication levels than the other recombinant constructs.

Example 7

RNA Replication Efficiencies of HCV Viruses in Different Cell Lines

Figure 8:
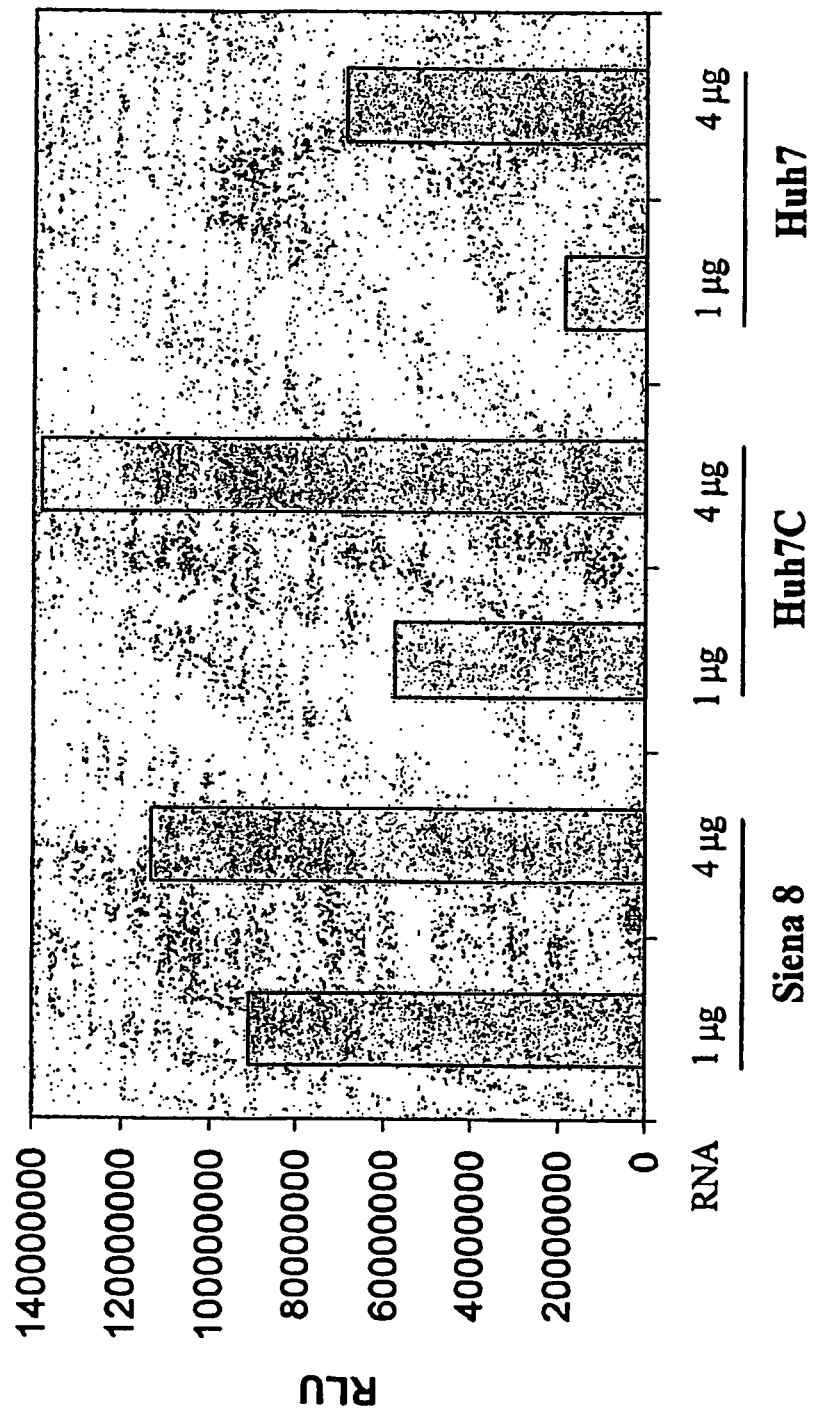
FIG. 8 compares RNA replication efficiencies of JFH-1 construct RLF2AUbJFH1 in the three cell lines, Siena 8, T7-11, and Huh7. Cells were transfected with either 1 μg or 4 μg of the construct.

The RNA replication efficiencies of JFH-1 in the three cell lines, Siena 8, Huh7C, and Huh7 were compared (FIG. 8).

5×10⁶ cells were transfected with either 1 μg or 4 μg of the genomic RNA transcript RLF2aUbJFH-1. Rluc was measured 3 days after electroporation in cell lysates.

Example 8

Influenza Virus NS1 Constructs for RNA Silencing Suppression

JFH1 is a type 2a virus that replicates efficiently and produces infectious virus in cell culture. Infectivity titers of JFH1 in Huh7.5 cells are limited to about $10^4$/ml, and titers of chimeric viruses, comprising genotype's other than 2a, are significantly lower (about $10^3$/ml). Viral titers can be improved by blocking host antiviral defense mechanisms that interfere with viral replication.

One trigger of host defense mechanisms is viral double-stranded RNA, which is produced as an intermediate during viral replication. Double stranded RNA induces host interferon and RNA silencing antiviral responses. Suppressors of interferon and RNA silencing responses are produced by certain viruses. For example, the NS1 protein of influenza virus is a double stranded RNA binding protein that blocks activation of host interferon-induced dsRNA-dependent protein kinase PKR and RNA interference (RNAi). NS1 is required for efficient influenza virus replication. The ability of NS1 to also improve HCV infectivity titers was therefore tested.

Figure 9:
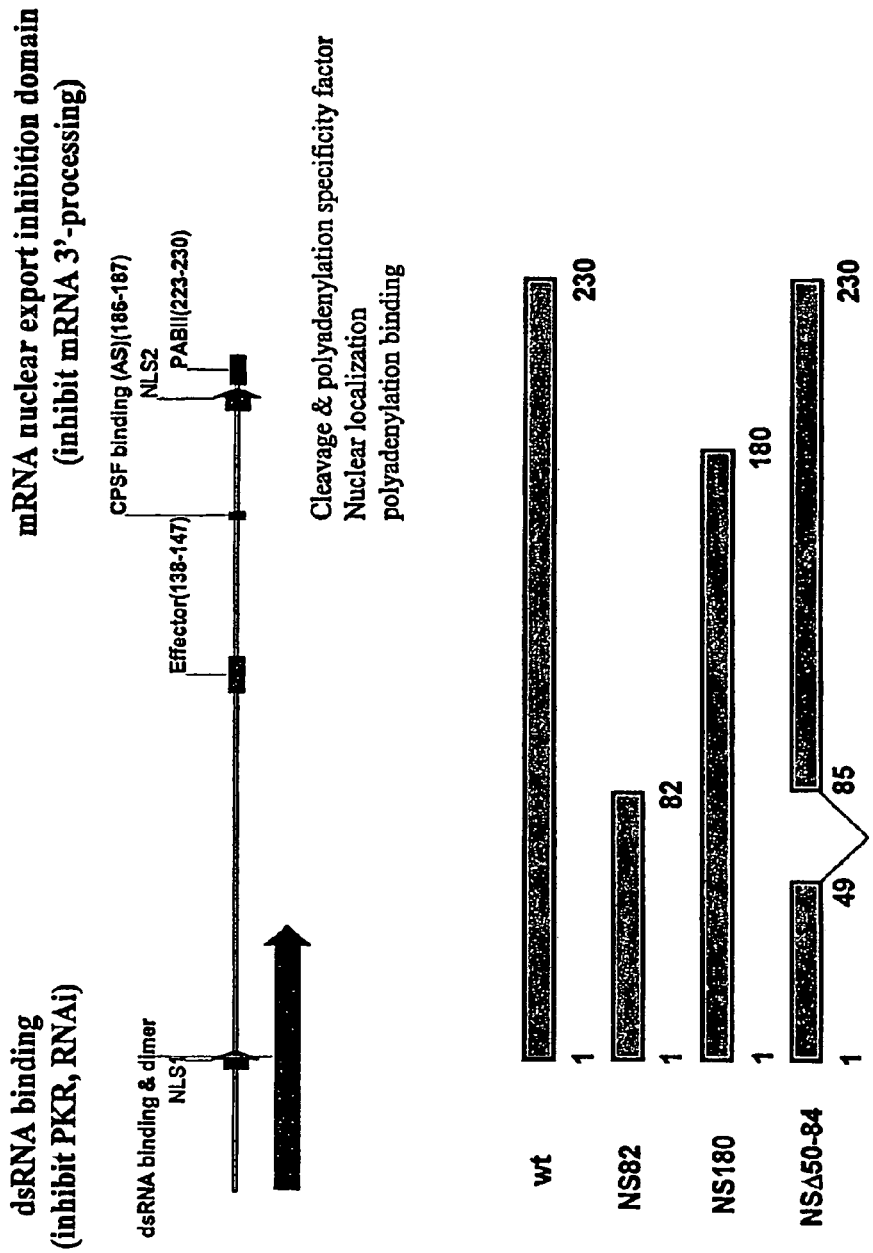
FIG. 9 depicts a schematic representation of NS1 of influenza. The MI-length NS1 protein contains a double-stranded RNA (dsRNA) binding domain, which inhibits the interferon-induced dsRNA-dependent protein kinase PKR and RNA interference (RNAi), and an effector domain, which functions in inhibiting pre-mRNA splicing and nuclear export of mRNA. The dsRNA binding domain and the effector domain reside at amino acid residues 1-82 and 138-147, respectively. In addition, the NS1 protein comprises two nuclear localization signals (NLS1 and NLS2), a cleavage and polyadenylation specificity factor (CPSF) binding site, and a polyadenylation binding protein II (PABII) binding site. Four RSS constructs are shown, including the full-length wild-type (wt) NS1 (residues 1-230); NS82, a truncated NS1 protein containing the dsRNA binding domain (residues 1-82); NS180, a longer truncated NS1 protein containing the dsRNA binding domain and the effector domain; and a mutant NS1 protein defective in dsRNA binding containing a deletion of residues 50-84.

Several RNA silencing suppressors comprising full-length and truncated forms of NS1 were constructed (FIG. 9). A representative NS1 gene can be found at GenBank accession number AAA43536. Other influenza strains available, or fragments thereof, can also be used in the practice of the invention. The full-length NS1 protein contains a dsRNA binding domain, which inhibits PKR and RNAi, and an effector domain, which functions in inhibiting pre-mRNA splicing and nuclear export of mRNA. The dsRNA binding domain and the effector domain reside at amino acid residues 1-82 and 138-147, respectively. In addition, the NS1 protein comprises two nuclear localization signals (VLSI and NLS2), a cleavage and polyadenylation specificity factor (CPSF) binding site, and a polyadenylation binding protein II (PABII) binding site.

Four constructs were prepared, including (i) the full-length wild-type (wt) NS1 (residues 1-230), comprising about nucleotide 2033 to about nucleotide 2723 of SEQ ID NO: 11; (ii) NS82, a truncated NS1 protein containing the dsRNA binding domain (residues 1-82 of Seq ID No. 15); (iii) NS180, a longer truncated NS1 protein containing the dsRNA binding domain and the effector domain, comprising residues 1-180 of SEQ ID NO:15; and (iv) a mutant NS1 protein defective in dsRNA binding containing a deletion of residues 50-84 of SEQ ID NO:15. Constructs were each cloned into a pCMV vector for expression and the constructs are represented by SEQ ID NOS:11-14.

Example 9

Effects of Influenza Virus NS1 and NS82 on Replication of JFH1

Figure 10:
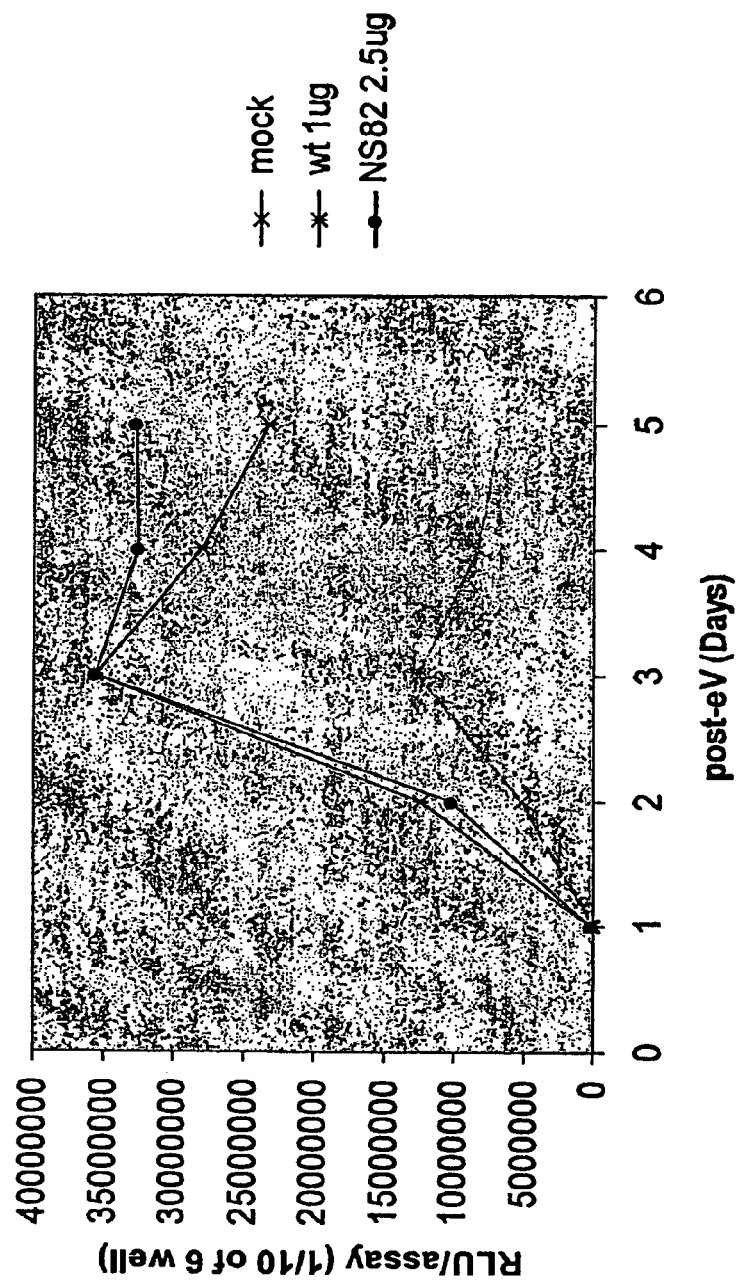
FIG. 10 shows the effects of the full-length wild type and NS82 constructs on replication of the monocistronic RLF2AUbJFH-1 construct in Huh7 cells.

The effects of NS1 and NS82 expression on JFH1 replication in Huh7 cells were tested. Interferon-cured Huh7 cells were transfected with pCMV-NS1 or pCMV-NS82, followed by electroporation with monocistronic JFH1 RNA. The level of JFH1 RNA replication in the electroporated cells was measured by (RLuc) assay on cell lysates. As shown in FIG. 10, the level of JFH1 replication peaked on day 3 after electroporation. The level of replication in NS1 transfected cells was about 3-fold higher than that of mock-transfected cells. High levels of JFH1 replication were maintained for up to 5 days after electroporation in cells transfected with NS82, whereas replication levels decreased in cells transfected with wild-type NS1.

Example 10

Effects of Influenza Virus NS1 and NS82 on Infectivity of JFH1

Figure 11:
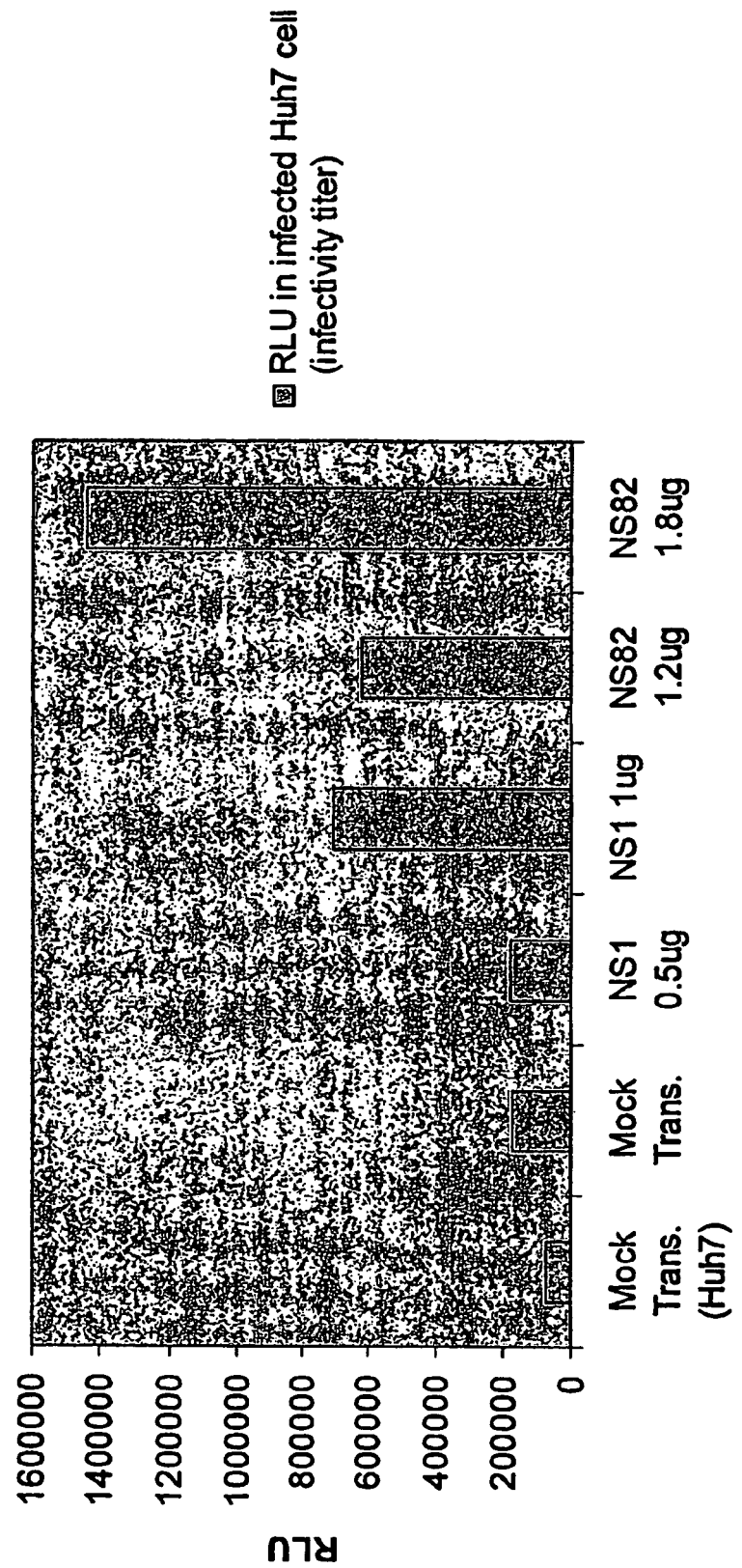
FIG. 11 shows the effects of the full-length wild-type and NS82 constructs on infectivity of virus produced from the monocistronic RLF2AUbJFH-1 construct in Huh7 cells.

JFH1 was produced from interferon-cured Huh7 cells by first transfecting cells with pCMV-NS1 (SEQ ID NO:11) or pCMV-NS82 (SEQ ID NO:12) and then electroporating cells with the monocistronic RLF2AUbJFH-1 RNA. Virus replication in electroporated cells was measured. Virus present in the culture supernatant was then used to infect naive Huh7 cells, and the level of infectious virus titer was measured by RLuc assay. As shown in FIG. 11, expression of NS82 (transfected with 1.8 μg of pCMV-NS82) prior to JFH1 electroporation of IFN-cured cells increased the infectious JFH1 titer by about 8-fold. The NS1 gene was cloned into the pCMV plasmid as an Asc1-Not1 fragment.

Example 11

Effects of CD81 on Replication and Infectivity of JFH1 in Interferon Cured Huh7 and Naive Huh7 Cells The effects of NS1 on JFH1 replication and infectivity were compared in interferon cured Huh7 cells (Huh7C) and naïve Huh7 cells. Expression of a portion of the NS1 coding region prior to viral RNA transfection resulted in a significant increase in infectious JFH1 titers in Huh7C cells compared to naïve Huh7 cells. Huh7C cells were more permissive for JHF1 replication compared to naïve Huh7 cells, but the infectivity of JFH1 in Huh7C cells was severely compromised.

The CD81 level on the Huh7C cell surface was about 1/10 that of Huh7 cells. In order to verify the role of CD81 and improve JFH1 infectivity, a variety of cell lines derived from Huh7 were transfected with a CD81 expression plasmid (Pileri et al. (1998) Science 282:938-941; herein incorporated by reference). CD81 was required for infection and improved JFH1 infectivity, but over-expression of CD81 beyond a threshold level inhibited JFH1 replication. Huh7C was optimal for supporting replication but was suboptimal for the infectivity assay. Huh7 was optimal for infection.

Example 12

Assays Using HCV Produced in Cell Culture

Culture Medium

Huh7.5 cells were grown in a culture medium containing 1 liter of Dulbecco's Modification of Eagle's Medium (DMEM) with 4.5 g/L glucose and L-glutamine without sodium pyruvate (Cellgro, Catalog No. 10-017-CN), 10 ml of penicillin-streptomycin solution (10,000 I.U. penicillin/ml and 10,000 μg streptomycin/ml; Cellgro, Catalog No. 30-002-CI), 10 ml of nonessential amino acids (Cellgro, Catalog No. 25-025-CI) and 100 ml of undialized fetal bovine serum (FBS).

Infection and Neutralization

Day 0:

$8 \times 10^4$ to $10 \times 10^4$ Huh7.5 cells (for luciferase assay) or $5 \times 10^4$ Huh7.5 cells (for indirect fluorescent antibody assay) were added per well to a 24-well plate.

Day 1:

The Huh7.5 cells were infected with HCV virus. The viral medium was warmed to 37° C. before adding to the wells. The culture medium in the wells was replaced with about 200 µl of the viral medium per well, and the 24-well plate was then placed in a $CO_2$ incubator and incubated overnight.

For studies of antibody neutralization, anti-HCV antibodies or serum containing anti-HCV antibodies were diluted as appropriate and added to the viral medium. The mixture was incubated at 37° C. for one hour and added to the cells at 200 µl per well. The cells were incubated in a $CO_2$ incubator for five hours (for RJ1 or JFH1) or overnight (for RCJ1 or HJ1). In some cases, the viral medium was removed (e.g., if RJ1 was used) and washed with fresh culture medium twice and replaced with 500 µl of fresh culture medium per well.

Day 2:

The viral medium was removed and washed twice and replaced with 500 µl of fresh culture medium.

Day 3:

The medium was replaced with fresh culture medium

Figure 14:
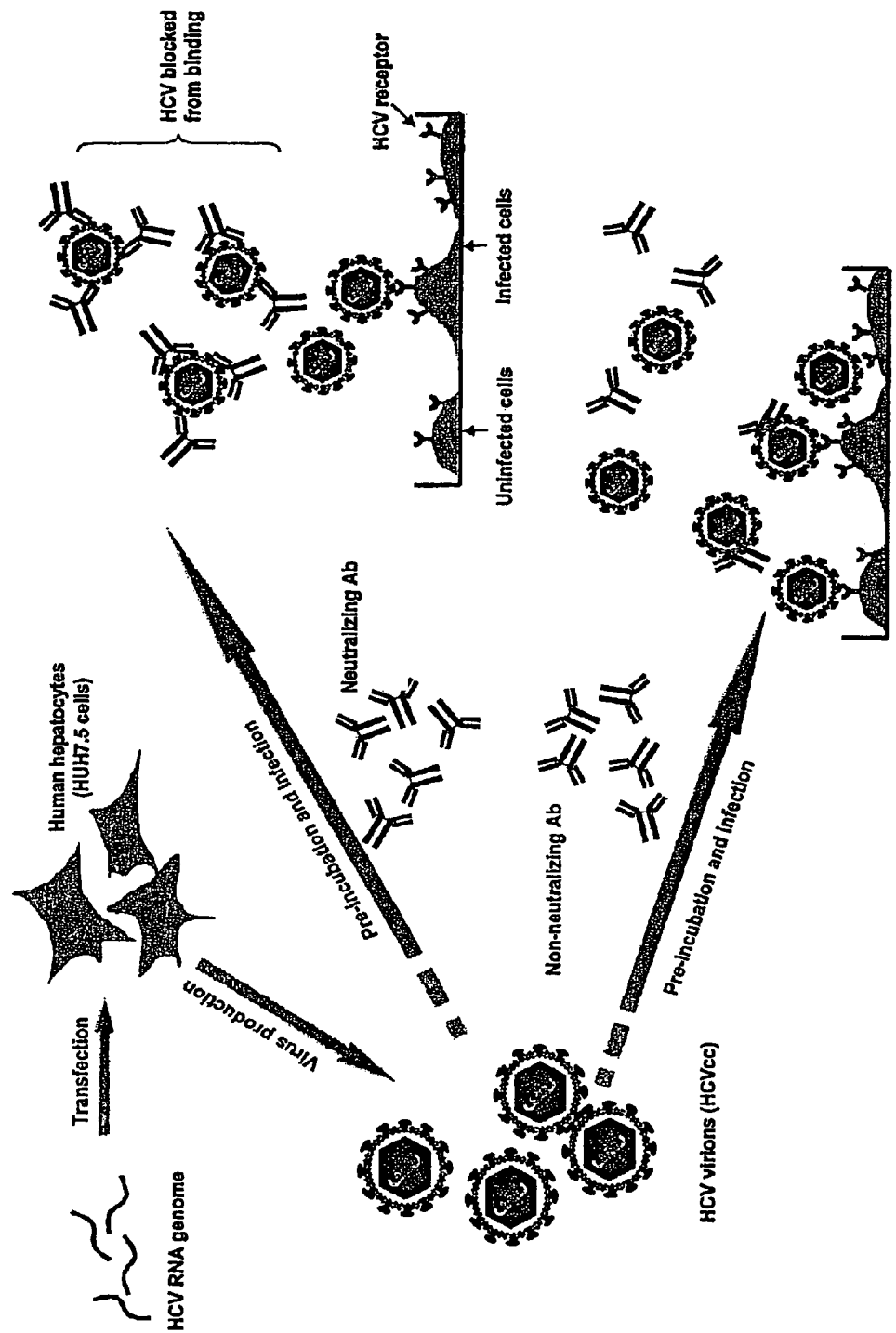
FIG. 14 shows a schematic representation of the viral neutralization assay performed with the HCV tissue culture system.
Figure 15:
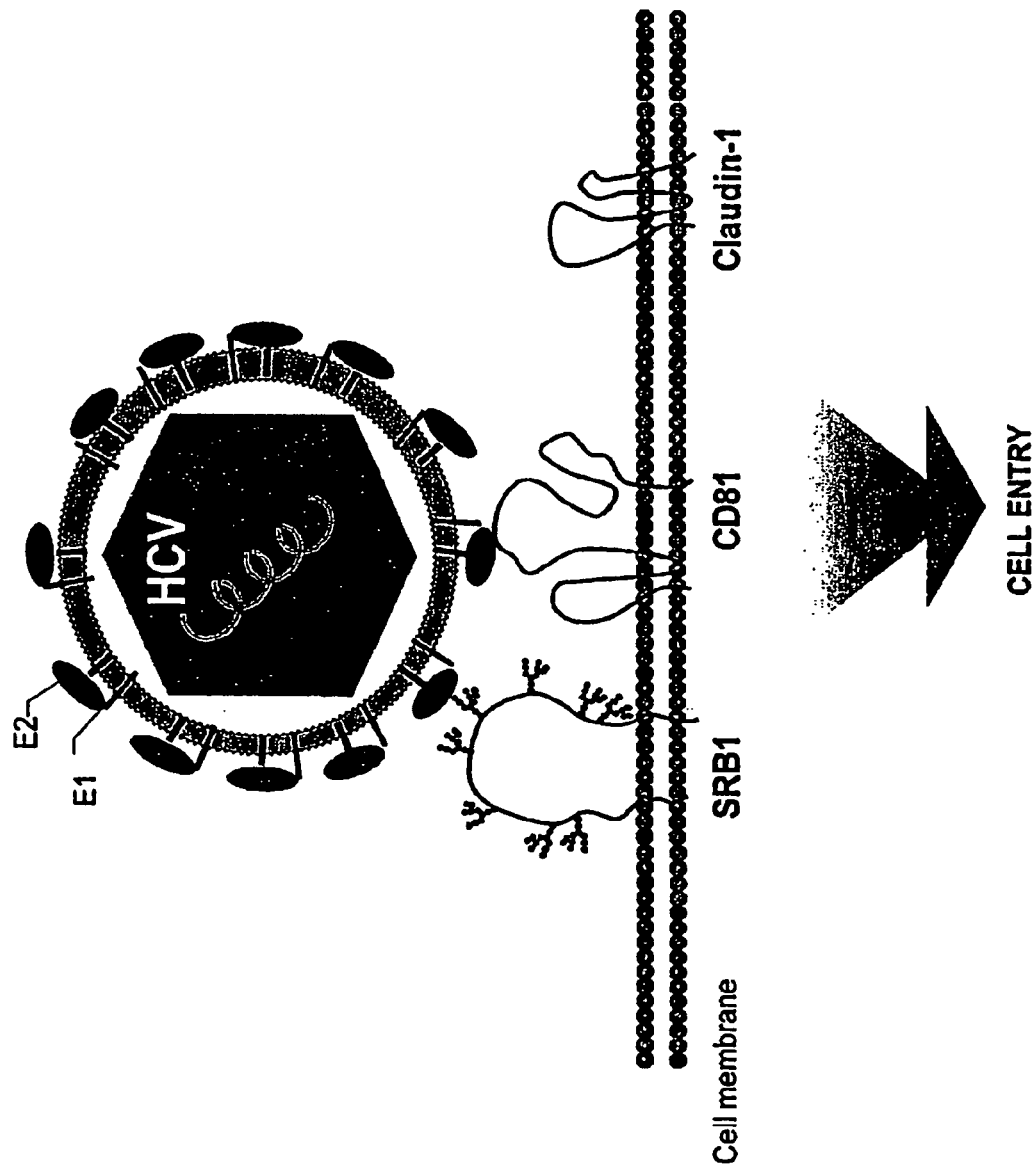
FIG. 15 depicts a model of HCV cell attachment and entry, showing the interactions of the HCV E1/E2 complex on the viral envelope with SRB1 and CD81 on cells during viral infection.

Day 4:

Luciferase and WA assays were performed on HCV produced in cell culture (HCVcc). See FIG. 14 for a schematic diagram of assaying viral neutralization of HCV infected hepatocytes grown in cell culture.

Luciferase Assay

Luciferase assays were performed using the *Renilla* luciferase assay system (Promega, Catalog No. E2820). The 24-well plate was washed twice with 500 µl phosphate buffered saline (PBS) per well, and the PBS was removed as completely as possible. 200 µl of 1× lysis buffer (Promega) was added per well, and the plate was shaken at room temperature for over one hour. 100 µl aliquots of luciferase assay buffer (Promega) mixed with the *Renilla* luciferase assay substrate (Promega) were added to luminometer cuvettes. 50 µl of lysate was added to the 100 µl of assay buffer in each cuvette and mixed. Luciferase activity was measured with a MOONLIGHT 3010 luminometer.

Indirect Fluorescent Antibody Assay

Indirect fluorescent antibody (IFA) assays were performed using the CYTOFIX/CYTOPERM kit for fixation and permeabilization of cells and immunofluorescent staining (BD Biosciences, Catalog No. 554714). The plate was washed twice with 500 µl PBS per well. The PBS was removed and replaced with 1× cytofixation/permeabilization solution (BD Biosciences) for overnight fixation. The plate was washed three times with PBS or 1× cytowash/permeabilization solution (BD Biosciences). 1× cytowash/permeabilization solution containing a blocking reagent was added and incubated at room temperature for about 30 minutes to 1 hour. The blocking reagent was removed and 150-200 µl of the primary antibody (rabbit anti-NS5A diluted by 1:1000 in 1× cytowash/permeablization solution) was added per well. The plate was incubated at room temperature for 1 hour and washed three times with 1× cytowash/permeabilization solution (BD Biosciences) before adding the secondary antibody (ALEXA FLUOR 488-conjugated goat-anti-rabbit antibody diluted 1:1000 in 1× cytowash/permeabilization solution). The plate was incubated at room temperature for about one hour and then washed twice with PBS. The PBS was removed and the wells were partially air dried and sealed. The plate was stored at −20° C. until observation under a fluorescence microscope.

Example 13

IFA Assay of HCV Infection in Huh7.5 Cells

Figure 16:
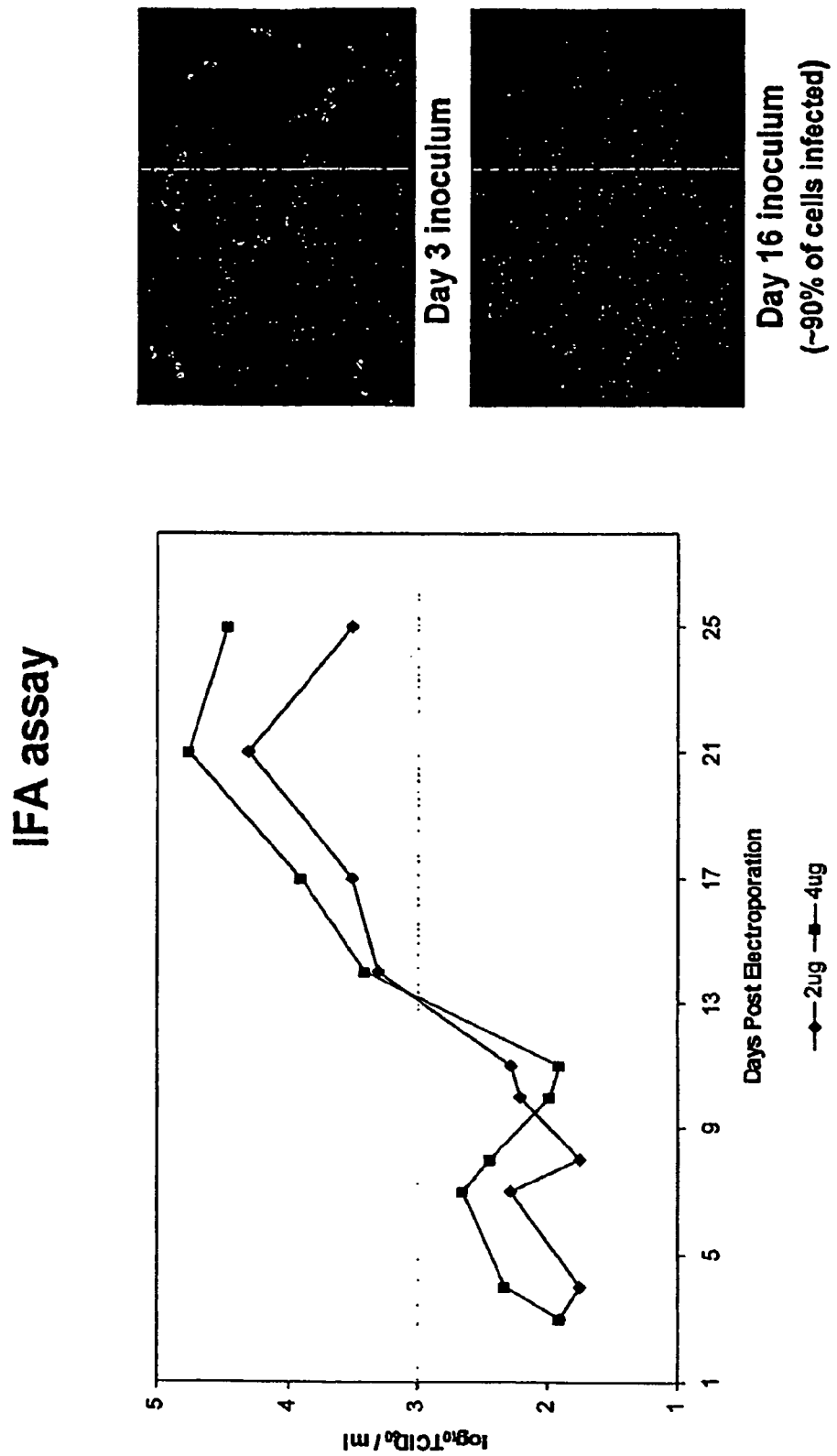
FIG. 16 shows JFH1 infectivity in Huh7.5 cells measured by indirect fluorescent antibody assay (IFA).

The IFA assay was performed on Huh7.5 cells infected with JFH-1 as described in Example 12. Huh7.5 cells were transfected with either 2 µg or 4 µg of the RLF2AUbJFH-1 RNA genomic transcript by electroporation. Cells were fixed and immunostained with anti-NS5a antibody at either day 3 or 16 after infection with JFH1. Viral titers were measured for 25 days after electroporation. As shown in FIG. 16, the synthetic JFH1 genome replicated in Huh7.5 cells and secreted infectious viral particles at high viral titers. By day 16 after electroporation, about 90% of the Huh7.5 cells were infected with virus.

Example 14

Effects of CD81 on Infectivity of JFH1 in Huh7 and Huh7.5 Cells

Figure 18:
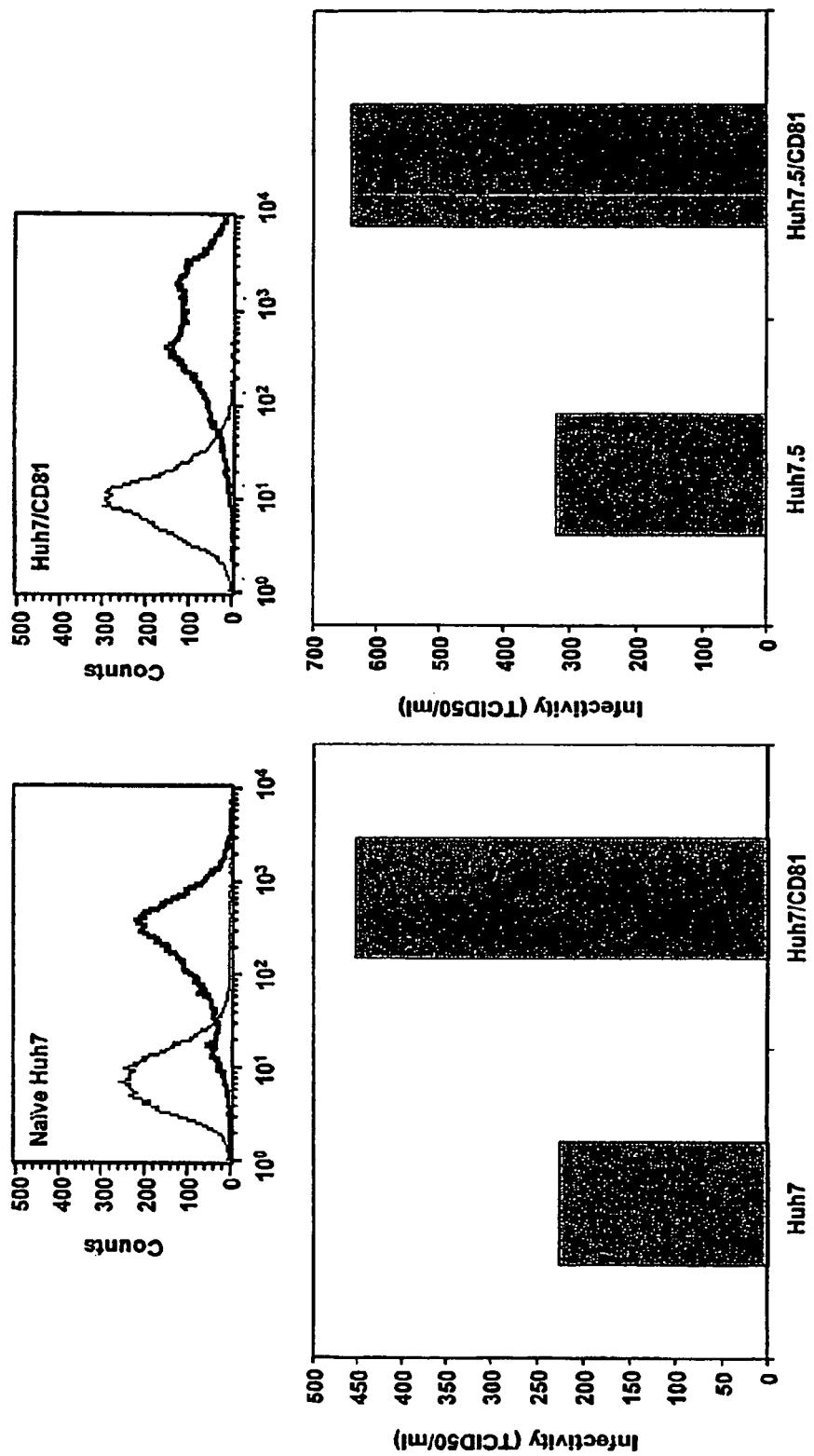
FIG. 18 shows the effects of CD81 on the infectivity of JFH1 in Huh7 and Huh7.5 cells.

The effect of CD81 on JFH1 infectivity was compared in Huh7 and Huh7.5 cells. CD81 is expected to improve infectivity by increasing the expression of the CD81 receptor on the surface of cells, which facilitates viral entry into cells. Huh7 and Huh7.5 cells were transfected with a CD81 expression plasmid (Pileri et al., supra) prior to viral RNA transfection. As shown in FIG. 18, both Huh7 and Huh7.5 cells showed significant increases in infectious JFH1 titers in the presence of CD81 compared to naive cells.

Example 15

Selection of Anti-HCV Antibodies Using Cell Culture System

Figure 19:
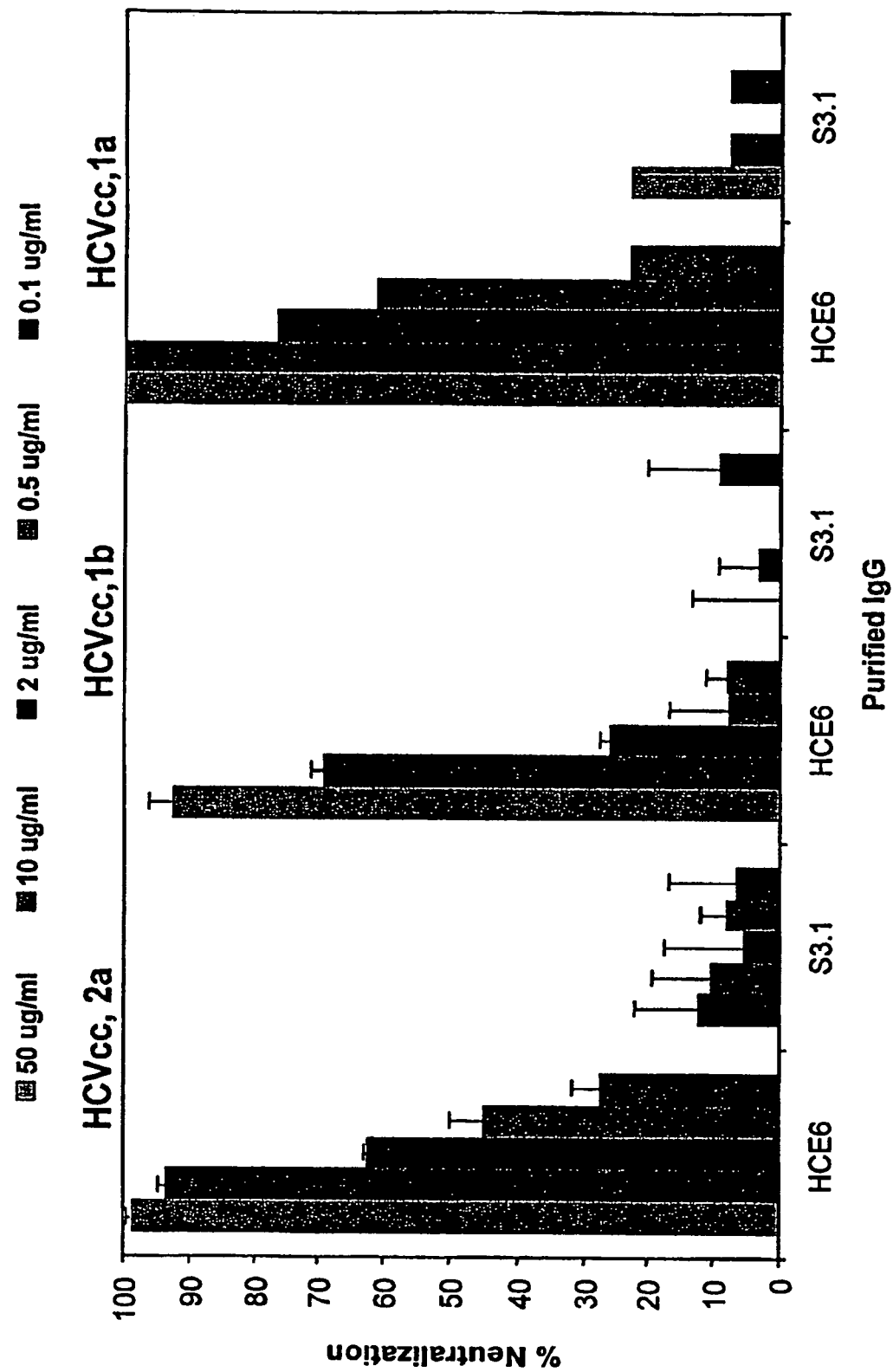
FIG. 19 shows neutralization antibody titers for HCV types 2a, 1b, and 1a, as measured with the HCV tissue culture system.

The HCV cell culture system was used to select neutralizing antibodies against HCV. HCV viruses were produced from RHJ1 (type 1a H77C:type 2a JFH1 chimera), RCJ1 (type 1b con1:type 2a JFH1 chimera), and RJ1 (type 2a JFH1) RNA genomic transcripts (see FIG. 17) in cell culture. Anti-HCV human monoclonal antibodies, HCE6 or S3.1, were tested in neutralization assays as described previously in Example 12. The antibodies were mixed with viral medium prior to infection and added to cells at concentrations of 50, 10, 2, 0.5, or 0.1 µg/ml. As shown in FIG. 19, the HCE6 monoclonal antibody showed superior neutralization of HCV compared to S3.1 for all of the HCV viruses tested, approaching nearly 100% HCV neutralization at the highest antibody concentrations (i.e., 10 and 50 µg/ml) for the JFH1 and the type 1a H77C:type 2a JFH1 chimera and about 90% neutralization at the highest antibody concentration (i.e., 50 µg/ml) for the type 1b con1:type 2a JFH1 chimera.

Example 16

Correlation Between Antibody Neutralization in Cell Culture Assay and Protection Against HCV Infection in an Animal Model Plasma samples were collected from four chimpanzees (Pan troglodytes; L357, L534, L559, and L470) vaccinated with HCV-1 E1 and E2 proteins, as described previously (Proc. Natl. Acad. Sci. U.S.A. (1994) 91:1294-1298, herein incorporated by reference). Three of the vaccinated chimpanzees, L357, L534, and L559 were completely protected from subsequent HCV infection. One of the chimpanzees, L470, showed partial protection, that is, vaccination significantly retarded infection and disease development. A plasma sample, collected from a fifth unvaccinated chimpanzee, was used as a control.

Figure 20:
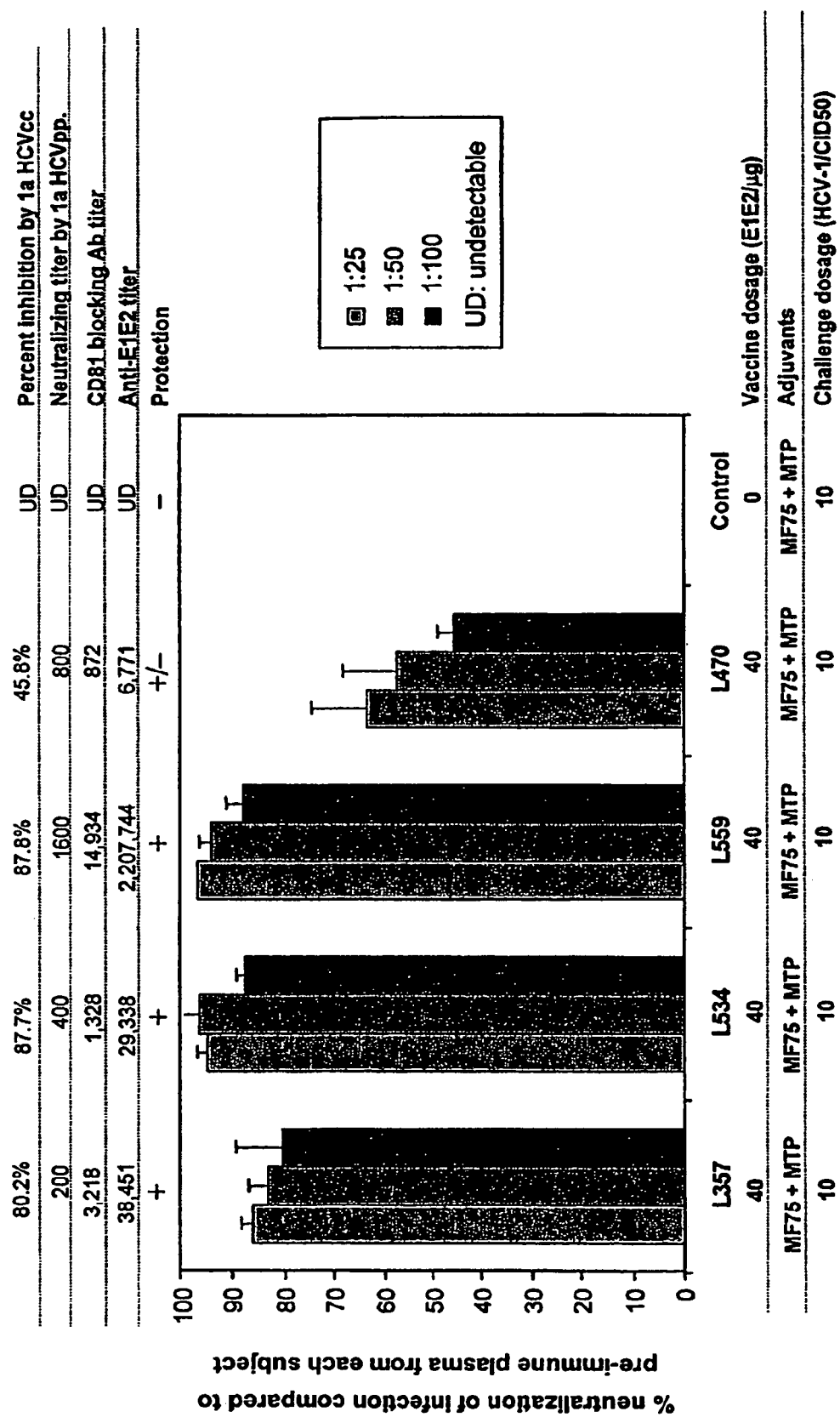
FIG. 20 compares protective immunity against HCV type 1a in chimpanzees vaccinated with E1E2. The percent inhibition of HCV type 1a, neutralizing antibody titer, CD81 blocking antibody titer, and anti-E1E2 antibody titer were measured using a cell culture assay.

Plasma samples were tested for the presence of neutralizing antibodies by using the cell culture assay described in Example 12. In FIG. 20, results are shown for neutralization of the type 1a H77C:type 2a JFH1 chimeric virus grown in cell culture. Plasma from the protected chimpanzees, L357, L534, and L559 neutralized 80% to 88% of the virus, whereas plasma from the partially protected chimpanzee, L470, neutralized 46% of the virus, and neutralization was undetectable for the control. These results indicate that viral neutralization in the cell culture assay correlates well with actual protection from HCV infection. For comparison, the results of previous work on the neutralizing titers of the same chimp plasma as assayed against an HCV type 4a pseudoparticle (HCVpp), CD81 blocking antibody titers, and anti-E1E2 antibody titers are also shown.

Figure 21:
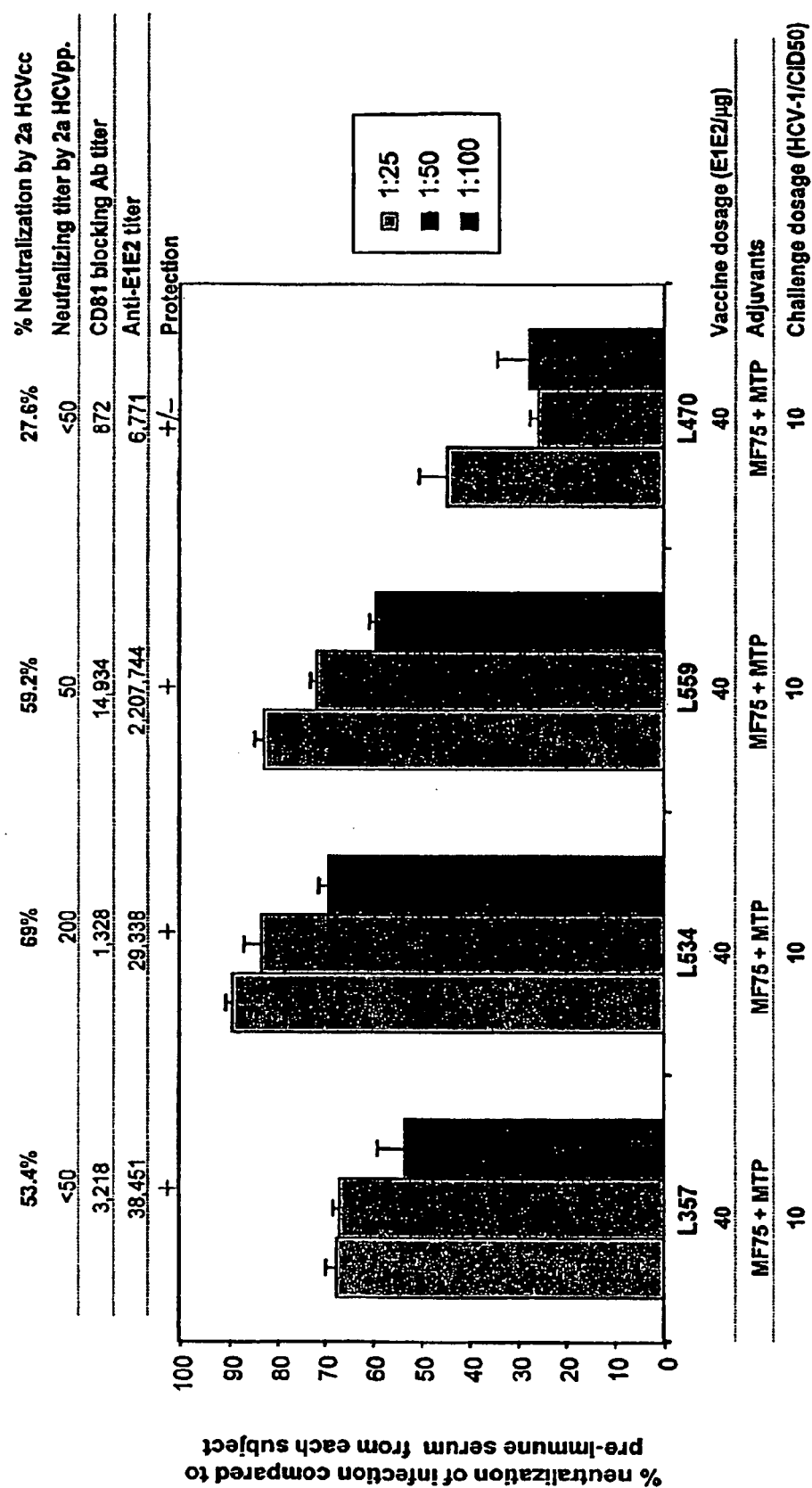
FIG. 21 shows cross-neutralization of HCV types 1a and 2a in chimpanzees, as measured using a cell culture assay.

In FIG. 21, results are shown for neutralization of the type 2a JFH1 virus grown in cell culture. Plasma from the protected chimpanzees, L357, L534, and L559 neutralized 53% to 69% of the virus, whereas plasma from the partially protected chimpanzee, L470, neutralized 28% of the virus. Thus, neutralizing titers are lower against the type 2a virus than the type 1a virus. The results of the cell culture assay correlate with cross-protection observed for HCV types 1a and 2a.

Thus, wild-type JFH1 and chimeric monocistronic and bicistronic genomic constructs, and methods of using the constructs for production of HCV in tissue culture are described. In addition, a neutralization assay using HCV grown in cell culture is described. Neutralization titers measured by this assay have been found to correlate well with actual protection from HCV infection in vaccinated animals. Although preferred embodiments of the subject invention have been described in some detail, it is understood that obvious variations can be made without departing from the spirit and the scope of the invention as defined herein. All references cited herein are hereby incorporate by reference in their entirety.

What is claimed is:

1. A recombinant hepatitis C virus (HCV) monocistronic genomic construct comprising in 5' to 3' order:
   a) an HCV 5' untranslated region, or a functional portion thereof;
   b) a polynucleotide comprising a coding sequence for an N-terminal fragment of the JFH1 core protein, wherein said fragment comprises at least the first 12 residues and up to the first 18 residues of the JFH1 core protein, wherein the coding sequence for the N-terminal fragment of the JFH1 core protein is linked to a reporter gene;
   c) a coding sequence for a foot-and-mouth disease virus (FMDV) 2A protease;
   d) a coding sequence for a ubiquitin protease cleavage site;
   e) a polynucleotide encoding an HCV polyprotein comprising core, E1, E2, and p7 regions from an HCV strain or isolate other than JFH1, a chimeric NS2 region comprising an N-terminal portion of NS2 from an HCV strain or isolate other than JFH1 and a C-terminal portion of NS2 from JFH1, and NS3, NS4a, NS4b, NS5a, and NS5b regions from JFH1; and
   f) an HCV 3' untranslated region, or a functional portion thereof.

2. The recombinant HCV genomic construct of claim 1, comprising a polynucleotide selected from the group consisting of:
   a) a polynucleotide comprising the contiguous sequence from nucleotide 7 to nucleotide 10953 of SEQ ID NO:8;
   b) a polynucleotide comprising the contiguous sequence from nucleotide 7 to nucleotide 10953 of SEQ ID NO:9;
   c) a polynucleotide comprising the contiguous sequence from nucleotide 7 to nucleotide 10971 of SEQ ID NO:10;
   d) a polynucleotide comprising the contiguous sequence from nucleotide 35 to nucleotide 9723 of SEQ ID NO:16
   e) a polynucleotide complementary to a polynucleotide of a)-d); and
   f) an RNA equivalent of a)-e).

3. The recombinant HCV genomic construct of claim 1, wherein the HCV strain or isolate other than JFH1 is selected from the group consisting of HCV 1a, 1b, 2a, 2b, 3a, 3b, 4, 5, and 6.

4. The recombinant HCV genomic construct of claim 3, wherein the HCV strain or isolate is H77C, Con1, NZ1, or 452.

5. The recombinant HCV genomic construct of claim 1, wherein the reporter gene encodes a firefly luciferase, Renilla luciferase, or, green fluorescent protein.

6. A vector comprising the recombinant HCV genomic construct of claim 1.

7. The vector of claim 6, comprising a nucleotide sequence selected from the group consisting of SEQ ID NO:8-10 and SEQ ID NO:16.

8. The vector of claim 6, further comprising a T7 promoter, wherein the T7 promoter is operably linked to the polynucleotide encoding an HCV polyprotein.

9. An HCV genomic RNA transcript comprising the recombinant HCV genomic construct of claim 1.

10. A tissue culture system for production of infectious HCV particles comprising a cell capable of supporting HCV infection transfected with the HCV genomic RNA transcript of claim 9.

11. The tissue culture system of claim 10, wherein the cell is a hepatocyte.

12. The tissue culture system of claim 10, further comprising a polynucleotide encoding an RNA silencing suppressor.

13. The tissue culture system of claim 12, wherein the RNA silencing suppressor is an influenza virus NS1 polypeptide or a functional fragment thereof that increases the yield of viral particles.

14. The tissue culture system of claim 13, wherein the NS1 polypeptide comprises the amino acid sequence of SEQ ID NO 15 or a functional fragment thereof that increases the yield of viral particles.

15. The tissue culture system of claim 13, wherein the polynucleotide encoding the RNA silencing suppressor comprises a nucleotide sequence selected from the group consisting of SEQ ID NOS:11-14.

16. The tissue culture system of claim 10, further comprising a polynucleotide encoding a CD81 polypeptide.

17. The tissue culture system of claim 11, wherein the hepatocyte cell is derived from human tissue.

18. The tissue culture system of claim 17, wherein the hepatocyte cell is a hepatocellular carcinoma cell.

19. The tissue culture system of claim 17, wherein the hepatocyte cell is from a cell line selected from the group consisting of Huh7, Huh7.5, Siena 8, Huh7C and T7-11.

20. The tissue culture system of claim 11, wherein the hepatocyte cell is interferon-cured.

21. The tissue culture system of claim 11, wherein replication of the HCV genomic RNA transcript is maintained for at least 10 days after the HCV genomic RNA transcript is introduced into the cell.

22. The tissue culture system of claim 21, wherein replication of the HCV genomic RNA transcript is maintained for at least 20 days after the HCV genomic RNA transcript is introduced into the cell.

23. The tissue culture system of claim 22, wherein replication of the HCV genomic RNA transcript is maintained for at least 30 days after the HCV genomic RNA transcript is introduced into the cell.

24. The tissue culture system of claim 11, wherein infectivity of virus produced from the HCV genomic RNA transcript is maintained for at least 9 days after the HCV genomic RNA transcript is introduced into the cell.

25. The tissue culture system of claim 24, wherein infectivity of virus produced from the HCV genomic RNA transcript is maintained for at least 15 days after the HCV genomic RNA transcript is introduced into the cell.

26. A method for producing HCV in tissue culture, comprising transfecting a cell with the HCV genomic RNA transcript of claim 9 and growing said cell in culture media under conditions suitable for replication of the construct and secretion of infectious viral particles into said culture media.

27. The method of claim 26, further comprising transfecting said cell with a polynucleotide encoding an RNA silencing suppressor prior to transfecting the cell with the HCV genomic RNA transcript.

28. The method of claim 27, wherein the RNA silencing suppressor is an influenza virus NS1 polypeptide or a functional fragment thereof that increases the yield of viral particles.

29. The method of claim 28, wherein the NS1 polypeptide comprises the amino acid sequence of SEQ ID NO 15 or a functional fragment thereof that increases the yield of viral particles.

30. The method of claim 28, wherein the polynucleotide encoding the RNA silencing suppressor comprises a nucleotide sequence selected from the group consisting of SEQ ID NOS:11-14.

31. The method of claim 26, further comprising a polynucleotide encoding a CD81 polypeptide.

32. The method of claim 26, wherein the cell is a hepatocyte cell is derived from human tissue.

33. The method of claim 32, wherein the hepatocyte cell is a hepatocellular carcinoma cell.

34. The method of claim 32, wherein the hepatocyte cell is from a cell line selected from the group consisting of Huh7, Huh7.5, Siena 8, Huh7C and T7-11.

35. The method of claim 32, wherein the hepatocyte cell is interferon-cured.

36. A chimeric hepatitis C virus produced by the method of claim 26.

37. A chimeric hepatitis C virus comprising the HCV genomic RNA transcript of claim 9.

38. A kit comprising a cell capable of supporting HCV infection and the vector of claim 7.

39. A kit comprising a cell capable of supporting HCV infection and the HCV genomic RNA transcript of claim 9.

40. A method of identifying a compound having anti-HCV activity, the method comprising:
   a) treating the tissue culture system of claim 10 with a compound;
   b) comparing HCV replication, expression of HCV proteins, or viral infectivity in said culture system treated with said compound to said tissue culture system not treated with said compound, wherein a reduction in the level of HCV replication, expression of HCV proteins, or viral infectivity in the tissue culture system treated with said compound is indicative of a compound with anti-HCV activity.

41. A method of identifying an antibody having anti-HCV activity, the method comprising:
   a) treating the tissue culture system of claim 10 with the antibody;
   b) comparing HCV replication, expression of HCV proteins, or viral infectivity in said culture system treated with said compound to said tissue culture system not treated with the antibody, wherein a reduction in the level of HCV replication, expression of HCV proteins, or viral infectivity in the tissue culture system treated with said compound is indicative of an antibody with anti-HCV activity.

42. A method for producing HCV in tissue culture, comprising transfecting a cell with the HCV genomic RNA transcript of claim 9 and growing said cell in culture media under conditions suitable for replication of the HCV genomic RNA transcript and secretion of infectious viral particles into said culture media, wherein the transfected cell expresses CD81 and an influenza NS1 polypeptide.

43. The method of claim 42, wherein the NS1 polypeptide comprises the amino acid sequence of SEQ ID NO 15 or a functional fragment thereof that increases the yield of viral particles.

44. The method of claim 42, wherein the transfected cell comprises a polynucleotide comprising a nucleotide sequence selected from the group consisting of SEQ ID NOS: 11-14.

45. The method of claim 42, wherein the cell is a hepatocyte cell and is derived from human tissue.

46. The method of claim 45, wherein the hepatocyte cell is a hepatocellular carcinoma cell.

47. The method of claim 45, wherein the hepatocyte cell is from a cell line selected from the group consisting of Huh7, Huh7.5, Siena 8, Huh7C and T7-11.

48. The method of claim 45, wherein the hepatocyte cell is interferon-cured.

* * * * *

SEQUENCE LISTING

<160> NUMBER OF SEQ ID NOS: 16

<210> SEQ ID NO 1
<211> LENGTH: 12369
<212> TYPE: DNA
<213> ORGANISM: Artificial Sequence
<220> FEATURE:
<223> OTHER INFORMATION: Synthetic plasmid: pUC18-JFH1

<400> SEQUENCE: 1

```
gaattcccaa acgcgttaat acgactcact atagacctgc ccctaatagg ggcgacactc      60
cgccatgaat cactcccctg tgaggaacta ctgtcttcac gcagaaagcg cctagccatg     120
gcgttagtat gagtgtcgta cagcctccag gcccccccct cccgggagag ccatagtggt     180
ctgcggaacc ggtgagtaca ccggaattgc cgggaagact gggtcctttc ttggataaac     240
ccactctatg cccggccatt tgggcgtgcc cccgcaagac tgctagccga gtagcgttgg     300
gttgcgaaag gccttgtggt actgcctgat agggcgcttg cgagtgcccc gggaggtctc     360
gtagaccgtg caccatgagc acaaatccta aacctcaaag aaaaaccaaa agaaacacca     420
accgtcgccc agaagacgtt aagttcccgg gcggcggcca gatcgttggc ggagtatact     480
tgttgccgcg caggggcccc aggttgggtg tgcgcacgac aaggaaaact tcggagcggt     540
cccagccacg tgggagacgc cagcccatcc ccaaagatcg gcgctccact ggcaaggcct     600
ggggaaaacc aggtcgcccc tggcccctat atgggaatga gggactcggc tgggcaggat     660
ggctcctgtc cccccgaggc tctcgcccct cctgggccc cactgacccc cggcataggt     720
cgcgcaacgt gggtaaagtc atcgacaccc taacgtgtgg ctttgccgac ctcatggggt     780
acatccccgt cgtaggcgcc ccgcttagtg gcgccgccag agctgtcgcg cacggcgtga     840
gagtcctgga ggacggggtt aattatgcaa cagggaacct acccggtttc ccctttttcta     900 tcttcttgct ggccctgttg tcctgcatca ccgttccggt ctctgctgcc caggtgaaga     960
ataccagtag cagctacatg gtgaccaatg actgctccaa tgacagcatc acttggcagc    1020
tcgaggctgc ggttctccac gtccccgggt gcgtcccgtg cgagagagtg gggaatacgt    1080
cacggtgttg ggtgccagtc tcgccaaaca tggctgtgcg gcagcccggt gccctcacgc    1140
```

```
agggtctgcg gacgcacatc gatatggttg tgatgtccgc caccttctgc tctgctctct    1200
acgtggggga cctctgtggc ggggtgatgc tcgcggccca ggtgttcatc gtctcgccgc    1260
agtaccactg gtttgtgcaa gaatgcaatt gctccatcta ccctggcacc atcactggac    1320
accgcatggc atgggacatg atgatgaact ggtcgcccac ggccaccatg atcctggcgt    1380
acgtgatgcg cgtccccgag gtcatcatag acatcgttag cggggctcac tgggcgtca     1440 tgttcggctt ggcctacttc tctatgcagg gagcgtgggc gaaggtcatt gtcatccttc    1500
tgctggccgc tggggtggac gcgggcacca ccaccgttgg aggcgctgtt gcacgttcca    1560
ccaacgtgat tgccggcgtg ttcagccatg ccctcagca gaacattcag ctcattaaca     1620
ccaacggcag ttggcacatc aaccgtactg ccttgaattg caatgactcc ttgaacaccg    1680
gctttctcgc ggccttgttc tacaccaacc gctttaactc gtcagggtgt ccagggcgcc    1740
tgtccgcctg ccgcaacatc gaggctttcc ggatagggtg gggcacccta cagtacgagg    1800
ataatgtcac caatccagag gatatgaggc cgtactgctg gcactacccc ccaaagccgt    1860
gtggcgtagt ccccgcgagg tctgtgtgtg gcccagtgta ctgtttcacc cccagcccgg    1920
tagtagtggg cacgaccgac agacgtggag tgcccaccta cacatgggga gagaatgaga    1980
cagatgtctt cctactgaac agcacccgac cgccgcaggg ctcatggttc ggctgcacgt    2040
ggatgaactc cactggtttc accaagactt gtggcgcgcc accttgccgc accagagctg    2100
acttcaacgc cagcacggac ttgttgtgcc ctacggattg ttttaggaag catcctgatg    2160
ccacttatat taagtgtggt tctgggccct ggctcacacc aaagtgcctg gtccactacc    2220
cttacagact ctggcattac ccctgcacag tcaattttac catcttcaag ataagaatgt    2280
atgtaggggg ggttgagcac aggctcacgg ccgcatgcaa cttcactcgt ggggatcgct    2340
gcgacttgga ggacagggac aggagtcagc tgtctcctct gttgcactct accacggaat    2400
gggccatcct gccctgcacc tactcagact tacccgcttt gtcaactggt cttctccacc    2460
ttcaccagaa catcgtggac gtacaataca tgtatggcct ctcacctgct atcacaaaat    2520
acgtcgttcg atgggagtgg gtggtactct tattcctgct cttagcggac gccagagtct    2580
gcgcctgctt gtggatgctc atcttgttgg gccaggccga agcagcattg gagaagttgg    2640
tcgtcttgca cgctgcgagt gcggctaact gccatggcct cctatatttt gccatcttct    2700
tcgtggcagc ttggcacatc aggggtcggg tggtcccctt gaccacctat tgcctcactg    2760
gcctatggcc cttctgccta ctgctcatgg cactgccccg gcaggcttat gcctatgacg    2820
cacctgtgca cggacagata ggcgtgggtt tgttgatatt gatcaccctc ttcacactca    2880
ccccggggta taagaccctc tcggccagtg tctctgtggt gttgtgctat ctcctgaccc    2940
tgggggaagc catgattcag gagtgggtac cacccatgca ggtgcgcggc ggccgcgatg    3000
gcatcgcgtg gccgtcact atattctgcc cgggtgtggt gtttgacatt accaaatggc    3060
ttttggcgtt gcttgggcct gcttacctct aagggccgc tttgacacat gtgccgtact    3120
tcgtcagagc tcacgctctg ataagggtat gcgctttggt gaagcagctc gcggggggta    3180
ggtatgttca ggtggcgcta ttggcccttg gcaggtggac tggcacctac atctatgacc    3240
acctcacacc tatgtcggac tgggccgcta gcggcctgcg cgacttagcg gtcgccgtgg    3300
aacccatcat cttcagtccg atggagaaga aggtcatcgt ctggggagcg agacggctg    3360 catgtgggga cattctacat ggacttcccg tgtccgcccg actcggccag gagatcctcc    3420
tcggcccagc tgatgctac acctccaagg ggtggaagct ccttgctccc atcactgctt    3480
atgcccagca aacacgaggc ctcctgggcg ccatagtggt gagtatgacg gggcgtgaca    3540
```

```
ggacagaaca ggccggggaa gtccaaatcc tgtccacagt ctctcagtcc ttcctcggaa    3600
caaccatctc gggggttttg tggactgttt accacggagc tggcaacaag actctagccg    3660
gcttacgggg tccggtcacg cagatgtact cgagtgctga gggggacttg gtaggctggc    3720 ccagccccc tgggaccaag tctttggagc cgtgcaagtg tggagccgtc gacctatatc     3780
tggtcacgcg gaacgctgat gtcatcccgg ctcggagacg cggggacaag cggggagcat    3840
tgctctcccc gagacccatt tcgaccttga aggggtcctc ggggggcccg gtgctctgcc    3900
ctagggccca cgtcgttggg ctcttccgag cagctgtgtg ctctcgggc gtggccaaat     3960 ccatcgattt catccccgtt gagacactcg acgttgttac aaggtctccc actttcagtg    4020
acaacagcac gccaccggct gtgccccaga cctatcaggt cgggtacttg catgctccaa    4080
ctggcagtgg aaagagcacc aaggtccctg tcgcgtatgc cgcccagggg tacaaagtac    4140
tagtgcttaa cccctcggta gctgccaccc tggggtttgg ggcgtaccta tccaaggcac    4200
atggcatcaa tcccaacatt aggactggag tcaggaccgt gatgacgggg gaggccatca    4260
cgtactccac atatggcaaa tttctcgccg atgggggctg cgctagcggc gcctatgaca    4320
tcatcatatg cgatgaatgc cacgctgtgg atgctacctc cattctcggc atcggaacgg    4380
tccttgatca agcagagaca gccggggtca gactaactgt gctggctacg gccacacccc    4440
ccgggtcagt gacaaccccc catcccgata tagaagaggg aggcctcggg cgggagggtg    4500
agatcccctt ctatgggagg gcgattcccc tatcctgcat caagggaggg agacacctga    4560
ttttctgcca ctcaaagaaa aagtgtgacg agctcgcggc ggcccttcgg ggcatgggct    4620
tgaatgccgt ggcatactat agagggttgg acgtctccat aataccagct caggagatg     4680 tggtggtcgt cgccaccgac gccctcatga cggggtacac tggagacttt gactccgtga    4740
tcgactgcaa tgtagcggtc acccaagctg tcgacttcag cctggacccc accttcacta    4800
taaccacaca gactgtccca caagacgctg tctcacgcag tcagcgccgc gggcgcacag    4860
gtagaggaag acagggcact tataggtatg tttccactgg tgaacgagcc tcaggaatgt    4920
ttgacagtgt agtgctttgt gagtgctacg acgcaggggc tgcgtggtac gatctcacac    4980
cagcggagac caccgtcagg cttagagcgt atttcaacac gcccggccta cccgtgtgtc    5040
aagaccatct tgaatttggg gaggcagttt tcaccggcct cacacacata gacgcccact    5100
tcctctccca aacaaagcaa gcgggggaga acttcgcgta cctagtagcc taccaagcta    5160
cggtgtgcgc cagagccaag gcccctcccc cgtcctggga cgccatgtgg aagtgcctgg    5220
cccgactcaa gcctacgctt gcgggcccca cacctctcct gtaccgtttg ggccctatta    5280
ccaatgaggt caccctcaca caccctggga cgaagtacat cgccacatgc atgcaagctg    5340
accttgaggt catgaccagc acgtgggtcc tagctggagg agtcctggca gccgtcgccg    5400
catattgcct ggcgactgga tgcgtttcca tcatcggccg cttgcacgtc aaccagcgag    5460
tcgtcgttgc gccggataag gaggtcctgt atgaggcttt tgatgagatg gaggaatgcg    5520
cctctagggc ggctctcatc gaagaggggc agcggatagc cgagatgttg aagtccaaga    5580
tccaaggctt gctgcagcag gcctctaagc aggcccagga catacaaccc gctatgcagg    5640
cttcatggcc caaagtggaa caattttggg ccagacacat gtggaacttc attagcggca    5700
tccaatacct cgcaggattg tcaacactgc agggaaccc cgcggtggct tccatgatgg    5760
cattcagtgc cgccctcacc agtccgttgt cgaccagtac caccatcctt ctcaacatca    5820
tgggaggctg gttagcgtcc cagatcgcac caccgcgggg ggccaccggc tttgtcgtca    5880
gtggcctggt gggggctgcc gtgggcagca taggcctggg taaggtgctg gtggacatcc    5940
```

-continued

```
tggcaggata tggtgcgggc atttcggggg ccctcgtcgc attcaagatc atgtctggcg    6000
agaagccctc tatggaagat gtcatcaatc tactgcctgg gatcctgtct ccgggagccc    6060
tggtggtggg ggtcatctgc gcggccattc tgcgccgcca cgtggaccgg ggggaggggcg   6120
cggtccaatg gatgaacagg cttattgcct ttgcttccag aggaaaccac gtcgcccta    6180
ctcactacgt gacggagtcg gatgcgtcgc agcgtgtgac ccaactactt ggctctctta    6240
ctataaccag cctactcaga agactccaca attggataac tgaggactgc cccatcccat    6300
gctccggatc ctggctccgc gacgtgtggg actgggtttg caccatcttg acagacttca    6360
aaaattggct gacctctaaa ttgttcccca agctgcccgg cctcccttc atctcttgtc     6420
aaaagggta caagggtgtg tgggccggca ctggcatcat gaccacgcgc tgcccttgcg     6480
gcgccaacat ctctggcaat gtccgcctgg gctctatgag gatcacaggg cctaaaacct    6540
gcatgaacac ctggcagggg accttttccta tcaattgcta cacggagggc cagtgcgcgc   6600
cgaaacccc cacgaactac aagaccgcca tctggagggt ggcggcctcg gagtacgcgg     6660
aggtgacgca gcatgggtcg tactcctatg taacaggact gaccactgac aatctgaaaa    6720
ttccttgcca actaccttct ccagagtttt tctcctgggt ggacggtgtg cagatccata    6780
ggtttgcacc cacaccaaag ccgttttttcc gggatgaggt ctcgttctgc gttgggctta   6840
attcctatgc tgtcgggtcc cagcttccct gtgaacctga gcccgacgca gacgtattga    6900
ggtccatgct aacagatccg ccccacatca cggcggagac tgcggcgcgg cgcttggcac    6960
ggggatcacc tccatctgag gcgagctcct cagtgagcca gctatcagca ccgtcgctgc    7020
gggccacctg caccacccac agcaacacct atgacgtgga catggtcgat gccaacctgc    7080
tcatggaggg cggtgtggct cagacagagc ctgagtccag ggtgcccgtt ctggactttc    7140
tcgagccaat ggccgaggaa gagagcgacc ttgagccctc aataccatcg gagtgcatgc    7200
tccccaggag cgggtttcca cgggccttac cggcttgggc acggcctgac tacaacccgc    7260
cgctcgtgga atcgtggagg aggccagatt accaaccgcc caccgttgct ggttgtgctc    7320
tccccccccc caagaaggcc ccgacgcctc ccccaaggag acgccggaca gtgggtctga    7380
gcgagagcac catatcagaa gccctccagc aactggccat caagaccttt ggccagcccc    7440
cctcgagcgt tgatgcaggc tcgtccacgg gggcgggcgc cgccgaatcc ggcggtccga    7500
cgtcccctgg tgagccggcc ccctcagaga caggttccgc ctcctctatg cccccctcg    7560
aggggagcc tggagatccg gacctggagt ctgatcaggt agagcttcaa cctcccccc    7620
agggggggg ggtagctccc ggttcgggct cggggtcttg gtctacttgc tccgaggagg    7680
acgataccac cgtgtgctgc tccatgtcat actcctggac cggggctcta ataactccct    7740
gtagccccga agaggaaaag ttgccaatca acccttttgag taactcgctg ttgcgatacc    7800
ataacaaggt gtactgtaca acatcaaaga gcgcctcaca gagggctaaa aaggtaactt    7860
ttgacaggac gcaagtgctc gacgcccatt atgactcagt cttaaaggac atcaagctag    7920
cggcttccaa ggtcagcgca aggctcctca ccttggagga ggcgtgccag ttgactccac    7980
cccattctgc aagatccaag tatggattcg gggccaagga ggtccgcagc ttgtccggga    8040
gggccgttaa ccacatcaag tccgtgtgga aggacctcct ggaagaccca caaacaccaa    8100
ttcccacaac catcatggcc aaaaatgagg tgttctgcgt ggaccccgcc aaggggggta    8160
agaaaccagc tcgcctcatc gtttaccctg acctcggcgt ccgggtctgc gagaaaatgg    8220
ccctctatga cattacacaa aagcttcctc aggcggtaat gggagcttcc tatggcttcc    8280
agtactcccc tgcccaacgg gtggagtatc tcttgaaagc atgggcggaa aagaaggacc    8340
```

```
ccatgggttt tcgtatgat acccgatgct tcgactcaac cgtcactgag agagacatca    8400
ggaccgagga gtccatatac caggcctgct ccctgcccga ggaggcccgc actgccatac    8460
actcgctgac tgagagactt tacgtaggag ggcccatgtt caacagcaag ggtcaaacct    8520
gcggttacag acgttgccgc gccagcgggg tgctaaccac tagcatgggt aacaccatca    8580
catgctatgt gaaagcccta gcggcctgca aggctgcggg gatagttgcg cccacaatgc    8640
tggtatgcgg cgatgaccta gtagtcatct cagaaagcca ggggactgag gaggacgagc    8700
ggaacctgag agccttcacg gaggccatga ccaggtactc tgcccctcct ggtgatcccc    8760
ccagaccgga atatgacctg gagctaataa catcctgttc ctcaaatgtg tctgtggcgt    8820
tgggcccgcg gggccgccgc agatactacc tgaccagaga cccaaccact ccactcgccc    8880
gggctgcctg ggaaacagtt agacactccc ctatcaattc atggctggga aacatcatcc    8940
agtatgctcc aaccatatgg gttcgcatgg tcctaatgac acacttcttc tccattctca    9000
tggtccaaga caccctggac cagaacctca actttgagat gtatggatca gtatactccg    9060
tgaatccttt ggaccttcca gccataattg agaggttaca cgggcttgac gccttttcta    9120
tgcacacata ctctcaccac gaactgacgc gggtggcttc agccctcaga aaacttgggg    9180
cgccacccct cagggtgtgg aagagtcggg ctcgcgcagt cagggcgtcc ctcatctccc    9240
gtggagggaa agcggccgtt tgcggccgat atctcttcaa ttgggcggtg aagaccaagc    9300
tcaaactcac tccattgccg gaggcgcgcc tactggactt atccagttgg ttcaccgtcg    9360
gcgccggcgg gggcgacatt tttcacagcg tgtcgcgcgc ccgaccccgc tcattactct    9420
tcggcctact cctactttc gtaggggtag gcctcttcct actccccgct cggtagagcg    9480
gcacacacta ggtacactcc atagctaact gttcctttt ttttttttt ttttttttt     9540
ttttttttt tttttttct ttttttttt tttccctctt tcttcccttc tcatcttatt    9600
ctactttctt tcttggtggc tccatcttag ccctagtcac ggctagctgt gaaaggtccg    9660
tgagccgcat gactgcagag agtgccgtaa ctggtctctc tgcagatcat gtctagagtc    9720
gacctgcagg catgcaagct tggcactggc cgtcgtttta caacgtcgtg actgggaaaa    9780
ccctggcgtt acccaactta atcgccttgc agcacatccc cctttcgcca gctggcgtaa    9840
tagcgaagag gcccgcaccg atcgcccttc ccaacagttg cgcagcctga atggcgaatg    9900
gcgcctgatg cggtattttc tccttacgca tctgtgcggt atttcacacc gcatatggtg    9960
cactctcagt acaatctgct ctgatgccgc atagttaagc cagccccgac acccgccaac   10020
acccgctgac gcgccctgac gggcttgtct gctcccggca tccgcttaca gacaagctgt   10080
gaccgtctcc gggagctgca tgtgtcagag gttttcaccg tcatcaccga aacgcgcgag   10140
acgaaagggc ctcgtgatac gcctattttt ataggttaat gtcatgataa taatggtttc   10200
ttagacgtca ggtggcactt ttcggggaaa tgtgcgcgga acccctattt gtttatttt    10260
ctaaatacat tcaaatatgt atccgctcat gagacaataa ccctgataaa tgcttcaata   10320
atattgaaaa aggaagagta tgagtattca acatttccgt gtcgccctta ttcccttttt   10380
tgcggcattt tgccttcctg tttttgctca cccagaaacg ctggtgaaag taaaagatgc   10440
tgaagatcag ttgggtgcac gagtgggtta tcgaactg gatctcaaca gcggtaagat   10500
ccttgagagt tttcgccccg aagaacgttt tccaatgatg agcactttta aagttctgct   10560
atgtggcgcg gtattatccc gtattgacgc cgggcaagag caactcggtc gccgcataca   10620
ctattctcag aatgacttgg ttgagtactc accagtcaca gaaaagcatc ttacggatgg   10680
catgacagta agagaattat gcagtgctgc cataaccatg agtgataaca ctgcggccaa   10740
```

```
cttacttctg acaacgatcg gaggaccgaa ggagctaacc gcttttttgc acaacatggg    10800
ggatcatgta actcgccttg atcgttggga accggagctg aatgaagcca taccaaacga    10860
cgagcgtgac accacgatgc ctgtagcaat ggcaacaacg ttgcgcaaac tattaactgg    10920
cgaactactt actctagctt cccggcaaca attaatagac tggatggagg cggataaagt    10980
tgcaggacca cttctgcgct cggcccttcc ggctggctgg tttattgctg ataaatctgg    11040
agccggtgag cgtgggtctc gcggtatcat tgcagcactg gggccagatg gtaagccctc    11100
ccgtatcgta gttatctaca cgacggggag tcaggcaact atggatgaac gaaatagaca    11160
gatcgctgag ataggtgcct cactgattaa gcattggtaa ctgtcagacc aagtttactc    11220
atatatactt tagattgatt taaaacttca ttttttaattt aaaaggatct aggtgaagat    11280
cctttttgat aatctcatga ccaaaatccc ttaacgtgag ttttcgttcc actgagcgtc    11340
agacccgta gaaagatca aaggatcttc ttgagatcct ttttttctgc gcgtaatctg    11400
ctgcttgcaa acaaaaaac caccgctacc agcggtggtt tgtttgccgg atcaagagct    11460
accaactctt tttccgaagg taactggctt cagcagagcg cagataccaa atactgttct    11520
tctagtgtag ccgtagttag gccaccactt caagaactct gtagcaccgc ctacatacct    11580
cgctctgcta atcctgttac cagtggctgc tgccagtggc gataagtcgt gtcttaccgg    11640
gttggactca agacgatagt taccggataa ggcgcagcgg tcgggctgaa cggggggttc    11700
gtgcacacag cccagcttgg agcgaacgac ctacaccgaa ctgagatacc tacagcgtga    11760
gctatgagaa agcgccacgc ttcccgaagg agaaaggcg gacaggtatc cggtaagcgg    11820
cagggtcgga acaggagagc gcacgaggga gcttccaggg ggaaacgcct ggtatcttta    11880
tagtcctgtc gggtttcgcc acctctgact tgagcgtcga ttttttgtgat gctcgtcagg    11940
ggggcggagc ctatggaaaa acgccagcaa cgcggccttt ttacggttcc tggccttttg    12000
ctggcctttt gctcacatgt tctttcctgc gttatcccct gattctgtgg ataaccgtat    12060
taccgccttt gagtgagctg ataccgctcg ccgcagccga acgaccgagc gcagcgagtc    12120
agtgagcgag gaagcggaag agcgcccaat acgcaaaccg cctctccccg cgcgttggcc    12180
gattcattaa tgcagctggc acgacaggtt cccgactgg aaagcgggca gtgagcgcaa    12240
cgcaattaat gtgagttagc tcactcatta ggcaccccag gctttacact ttatgcttcc    12300
ggctcgtatg ttgtgtggaa ttgtgagcgg ataacaattt cacacaggaa acagctatga    12360
catgattac                                                             12369

<210> SEQ ID NO 2
<211> LENGTH: 14683
<212> TYPE: DNA
<213> ORGANISM: Artificial Sequence
<220> FEATURE:
<223> OTHER INFORMATION: Synthetic plasmid: pLucJFH1

<400> SEQUENCE: 2
gaattcccaa acgcgttaat acgactcact atagacctgc cctaataggg ggcgacactc      60
cgccatgaat cactcccctg tgaggaacta ctgtcttcac gcagaaagcg cctagccatg     120
gcgttagtat gagtgtcgta cagcctccag gccccccccct cccggagag ccatagtggt     180
ctgcggaacc ggtgagtaca ccggaattgc cgggaagact gggtcctttc ttggataaac     240
ccactctatg cccggccatt tgggcgtgcc cccgcaagac tgctagccga gtagcgttgg     300
gttgcgaaag gccttgtggt actgcctgat agggcgcttg cgagtgcccc ggaggtctc     360
gtagaccgtg caccatgagc acaaatccta aacctcaaag aaaaaccaaa agaaacacca     420
```

```
accgtgaaga cgccaaaaac ataaagaaag gcccggcgcc attctatccc ctagaggatg    480
gaaccgctgg agagcaactg cataaggcta tgaagagata cgccctggtt cctggaacaa    540
ttgcttttac agatgcacat atcgaggtga acatcacgta cgcggaatac ttcgaaatgt    600
ccgttcggtt ggcagaagct atgaaacgat atgggctgaa tacaaatcac agaatcgtcg    660
tatgcagtga aaactctctt caattcttta tgccggtgtt gggcgcgtta tttatcggag    720
ttgcagttgc gcccgcgaac gacatttata tgaacgtgaa attgctcaac agtatgaaca    780
tttcgcagcc taccgtagtg tttgtttcca aaaggggtt gcaaaaaatt ttgaacgtgc     840
aaaaaaatt accaataatc cagaaaatta ttatcatgga ttctaaaacg gattaccagg     900
gatttcagtc gatgtacacg ttcgtcacat ctcatctacc tcccggtttt aatgaatacg    960
attttgtacc agagtccttt gatcgtgaca aaacaattgc actgataatg aattcctctg   1020
gatctactgg gttacctaag ggtgtggccc ttccgcatag aactgcctgc gtcagattct   1080
cgcatgccag agatcctatt tttggcaatc aaatcattcc ggatactgcg attttaagtg   1140
ttgttccatt ccatcacggt tttggaatgt ttactacact cggatatttg atatgtggat   1200
ttcgagtcgt cttaatgtat agatttgaag aagagctgtt tttacgatcc cttcaggatt   1260
acaaaattca agtgcgttg ctagtaccaa ccctattttc attcttcgcc aaaagcactc     1320
tgattgacaa atacgattta tctaatttac acgaaattgc ttctggggc gcacctcttt     1380
cgaaagaagt cggggaagcg gttgcaaaac gcttccatct tccagggata cgacaaggat   1440
atgggctcac tgagactaca tcagctattc tgattacacc cgaggggat gataaaccgg     1500
gcgcggtcgg taaagttgtt ccatttttg aagcgaaggt tgtggatctg ataccgggga     1560
aaacgctggg cgttaatcag agaggcgaat tatgtgtcag aggacctatg attatgtccg   1620
gttatgtaaa caatccggaa gcgaccaacg ccttgattga caaggatgga tggctacatt   1680
ctggagacat agcttactgg gacgaagacg aacacttctt catagttgac cgcttgaagt   1740
ctttaattaa atacaaagga tatcaggtgg ccccccgctga attggaatcg atattgttac   1800
aacaccccaa catcttcgac gcgggcgtgg caggtcttcc cgacgatgac gccggtgaac   1860
ttcccgccgc cgttgttgtt ttggagcacg gaaagacgat gacggaaaaa gagatcgtgg   1920
attacgtcgc cagtcaagta acaaccgcga aaaagttgcg cggaggagtt gtgtttgtgg   1980
acgaagtacc gaaaggtctt accggaaaac tcgacgcaag aaaaatcaga gagatcctca   2040
taaaggccaa gaagggcgga aagtccaaat tgtgagttgt taaacagacc acaacgtttt   2100
ccctctagcg ggatcaattc cgcccccccc cctaacgtt actggccgaa gccgcttgga    2160
ataaggccgg tgtgcgtttg tctatatgtt attttccacc atattgccgt cttttggcaa   2220
tgtgagggcc cggaaacctg gccctgtctt cttgacgagc attcctaggg gtctttcccc   2280
tctcgccaaa ggaatgcaag gtctgttgaa tgtcgtgaag gaagcagttc ctctggaagc   2340
ttcttgaaga caaacaacgt ctgtagcgac cctttgcagg cagcggaacc ccccacctgg   2400
cgacaggtgc ctctgcggcc aaaagccacg tgtataagat acacctgcaa aggcggcaca   2460
accccagtgc cacgttgtga gttggatagt tgtggaaaga gtcaaatggc tctcctcaag   2520
cgtattcaac aaggggctga aggatgccca gaaggtaccc cattgtatgg gatctgatct   2580
ggggcctcgg tgcacatgct ttacatgtgt ttagtcgagg ttaaaaaaac gtctaggccc   2640
cccgaaccac ggggacgtgg ttttcctttg aaaacacga taataccatg agcacaaatc    2700
ctaaacctca agaaaaacc aaaagaaaca ccaaccgtcg cccagaagac gttaagttcc     2760
cgggcggcgg ccagatcgtt ggcggagtat acttgttgcc gcgcaggggc cccaggttgg   2820
```

```
gtgtgcgcac gacaaggaaa acttcggagc ggtcccagcc acgtgggaga cgccagccca    2880
tccccaaaga tcggcgctcc actggcaagg cctggggaaa accaggtcgc ccctggcccc    2940
tatatgggaa tgagggactc ggctgggcag gatggctcct gtcccccga ggctctcgcc     3000 cctcctgggg ccccactgac ccccggcata ggtcgcgcaa cgtgggtaaa gtcatcgaca    3060
ccctaacgtg tggctttgcc gacctcatgg ggtacatccc cgtcgtaggc gccccgctta    3120
gtggcgccgc cagagctgtc gcgcacggcg tgagagtcct ggaggacggg gttaattatg    3180
caacagggaa cctacccggt ttccccttt ctatcttctt gctggccctg ttgtcctgca     3240
tcaccgttcc ggtctctgct gcccaggtga agaataccag tagcagctac atggtgacca    3300
atgactgctc caatgacagc atcacttggc agctcgaggc tgcggttctc cacgtccccg    3360
ggtgcgtccc gtgcgagaga gtggggaata cgtcacggtg ttgggtgcca gtctcgccaa    3420
acatggctgt gcggcagccc ggtgccctca cgcagggtct gcggacgcac atcgatatgg    3480
ttgtgatgtc cgccaccttc tgctctgctc tctacgtggg ggacctctgt ggcggggtga    3540
tgctcgcggc ccaggtgttc atcgtctcgc cgcagtacca ctggtttgtg caagaatgca    3600
attgctccat ctaccctggc accatcactg gacaccgcat ggcatgggac atgatgatga    3660
actggtcgcc cacggccacc atgatcctgg cgtacgtgat gcgcgtcccc gaggtcatca    3720
tagacatcgt tagcggggct cactgggggcg tcatgttcgg cttggcctac ttctctatgc    3780
agggagcgtg ggcgaaggtc attgtcatcc ttctgctggc cgctgggggtg gacgcgggca    3840 ccaccaccgt tggaggcgct gttgcacgtt ccaccaacgt gattgccggc gtgttcagcc    3900
atggccctca gcagaacatt cagctcatta acaccaacgg cagttggcac atcaaccgta    3960
ctgccttgaa ttgcaatgac tccttgaaca ccggctttct cgcggccttg ttctacacca    4020
accgctttaa ctcgtcaggg tgtccagggc gcctgtccgc ctgccgcaac atcgaggctt    4080
tccggatagg gtgggcacc ctacagtacg aggataatgt caccaatcca gaggatatga     4140
ggccgtactg ctggcactac cccccaaagc cgtgtggcgt agtcccgcg aggtctgtgt     4200 gtggcccagt gtactgtttc accccagccc cggtagtagt gggcacgacc gacagacgtg    4260
gagtgcccac ctacacatgg ggagagaatg agacagatgt cttcctactg aacagcaccc    4320
gaccgccgca gggctcatgg ttcggctgca cgtggatgaa ctccactggt ttcaccaaga    4380
cttgtggcgc gccaccttgc cgcaccagag ctgacttcaa cgccagcacg gacttgttgt    4440
gccctacgga ttgttttagg aagcatcctg atgccactta tattaagtgt ggttctgggc    4500
cctggctcac accaaagtgc ctggtccact acccttacag actctggcat taccccctgca   4560 cagtcaattt taccatcttc aagataagaa tgtatgtagg ggggttgag cacaggctca    4620 cggccgcatg caacttcact cgtgggatc gctgcgactt ggaggacagg gacaggagtc    4680
agctgtctcc tctgttgcac tctaccacgg aatgggccat cctgcccctgc acctactcag    4740 acttacccgc tttgtcaact ggtcttctcc accttcacca gaacatcgtg gacgtacaat    4800
acatgtatgg cctctcacct gctatcacaa aatacgtcgt tcgatgggag tgggtggtac    4860
tcttattcct gctcttagcg gacgccgagc tctgcgcctg cttgtggatg ctcatcttgt    4920
tgggccaggc cgaagcagca ttggagaagt tggtcgtctt gcacgctgcg agtgcggcta    4980
actgccatgg cctcctatat tttgccatct tcttcgtggg agcttggcac atcagggggtc    5040 gggtggtccc cttgaccacc tattgcctca ctggcctatg gcccttctgc ctactgctca    5100
tggcactgcc ccggcaggct tatgcctatg acgcacctgt gcacgacagg ataggcgtgg    5160
gtttgttgat attgatcacc ctcttcacac tcaccccggg gtataagacc ctcctcggcc    5220
```

```
agtgtctgtg gtggttgtgc tatctcctga ccctggggga agccatgatt caggagtggg    5280
taccacccat gcaggtgcgc ggcggccgcg atggcatcgc gtgggccgtc actatattct    5340
gcccgggtgt ggtgtttgac attaccaaat ggcttttggc gttgcttggg cctgcttacc    5400
tcttaagggc cgctttgaca catgtgccgt acttcgtcag agctcacgct ctgataaggg    5460
tatgcgcttt ggtgaagcag ctcgcggggg gtaggtatgt tcaggtggcg ctattggccc    5520
ttggcaggtg gactggcacc tacatctatg accacctcac acctatgtcg gactgggccg    5580
ctagcggcct cgcgcgactta gcggtcgccg tggaacccat catcttcagt ccgatggaga    5640
agaaggtcat cgtctgggga gcggagacgg ctgcatgtgg ggacattcta catggacttc    5700
ccgtgtccgc ccgactcggc caggagatcc tcctcggccc agctgatggc tacacctcca    5760
aggggtggaa gctccttgct cccatcactg cttatgccca gcaaacacga ggcctcctgg    5820
gcgccatagt ggtgagtatg acggggcgtg acaggacaga acaggccggg gaagtccaaa    5880
tcctgtccac agtctctcag tccttcctcg gaacaaccat ctcgggggtt ttgtggactg    5940
tttaccacgg agctggcaac aagactctag ccggcttacg gggtccggtc acgcagatgt    6000
actcgagtgc tgaggggggac ttggtaggct ggcccagccc cctgggacc aagtctttgg    6060 agccgtgcaa gtgtggagcc gtcgacctat atctggtcac gcggaacgct gatgtcatcc    6120
cggctcggag acgcggggac aagcggggag cattgctctc cccgagaccc atttcgacct    6180
tgaaggggtc ctcgggggggg ccggtgctct gccctagggg ccacgtcgtt gggctcttcc    6240
gagcagctgt tgctctcgg ggcgtggcca aatccatcga tttcatcccc gttgagacac    6300
tcgacgttgt tacaaggtct cccactttca gtgacaacag cacgccaccg ctgtgccccc    6360
agacctatca ggtcgggtac ttgcatgctc caactggcag tggaaagagc accaaggtcc    6420
ctgtcgcgta tgccgcccag gggtacaaag tactagtgct taacccctcg gtagctgcca    6480 ccctgggggtt tggggcgtac ctatccaagg cacatgggcat caatcccaac attaggactg    6540
gagtcaggac cgtgatgacc ggggaggcca tcacgtactc cacatatggc aaatttctcg    6600
ccgatggggg ctgcgctagc ggcgcctatg acatcatcat atgcgatgaa tgccacgctg    6660
tggatgctac ctccattctc ggcatcggaa cggtccttga tcaagcagag acagccgggg    6720
tcagactaac tgtgctggct acggccacac ccccgggtc agtgacaacc ccccatcccg    6780
atatagaaga ggtaggcctc gggcgggagg gtgagatccc cttctatggg agggcgattc    6840
ccctatcctg catcaaggga gggagacacc tgattttctg ccactcaaag aaaaagtgtg    6900
acgagctcgc ggcggcccctt cggggcatgg gcttgaatgc cgtggcatac tatagagggt    6960
tggacgtctc cataataccca gctcagggag atgtggtggt cgtcgccacc gacgccctca    7020
tgacggggta cactggagac tttgactccg tgatcgactg caatgtagcg gtcacccaag    7080
ctgtcgactt cagcctggac cccaccttca ctataaccac acagactgtc ccacaagacg    7140
ctgtctcacg cagtcagcgc cgcgggcgca caggtagagg aagacagggc acttataggt    7200
atgtttccac tggtgaacga gcctcaggaa tgtttgacag tgtagtgctt tgtgagtgct    7260
acgacgcagg ggctgcgtgg tacgatctca caccagcgga gaccaccgtc aggcttagag    7320
cgtatttcaa cacgcccggc ctaccgtgt gtcaagacca tcttgaattt tgggaggcag    7380
ttttcaccgg cctcacacac atagacgccc acttcctctc ccaaacaaag caagcggggg    7440
agaacttcgc gtacctagta gcctaccaag ctacggtgtg cgccagagcc aaggcccctc    7500
ccccgtcctg ggacgccatg tggaagtgcc tggcccgact caagcctacg cttgcgggcc    7560
ccacacctct cctgtaccgt ttgggcccta ttaccaatga ggtcaccctc acacaccctg    7620
```

-continued

```
ggacgaagta catcgccaca tgcatgcaag ctgaccttga ggtcatgacc agcacgtggg    7680
tcctagctgg aggagtcctg gcagccgtcg ccgcatattg cctggcgact ggatgcgttt    7740
ccatcatcgg ccgcttgcac gtcaaccagc gagtcgtcgt tgcgccggat aaggaggtcc    7800
tgtatgaggc ttttgatgag atggaggaat gcgcctctag ggcggctctc atcgaagagg    7860
ggcagcggat agccgagatg ttgaagtcca agatccaagg cttgctgcag caggcctcta    7920
agcaggccca ggacatacaa cccgctatgc aggcttcatg gcccaaagtg gaacaatttt    7980
gggccagaca catgtggaac ttcattagcg gcatccaata cctcgcagga ttgtcaacac    8040
tgccagggaa ccccgcggtg gcttccatga tggcattcag tgccgccctc accagtccgt    8100
tgtcgaccag taccaccatc cttctcaaca tcatgggagg ctggttagcg tcccagatcg    8160
caccacccgc gggggccacc ggcttttgtcg tcagtggcct ggtgggggct gccgtgggca    8220
gcataggcct gggtaaggtg ctggtggaca tcctggcagg atatggtgcg ggcatttcgg    8280
gggccctcgt cgcattcaag atcatgtctg gcgagaagcc ctctatggaa gatgtcatca    8340
atctactgcc tgggatcctg tctccgggag ccctggtggt gggggtcatc tgcgcggcca    8400
ttctgcgccg ccacgtggga ccgggggagg gcgcggtcca atggatgaac aggcttattg    8460
cctttgcttc cagaggaaac cacgtcgccc ctactcacta cgtgacggag tcggatgcgt    8520
cgcagcgtgt gacccaacta cttggctctc ttactataac cagcctactc agaagactcc    8580
acaattggat aactgaggac tgccccatcc catgctccgg atcctggctc cgcgacgtgt    8640
gggactgggt ttgcaccatc ttgacagact tcaaaaattg gctgacctct aaattgttcc    8700
ccaagctgcc cggcctcccc ttcatctctt gtcaaaaggg gtacaagggt gtgtgggccg    8760
gcactggcat catgaccacg cgctgcccct gcggcgccaa catctctggc aatgtccgcc    8820
tgggctctat gaggatcaca gggcctaaaa cctgcatgaa cacctggcag gggaccttc    8880 ctatcaattg ctacacggag ggccagtgcg cgccgaaacc ccccacgaac tacaagaccg    8940
ccatctggag ggtggcggcc tcggagtacg cggaggtgac gcagcatggg tcgtactcct    9000
atgtaacagg actgaccact gacaatctga aaattccttg ccaactacct tctccagagt    9060
ttttctcctg ggtggacggt gtgcagatcc ataggtttgc acccacacca aagccgtttt    9120
tccgggatga ggtctcgttc tgcgttgggc ttaattccta tgctgtcggg tcccagcttc    9180
cctgtgaacc tgagcccgac gcagacgtat tgaggtccat gctaacagat ccgccccaca    9240
tcacggcgga gactgcggcg cggcgcttgg cacggggatc acctccatct gaggcgagct    9300
cctcagtgag ccagctatca gcaccgtcgc tgcgggccac ctgcaccacc cacagcaaca    9360
cctatgacgt ggacatggtc gatgccaacc tgctcatgga gggcggtgtg gctcagacag    9420
agcctgagtc cagggtgccc gttctggact ttctcgagcc aatggccgag gaagagagcg    9480
accttgagcc ctcaatacca tcggagtgca tgctccccag gagcgggttt ccacgggcct    9540
taccggcttg ggcacggcct gactacaacc cgccgctcgt ggaatcgtgg aggaggccag    9600
attaccaacc gcccaccgtt gctggttgtg ctctccccc cccaagaag gccccgacgc    9660 ctcccccaag gagacgccgg acagtgggtc tgagcgagag caccatatca gaagccctcc    9720
agcaactggc catcaagacc tttgccagc ccccctcgag cggtgatgca ggctcgtcca    9780 cggggcggg cgccgccgaa tccggcggtc cgacgtcccc tggtgagccg gccccctcag    9840
agacaggttc cgcctcctct atgccccccc tcgaggggga gcctggagat ccggacctgg    9900
agtctgatca ggtagagctt caacctcccc ccagggggg ggggtagct cccggttcgg    9960 gctcggggtc ttggtctact tgctccgagg aggacgatac caccgtgtgc tgctccatgt    10020
```

```
catactcctg gaccggggct ctaataactc cctgtagccc cgaagaggaa aagttgccaa    10080
tcaacccttt gagtaactcg ctgttgcgat accataacaa ggtgtactgt acaacatcaa    10140
agagcgcctc acagagggct aaaaaggtaa cttttgacag gacgcaagtg ctcgacgccc    10200
attatgactc agtcttaaag gacatcaagc tagcggcttc caaggtcagc gcaaggctcc    10260
tcaccttgga ggaggcgtgc cagttgactc cacccattc tgcaagatcc aagtatggat     10320
tcggggccaa ggaggtccgc agcttgtccg ggagggccgt taaccacatc aagtccgtgt    10380
ggaaggacct cctggaagac ccacaaacac caattcccac aaccatcatg gccaaaaatg    10440
aggtgttctg cgtggacccc gccaagggg gtaagaaacc agctcgcctc atcgtttacc     10500
ctgacctcgg cgtccgggtc tgcgagaaaa tggccctcta tgacattaca caaaagcttc    10560
ctcaggcggt aatgggagct tcctatggct tccagtactc ccctgcccaa cgggtggagt    10620
atctcttgaa agcatgggcg aaaagaagg accccatggg tttttcgtat gatacccgat     10680
gcttcgactc aaccgtcact gagagagaca tcaggaccga ggagtccata taccaggcct    10740
gctccctgcc cgaggaggcc cgcactgcca tacactcgct gactgagaga ctttacgtag    10800
gagggcccat gttcaacagc aagggtcaaa cctgcggtta cagacgttgc cgcgccagcg    10860
gggtgctaac cactagcatg ggtaacacca tcacatgcta tgtgaaagcc ctagcggcct    10920
gcaaggctgc ggggatagtt cgcccacaa tgctggtatg cggcgatgac ctagtagtca     10980
tctcagaaag ccaggggact gaggaggacg agcggaacct gagagccttc acggaggcca    11040
tgaccaggta ctctgccct cctggtgatc ccccagacc ggaatatgac ctggagctaa      11100
taacatcctg ttcctcaaat gtgtctgtgg cgttgggccc gcgggccgc cgcagatact     11160
acctgaccag agacccaacc actccactcg cccgggctgc ctgggaaaca gttagacact    11220
cccctatcaa ttcatggctg ggaaacatca tccagtatgc tccaaccata tgggttcgca    11280
tggtcctaat gacacacttc ttctccattc tcatggtcca agacacctg gaccagaacc      11340
tcaactttga gatgtatgga tcagtatact ccgtgaatcc tttggacctt ccagccataa    11400
ttgagaggtt acacgggctt gacgcctttt ctatgcacac atactctcac cacgaactga    11460
cgcgggtggc ttcagccctc agaaaacttg gggcgccacc cctcagggtg tggaagagtc    11520
gggctcgcgc agtcagggcg tccctcatct cccgtggagg gaaagcggcc gtttgcggcc    11580
gatatctctt caattgggcg gtgaagacca agctcaaact cactccattg ccggaggcgc    11640
gcctactgga cttatccagt tggttcaccg tcggcgccgg cggggcgac atttttcaca     11700
gcgtgtcgcg cgcccgaccc cgctcattac tcttcggcct actcctactt ttcgtagggg    11760
taggcctctt cctactcccc gctcggtaga gcggcacaca ctaggtacac tccatagcta    11820
actgttcctt ttttttttt tttttttt tttttttt tttttttt tcttttttt             11880
ttttttccct ctttcttccc ttctcatctt attctacttt ctttcttggt ggctccatct    11940
tagccctagt cacggctagc tgtgaaaggt ccgtgagccg catgactgca gagagtgccg    12000
taactggtct ctctgcagat catgtctaga gtcgacctgc aggcatgcaa gcttggcact    12060
ggccgtcgtt ttacaacgtc gtgactggga aaaccctggc gttacccaac ttaatcgcct    12120
tgcagcacat ccccctttcg ccagctggcg taatagcgaa gaggcccgca ccgatcgccc    12180
ttcccaacag ttgcgcagcc tgaatggcga atggcgcctg atgcggtatt ttctccttac    12240
gcatctgtgc ggtatttcac accgcatatg gtgcactctc agtacaatct gctctgatgc    12300
cgcatagtta agccagcccc gacacccgcc aacacccgct gacgcgccct gacgggcttg    12360
tctgctcccg gcatccgctt acagacaagc tgtgaccgtc tccgggagct gcatgtgtca    12420
```

```
gaggttttca ccgtcatcac cgaaacgcgc gagacgaaag ggcctcgtga tacgcctatt    12480
tttataggtt aatgtcatga taataatggt ttcttagacg tcaggtggca cttttcgggg    12540
aaatgtgcgc ggaacccta tttgtttatt tttctaaata cattcaaata tgtatccgct     12600
catgagacaa taaccctgat aaatgcttca ataatattga aaaggaaga gtatgagtat     12660
tcaacatttc cgtgtcgccc ttattccctt ttttgcggca ttttgccttc ctgtttttgc    12720
tcacccagaa acgctggtga agtaaaaga tgctgaagat cagttgggtg cacgagtggg     12780
ttacatcgaa ctggatctca acagcggtaa gatccttgag agttttcgcc ccgaagaacg    12840
ttttccaatg atgagcactt ttaaagttct gctatgtggc gcggtattat cccgtattga    12900
cgccgggcaa gagcaactcg gtcgccgcat acactattct cagaatgact tggttgagta    12960
ctcaccagtc acagaaaagc atcttacgga tggcatgaca gtaagagaat tatgcagtgc    13020
tgccataacc atgagtgata acactgcggc caacttactt ctgacaacga tcggaggacc    13080
gaaggagcta accgcttttt tgcacaacat gggggatcat gtaactcgcc ttgatcgttg    13140
ggaaccggag ctgaatgaag ccataccaaa cgacgagcgt gacaccacga tgcctgtagc    13200
aatggcaaca acgttgcgca aactattaac tggcgaacta cttactctag cttcccggca    13260
acaattaata gactggatgg aggcggataa agttgcagga ccacttctgc gctcggccct    13320
tccggctggc tggtttattg ctgataaatc tggagccggt gagcgtgggt ctcgcggtat    13380
cattgcagca ctggggccag atggtaagcc ctcccgtatc gtagttatct acacgacggg    13440
gagtcaggca actatggatg aacgaaatag acagatcgct gagataggtg cctcactgat    13500
taagcattgg taactgtcag accaagttta ctcatatata ctttagattg atttaaaact    13560
tcatttttaa tttaaaagga tctaggtgaa gatcctttt gataatctca tgaccaaaat     13620
cccttaacgt gagttttcgt tccactgagc gtcagacccc gtagaaaaga tcaaaggatc    13680
ttcttgagat ccttttttc tgcgcgtaat ctgctgcttg caaacaaaaa aaccaccgct      13740
accagcggtg gtttgtttgc cggatcaaga gctaccaact cttttccga aggtaactgg     13800
cttcagcaga gcgcagatac caaatactgt ccttctagtg tagccgtagt taggccacca    13860
cttcaagaac tctgtagcac cgcctacata cctcgctctg ctaatcctgt taccagtggc    13920
tgctgccagt ggcgataagt cgtgtcttac cgggttggac tcaagacgat agttaccgga    13980
taaggcgcag cggtcgggct gaacggggg ttcgtgcaca cagcccagct tggagcgaac     14040
gacctacacc gaactgagat acctacagcg tgagctatga gaaagcgcca cgcttcccga    14100
agggagaaag gcggacaggt atccggtaag cggcagggtc ggaacaggag agcgcacgag    14160
ggagcttcca gggggaaacg cctggtatct ttatagtcct gtcgggtttc gccacctctg    14220
acttgagcgt cgatttttgt gatgctcgtc aggggggcgg agcctatgga aaaacgccag    14280
caacgcggcc ttttacggt tcctggcctt ttgctggcct tttgctcaca tgttctttcc      14340
tgcgttatcc cctgattctg tggataaccg tattaccgcc tttgagtgag ctgataccgc    14400
tcgccgcagc cgaacgaccg agcgcagcga gtcagtgagc gaggaagcgg aagagcgccc    14460
aatacgcaaa ccgcctctcc ccgcgcgttg gccgattcat taatgcagct ggcacgacag    14520
gtttcccgac tggaaagcgg gcagtgagcg caacgcaatt aatgtgagtt agctcactca    14580
ttaggcaccc caggctttac actttatgct tccggctcgt atgttgtgtg gaattgtgag    14640
cggataacaa tttcacacag gaaacagcta tgaccatgat tac                      14683
```

<210> SEQ ID NO 3
<211> LENGTH: 14671

<212> TYPE: DNA
<213> ORGANISM: Artificial Sequence
<220> FEATURE:
<223> OTHER INFORMATION: Synthetic plasmid: pLucHJ1

<400> SEQUENCE: 3

```
gaattcccaa acgcgttaat acgactcact atagacctgc ccctaatagg ggcgacactc      60
cgccatgaat cactcccctg tgaggaacta ctgtcttcac gcagaaagcg cctagccatg     120
gcgttagtat gagtgtcgta cagcctccag gccccccct cccgggagag ccatagtggt      180
ctgcggaacc ggtgagtaca ccggaattgc cgggaagact gggtcctttc ttggataaac     240
ccactctatg cccggccatt tgggcgtgcc cccgcaagac tgctagccga gtagcgttgg     300
gttgcgaaag gccttgtggt actgcctgat agggcgcttg cgagtgcccc gggaggtctc     360
gtagaccgtg caccatgagc acaaatccta aacctcaaag aaaaaccaaa agaaacacca     420
accgtgaaga cgccaaaaac ataaagaaag gcccggcgcc attctatccc ctagaggatg     480
gaaccgctgg agagcaactg cataaggcta tgaagagata cgccctggtt cctggaacaa     540
ttgcttttac agatgcacat atcgaggtga acatcacgta cgcggaatac ttcgaaatgt     600
ccgttcggtt ggcagaagct atgaaacgat atgggctgaa tacaaatcac agaatcgtcg     660
tatgcagtga aaactctctt caattcttta tgccggtgtt gggcgcgtta tttatcggag     720
ttgcagttgc gcccgcgaac gacatttata tgaacgtga attgctcaac agtatgaaca      780
tttcgcagcc taccgtagtg tttgttccca aaaggggtt gcaaaaaatt ttgaacgtgc      840
aaaaaaatt accaataatc cagaaaatta ttatcatgga ttctaaaacg gattaccagg      900
gatttcagtc gatgtacacg ttcgtcacat ctcatctacc tcccggtttt aatgaatacg      960
attttgtacc agagtccttt gatcgtgaca aaacaattgc actgataatg aattcctctg    1020
gatctactgg gttacctaag ggtgtggccc ttccgcatag aactgcctgc gtcagattct    1080
cgcatgccag agatcctatt tttggcaatc aaatcattcc ggatactgcg attttaagtg    1140
ttgttccatt ccatcacggt tttggaatgt ttactacact cggatatttg atatgtggat    1200
ttcgagtcgt cttaatgtat agatttgaag aagagctgtt tttacgatcc cttcaggatt    1260
acaaaattca agtgcgttg ctagtaccaa ccctattttc attcttcgcc aaaagcactc     1320
tgattgacaa atacgattta tctaatttac acgaaattgc ttctggggc gcacctcttt     1380
cgaaagaagt cggggaagcg gttgcaaaac gcttccatct tccagggata cgacaaggat    1440
atgggctcac tgagactaca tcagctattc tgattacacc cgaggggat gataaaccgg     1500
gcgcggtcgg taaagttgtt ccatttttg aagcgaaggt tgtggatctg gataccggga     1560
aaacgctggg cgttaatcag agaggcgaat tatgtgtcag aggacctatg attatgtccg    1620
gttatgtaaa caatccggaa gcgaccaacg ccttgattga caaggatgga tggctacatt    1680
ctggagacat agcttactgg gacgaagacg aacacttctt catagttgac cgcttgaagt    1740
ctttaattaa atacaaagga tatcaggtgg cccccgctga attggaatcg atattgttac    1800
aacaccccaa catcttcgac gcgggcgtgg caggtcttcc cgacgatgac gccggtgaac    1860
ttcccgccgc cgttgttgtt ttggagcacg gaaagacgat gacggaaaaa gagatcgtgg    1920
attacgtcgc cagtcaagta acaaccgcga aaaagttgcg cggaggagtt gtgtttgtgg    1980
acgaagtacc gaaaggtctt accggaaaac tcgacgcaag aaaaatcaga gagatcctca    2040
taaaggccaa gaagggcgga aagtccaaat tgtgagttgt taaacagacc acaacggttt    2100
ccctctagcg ggatcaattc cgccccccc cctaacgtt actggccgaa gccgcttgga     2160
ataaggccgg tgtgcgtttg tctatatgtt attttccacc atattgccgt cttttggcaa    2220
```

```
tgtgagggcc cggaaacctg gccctgtctt cttgacgagc attcctaggg gtctttcccc   2280
tctcgccaaa ggaatgcaag gtctgttgaa tgtcgtgaag gaagcagttc ctctggaagc   2340
ttcttgaaga caaacaacgt ctgtagcgac cctttgcagg cagcggaacc ccccaccctgg  2400 cgacaggtgc ctctgcggcc aaaagccacg tgtataagat acacctgcaa aggcggcaca   2460
accccagtgc cacgttgtga gttggatagt tgtggaaaga gtcaaatggc tctcctcaag   2520
cgtattcaac aaggggctga aggatgccca gaaggtaccc cattgtatgg gatctgatct   2580
ggggcctcgg tgcacatgct ttacatgtgt ttagtcgagg ttaaaaaaac gtctaggccc   2640
cccgaaccac ggggacgtgg ttttcctttg aaaaacacga taataccatg agcacgaatc   2700
ctaaacctca agaaaaaacc aaacgtaaca ccaaccgtcg cccacaggac gtcaagttcc   2760
cgggtggcgg tcagatcgtt ggtggagttt acttgttgcc gcgcagggc cctagattgg     2820 gtgtgcgcgc gacgaggaag acttccgagc ggtcgcaacc tcgaggtaga cgtcagccta   2880
tccccaaggc acgtcggccc gagggcagga cctgggctca gcccgggtac ccttggcccc   2940
tctatggcaa tgagggttgc gggtgggcgg gatggctcct gtctccccgt ggctctcggc   3000
ctagctgggg ccccacagac ccccggcgta ggtcgcgcaa tttgggtaag gtcatcgata   3060
cccttacgtg cggcttcgcc gacctcatgg ggtacatacc gctcgtcggc gcccctcttg   3120
gaggcgctgc cagggccctg gcgcatggcg tccgggttct ggaagacggc gtgaactatg   3180
caacagggaa ccttcctggt tgctcttcct ctatcttcct tctggccctg ctctcttgcc   3240
tgactgtgcc cgcttcagcc taccaagtgc gcaattcctc ggggctttac catgtcacca   3300
atgattgccc taactcgagt attgtgtacg aggcggccga tgccatcctg cacactccgg   3360
ggtgtgtccc ttgcgttcgc gagggtaacg cctcgaggtg ttgggtggcg gtgaccccca   3420
cggtggccac cagggacggc aaactcccca caacgcagct tcgacgtcat atcgatctgc   3480
ttgtcgggag cgccaccctc tgctcggccc tctacgtggg ggacctgtgc gggtctgtct   3540
ttcttgttgg tcaactgttt accttctctc ccaggcgcca ctggacgacg caagactgca   3600
attgttctat ctatcccggc catataacgg gtcatcgcat ggcatgggat atgatgatga   3660
actggtcccc tacggcagcg ttggtggtag ctcagctgct ccggatccca caagccatca   3720
tggacatgat cgctggtgct cactgggggag tcctggcggg catagcgtat ttctccatgg   3780
tggggaactg ggcgaaggtc ctggtagtgc tgctgctatt tgccggcgtc gacgcggaaa   3840
cccacgtcac cggggggaagt gccggccgca ccacggctgg gcttgttggt ctccttacac   3900
caggcgccaa gcagaacatc caactgatca acaccaacgg cagttggcac atcaatagca   3960
cggccttgaa ctgcaatgaa agccttaaca ccggctggtt agcagggctc ttctatcagc   4020
acaaattcaa ctcttcaggc tgtcctgaga ggttggccag ctgccgacgc cttaccgatt   4080
ttgcccaggg ctggggtcct atcagttatg ccaacggaag cggcctcgac gaacgcccct   4140
actgctggca ctaccctcca agaccttgtg gcattgtgcc cgcaaagagc gtgtgtggcc   4200
cggtatattg cttcactccc agcccgtgg tggtgggaac gaccgacagg tcggcgcgc     4260 ctacctacag ctggggtgca aatgatacgg atgtcttcgt ccttaacaac accaggccac   4320
cgctgggcaa ttggttcggt tgtacctgga tgaactcaac tggattcacc aaagtgtgcg   4380
gagcgccccc ttgtgtcatc ggaggggtgg gcaacaacac cttgctctgc cccactgatt   4440
gtttccgcaa gcatccggaa gccacatact ctcggtgcgg ctccggtccc tggattacac   4500
ccaggtgcat ggtcgactac ccgtataggc tttggcacta tccttgtacc atcaattaca   4560
ccatattcaa agtcaggatg tacgtgggag gggtcgagca caggctggaa gcggcctgca   4620
```

```
actggacgcg gggcgaacgc tgtgatctgg aagacaggga caggtccgag ctcagcccat    4680
tgctgctgtc caccacacag tggcaggtcc ttccgtgttc tttcacgacc ctgccagcct    4740
tgtccaccgg cctcatccac ctccaccaga acattgtgga cgtgcagtac ttgtacgggg    4800
tagggtcaag catcgcgtcc tgggccatta agtgggagta cgtcgttctc ctgttcctcc    4860
tgcttgcaga cgcgcgcgtc tgctcctgct tgtggatgat gttactcata tcccaagcgg    4920
aggcggcttt ggagaacctc gtaatactca atgcagcatc cctggccggg acgcacggtc    4980
ttgtgtcctt cctcgtgttc ttctgctttg cgtggtatct gaagggtagg tgggtgcccg    5040
gagcggtcta cgccttctac gggatgtggc ctctcctcct gctcctgctg gcgttgcctc    5100
agcgggcata cgcactggac acggaggtgg ccgcgtcgtg tggcggcgtt gttcttgtcg    5160
ggttaatggc gctgactctg tcgccatatt acaagcgcta catcagctgg tgcatgtggt    5220
ggcttcagta ttttctgacc agagtagaag cgcaactgca cgtgtgggtt ccccccctca    5280
acgtccgggg ggggcgcgat ggcatcgcgt gggccgtcac tatattctgc ccgggtgtgg    5340
tgtttgacat taccaaatgg cttttggcgt tgcttgggcc tgcttacctc ttaagggccg    5400 cttttgacaca tgtgccgtac ttcgtcagag ctcacgctct gataagggta tgcgctttgg    5460
tgaagcagct cgcggggggt aggtatgttc aggtggcgct attggcccct ggcaggtgga    5520
ctggcaccta catctatgac cacctcacac ctatgtcgga ctgggccgct agcggcctgc    5580
gcgacttagc ggtcgccgtg aacccatca tcttcagtcc gatggagaag aaggtcatcg    5640
tctggggagc ggagacggct gcatgtgggg acattctaca tggacttccc gtgtccgccc    5700
gactcggcca ggagatcctc ctcggcccag ctgatggcta cacctccaag gggtggaagc    5760
tccttgctcc catcactgct tatgcccagc aaacacgagg cctcctgggc gccatagtgg    5820
tgagtatgac ggggcgtgac aggacagaac aggccgggga agtccaaatc ctgtccacag    5880
tctctcagtc cttcctcgga acaaccatct cggggttttt gtggactgtt taccacggag    5940
ctggcaacaa gactctagcc ggcttacggg gtccggtcac gcagatgtac tcgagtgctg    6000 aggggggactt ggtaggctgg cccagccccc ctgggaccaa gtctttggag ccgtgcaagt    6060
gtggagccgt cgacctatat ctggtcacgc ggaacgctga tgtcatcccg gctcggagac    6120
gcggggacaa gcggggagca ttgctctccc cgagacccat ttcgaccttg aaggggtcct    6180 cggggggggcc ggtgctctgc cctaggggcc acgtcgttgg gctcttccga gcagctgtgt    6240
gctctcgggg cgtggccaaa tccatcgatt tcatccccgt tgagacactc gacgttgtta    6300
caaggtctcc cactttcagt gacaacagca cgccaccggc tgtgccccag acctatcagg    6360
tcgggtactt gcatgctcca actggcagtg gaaagagcac caaggtccct gtcgcgtatg    6420
ccgcccaggg gtacaaagta ctagtgctta accctcggt agctgccacc ctggggtttg    6480
gggcgtacct atccaaggca catggcatca atcccaacat taggactgga gtcaggaccg    6540
tgatgaccgg ggaggccatc acgtactcca catatggcaa atttctcgcc gatgggggct    6600
gcgctagcgg cgcctatgac atcatcatat gcgatgaatg ccacgctgtg gatgctacct    6660
ccattctcgg catcggaacg gtccttgatc aagcagagac agccggggtc agactaactg    6720
tgctggctac ggccacaccc cccgggtcag tgacaacccc ccatcccgat atagaagagg    6780
taggcctcgg cgggagggt gagatccct tctatgggag ggcgattccc ctatcctgca    6840 tcaaggagg gagacacctg attttctgcc actcaaagaa aaagtgtgac gagctcgcgg    6900
cggcccttcg gggcatgggc ttgaatgccg tggcatacta tagagggttg gacgtctcca    6960
taataccagc tcagggagat gtggtggtcg tcgccaccga cgccctcatg acggggtaca    7020
```

```
ctggagactt tgactccgtg atcgactgca atgtagcggt cacccaagct gtcgacttca   7080
gcctggaccc caccttcact ataaccacac agactgtccc acaagacgct gtctcacgca   7140
gtcagcgccg cgggcgcaca ggtagaggaa gacagggcac ttataggtat gtttccactg   7200
gtgaacgagc ctcaggaatg tttgacagtg tagtgctttg tgagtgctac gacgcagggg   7260
ctgcgtggta cgatctcaca ccagcggaga ccaccgtcag gcttagagcg tatttcaaca   7320
cgcccggcct acccgtgtgt caagaccatc ttgaattttg ggaggcagtt ttcaccggcc   7380
tcacacacat agacgcccac ttcctctccc aaacaaagca agcggggag aacttcgcgt    7440 acctagtagc ctaccaagct acggtgtgcg ccagagccaa ggcccctccc ccgtcctggg   7500
acgccatgtg gaagtgcctg gcccgactca agcctacgct gcgggcccc acacctctcc    7560 tgtaccgttt gggccctatt accaatgagg tcaccctcac acaccctggg acgaagtaca   7620
tcgccacatg catgcaagct gaccttgagg tcatgaccag cacgtgggtc ctagctggag   7680
gagtcctggc agccgtcgcc gcatattgcc tggcgactgg atgcgtttcc atcatcggcc   7740
gcttgcacgt caaccagcga gtcgtcgttg cgccggataa ggaggtcctg tatgaggctt   7800
ttgatgagat ggaggaatgc gcctctaggg cggctctcat cgaagagggg cagcggatag   7860
ccgagatgtt gaagtccaag atccaaggct tgctgcagca ggcctctaag caggcccagg   7920
acatacaacc cgctatgcag gcttcatggc ccaaagtgga acaattttgg gccagacaca   7980
tgtggaactt cattagcggc atccatacc tcgcaggatt gtcaacactg ccagggaacc     8040
ccgcggtggc ttcatgatg gcattcagtg ccgccctcac cagtccgttg tcgaccagta     8100
ccaccatcct tctcaacatc atgggaggct ggttagcgtc ccagatcgca ccacccgcgg   8160
gggccaccgg ctttgtcgtc agtggcctgg tgggggctgc cgtgggcagc ataggcctgg   8220
gtaaggtgct ggtggacatc ctggcaggat atggtgcggg catttcgggg gccctcgtcg   8280
cattcaagat catgtctggc gagaagccct ctatggaaga tgtcatcaat ctactgcctg   8340
ggatcctgtc tccgggagcc ctggtggtgg gggtcatctg cgcggccatt ctgcgccgcc   8400
acgtgggacc gggggagggc gcggtccaat ggatgaacag gcttattgcc tttgcttcca   8460
gaggaaacca cgtcgcccct actcactacg tgacggagtc ggatgcgtcg cagcgtgtga   8520
cccaactact tggctctctt actataacca gcctactcag aagactccac aattggataa   8580
ctgaggactg ccccatccca tgctccggat cctggctccg cgacgtgtgg gactgggttt   8640
gcaccatctt gacagacttc aaaaattggc tgacctctaa attgttcccc aagctgcccg   8700
gcctccccgt catctcttgt caaaaggggt acaagggtgt gtgggccggc actggcatca   8760
tgaccacgcg ctgcccttgc ggcgccaaca tctctggcaa tgtccgcctg ggctctatga   8820
ggatcacagg gcctaaaacc tgcatgaaca cctggcaggg gacctttcct atcaattgct   8880
acacggaggg ccagtgcgcg ccgaaacccc ccacgaacta caagaccgcc atctggaggg   8940
tggcggcctc ggagtacgcg gaggtgacgc agcatgggtc gtactcctat gtaacaggac   9000
tgaccactga caatctgaaa attccttgcc aactaccttc tccagagttt ttctcctggg   9060
tggacggtgt gcagatccat aggtttgcac ccacaccaaa gccgttttc cgggatgagg    9120 tctcgttctg cgttgggctt aattcctatg ctgtcgggtc ccagcttccc tgtgaacctg   9180
agcccgacgc agacgtattg aggtccatgc taacagatcc gccccacatc acggcggaga   9240
ctgcggcgcg gcgcttggca cggggatcac ctccatctga ggcgagctcc tcagtgagcc   9300
agctatcagc accgtcgctg cgggccacct gcaccaccca cagcaacacc tatgacgtgg   9360
acatggtcga tgccaacctg ctcatggagg gcggtgtggc tcagacagag cctgagtcca   9420
```

```
gggtgcccgt tctggacttt ctcgagccaa tggccgagga agagagcgac cttgagccct   9480
caataccatc ggagtgcatg ctccccagga gcgggtttcc acgggcctta ccggcttggg   9540
cacggcctga ctacaacccg ccgctcgtgg aatcgtggag gaggccagat taccaaccgc   9600
ccaccgttgc tggttgtgct ctccccccc ccaagaaggc cccgacgcct cccccaagga    9660
gacgccggac agtgggtctg agcgagagca ccatatcaga agccctccag caactggcca   9720
tcaagacctt tggccagccc ccctcgagcg gtgatgcagg ctcgtccacg ggggcgggcg   9780
ccgccgaatc cggcggtccg acgtcccctg tgagccggc ccctcagag acaggttccg     9840
cctcctctat gccccccctc gagggggagc ctggagatcc ggacctggag tctgatcagg   9900
tagagcttca acctcccccc caggggggg gggtagctcc cggttcgggc tcggggtctt    9960
ggtctacttg ctccgaggag gacgatacca ccgtgtgctg ctccatgtca tactcctgga  10020
ccggggctct aataactccc tgtagccccg aagaggaaaa gttgccaatc aacccttga   10080
gtaactcgct gttgcgatac cataacaagg tgtactgtac aacatcaaag agcgcctcac  10140
agagggctaa aaaggtaact tttgacagga cgcaagtgct cgacgcccat tatgactcag  10200
tcttaaagga catcaagcta gcggcttcca aggtcagcgc aaggctcctc accttggagg  10260
aggcgtgcca gttgactcca ccccattctg caagatccaa gtatggattc ggggccaagg  10320
aggtccgcag cttgtccggg agggccgtta accacatcaa gtccgtgtgg aaggacctcc  10380
tggaagaccc acaaacacca attcccacaa ccatcatggc caaaaatgag gtgttctgcg  10440
tggaccccgc caagggggt aagaaaccag ctcgcctcat cgtttaccct gacctcggcg   10500
tccgggtctg cgagaaaatg gccctctatg acattacaca aaagcttcct caggcggtaa  10560
tgggagcttc ctatggcttc cagtactccc ctgcccaacg ggtggagtat ctcttgaaag  10620
catgggcgga aaagaaggac cccatgggtt tttcgtatga tacccgatgc ttcgactcaa  10680
ccgtcactga gagagacatc aggaccgagg agtccatata ccaggcctgc tccctgcccg  10740
aggaggcccg cactgccata cactcgctga ctgagagact ttacgtagga gggcccatgt  10800
tcaacagcaa gggtcaaacc tgcggttaca gacgttgccg cgccagcggg gtgctaacca  10860
ctagcatggg taacaccatc acatgctatg tgaaagccct agcggcctgc aaggctgcgg  10920
ggatagttgc gcccacaatg ctggtatgcg gcgatgacct agtagtcatc tcagaaagcc  10980
agggggactga ggaggacgag cggaacctga gagccttcac ggaggccatg accaggtact  11040
ctgcccctcc tggtgatccc cccagaccgg aatatgacct ggagctaata acatcctgtt  11100
cctcaaatgt gtctgtggcg ttgggcccgc ggggccgccg cagatactac ctgaccagag  11160
acccaaccac tccactcgcc cgggctgcct gggaaacagt tagacactcc cctatcaatt  11220
catggctggg aaacatcatc cagtatgctc caaccatatg ggttcgcatg gtcctaatga  11280
cacacttctt ctccattctc atggtccaag acaccctgga ccagaacctc aactttgaga  11340
tgtatggatc agtatactcc gtgaatcctt tggaccttcc agccataatt gagaggttac  11400
acggcttga cgccttttct atgcacacat actctcacca cgaactgacg cgggtggctt    11460
cagccctcag aaaacttggg gcgccacccc tcagggtgtg aagagtcgg gctcgcgcag    11520
tcagggcgtc cctcatctcc cgtggaggga agcggccgt ttgcggccga tatctcttca    11580
attgggcggt gaagaccaag ctcaaactca ctccattgcc ggaggcgcgc ctactggact   11640
tatccagttg gttcaccgtc ggcgccggcg ggggcgacat ttttcacagc gtgtcgcgcg   11700
cccgaccccg ctcattactc ttcggcctac tcctactttt cgtaggggta ggcctcttcc   11760
tactccccgc tcggtagagc ggcacacact aggtacactc catagctaac tgttcctttt   11820
```

```
tttttttttt tttttttttt tttttttttt ttttttttttc ttttttttttt ttttccctct  11880
ttcttccctt ctcatcttat tctactttct ttcttggtgg ctccatctta gccctagtca  11940
cggctagctg tgaaaggtcc gtgagccgca tgactgcaga gagtgccgta actggtctct  12000
ctgcagatca tgtctagagt cgacctgcag gcatgcaagc ttggcactgg ccgtcgtttt  12060
acaacgtcgt gactgggaaa accctggcgt tacccaactt aatcgccttg cagcacatcc  12120
ccctttcgcc agctggcgta atagcgaaga ggcccgcacc gatcgccctt cccaacagtt  12180
gcgcagcctg aatggcgaat ggcgcctgat gcggtatttt ctccttacgc atctgtgcgg  12240
tatttcacac cgcatatggt gcactctcag tacaatctgc tctgatgccg catagttaag  12300
ccagccccga cacccgccaa cacccgctga cgcgccctga cgggcttgtc tgctcccggc  12360
atccgcttac agacaagctg tgaccgtctc cgggagctgc atgtgtcaga ggttttcacc  12420
gtcatcaccg aaacgcgcga gacgaaaggg cctcgtgata cgcctatttt tataggttaa  12480
tgtcatgata ataatggttt cttagacgtc aggtggcact tttcggggaa atgtgcgcgg  12540
aaccccTatt tgtttatttt tctaaataca ttcaaatatg tatccgctca tgagacaata  12600
accctgataa atgcttcaat aatattgaaa aggaagagt atgagtattc aacatttccg  12660
tgtcgccctt attccctttt ttgcggcatt ttgccttcct gtttttgctc acccagaaac  12720
gctggtgaaa gtaaaagatg ctgaagatca gttgggtgca cgagtgggtt acatcgaact  12780
ggatctcaac agcggtaaga tccttgagag ttttcgcccc gaagaacgtt ttccaatgat  12840
gagcactttt aaagttctgc tatgtggcgc ggtattatcc cgtattgacg ccgggcaaga  12900
gcaactcggt cgccgcatac actattctca gaatgacttg gttgagtact caccagtcac  12960
agaaaagcat cttacggatg gcatgacagt aagagaatta tgcagtgctg ccataaccat  13020
gagtgataac actgcggcca acttacttct gacaacgatc ggaggaccga aggagctaac  13080
cgcttttttg cacaacatgg gggatcatgt aactcgcctt gatcgttggg aaccggagct  13140
gaatgaagcc ataccaaacg acgagcgtga caccacgatg cctgtagcaa tggcaacaac  13200
gttgcgcaaa ctattaactg gcgaactact tactctagct tcccggcaac aattaataga  13260
ctggatggag gcggataaag ttgcaggacc acttctgcgc tcggcccttc cggctggctg  13320
gtttattgct gataaatctg gagccggtga gcgtgggtct cgcggtatca ttgcagcact  13380
ggggccagat ggtaagccct cccgtatcgt agttatctac acgacgggga gtcaggcaac  13440
tatggatgaa cgaaatagac agatcgctga gataggtgcc tcactgatta agcattggta  13500
actgtcagac caagtttact catatatact ttagattgat ttaaaacttc attttTaatt  13560
taaaaggatc taggtgaaga tcctttttga atctcatg accaaaatcc cttaacgtga  13620
gttttcgttc cactgagcgt cagaccccgt agaaaagatc aaaggatctt cttgagatcc  13680
ttttttctg cgcgtaatct gctgcttgca acaaaaaaa ccaccgctac cagcggtggt  13740
ttgtttgccg gatcaagagc taccaactct ttttccgaag gtaactggct tcagcagagc  13800
gcagatacca atactgtcc ttctagtgta gccgtagtta ggccaccact tcaagaactc  13860
tgtagcaccg cctacatacc tcgctctgct aatcctgtta ccagtggctg ctgccagtgg  13920
cgataagtcg tgtcttaccg ggttggactc aagacgatag ttaccggata aggcgcagcg  13980
gtcgggctga acggggggtt cgtgcacaca gcccagcttg gagcgaacga cctacaccga  14040
actgagatac ctacagcgtg agctatgaga aagcgccacg cttcccgaag ggagaaaggc  14100
ggacaggtat ccggtaagcg gcagggtcgg aacaggagag cgcacgaggg agcttccagg  14160
gggaaacgcc tggtatcttt atagtcctgt cgggtttcgc cacctctgac ttgagcgtcg  14220
```

```
attttttgtga tgctcgtcag gggggcggag cctatggaaa aacgccagca acgcggcctt    14280
tttacggttc ctggccttt gctggccttt tgctcacatg ttctttcctg cgttatcccc    14340
tgattctgtg gataaccgta ttaccgcctt tgagtgagct gataccgctc gccgcagccg    14400
aacgaccgag cgcagcgagt cagtgagcga ggaagcggaa gagcgcccaa tacgcaaacc    14460
gcctctcccc gcgcgttggc cgattcatta atgcagctgg cacgacaggt ttcccgactg    14520
gaaagcgggc agtgagcgca acgcaattaa tgtgagttag ctcactcatt aggcacccca    14580
ggctttacac tttatgcttc cggctcgtat gttgtgtgga attgtgagcg ataacaatt     14640 tcacacagga aacagctatg accatgatta c                                   14671

<210> SEQ ID NO 4
<211> LENGTH: 14671
<212> TYPE: DNA
<213> ORGANISM: Artificial Sequence
<220> FEATURE:
<223> OTHER INFORMATION: Synthetic plasmid: pLucCJ1

<400> SEQUENCE: 4
gaattcccaa acgcgttaat acgactcact atagacctgc ccctaatagg ggcgacactc      60
cgccatgaat cactcccctg tgaggaacta ctgtcttcac gcagaaagcg cctagccatg    120
gcgttagtat gagtgtcgta cagcctccag gccccccct cccgggagag ccatagtggt    180
ctgcggaacc ggtgagtaca ccggaattgc cgggaagact gggtcctttc ttggataaac    240
ccactctatg cccggccatt gggcgtgcc cccgcaagac tgctagccga gtagcgttgg    300
gttgcgaaag gccttgtggt actgcctgat agggcgcttg cgagtgcccc gggaggtctc    360
gtagaccgtg caccatgagc acaaatccta aacctcaaag aaaaaccaaa agaaacacca    420
accgtgaaga cgccaaaaac ataagaaag gcccggcgcc attctatccc ctagaggatg    480
gaaccgctgg agagcaactg cataaggcta tgaagagata cgccctggtt cctggaacaa    540
ttgcttttac agatgcacat atcgaggtga acatcacgta cgcggaatac ttcgaaatgt    600
ccgttcggtt ggcagaagct atgaaacgat atgggctgaa tacaaatcac agaatcgtcg    660
tatgcagtga aaactctctt caattcttta tgccggtgtt gggcgcgtta tttatcggag    720
ttgcagttgc gcccgcgaac gacatttata atgaacgtga attgctcaac agtatgaaca    780
tttcgcagcc taccgtagtg tttgttccca aaaaggggt gcaaaaaatt ttgaacgtgc    840
aaaaaaaatt accaataatc cagaaaatta ttatcatgga ttctaaaacg gattaccagg    900
gatttcagtc gatgtacacg ttcgtcacat ctcatctacc tcccggtttt aatgaatacg    960
attttgtacc agagtccttt gatcgtgaca aaacaattgc actgataatg aattcctctg    1020
gatctactgg gttacctaag ggtgtggccc ttccgcatag aactgcctgc gtcagattct    1080
cgcatgccag agatcctatt tttggcaatc aaatcattcc ggatactgcg attttaagtg    1140
ttgttccatt ccatcacggt tttggaatgt ttactacact cggatatttg atatgtggat    1200
ttcgagtcgt cttaatgtat agatttgaag aagagctgtt tttacgatcc cttcaggatt    1260
acaaaattca aagtgcgttg ctagtaccaa cctatttc attcttcgcc aaaagcactc    1320
tgattgacaa atacgattta tctaatttac acgaaattgc ttctggggc gcacctcttt    1380 cgaaagaagt cggggaagcg gttgcaaaac gcttccatct tccagggata cgacaaggat    1440
atgggctcac tgagactaca tcagctattc tgattacacc cgagggggat gataaaccgg    1500
gcgcggtcgg taaagttgtt ccattttttg aagcgaaggt tgtggatctg gataccggga    1560
aaacgctggg cgttaatcag agaggcgaat tatgtgtcag aggacctatg attatgtccg    1620
```

```
gttatgtaaa caatccggaa gcgaccaacg ccttgattga caaggatgga tggctacatt    1680
ctggagacat agcttactgg gacgaagacg aacacttctt catagttgac cgcttgaagt    1740
ctttaattaa atacaaagga tatcaggtgg cccccgctga attggaatcg atattgttac    1800
aacaccccaa catcttcgac gcgggcgtgg caggtcttcc cgacgatgac gccggtgaac    1860
ttcccgccgc cgttgttgtt ttggagcacg gaaagacgat gacggaaaaa gagatcgtgg    1920
attacgtcgc cagtcaagta acaaccgcga aaaagttgcg cggaggagtt gtgtttgtgg    1980
acgaagtacc gaaaggtctt accggaaaac tcgacgcaag aaaaatcaga gagatcctca    2040
taaaggccaa gaagggcgga aagtccaaat tgtgagttgt taaacagacc acaacggttt    2100
ccctctagcg ggatcaattc cgccccccc cctaacgtt actggccgaa gccgcttgga     2160
ataaggccgg tgtgcgtttg tctatatgtt attttccacc atattgccgt cttttggcaa    2220
tgtgagggcc cggaaacctg gccctgtctt cttgacgagc attcctaggg gtcttttcccc   2280 tctcgccaaa ggaatgcaag gtctgttgaa tgtcgtgaag gaagcagttc ctctggaagc    2340
ttcttgaaga caaacaacgt ctgtagcgac cctttgcagg cagcggaacc ccccacctgg    2400
cgacaggtgc ctctgcggcc aaaagccacg tgtataagat acacctgcaa aggcggcaca    2460
accccagtgc cacgttgtga gttggatagt tgtggaaaga gtcaaatggc tctcctcaag    2520
cgtattcaac aaggggctga aggatgccca gaaggtaccc cattgtatgg gatctgatct    2580
ggggcctcgg tgcacatgct ttacatgtgt ttagtcgagg ttaaaaaaac gtctaggccc    2640
cccgaaccac ggggacgtgg ttttcctttg aaaaacacga taataccatg agcacgaatc    2700
ctaaacctca agaaaaaacc aaacgtaaca ccaaccgccg cccacaggac gtcaagttcc    2760
cgggcggtgg tcagatcgtc ggtggagttt acctgttgcc gcgcagggc cccaggttgg     2820 gtgtgcgcgc gactaggaag acttccgagc ggtcgcaacc tcgtggaagg cgacaaccta    2880
tccccaaggc tcgccagccc gagggtaggg cctgggctca gcccgggtac ccctggcccc    2940
tctatggcaa tgagggcttg gggtgggcag gatggctcct gtcaccccgt ggctctcggc    3000
ctagttgggg cccacggac ccccggcgta ggtcgcgcaa tttgggtaag gtcatcgata    3060
ccctcacgtg cggcttcgcc gatctcatgg ggtacattcc gctcgtcggc gccccctag    3120 ggggcgctgc cagggccctg gcgcatggcg tccgggttct ggaggacggc gtgaactatg    3180
caacagggaa tctgcccggt tgctcctttt ctatcttcct tttggctttg ctgtcctgtt    3240
tgaccatccc agcttccgct tatgaagtgc gcaacgtatc cggagtgtac catgtcacga    3300
acgactgctc caacgcaagc attgtgtatg aggcagcgga catgatcatg cataccccg    3360 ggtgcgtgcc ctgcgttcgg gagaacaact cctcccgctg ctgggtagcg ctcactccca    3420
cgctcgcggc caggaacgct agcgtcccca ctacgacgat acgacgccat gtcgatttgc    3480 tcgttgggc ggctgctctc tgctccgcta tgtacgtggg agatctctgc ggatctgttt    3540
tcctcgtcgc ccagctgttc accttctcgc ctcgccggca cgagacagta caggactgca    3600
attgctcaat atatcccggc cacgtgacag gtcaccgtat ggcttgggat atgatgatga    3660
actggtcacc tacagcagcc ctagtggtat cgcagttact ccggatccca caagctgtcg    3720
tggatatggt ggcggggcc cattgggag tcctagcggg ccttgcctac tattccatgg     3780
tggggaactg ggctaaggtt ctgattgtga tgctactctt tgccggcgtt gacggggaa     3840 cctatgtgac agggggacg atggccaaaa acaccctcgg gattacgtcc ctcttttcac    3900
ccgggtcatc ccagaaaatc cagcttgtaa acaccaacgg cagctggcac atcaacagga    3960
ctgccctgaa ctgcaatgac tccctcaaca ctgggttcct tgctgcgctg ttctacgtgc    4020
```

```
acaagttcaa ctcatctgga tgcccagagc gcatggccag ctgcagcccc atcgacgcgt   4080
tcgctcaggg gtgggggccc atcacttaca atgagtcaca cagctcggac cagaggcctt   4140
attgttggca ctacgcaccc cggccgtgcg gtatcgtacc cgcggcgcag gtgtgtggtc   4200
cagtgtactg cttcacccca agccctgtcg tggtggggac gaccgaccgg ttcggcgtcc   4260
ctacgtacag ttgggggggag aatgagacgg acgtgctgct tcttaacaac acgcggccgc   4320
cgcaaggcaa ctggtttggc tgtacatgga tgaatagcac tgggttcacc aagacgtgcg   4380
ggggccccccc gtgtaacatc ggggggatcg gcaataaaac cttgacctgc cccacggact   4440
gcttccggaa gcaccccgag gccacttaca ccaagtgtgg ttcggggcct tggttgacac   4500
ccagatgctt ggtccactac ccatacaggc tttggcacta ccccctgcact gtcaacttta   4560
ccatcttcaa ggttaggatg tacgtggggg gagtggagca caggctcgaa gccgcatgca   4620
attggactcg aggagagcgt tgtaacctgg aggacaggga cagatcagag cttagcccgc   4680
tgctgctgtc tacaacggag tggcaggtat tgccctgttc cttcaccacc ctaccggctc   4740
tgtccactgg tttgatccat ctccatcaga acgtcgtgga cgtacaatac ctgtacggta   4800
tagggtcggc ggttgtctcc tttgcaatca aatgggagta tgtcctgttg ctcttccttc   4860
ttctggcgga cgcgcgcgtc tgtgcctgct tgtggatgat gctgctgata gctcaagctg   4920
aggccgccct agagaacctg gtggtcctca acgcggcatc cgtggccggg gcgcatggca   4980
ttctctcctt cctcgtgttc ttctgtgctg cctggtacat caagggcagg ctggtccctg   5040
gggcggcata tgccctctac ggcgtatggc cgctactcct gctcctgctg gcgttaccac   5100
cacgagcata cgccatggac cgggagatgg cagcatcgtg cggaggcgcg gttttcgtag   5160
gtctgatact cttgaccttg tcaccgcact ataagctgtt cctcgctagg ctcatatggt   5220
ggttacaata ttttatcacc agggccgagg cacacttgca agtgtggatc cccccccctca   5280
acgttcgggg gggccgcgat ggcatcgcgt gggccgtcac tatattctgc ccgggtgtgg   5340
tgtttgacat taccaaatgg cttttggcgt tgcttgggcc tgcttacctc ttaagggccg   5400
ctttgacaca tgtgccgtac ttcgtcagag ctcacgctct gataagggta tgcgctttgg   5460
tgaagcagct cgcggggggt aggtatgttc aggtggcgct attggcccctt ggcaggtgga   5520
ctggcaccta catctatgac cacctcacac ctatgtcgga ctgggccgct agcggcctgc   5580
gcgacttagc ggtcgccgtg gaacccatca tcttcagtcc gatggagaag aaggtcatcg   5640
tctggggagc ggagacggct gcatgtgggg acattctaca tggacttccc gtgtccgccc   5700
gactcggcca ggagatcctc ctcggcccag ctgatggcta cacctccaag gggtggaagc   5760
tccttgctcc catcactgct tatgcccagc aaacacgagg cctcctgggc gccatagtgg   5820
tgagtatgac ggggcgtgac aggacagaac aggccgggga agtccaaatc ctgtccacag   5880
tctctcagtc cttcctcgga caaccatct cggggggtttt gtggactgtt taccacggag   5940
ctggcaacaa gactctagcc ggcttacggg gtccggtcac gcagatgtac tcgagtgctg   6000
aggggggactt ggtaggctgg cccagccccc ctgggaccaa gtctttggag ccgtgcaagt   6060
gtggagccgt cgacctatat ctggtcacgc ggaacgctga tgtcatcccg gctcggagac   6120
gcggggacaa gcggggagca ttgctctccc cgagacccat ttcgaccttg aagggggtcct   6180
cggggggggcc ggtgctctgc cctaggggcc acgtcgttgg gctcttccga gcagctgtgt   6240
gctctcgggg cgtggccaaa tccatcgatt tcatccccgt tgagacactc gacgttgtta   6300
caaggtctcc cactttcagt gacaacagca cgcaccggc tgtgccccag acctatcagg   6360
tcgggtactt gcatgctcca actggcagtg gaaagagcac caaggtccct gtcgcgtatg   6420
```

```
ccgcccaggg gtacaaagta ctagtgctta acccctcggt agctgccacc ctggggtttg   6480
gggcgtacct atccaaggca catggcatca atcccaacat taggactgga gtcaggaccg   6540
tgatgaccgg ggaggccatc acgtactcca catatggcaa atttctcgcc gatgggggct   6600
gcgctagcgg cgcctatgac atcatcatat gcgatgaatg ccacgctgtg gatgctacct   6660
ccattctcgg catcggaacg gtccttgatc aagcagagac agccgggtc agactaactg   6720 tgctggctac ggccacaccc cccgggtcag tgacaacccc ccatcccgat atagaagagg   6780
taggcctcgg gcgggagggt gagatcccct tctatgggag ggcgattccc ctatcctgca   6840
tcaagggagg gagacacctg attttctgcc actcaaagaa aaagtgtgac gagctcgcgg   6900
cggcccttcg gggcatgggc ttgaatgccg tggcatacta tagagggttg gacgtctcca   6960
taataccagc tcagggagat gtggtggtcg tcgccaccga cgccctcatg acggggtaca   7020
ctggagactt tgactccgtg atcgactgca atgtagcggt cacccaagct gtcgacttca   7080
gcctggaccc caccttcact ataaccacac agactgtccc acaagacgct gtctcacgca   7140
gtcagcgccg cgggcgcaca ggtagaggaa gacagggcac ttataggtat gtttccactg   7200
gtgaacgagc ctcaggaatg tttgacagtg tagtgctttg tgagtgctac gacgcagggg   7260
ctgcgtggta cgatctcaca ccagcggaga ccaccgtcag gcttagagcg tatttcaaca   7320 cgccggcct accgtgtgt caagaccatc ttgaattttg ggaggcagtt ttcaccggcc   7380
tcacacacat agacgcccac ttcctctccc aaacaaagca agcgggggag aacttcgcgt   7440
acctagtagc ctaccaagct acggtgtgcg ccagagccaa ggcccctccc cgtcctgggg   7500
acgccatgtg gaagtgcctg gcccgactca agcctacgct tgcgggcccc acacctctcc   7560
tgtaccgttt gggcccctatt accaatgagg tcacccctcac acaccctggg acgaagtaca   7620
tcgccacatg catgcaagct gaccttgagg tcatgaccag cacgtgggtc ctagctggag   7680
gagtcctggc agccgtcgcc gcatattgcc tggcgactgg atgcgtttcc atcatcggcc   7740
gcttgcacgt caaccagcga gtcgtcgttg cgccggataa ggaggtcctg tatgaggctt   7800
ttgatgagat ggaggaatgc gcctctaggg cggctctcat cgaagagggg cagcggatag   7860
ccgagatgtt gaagtccaag atccaaggct tgctgcagca ggcctctaag caggcccagg   7920
acatacaacc cgctatgcag gcttcatggc ccaaagtgga acaattttgg gccagacaca   7980
tgtggaactt cattagcggc atccaatacc tcgcaggatt gtcaacactg ccagggaacc   8040
ccgcggtggc ttccatgatg gcattcagtg ccgccctcac cagtccgttg tcgaccagta   8100
ccaccatcct tctcaacatc atgggaggct ggttagcgtc ccagatcgca ccacccgcgg   8160
gggccaccgg ctttgtcgtc agtggcctgg tggggctgc cgtgggcagc ataggcctgg   8220
gtaaggtgct ggtggacatc ctggcaggat atggtgcggg catttcgggg gccctcgtcg   8280
cattcaagat catgtctggc gagaagccct ctatggaaga tgtcatcaat ctactgcctg   8340
ggatcctgtc tccgggagcc ctggtggtgg gggtcatctg cgcggccatt ctgcgccgcc   8400
acgtgggacc gggggagggc gcggtccaat ggatgaacag gcttattgcc tttgcttcca   8460
gaggaaacca cgtcgcccct actcactacg tgacggagtc ggatgcgtcg cagcgtgtga   8520
cccaactact tggctctctt actataacca gcctactcag aagactccac aattggataa   8580
ctgaggactg ccccatccca tgctccggat cctggctccg cgacgtgtgg gactgggttt   8640
gcaccatctt gacagacttc aaaaattggc tgacctctaa attgttcccc aagctgcccg   8700
gcctcccctt catctcttgt caaaaggggt acaagggtgt gtgggccggc actggcatca   8760
tgaccacgcg ctgcccttgc ggcgccaaca tctctggcaa tgtccgcctg ggctctatga   8820
```

```
ggatcacagg gcctaaaacc tgcatgaaca cctggcaggg gacctttcct atcaattgct    8880
acacggaggg ccagtgcgcg ccgaaacccc ccacgaacta caagaccgcc atctggaggg    8940
tggcggcctc ggagtacgcg gaggtgacgc agcatgggtc gtactcctat gtaacaggac    9000
tgaccactga caatctgaaa attccttgcc aactaccttc tccagagttt ttctcctggg    9060
tggacggtgt gcagatccat aggtttgcac ccacaccaaa gccgtttttc cgggatgagg    9120
tctcgttctg cgttgggctt aattcctatg ctgtcgggtc ccagcttccc tgtgaacctg    9180
agcccgacgc agacgtattg aggtccatgc taacagatcc gccccacatc acggcggaga    9240
ctgcggcgcg gcgcttggca cggggatcac ctccatctga ggcgagctcc tcagtgagcc    9300
agctatcagc accgtcgctg cgggccacct gcaccaccca cagcaacacc tatgacgtgg    9360
acatggtcga tgccaacctg ctcatggagg gcggtgtggc tcagacagag cctgagtcca    9420
gggtgcccgt tctggacttt ctcgagccaa tggccgagga agagagcgac cttgagccct    9480
caataccatc ggagtgcatg ctccccagga gcgggtttcc acgggcctta ccggcttggg    9540
cacggcctga ctacaacccg ccgctcgtgg aatcgtggag gaggccagat taccaaccgc    9600
ccaccgttgc tggttgtgct ctcccccccc ccaagaaggc cccgacgcct cccccaagga    9660
gacgccggac agtgggtctg agcgagagca ccatatcaga agccctccag caactggcca    9720
tcaagacctt tggccagccc ccctcgacgc gtgatgcagg ctcgtccacg ggggcgggcg    9780
ccgccgaatc cggcggtccg acgtcccctg gtgagccggc cccctcagag acaggttccg    9840
cctcctctat gccccccctc gaggggggagc ctggagatcc ggacctggag tctgatcagg    9900
tagagcttca acctcccccc cagggggggg gggtagctcc cggttcgggc tcggggtctt    9960
ggtctacttg ctccgaggag gacgatacca ccgtgtgctg ctccatgtca tactcctgga   10020
ccggggctct aataactccc tgtagccccg aagaggaaaa gttgccaatc aacccttgga   10080
gtaactcgct gttgcgatac cataacaagg tgtactgtac aacatcaaag agcgcctcac   10140
agagggctaa aaaggtaact tttgacagga cgcaagtgct cgacgcccat tatgactcag   10200
tcttaaagga catcaagcta gcggcttcca aggtcagcgc aaggctcctc accttggagg   10260
aggcgtgcca gttgactcca ccccattctg caagatccaa gtatggattc ggggccaagg   10320
aggtccgcag cttgtccggg agggccgtta accacatcaa gtccgtgtgg aaggacctcc   10380
tggaagaccc acaaacacca attcccacaa ccatcatggc caaaaatgag gtgttctgcg   10440
tggaccccgc caagggggggt aagaaaccag ctcgcctcat cgtttaccct gacctcggcg   10500
tccgggtctg cgagaaaatg gccctctatg acattacaca aaagcttcct caggcggtaa   10560
tgggagcttc ctatggcttc cagtactccc ctgcccaacg ggtggagtat ctcttgaaag   10620
catgggcgga aaagaaggac cccatggggtt tttcgtatga tacccgatgc ttcgactcaa   10680
ccgtcactga gagagacatc aggaccgagg agtccatata ccaggcctgc tccctgcccg   10740
aggaggcccg cactgccata cactcgctga ctgagagact ttacgtagga gggcccatgt   10800
tcaacagcaa gggtcaaacc tgcggttaca gacgttgccg cgccagcggg gtgctaacca   10860
ctagcatggg taacaccatc acatgctatg tgaaagccct agcggcctgc aaggctgcgg   10920
ggatagttgc gcccacaatg ctggtatgcg gcgatgacct agtagtcatc tcagaaagcc   10980 agggggactga ggaggacgag cggaacctga gagccttcac ggaggccatg accaggtact   11040
ctgcccctcc tggtgatccc cccagaccgg aatatgacct ggagctaata acatcctgtt   11100 cctcaaaatgt gtcctgtggcg ttgggcccgc ggggccgccg cagatactac ctgaccagag   11160
acccaaccac tccactcgcc cgggctgcct gggaaacagt tagacactcc cctatcaatt   11220
```

```
catggctggg aaacatcatc cagtatgctc caaccatatg ggttcgcatg gtcctaatga    11280
cacacttctt ctccattctc atggtccaag acaccctgga ccagaacctc aactttgaga    11340
tgtatggatc agtatactcc gtgaatcctt tggaccttcc agccataatt gagaggttac    11400
acgggcttga cgccttttct atgcacacat actctcacca cgaactgacg cgggtggctt    11460
cagccctcag aaaacttggg gcgccacccc tcagggtgtg aaagagtcgg gctcgcgcag    11520
tcagggcgtc cctcatctcc cgtggaggga aagcggccgt ttgcggccga tatctcttca    11580
attgggcggt gaagaccaag ctcaaaactca ctccattgcc ggaggcgcgc ctactggact    11640
tatccagttg gttcaccgtc ggcgccggcg ggggcgacat ttttcacagc gtgtcgcgcg    11700
cccgaccccg ctcattactc ttcggcctac tcctactttt cgtaggggta ggcctcttcc    11760
tactccccgc tcggtagagc ggcacacact aggtacactc catagctaac tgttcctttt    11820
tttttttttt tttttttttt tttttttttt tttttttttc tttttttttt ttttccctct    11880
ttcttccctt ctcatcttat tctactttct tcttggtgg ctccatctta gccctagtca    11940
cggctagctg tgaaaggtcc gtgagccgca tgactgcaga gagtgccgta actggtctct    12000
ctgcagatca tgtctagagt cgacctgcag gcatgcaagc ttggcactgg ccgtcgtttt    12060
acaacgtcgt gactgggaaa accctggcgt tacccaactt aatcgccttg cagcacatcc    12120
cccttcgcc agctggcgta atagcgaaga ggcccgcacc gatcgccctt cccaacagtt    12180
gcgcagcctg aatggcgaat ggcgcctgat gcggtatttt ctccttacgc atctgtgcgg    12240
tatttcacac cgcatatggt gcactctcag tacaatctgc tctgatgccg catagttaag    12300
ccagccccga cacccgccaa cacccgctga cgcgccctga cgggcttgtc tgctcccggc    12360
atccgcttac agacaagctg tgaccgtctc cgggagctgc atgtgtcaga ggttttcacc    12420
gtcatcaccg aaacgcgcga gacgaaaggg cctcgtgata cgcctatttt tataggttaa    12480
tgtcatgata ataatggttt cttagacgtc aggtggcact tttcggggaa atgtgcgcgg    12540
aaccctatt tgtttatttt tctaaataca ttcaaatatg tatccgctca tgagacaata    12600
accctgataa atgcttcaat aatattgaaa aaggaagagt atgagtattc aacatttccg    12660
tgtcgccctt attcccttt ttgcggcatt ttgccttcct gttttgctc acccagaaac    12720
gctggtgaaa gtaaaagatg ctgaagatca gttgggtgca cgagtgggtt acatcgaact    12780
ggatctcaac agcggtaaga tccttgagag ttttcgcccc gaagaacgtt ttccaatgat    12840
gagcactttt aaagttctgc tatgtggcgc ggtattatcc cgtattgacg ccgggcaaga    12900
gcaactcggt cgccgcatac actattctca gaatgacttg gttgagtact caccagtcac    12960
agaaaagcat cttacggatg gcatgacagt aagagaatta tgcagtgctg ccataaccat    13020
gagtgataac actgcggcca acttacttct gacaacgatc ggaggaccga aggagctaac    13080
cgcttttttg cacaacatgg ggatcatgt aactcgcctt gatcgttggg aaccggagct    13140
gaatgaagcc ataccaaacg acgagcgtga caccacgatg cctgtagcaa tggcaacaac    13200
gttgcgcaaa ctattaactg gcgaactact tactctagct tcccggcaac aattaataga    13260
ctggatggag gcggataaag ttgcaggacc acttctgcgc tcggcccttc cggctggctg    13320
gtttattgct gataaatctg gagccggtga gcgtgggtct cgcggtatca ttgcagcact    13380
ggggccagat ggtaagccct cccgtatcgt agttatctac acgacgggga gtcaggcaac    13440
tatggatgaa cgaaatagac agatcgctga gataggtgcc tcactgatta agcattggta    13500
actgtcagac caagtttact catatatact ttagattgat ttaaaacttc atttttaatt    13560
taaaaggatc taggtgaaga tcctttttga taatctcatg accaaaatcc cttaacgtga    13620
```

```
gttttcgttc cactgagcgt cagacccgt agaaaagatc aaaggatctt cttgagatcc    13680 ttttttctg cgcgtaatct gctgcttgca acaaaaaaa ccaccgctac cagcggtggt    13740
ttgtttgccg gatcaagagc taccaactct ttttccgaag gtaactggct tcagcagagc    13800
gcagatacca aatactgtcc ttctagtgta gccgtagtta ggccaccact tcaagaactc    13860
tgtagcaccg cctacatacc tcgctctgct aatcctgtta ccagtggctg ctgccagtgg    13920
cgataagtcg tgtcttaccg ggttggactc aagacgatag ttaccggata aggcgcagcg    13980
gtcgggctga acgggggggtt cgtgcacaca gcccagcttg gagcgaacga cctacaccga    14040
actgagatac ctacagcgtg agctatgaga aagcgccacg cttcccgaag ggagaaaggc    14100
ggacaggtat ccggtaagcg gcagggtcgg aacaggagag cgcacgaggg agcttccagg    14160
gggaaacgcc tggtatcttt atagtcctgt cgggtttcgc cacctctgac ttgagcgtcg    14220
atttttgtga tgctcgtcag gggggcggag cctatgaaaa aacgccagca acgcggcctt    14280
tttacggttc ctggcctttt gctggccttt tgctcacatg ttctttcctg cgttatcccc    14340
tgattctgtg gataaccgta ttaccgcctt tgagtgagct gataccgctc gccgcagccg    14400
aacgaccgag cgcagcgagt cagtgagcga ggaagcggaa gagcgcccaa tacgcaaacc    14460
gcctctcccc gcgcgttggc cgattcatta atgcagctgg cacgacaggt ttcccgactg    14520
gaaagcgggc agtgagcgca acgcaattaa tgtgagttag ctcactcatt aggcacccca    14580
ggctttacac tttatgcttc cggctcgtat gttgtgtgga attgtgagcg gataacaatt    14640
tcacacagga aacagctatg accatgatta c                                   14671

<210> SEQ ID NO 5
<211> LENGTH: 14689
<212> TYPE: DNA
<213> ORGANISM: Artificial Sequence
<220> FEATURE:
<223> OTHER INFORMATION: Synthetic plasmid: pLucNJ1

<400> SEQUENCE: 5
gaattcccaa acgcgttaat acgactcact atagacctgc ccctaatagg ggcgacactc      60
cgccatgaat cactcccctg tgaggaacta ctgtcttcac gcagaaagcg cctagccatg     120
gcgttagtat gagtgtcgta cagcctccag gccccccccct cccgggagag ccatagtggt     180
ctgcggaacc ggtgagtaca ccggaattgc cgggaagact gggtcctttc ttggataaac     240
ccactctatg cccggccatt tgggcgtgcc cccgcaagac tgctagccga gtagcgttgg     300
gttgcgaaag gccttgtggt actgcctgat agggcgcttg cgagtgcccc gggaggtctc     360
gtagaccgtg caccatgagc acaaatccta aacctcaaag aaaaaccaaa agaaacacca     420
accgtgaaga cgccaaaaac ataaagaaag gcccggcgcc attctatccc ctagaggatg     480
gaaccgctgg agagcaactg cataaggcta tgaagagata cgccctggtt cctggaacaa     540
ttgcttttac agatgcacat atcgaggtga acatcacgta cgcggaatac ttcgaaatgt     600
ccgttcggtt ggcagaagct atgaaacgat atgggctgaa tacaaatcac agaatcgtcg     660
tatgcagtga aaactctctt caattcttta tgccggtgtt gggcgcgtta tttatcggag     720
ttgcagttgc gcccgcgaac gacatttata tgaacgtga attgctcaac agtatgaaca     780
tttcgcagcc taccgtagtg tttgtttcca aaaagggggtt gcaaaaaatt ttgaacgtgc     840
aaaaaaaatt accaataatc cagaaaatta ttatcatgga ttctaaaacg gattaccagg     900
gatttcagtc gatgtacacg ttcgtcacat ctcatctacc tcccggtttt aatgaatacg     960
attttgtacc agagtccttt gatcgtgaca aaacaattgc actgataatg aattcctctg    1020
```

```
gatctactgg gttacctaag ggtgtggccc ttccgcatag aactgcctgc gtcagattct    1080
cgcatgccag agatcctatt tttggcaatc aaatcattcc ggatactgcg attttaagtg    1140
ttgttccatt ccatcacggt tttggaatgt ttactacact cggatatttg atatgtggat    1200
ttcgagtcgt cttaatgtat agatttgaag aagagctgtt tttacgatcc cttcaggatt    1260
acaaaattca aagtgcgttg ctagtaccaa ccctattttc attcttcgcc aaaagcactc    1320
tgattgacaa atacgattta tctaatttac acgaaattgc ttctgggggc gcacctcttt    1380
cgaaagaagt cggggaagcg gttgcaaaac gcttccatct tccagggata cgacaaggat    1440
atgggctcac tgagactaca tcagctattc tgattacacc cgagggggat gataaaccgg    1500
gcgcggtcgg taaagttgtt ccattttttg aagcgaaggt tgtggatctg ataccgggaa   1560
aaacgctggg cgttaatcag agaggcgaat tatgtgtcag aggacctatg attatgtccg    1620
gttatgtaaa caatccggaa gcgaccaacg ccttgattga caaggatgga tggctacatt    1680
ctggagacat agcttactgg gacgaagacg aacacttctt catagttgac cgcttgaagt    1740
ctttaattaa atacaaagga tatcaggtgg ccccgctga attggaatcg atattgttac     1800
aacaccccaa catcttcgac gcgggcgtgg caggtcttcc cgacgatgac gccggtgaac    1860
ttcccgccgc cgttgttgtt ttggagcacg aaagacgat gacggaaaaa gagatcgtgg     1920
attacgtcgc cagtcaagta acaaccgcga aaaagttgcg cggaggagtt gtgtttgtgg    1980
acgaagtacc gaaaggtctt accggaaaac tcgacgcaag aaaaatcaga gagatcctca    2040
taaaggccaa gaagggcgga aagtccaaat tgtgagttgt taaacagacc acaacggttt    2100
ccctctagcg ggatcaattc cgcccccccc ccctaacgtt actggccgaa gccgcttgga    2160
ataaggccgg tgtgcgtttg tctatatgtt attttccacc atattgccgt cttttggcaa    2220
tgtgagggcc cggaaacctg gccctgtctt cttgacgagc attcctaggg gtcttttccc    2280
tctcgccaaa ggaatgcaag gtctgttgaa tgtcgtgaag gaagcagttc ctctggaagc    2340
ttcttgaaga caaacaacgt ctgtagcgac cctttgcagg cagcggaacc ccccacctgg    2400
cgacaggtgc ctctgcggcc aaaagccacg tgtataagat acacctgcaa aggcggcaca    2460
accccagtgc cacgttgtga gttggatagt tgtggaaaga gtcaaatggc tctcctcaag    2520
cgtattcaac aaggggctga aggatgccca gaaggtaccc cattgtatgg gatctgatct    2580
ggggcctcgg tgcacatgct ttacatgtgt ttagtcgagg ttaaaaaaac gtctaggccc    2640
cccgaaccac ggggacgtgg ttttcctttg aaaaacacga taataccatg agcacacttc    2700
ctaaacctca agaaaaaacc aaaagaaaca ccatccgtcg cccacaggac gtcaagttcc    2760
cgggtggcgg acagatcgtt ggtggagtat acgtgttgcc gcgcaggggc ccacgattgg    2820
gtgtgcgcgc gacgcgtaaa acttctgaac ggtcacagcc tcgcggacga cgacagccta    2880
tccccaaggc gcgtcggagc gaaggccggt cctgggctca gcccgggtac ccttggcccc    2940
tctatggtaa cgagggctgc gggtgggcag ggtggctcct gtccccacgc ggctcccgtc    3000
catcctgggg cccaaatgac ccccggcgga ggtcccgcaa tttgggtaaa gtcatcgata    3060
ccctaacgtg cggattcgcc gacctcatgg ggtacatccc gctcgtcggc gctcctgtag    3120
gaggcgtcgc aagagccctc gcgcatggcg tgagggccct tgaagacggg ataaatttcg    3180
caacagggaa cttgccgggt tgctcctttt ctatcttcct tcttgctctg ttctcttgct    3240
taattcatcc agcagccagt cttgagtggc ggaatacgtc tggcctctac gtccttacca    3300
acgactgttc caatagcagt attgtgtatg aggccgatga tgtcattctg cacacacccg    3360
gctgtgtacc ttgtgtccag gacggcaata catctacgtg ctggacccca gtgacaccta    3420
```

```
cagtggcagt caggtacgtc ggagcaacta ctgcttcgat acgcagtcat gtggacctat    3480
tagtaggcgc ggccacgatg tgctctgcgc tctacgtggg tgatatgtgt ggggctgtct    3540
ttctcgtggg acaagccttc acgttcagac ctcgacgcca tcaaacggtc cagacctgta    3600
actgctcgct gtacccaggc catctttcag gacatcgaat ggcttgggat atgatgatga    3660
attggtcccc cgctgtgggt atggtggtgg cgcatgtcct gcgtttaccc cagaccttgt    3720
tcgacataat ggccggggcc cattggggca tcttggcggg cctggcctat tactccatgc    3780
agggcaactg ggccaaggtc gcaatcatca tggttatgtt ctcaggggtc gatgcccaca    3840
catataccac cggtggcact gcatctcgtc atacccaagc gtttgctggt cttttttgaca   3900 taggccccca acagaaactg cagctggtca acaccaatgg ctcgtggcac atcaacagta    3960
ctgccctaaa ttgcaatgag tccataaaca ccgggtttat agctgggttg ttttattacc    4020
ataagttcaa ctctactgga tgtcctcaaa ggctcagcag ctgcaagccc atcactttct    4080
tcaggcaggg atgggccccc ttaacagatg ctaacatcac cggtccttct gatgacagac    4140
catactgctg gcactacgca cctagaccct tgtgacattgt cccggcatca agtgtctgcg    4200
gccctgtgta ctgcttcaca ccatcgccag tggtcgtagg cactactgat gccaggggcg    4260
tgccaaccta cacctggggt gagaatgaga aagatgtgtt cctgctgaag tcccagcggc    4320
ctcccagtgg tcggtggttt gggtgctcgt ggatgaactc cacggggttt ctcaagacgt    4380
gcggagctcc ccctgtaac atctatgggg gcgaggggaa tccccacaat gaatcagatc    4440
ttttctgccc cactgactgc ttcaggaaac atcccgagac cacgtacagc cggtgtggtg    4500
cagggccctg gttgacacct cgttgcatgg ttgactaccc ataccggctt tggcattacc    4560
catgtacagt cgatttcaga ttgttcaagg tgaggatgtt tgtgggtggg tttgaacatc    4620
gatttaccgc cgcttgcaac tggaccaggg gggagcgctg cgatatcgag gatcgtgacc    4680
gcagtgagca acatccgctg ctgcattcaa caactgagct tgctatactg ccttgctctt    4740
tcacgcccat gcctgcgctg tcaacaggtc tgatacacct ccaccaaaac atcgtggatg    4800 tccaataccct ttatggcgtt ggatctggca tggtgggatg ggcgctgaaa tgggagttcg    4860
tcatcctcgt tttcctcctt ctggcggacg cacgcgtgtg cgttgccctt tggctgatgc    4920
tgatgatatc acagacagaa gcagccttgg agaacctggt cacgctgaac gccgtcgctg    4980
ctgctgggac acatggtatc ggctggtacc tggtagcttt ttgcgcggcg tggtacgtgc    5040
ggggtaaact cgtcccgctg gtgacctaca gcctgacggg tctttggtcc ctagcattgc    5100
tcgtcctctt gctcccccaa cgtgcgtatg cttggtcggg tgaagacagc gccactcttg    5160
gcgctggggt cttggtcctc ttcggcttct taccttgtc accctggtat aagcattgga    5220
tcggccgcct catgtggtgg aaccagtaca ccatatgcag atgcgagtcc gcccttcacg    5280
tgtgggttcc cccctactc gcacgcggga gtagggatgg catcgcgtgg gccgtcacta    5340
tattctgccc gggtgtggtg tttgacatta ccaaatggct tttggcgttg cttgggcctg    5400
cttacctctt aagggccgct ttgacacatg tgccgtactt cgtcagagct cacgctctga    5460
taagggtatg cgctttggtg aagcagctcg cgggggggtag gtatgttcag gtggcgctat    5520
tggcccttgg caggtggact ggcacctaca tctatgacca cctcacacct atgtcggact    5580
gggccgctag cggcctgcgc gacttagcgg tcgccgtgga accatcatc ttcagtccga    5640 tggagaagaa ggtcatcgtc tggggagcgg agacggctgc atgtgggac attctacatg    5700 gacttcccgt gtccgcccga ctcggccagg agatcctcct cggcccagct gatggctaca    5760
cctccaaggg gtggaagctc cttgctccca tcactgctta tgcccagcaa acacgaggcc    5820
```

```
tcctgggcgc catagtggtg agtatgacgg ggcgtgacag gacagaacag gccggggaag   5880
tccaaatcct gtccacagtc tctcagtcct tcctcggaac aaccatctcg ggggttttgt   5940
ggactgttta ccacggagct ggcaacaaga ctctagccgg cttacggggt ccggtcacgc   6000
agatgtactc gagtgctgag ggggacttgg taggctggcc cagccccct gggaccaagt    6060 ctttggagcc gtgcaagtgt ggagccgtcg acctatatct ggtcacgcgg aacgctgatg   6120
tcatcccggc tcggagacgc ggggacaagc ggggagcatt gctctccccg agacccattt   6180
cgaccttgaa ggggtcctcg ggggggccgg tgctctgccc tagggccac gtcgttgggc    6240 tcttccgagc agctgtgtgc tctcggggcg tggccaaatc catcgatttc atccccgttg   6300
agacactcga cgttgttaca aggtctccca ctttcagtga caacagcacg ccaccggctg   6360
tgccccagac ctatcaggtc gggtacttgc atgctccaac tggcagtgga aagagcacca   6420
aggtccctgt cgcgtatgcc gcccaggggt acaaagtact agtgcttaac ccctcggtag   6480
ctgccaccct ggggtttggg gcgtacctat ccaaggcaca tggcatcaat cccaacatta   6540
ggactggagt caggaccgtg atgaccgggg aggccatcac gtactccaca tatggcaaat   6600
ttctcgccga tgggggctgc gctagcgcg cctatgacat catcatatgc gatgaatgcc    6660
acgctgtgga tgctacctcc attctcggca tcggaacggt ccttgatcaa gcagagacag   6720
ccggggtcag actaactgtg ctggctacgg ccacaccccc cggtcagtg acaaccccc     6780 atcccgatat agaagaggta ggcctcgggc gggagggtga gatcccttc tatgggaggg    6840 cgattccccc atcctgcatc aagggaggga gacacctgat tttctgccac tcaaagaaaa   6900
agtgtgacga gctcgcggcg gcccttcggg gcatgggctt gaatgccgtg gcatactata   6960
gagggttgga cgtctccata ataccagctc agggagatgt ggtggtcgtc gccaccgacg   7020
ccctcatgac ggggtacact ggagactttg actccgtgat cgactgcaat gtagcggtca   7080
cccaagctgt cgacttcagc ctggaccca ccttcactat aaccacacag actgtcccac     7140
aagacgctgt ctcacgcagt cagcgccgcg gccgcacagg tagaggaaga cagggcactt   7200
ataggtatgt ttccactggt gaacgagcct caggaatgtt tgacagtgta gtgctttgtg   7260
agtgctacga cgcaggggct gcgtggtacg atctcacacc agcggagacc accgtcaggc   7320
ttagagcgta tttcaacacg cccggcctac ccgtgtgtca agaccatctt gaattttggg   7380
aggcagtttt caccggcctc acacacatag acgcccactt cctctcccaa acaaagcaag   7440
cgggggagaa cttcgcgtac ctagtagcct accaagctac ggtgtgcgcc agagccaagg   7500 cccctcccc gtcctgggac gccatgtgga agtgcctggc ccgactcaag cctacgcttg   7560
cgggccccac acctctcctg taccgttttgg gccctattac caatgaggtc accctcacac   7620
accctgggac gaagtacatc gccacatgca tgcaagctga ccttgaggtc atgaccagca   7680
cgtgggtcct agctggagga gtcctggcag ccgtcgccgc atattgcctg gcgactggat   7740
gcgtttccat catcggccgc ttgcacgtca accagcgagt cgtcgttgcg ccggataagg   7800
aggtcctgta tgaggctttt gatgagatgg aggaatgcgc ctctaggcg gctctcatcg     7860 aagagggca gcggatagcc gagatgttga gtccaagat ccaaggcttg ctgcagcagg      7920
cctctaagca ggcccaggac atacaacccg ctatgcaggc ttcatggccc aaagtggaac   7980
aattttgggc cagacacatg tggaacttca ttagcggcat ccaatacctc gcaggattgt   8040
caacactgcc agggaacccc gcggtggctt ccatgatggc attcagtgcc gccctcacca   8100
gtccgttgtc gaccagtacc accatcctcc tcaacatcat gggaggctgg ttagcgtccc   8160
agatcgcacc cccgcgggg gccaccggct ttgtcgtcag tggcctggtg ggggctgccg   8220
```

-continued

```
tgggcagcat aggcctgggt aaggtgctgg tggacatcct ggcaggatat ggtgcgggca      8280
tttcggggc  cctcgtcgca ttcaagatca tgtctggcga gaagccctct atggaagatg      8340
tcatcaatct actgcctggg atcctgtctc cgggagccct ggtggtgggg gtcatctgcg      8400
cggccattct gcgccgccac gtgggaccgg gggagggcgc ggtccaatgg atgaacaggc      8460
ttattgcctt tgcttccaga ggaaaccacg tcgcccctac tcactacgtg acggagtcgg      8520
atgcgtcgca gcgtgtgacc caactacttg gctctcttac tataaccagc ctactcagaa      8580
gactccacaa ttggataact gaggactgcc ccatcccatg ctccggatcc tggctccgcg      8640
acgtgtggga ctgggtttgc accatcttga cagacttcaa aaattggctg acctctaaat      8700
tgttccccaa gctgcccggc ctcccctcca tctcttgtca aaaggggtac aagggtgtgt      8760
gggccggcac tggcatcatg accacgcgct gcccttgcgg cgccaacatc tctggcaatg      8820
tccgcctggg ctctatgagg atcacagggc ctaaaacctg catgaacacc tggcagggga      8880
cctttcctat caattgctac acggagggcc agtgcgcgcc gaaaccccc  acgaactaca      8940
agaccgccat ctggagggtg gcggcctcgg agtacgcgga ggtgacgcag catgggtcgt      9000
actcctatgt aacaggactg accactgaca atctgaaaat tccttgccaa ctaccttctc      9060
cagagttttt ctcctgggtg gacggtgtgc agatccatag gtttgcaccc acaccaaagc      9120
cgttttccg  ggatgaggtc tcgttctgcg ttgggcttaa ttcctatgct gtcgggtccc      9180
agcttccctg tgaacctgag cccgacgcag acgtattgag gtccatgcta acagatccgc      9240
cccacatcac ggcggagact gcggcgcggc gcttggcacg gggatcacct ccatctgagg      9300
cgagctcctc agtgagccag ctatcagcac cgtcgctgcg ggccacctgc accacccaca      9360
gcaacaccta tgacgtggac atggtcgatg ccaacctgct catggagggc ggtgtggctc      9420
agacagagcc tgagtccagg gtgcccgttc tggactttct cgagccaatg gccgaggaag      9480
agagcgacct tgagccctca ataccatcgg agtgcatgct ccccaggagc gggttttccac    9540
gggccttacc ggcttgggca cggcctgact acaacccgcc gctcgtggaa tcgtggagga      9600
ggccagatta ccaaccgccc accgttgctg gttgtgctct cccccccccc aagaaggccc      9660
cgacgcctcc cccaaggaga cgccggacag tgggtctgag cgagagcacc atatcagaag      9720
ccctccagca actggccatc aagacctttg ccagccccc  ctcgagcggt gatgcaggct      9780
cgtccacggg ggcgggcgcc gccgaatccg gcggtccgac gtccctggt  gagccggccc      9840
cctcagagac aggttccgcc tcctctatgc ccccctcga  gggggagcct ggagatccgg      9900
acctggagtc tgatcaggta gagcttcaac ctcccccca  gggggggggg gtagctcccg      9960
gttcgggctc ggggtcttgg tctacttgct ccgaggagga cgataccacc gtgtgctgct    10020
ccatgtcata ctcctggacc ggggctctaa taactccctg tagccccgaa gaggaaaagt    10080
tgccaatcaa ccctttgagt aactcgctgt tgcgatacca taacaaggtg tactgtacaa    10140
catcaaagag cgcctcacag agggctaaaa aggtaacttt tgacaggacg caagtgctcg    10200
acgcccatta tgactcagtc ttaaaggaca tcaagctagc ggcttccaag gtcagcgcaa    10260
ggctcctcac cttggaggag gcgtgccagt tgactccacc ccattctgca agatccaagt    10320
atggattcgg ggccaaggag gtccgcagct tgtccgggag ggccgttaac cacatcaagt    10380
ccgtgtggaa ggacctcctg gaagacccac aaacaccaat tccacaaacc atcatggcca    10440
aaaatgaggt gttctgcgtg gacccgcca  aggggggtaa gaaaccagct cgcctcatcg    10500
tttaccctga cctcggcgtc cgggtctgcg agaaaatggc cctctatgac attacacaaa    10560
agcttcctca ggcggtaatg ggagcttcct atggcttcca gtactcccct gcccaacggg    10620
```

```
tggagtatct cttgaaagca tgggcggaaa agaaggaccc catgggtttt tcgtatgata   10680
cccgatgctt cgactcaacc gtcactgaga gagacatcag gaccgaggag tccatatacc   10740
aggcctgctc cctgcccgag gaggcccgca ctgccataca ctcgctgact gagagacttt   10800
acgtaggagg gcccatgttc aacagcaagg gtcaaacctg cggttacaga cgttgccgcg   10860 ccagcgggt gctaaccact agcatgggta acaccatcac atgctatgtg aaagccctag    10920
cggcctgcaa ggctgcgggg atagttgcgc ccacaatgct ggtatgcggc gatgacctag   10980
tagtcatctc agaaagccag gggactgagg aggacgagcg gaacctgaga gccttcacgg   11040
aggccatgac caggtactct gcccctcctg gtgatccccc cagaccggaa tatgacctgg   11100
agctaataac atcctgttcc tcaaatgtgt ctgtggcgtt gggcccgcgg ggccgccgca   11160
gatactacct gaccagagac ccaaccactc cactcgcccg ggctgcctgg gaaacagtta   11220
gacactcccc tatcaattca tggctgggaa acatcatcca gtatgctcca accatatggg   11280
ttcgcatggt cctaatgaca cacttcttct ccattctcat ggtccaagac ccctggacc    11340 agaacctcaa cttttgagatg tatggatcag tatactccgt gaatcctttg gaccttccag   11400
ccataattga gaggttacac gggcttgacg ccttttctat gcacacatac tctcaccacg   11460
aactgacgcg ggtggcttca gccctcagaa aacttggggc gccacccctc agggtgtgga   11520
agagtcgggc tcgcgcagtc agggcgtccc tcatctcccg tggagggaaa gcggccgttt   11580
gcggccgata tctcttcaat tgggcggtga agaccaagct caaactcact ccattgccgg   11640
aggcgcgcct actggactta ccagttggt tcaccgtcgg cgccggcggg ggcgacattt    11700
ttcacagcgt gtcgcgcgcc cgaccccgct cattactctt cggcctactc ctacttttcg   11760 tagggggtagg cctcttccta ctccccgctc ggtagagcgg cacacactag gtacactcca   11820
tagctaactg ttccttttt tttttttttt tttttttttt tttttttttt ttttttcttt    11880
tttttttttt ttccctcttt cttcccttct catcttattc tactttcttt cttggtggct   11940
ccatcttagc cctagtcacg gctagctgtg aaaggtccgt gagccgcatg actgcagaga   12000
gtgccgtaac tggtctctct gcagatcatg tctagagtcg acctgcaggc atgcaagctt   12060
ggcactggcc gtcgttttac aacgtcgtga ctgggaaaac cctggcgtta cccaacttaa   12120
tcgccttgca gcacatcccc ctttcgccag ctggcgtaat agcgaagagg cccgcaccga   12180
tcgcccttcc caacagttgc gcagcctgaa tggcgaatgg cgcctgatgc ggtattttct   12240
ccttacgcat ctgtgcggta tttcacaccg catatggtgc actctcagta caatctgctc   12300
tgatgccgca tagttaagcc agccccgaca cccgccaaca cccgctgacg cgccctgacg   12360
ggcttgtctg ctcccggcat ccgcttacag acaagctgtg accgtctccg ggagctgcat   12420
gtgtcagagg ttttcaccgt catcaccgaa acgcgcgaga cgaaagggcc tcgtgatacg   12480 cctatttta taggttaatg tcatgataat aatggtttct tagacgtcag gtggcacttt    12540
tcggggaaat gtgcgcggaa cccctatttg tttatttttc taaatacatt caaatatgta   12600
tccgctcatg agacaataac cctgataaat gcttcaataa tattgaaaaa ggaagagtat   12660
gagtattcaa catttccgtg tcgcccttat tccctttttt gcggcatttt gccttcctgt   12720
ttttgctcac ccagaaacgc tggtgaaagt aaaagatgct gaagatcagt tgggtgcacg   12780
agtgggttac atcgaactgg atctcaacag cggtaagatc cttgagagtt ttcgccccga   12840
agaacgtttt ccaatgatga gcacttttaa agttctgcta tgtggcgcgg tattatcccg   12900
tattgacgcc gggcaagagc aactcggtcg ccgcatacac tattctcaga atgacttggt   12960
tgagtactca ccagtcacag aaaagcatct tacggatggc atgacagtaa gagaattatg   13020
```

```
cagtgctgcc ataaccatga gtgataacac tgcggccaac ttacttctga caacgatcgg   13080
aggaccgaag gagctaaccg cttttttgca caacatgggg gatcatgtaa ctcgccttga   13140
tcgttgggaa ccggagctga atgaagccat accaaacgac gagcgtgaca ccacgatgcc   13200
tgtagcaatg gcaacaacgt tgcgcaaact attaactggc gaactactta ctctagcttc   13260
ccggcaacaa ttaatagact ggatggaggc ggataaagtt gcaggaccac ttctgcgctc   13320
ggcccttccg gctggctggt ttattgctga taaatctgga gccggtgagc gtgggtctcg   13380
cggtatcatt gcagcactgg ggccagatgg taagccctcc cgtatcgtag ttatctacac   13440
gacggggagt caggcaacta tggatgaacg aaatagacag atcgctgaga taggtgcctc   13500
actgattaag cattggtaac tgtcagacca agtttactca tatatacttt agattgattt   13560
aaaacttcat ttttaattta aaaggatcta ggtgaagatc ctttttgata atctcatgac   13620
caaaatccct taacgtgagt tttcgttcca ctgagcgtca gaccccgtag aaaagatcaa   13680
aggatcttct tgagatcctt ttttttctgcg cgtaatctgc tgcttgcaaa caaaaaaacc   13740
accgctacca gcggtggttt gtttgccgga tcaagagcta ccaactcttt ttccgaaggt   13800
aactggcttc agcagagcgc agataccaaa tactgtcctt ctagtgtagc cgtagttagg   13860
ccaccacttc aagaactctg tagcaccgcc tacatacctc gctctgctaa tcctgttacc   13920
agtggctgct gccagtggcg ataagtcgtg tcttaccggg ttggactcaa gacgatagtt   13980
accggataag gcgcagcggt cgggctgaac ggggggttcg tgcacacagc ccagcttgga   14040
gcgaacgacc tacaccgaac tgagatacct acagcgtgag ctatgagaaa gcgccacgct   14100
tcccgaaggg agaaaggcgg acaggtatcc ggtaagcggc agggtcggaa caggagagcg   14160
cacgaggagc ttccaggggg aaacgcctg gtatctttat agtcctgtcg ggtttcgcca   14220
cctctgactt gagcgtcgat ttttgtgatg ctcgtcaggg gggcggagcc tatggaaaaa   14280
cgccagcaac gcggcctttt tacggttcct ggccttttgc tggccttttg ctcacatgtt   14340
ctttcctgcg ttatcccctg attctgtgga taaccgtatt accgcctttg agtgagctga   14400
taccgctcgc cgcagccgaa cgaccgagcg cagcgagtca gtgagcgagg aagcggaaga   14460
gcgcccaata cgcaaaccgc ctctccccgc gcgttggccg attcattaat gcagctggca   14520
cgacaggttt cccgactgga aagcgggcag tgagcgcaac gcaattaatg tgagttagct   14580
cactcattag gcaccccagg ctttacactt tatgcttccg gctcgtatgt tgtgtggaat   14640
tgtgagcgga taacaatttc acacaggaaa cagctatgac catgattac   14689
```

<210> SEQ ID NO 6
<211> LENGTH: 13623
<212> TYPE: DNA
<213> ORGANISM: Artificial Sequence
<220> FEATURE:
<223> OTHER INFORMATION: Synthetic plasmid: pRLF2AUbJFH1

<400> SEQUENCE: 6

```
gaattcccaa acgcgttaat acgactcact atagacctgc ccctaatagg ggcgacactc     60
cgccatgaat cactcccctg tgaggaacta ctgtcttcac gcagaaagcg cctagccatg    120
gcgttagtat gagtgtcgta cagcctccag gccccccct cccggagag ccatagtggt    180 ctgcggaacc ggtgagtaca ccggaattgc cgggaagact gggtcctttc ttggataaac    240
ccactctatg cccggccatt tgggcgtgcc cccgcaagac tgctagccga gtagcgttgg    300
gttgcgaaag gccttgtggt actgcctgat agggcgcttg cgagtgcccc gggaggtctc    360
gtagaccgtg caccatgagc acaaatccta aacctcaaag aaaaaccaaa atggcttcca    420
```

```
aggtgtacga ccccgagcaa cgcaaacgca tgatcactgg gcctcagtgg tgggctcgct        480
gcaagcaaat gaacgtgctg gactccttca tcaactacta tgattccgag aagcacgccg        540
agaacgccgt gattttctg catggtaacg ctgcctccag ctacctgtgg aggcacgtcg         600
tgcctcacat cgagcccgtg gctagatgca tcatccctga tctgatcgga atgggtaagt       660
ccggcaagag cgggaatggc tcatatcgcc tcctggatca ctacaagtac ctcaccgctt        720
ggttcgagct gctgaacctt ccaaagaaaa tcatctttgt gggccacgac tgggggggctt       780 gtctggcctt tcactactcc tacgagcacc aagacaagat caaggccatc gtccatgctg        840
agagtgtcgt ggacgtgatc gagtcctggg acagtggcc tgacatcgag gaggatatcg         900
ccctgatcaa gagcgaagag ggcgagaaaa tggtgcttga gaataacttc ttcgtcgaga        960
ccatgctccc aagcaagatc atgcggaaac tggagcctga ggagttcgct gcctacctgg       1020
agccattcaa ggagaagggc gaggttagac ggcctaccct ctcctggcct cgcgagatcc       1080
ctctcgttaa gggaggcaag cccgacgtcg tccagattgt ccgcaactac aacgcctacc       1140
ttcgggccag cgacgatctg cctaagatgt tcatcgagtc cgaccctggg ttcttttcca       1200
acgctattgt cgagggagct aagaagttcc ctaacaccga gttcgtgaag gtgaagggcc       1260
tccacttcag ccaggaggac gctccagatg aaatgggtaa gtacatcaag agcttcgtgg       1320
agcgcgtgct gaagaacgag cagctgttga attttgacct tcttaagctt gcgggagacg       1380
tcgagtccaa ccctgggccc atgcagatct cgtgaagac cctgacgggc aagaccatca        1440
ctcttgaggt cgagcccagt gacaccatcg agaatgtcaa ggccaagatc caagacaagg       1500
aaggcatccc acctgaccag cagaggctga tattcgcggg caaacagctg gaggatggcc       1560
gcaccctgtc cgactacaac atccagaaag agtccacctt gcacctggtg ctgcgtctcc       1620
gcggtggtat gagcacaaat cctaaacctc aaagaaaaac caaagaaac accaaccgtc        1680 gcccagaaga cgttaagttc ccgggcggcg gccagatcgt tggcggagta tacttgttgc       1740
cgcgcagggg ccccaggttg ggtgtgcgca cgacaaggaa aacttcggag cggtcccagc       1800
cacgtgggag acgccagccc atccccaaag atcggcgctc cactggcaag gcctggggaa       1860
aaccaggtcg cccctggccc ctatatggga atgagggact cggctgggca ggatggctcc       1920 tgtcccccg aggctctcgc ccctcctggg gccccactga ccccggcat aggtcgcgca         1980 acgtgggtaa agtcatcgac ccctaacgt gtggctttgc cgacctcatg gggtacatcc       2040
ccgtcgtagg cgccccgctt agtggcgccg ccagagctgt cgcgcacggc gtgagagtcc       2100
tggaggacgg ggttaattat gcaacaggga acctacccgg tttccccttt tctatcttct       2160
tgctggccct gttgtcctgc atcaccgttc cggtctctgc tgcccaggtg aagaatacca       2220
gtagcagcta catggtgacc aatgactgct ccaatgacag catcacttgg cagctcgagg       2280
ctgcggttct ccacgtcccc gggtgcgtcc cgtgcgagag agtggggaat acgtcacggt       2340
gttgggtgcc agtctcgcca aacatggctg tgcggcagcc cggtgccctc acgcagggtc       2400
tgcggacgca catcgatatg gttgtgatgt ccgccacctt ctgctctgct ctctacgtgg       2460
gggacctctg tggcggggtg atgctcgcgg cccaggtgtt catcgtctcg ccgcagtacc       2520
actggtttgt gcaagaatgc aattgctcca tctaccctgg caccatcact ggacaccgca       2580
tggcatggga catgatgatg aactggtcgc ccacggccac catgatcctg gcgtacgtga       2640
tgcgcgtccc cgaggtcatc atagacatcg ttagcggggc tcactggggc gtcatgttcg       2700
gcttggccta cttctctatg cagggagcgt gggcgaaggt cattgtcatc cttctgctgg       2760
ccgctggggt ggacgcgggc accaccaccg ttggaggcgc tgttgcacgt tccaccaacg       2820
```

```
tgattgccgg cgtgttcagc catggccctc agcagaacat tcagctcatt aacaccaacg   2880
gcagttggca catcaaccgt actgccttga attgcaatga ctccttgaac accggctttc   2940
tcgcggcctt gttctacacc aaccgcttta actcgtcagg gtgtccaggg cgcctgtccg   3000
cctgccgcaa catcgaggct ttccggatag ggtggggcac cctacagtac gaggataatg   3060
tcaccaatcc agaggatatg aggccgtact gctggcacta ccccccaaag ccgtgtggcg   3120
tagtccccgc gaggtctgtg tgtggcccag tgtactgttt cacccccagc ccggtagtag   3180
tgggcacgac cgacagacgt ggagtgccca cctacacatg gggagagaat gagacagatg   3240
tcttcctact gaacagcacc cgaccgccgc agggctcatg gttcggctgc acgtggatga   3300
actccactgg tttcaccaag acttgtggcg cgccaccttg ccgcaccaga gctgacttca   3360
acgccagcac ggacttgttg tgccctacgg attgttttag gaagcatcct gatgccactt   3420
atattaagtg tggttctggg ccctggctca caccaaagtg cctggtccac taccccttaca  3480
gactctggca ttacccctgc acagtcaatt ttaccatctt caagataaga atgtatgtag   3540
ggggggttga gcacaggctc acggccgcat gcaacttcac tcgtggggat cgctgcgact   3600
tggaggacag ggacaggagt cagctgtctc ctctgttgca ctctaccacg gaatgggcca   3660
tcctgccctg cacctactca gacttacccg ctttgtcaac tggtcttctc caccttcacc   3720
agaacatcgt ggacgtacaa tacatgtatg gcctctcacc tgctatcaca aaatacgtcg   3780
ttcgatggga gtgggtggta ctcttattcc tgctcttagc ggacgccaga gtctgcgcct   3840
gcttgtggat gctcatcttg ttgggccagg ccgaagcagc attggagaag ttggtcgtct   3900
tgcacgctgc gagtgcggct aactgccatg gcctcctata ttttgccatc ttcttcgtgg   3960
cagcttggca catcagggt cgggtggtcc ccttgaccac ctattgcctc actggcctat   4020
ggcccttctg cctactgctc atggcactgc cccggcaggc ttatgcctat gacgcacctg   4080
tgcacggaca gataggcgtg ggtttgttga tattgatcac cctcttcaca ctcaccccgg   4140
ggtataagac cctcctcggc cagtgtctgt ggtggttgtg ctatctcctg accctggggg   4200
aagccatgat tcaggagtgg gtaccaccca tgcaggtgcg cggcggccgc gatggcatcg   4260
cgtgggccgt cactatattc tgcccgggtg tggtgtttga cattaccaaa tggcttttgg   4320
cgttgcttgg gcctgcttac ctcttaaggg ccgctttgac acatgtgccg tacttcgtca   4380
gagctcacgc tctgataagg gtatgcgctt tggtgaagca gctcgcgggg ggtaggtatg   4440
ttcaggtggc gctattggcc cttggcaggt ggactggcac ctacatctat gaccacctca   4500
cacctatgtc ggactgggcc gctagcggcc tgcgcgactt agcggtcgcc gtggaaccca   4560
tcatcttcag tccgatggag aagaaggtca tcgtctgggg agcggagacg gctgcatgtg   4620
gggacattct acatggactt cccgtgtccg cccgactcgg ccaggagatc ctcctcggcc   4680
cagctgatgg ctacacctcc aaggggtgga gctccttgc tcccatcact gcttatgccc   4740
agcaaacacg aggcctcctg ggcgccatag tggtgagtat gacggggcgt gacaggacag   4800
aacaggccgg ggaagtccaa atcctgtcca cagtctctca gtccttcctc ggaacaacca   4860
tctcgggggt tttgtggact gtttaccacg gagctgcaa caagactcta gccggcttac   4920
ggggtccggt cacgcagatg tactcgagtc ctgagggga cttggtaggc tggcccagcc   4980
cccctgggac caagtctttg gagccgtgca agtgtgagc cgtcgaccta tatctggtca   5040
cgcggaacgc tgatgtcatc ccggctcgga gacgcgggga caagcgggga gcattgctct   5100
ccccgagacc catttcgacc ttgaaggggt cctcggggg gccggtgctc tgccctaggg   5160
gccacgtcgt tgggctcttc cgagcagctg tgtgctctcg gggcgtggcc aaatccatcg   5220
```

```
atttcatccc cgttgagaca ctcgacgttg ttacaaggtc tcccactttc agtgacaaca    5280
gcacgccacc ggctgtgccc cagacctatc aggtcgggta cttgcatgct ccaactggca    5340
gtggaaagag caccaaggtc cctgtcgcgt atgccgccca ggggtacaaa gtactagtgc    5400
ttaacccctc ggtagctgcc accctggggt ttggggcgta cctatccaag gcacatggca    5460
tcaatcccaa cattaggact ggagtcagga ccgtgatgac cggggaggcc atcacgtact    5520
ccacatatgg caaatttctc gccgatgggg gctgcgctag cggcgcctat gacatcatca    5580
tatgcgatga atgccacgct gtggatgcta cctccattct cggcatcgga acggtccttg    5640
atcaagcaga gacagccggg gtcagactaa ctgtgctggc tacggccaca ccccccgggt    5700
cagtgacaac cccccatccc gatatagaag aggtaggcct cggcgcggag ggtgagatcc    5760
ccttctatgg gagggcgatt cccctatcct gcatcaaggg agggagacac ctgattttct    5820
gccactcaaa gaaaaagtgt gacgagctcg cggcggccct tcggggcatg ggcttgaatg    5880
ccgtggcata ctatagaggg ttggacgtct ccataatacc agctcaggga gatgtggtgg    5940
tcgtcgccac cgacgccctc atgacggggt acactggaga ctttgactcc gtgatcgact    6000
gcaatgtagc ggtcacccaa gctgtcgact tcagcctgga ccccaccttc actataacca    6060
cacagactgt cccacaagac gctgtctcac gcagtcagcg ccgcgggcgc acaggtagag    6120
gaagacaggg cacttatagg tatgtttcca ctggtgaacg agcctcagga atgtttgaca    6180
gtgtagtgct tgtgagtgca tacgacgcag gggctgcgtg gtacgatctc accagcggg    6240 agaccaccgt caggcttaga gcgtatttca acacgcccgg cctacccgtg tgtcaagacc    6300
atcttgaatt ttgggaggca gttttcaccg gcctcacaca catagacgcc cacttcctct    6360
cccaaacaaa gcaagcgggg gagaacttcg cgtacctagt agcctaccaa gctacggtgt    6420
gcgccagagc caaggcccct cccccgtcct gggacgccat gtggaagtgc ctggcccgac    6480
tcaagcctac gcttgcgggc cccacacctc tcctgtaccg tttgggccct attaccaatg    6540
aggtcacccc cacacaccct gggacgaagt acatcgccac atgcatgcaa gctgaccttg    6600
aggtcatgac cagcacgtgg gtcctagctg gaggagtcct ggcagccgtc gccgcatatt    6660
gcctggcgac tggatgcgtt tccatcatcg gccgcttgca cgtcaaccag cgagtcgtcg    6720
ttgcgccgga taaggaggtc ctgtatgagg cttttgatga gatggaggaa tgcgcctcta    6780
gggcggctct catcgaagag gggcagcgga tagccgagat gttgaagtcc aagatccaag    6840
gcttgctgca gcaggcctct aagcaggccc aggacataca cccgctatg caggcttcat    6900 ggcccaaagt ggaacaattt tgggccagac acatgtggaa cttcattagc ggcatccaat    6960
acctcgcagg attgtcaaca ctgccaggga accccgcgt ggcttccatg atggcattca    7020
gtgccgccct caccagtccg ttgtcgacca gtaccaccat ccttctcaac atcatgggag    7080
gctggttagc gtcccagatc gcaccacccg cggggggccac cggctttgtc gtcagtggcc    7140 tggtggggc tgccgtgggc agcataggcc tgggtaaggt gctggtggac atcctggcag    7200
gatatggtgc gggcatttcg ggggccctcg tcgcattcaa gatcatgtct ggcgagaagc    7260
cctctatgga agatgtcatc aatctactgc ctgggatcct gtctccggga gccctggtgg    7320
tgggggtcat ctgcgcggcc attctgcgcc gccacgtggg accggggag ggcgcggtcc    7380 aatgatgaa caggcttatt gcctttgctt ccagaggaaa ccacgtcgcc ctactcact    7440 acgtgacgga gtcggatgcg tcgcagcgtg tgacccaact acttggctct cttactataa    7500
ccagcctact cagaagactc cacaattgga taactgagga ctgccccatc ccatgctccg    7560
gatcctggct ccgcgacgtg tgggactggg tttgcaccat cttgacagac ttcaaaaatt    7620
```

```
ggctgacctc taaattgttc cccaagctgc ccggcctccc cttcatctct tgtcaaaagg   7680
ggtacaaggg tgtgtgggcc ggcactggca tcatgaccac gcgctgccct tgcggcgcca   7740
acatctctgg caatgtccgc ctgggctcta tgaggatcac agggcctaaa acctgcatga   7800
acacctggca ggggaccttt cctatcaatt gctacacgga gggccagtgc gcgccgaaac   7860
cccccacgaa ctacaagacc gccatctgga gggtggcggc ctcggagtac gcggaggtga   7920
cgcagcatgg gtcgtactcc tatgtaacag gactgaccac tgacaatctg aaaattcctt   7980
gccaactacc ttctccagag ttttttctcct gggtggacgg tgtgcagatc cataggtttg   8040
cacccacacc aaagccgttt ttccgggatg aggtctcgtt ctgcgttggg cttaattcct   8100
atgctgtcgg gtcccagctt ccctgtgaac ctgagcccga cgcagacgta ttgaggtcca   8160
tgctaacaga tccgccccac atcacggcgg agactgcggc gcggcgcttg gcacggggat   8220
cacctccatc tgaggcgagc tcctcagtga gccagctatc agcaccgtcg ctgcgggcca   8280
cctgcaccac ccacagcaac acctatgacg tggacatggt cgatgccaac ctgctcatgg   8340
agggcggtgt ggctcagaca gagcctgagt ccagggtgcc cgttctggac tttctcgagc   8400
caatggccga ggaagagagc gaccttgagc cctcaatacc atcggagtgc atgctcccca   8460
ggagcgggtt tccacgggcc ttaccggctt gggcacggcc tgactacaac ccgccgctcg   8520
tggaatcgtg gaggaggcca gattaccaac cgcccaccgt tgctggttgt gctctccccc   8580
cccccaagaa ggccccgacg cctcccccaa ggagacgccg gacagtgggt ctgagcgaga   8640
gcaccatatc agaagccctc cagcaactgg ccatcaagac cttggccag cccccctcga   8700
gcggtgatgc aggctcgtcc acggggcgg gcgccgccga atccggcggt ccgacgtccc   8760
ctggtgagcc ggcccctca gagacaggtt ccgcctcctc tatgccccc ctcgagggg   8820
agcctggaga tccggacctg gagtctgatc aggtagagct tcaacctccc ccccaggggg   8880
ggggggtagc tcccggttcg ggctcggggt cttggtctac ttgctccgag gaggacgata   8940
ccaccgtgtg ctgctccatg tcatactcct ggaccggggc tctaataact ccctgtagcc   9000
ccgaagagga aaagttgcca atcaacccctt tgagtaactc gctgttgcga taccataaca   9060
aggtgtactg tacaacatca aagagcgcct cacagagggc taaaaaggta acttttgaca   9120
ggacgcaagt gctcgacgcc cattatgact cagtcttaaa ggacatcaag ctagcggctt   9180
ccaaggtcag cgcaaggctc ctcaccttgg aggaggcgtg ccagttgact ccaccccatt   9240
ctgcaagatc caagtatgga ttcggggcca aggaggtccg cagcttgtcc gggagggccg   9300
ttaaccacat caagtccgtg tggaaggacc tcctggaaga cccacaaaca ccaattccca   9360
caaccatcat ggccaaaaat gaggtgttct gcgtggaccc cgccaagggg ggtaagaaac   9420
cagctcgcct catcgtttac cctgacctcg gcgtccgggt ctgcgagaaa atggccctct   9480
atgacattac acaaaagctt cctcaggcgg taatgggagc ttcctatggc ttccagtact   9540
cccctgccca acgggtggag tatctcttga agcatgggc ggaaaagaag gaccccatgg   9600
gttttttcgta tgatacccga tgcttcgact caaccgtcac tgagagagac atcaggaccg   9660
aggagtccat ataccaggcc tgctccctgc ccgaggaggc ccgcactgcc atacactcgc   9720
tgactgagag actttacgta ggagggccca tgttcaacag caagggtcaa acctgcggtt   9780
acagacgttg ccgcgccagc ggggtgctaa ccactagcat gggtaacacc atcacatgct   9840
atgtgaaagc cctagcggcc tgcaaggctg cggggatagt tgcgcccaca atgctggtat   9900
gcggcgatga cctagtagtc atctcagaaa gccaggggac tgaggaggac gagcggaacc   9960
tgagagcctt cacggaggcc atgaccaggt actctgcccc tcctggtgat ccccccagac  10020
```

```
cggaatatga cctggagcta ataacatcct gttcctcaaa tgtgtctgtg gcgttgggcc   10080
cgcggggccg ccgcagatac tacctgacca gagacccaac cactccactc gcccgggctg   10140
cctgggaaac agttagacac tcccctatca attcatggct gggaaacatc atccagtatg   10200
ctccaaccat atgggttcgc atggtcctaa tgacacactt cttctccatt ctcatggtcc   10260
aagacaccct ggaccagaac ctcaactttg agatgtatgg atcagtatac tccgtgaatc   10320
ctttggacct tccagccata attgagaggt tacacgggct tgacgccttt tctatgcaca   10380
catactctca ccacgaactg acgcgggtgg cttcagccct cagaaaactt ggggcgccac   10440
ccctcagggt gtggaagagt cgggctcgcg cagtcagggc gtccctcatc tcccgtggag   10500
ggaaagcggc cgtttgcggc cgatatctct tcaattgggc ggtgaagacc aagctcaaac   10560
tcactccatt gccggaggcg cgcctactgg acttatccag ttggttcacc gtcggcgccg   10620 gcggggcga cattttcac agcgtgtcgc gcgcccgacc ccgctcatta ctcttcggcc   10680
tactcctact tttcgtaggg gtaggcctct tcctactccc cgctcggtag agcggcacac   10740
actaggtaca ctccatagct aactgttcct tttttttttt tttttttttt tttttttttt   10800
tttttttttt ttcttttttt tttttttccc tctttcttcc cttctcatct tattctactt   10860
tctttcttgg tggctccatc ttagccctag tcacggctag ctgtgaaagg tccgtgagcc   10920
gcatgactgc agagagtgcc gtaactggtc tctctgcaga tcatgtctag agtcgacctg   10980
caggcatgca agcttggcac tggccgtcgt tttacaacgt cgtgactggg aaaaccctgg   11040
cgttacccaa cttaatcgcc ttgcagcaca tccccctttc gccagctggc gtaatagcga   11100
agaggcccgc accgatcgcc cttcccaaca gttgcgcagc ctgaatggcg aatggcgcct   11160
gatgcggtat tttctcctta cgcatctgtg cggtatttca caccgcatat ggtgcactct   11220
cagtacaatc tgctctgatg ccgcatagtt aagccagccc cgacacccgc caacacccgc   11280
tgacgcgccc tgacgggctt gtctgctccc ggcatccgct tacagacaag ctgtgaccgt   11340
ctccgggagc tgcatgtgtc agaggttttc accgtcatca ccgaaacgcg cgagacgaaa   11400
gggcctcgtg atacgcctat ttttataggt taatgtcatg ataataatgg tttcttagac   11460
gtcaggtggc acttttcggg gaaatgtgcg cggaacccct atttgtttat ttttctaaat   11520
acattcaaat atgtatccgc tcatgagaca ataaccctga taaatgcttc aataatattg   11580
aaaaaggaag agtatgagta ttcaacattt ccgtgtcgcc cttattccct ttttgcggc    11640 attttgcctt cctgttttg ctcacccaga aacgctggtg aaagtaaaag atgctgaaga    11700
tcagttgggt gcacgagtgg gttacatcga actggatctc aacagcggta agatccttga   11760
gagttttcgc cccgaagaac gttttccaat gatgagcact tttaaagttc tgctatgtgg   11820
cgcggtatta tcccgtattg acgccgggca agagcaactc ggtcgccgca tacactattc   11880
tcagaatgac ttggttgagt actcaccagt cacagaaaag catcttacgg atggcatgac   11940
agtaagagaa ttatgcagtg ctgccataac catgagtgat aacactgcgg ccaacttact   12000
tctgacaacg atcggaggac cgaaggagct aaccgctttt ttgcacaaca tgggggatca   12060
tgtaactcgc cttgatcgtt gggaaccgga gctgaatgaa gccataccaa acgacgagcg   12120
tgacaccacg atgcctgtag caatggcaac aacgttgcgc aaactattaa ctggcgaact   12180
acttactcta gcttcccggc aacaattaat agactggatg gaggcggata agttgcagg    12240 accacttctg cgctcggccc ttccggctgg ctggtttatt gctgataaat ctggagccgg   12300
tgagcgtggg tctcgcggta tcattgcagc actggggcca gatggtaagc cctcccgtat   12360
cgtagttatc tacacgacgg ggagtcaggc aactatggat gaacgaaata gacagatcgc   12420
```

```
tgagataggt gcctcactga ttaagcattg gtaactgtca gaccaagttt actcatatat    12480
actttagatt gatttaaaac ttcatttta atttaaaagg atctaggtga agatcctttt    12540
tgataatctc atgaccaaaa tcccttaacg tgagttttcg ttccactgag cgtcagaccc    12600
cgtagaaaag atcaaaggat cttcttgaga tcctttttt ctgcgcgtaa tctgctgctt    12660
gcaaacaaaa aaaccaccgc taccagcggt ggtttgtttg ccggatcaag agctaccaac    12720 tcttttccg aaggtaactg gcttcagcag agcgcagata ccaaatactg ttcttctagt    12780
gtagccgtag ttaggccacc acttcaagaa ctctgtagca ccgcctacat acctcgctct    12840
gctaatcctg ttaccagtgg ctgctgccag tggcgataag tcgtgtctta ccgggttgga    12900
ctcaagacga tagttaccgg ataaggcgca gcggtcgggc tgaacggggg gttcgtgcac    12960
acagcccagc ttggagcgaa cgacctacac cgaactgaga tacctacagc gtgagctatg    13020
agaaagcgcc acgcttcccg aagggagaaa ggcggacagg tatccggtaa gcggcagggt    13080
cggaacagga gagcgcacga gggagcttcc agggggaaac gcctggtatc tttatagtcc    13140
tgtcgggttt cgccacctct gacttgagcg tcgatttttg tgatgctcgt caggggggcg    13200
gagcctatgg aaaaacgcca gcaacgcggc cttttacgg ttcctggcct tttgctggcc    13260
ttttgctcac atgttctttc ctgcgttatc ccctgattct gtggataacc gtattaccgc    13320
ctttgagtga gctgataccg ctcgccgcag ccgaacgacc gagcgcagcg agtcagtgag    13380
cgaggaagcg gaagagcgcc caatacgcaa accgcctctc ccgcgcgtt ggccgattca    13440 ttaatgcagc tggcacgaca ggtttcccga ctggaaagcg ggcagtgagc gcaacgcaat    13500
taatgtgagt tagctcactc attaggcacc ccaggcttta cactttatgc ttccggctcg    13560
tatgttgtgt ggaattgtga gcggataaca atttcacaca ggaaacagct atgacatgat    13620
tac                                                                  13623

<210> SEQ ID NO 7
<211> LENGTH: 13407
<212> TYPE: DNA
<213> ORGANISM: Artificial Sequence
<220> FEATURE:
<223> OTHER INFORMATION: Synthetic plasmid: pGFPF2AUbJFH1

<400> SEQUENCE: 7
gaattcccaa acgcgttaat acgactcact atagacctgc ccctaatagg ggcgacactc      60
cgccatgaat cactcccctg tgaggaacta ctgtcttcac gcagaaagcg cctagccatg     120
gcgttagtat gagtgtcgta cagcctccag gccccccct cccgggagag ccatagtggt     180
ctgcggaacc ggtgagtaca ccggaattgc cgggaagact gggtcctttc ttggataaac     240
ccactctatg cccggccatt tgggcgtgcc cccgcaagac tgctagccga gtagcgttgg     300
gttgcgaaag gccttgtggt actgcctgat agggcgcttg cgagtgcccc ggaggtctc      360 gtagaccgtg caccatgagc acaaatccta aacctcaaag aaaaaccaaa atggtgagca     420
agggcgagga gctgttcacc ggggtggtgc ccatcctggt cgagctggac ggcgacgtaa     480
acggccacaa gttcagcgtg tccggcgagg gcgagggcga tgccacctac ggcaagctga     540
ccctgaagtt catctgcacc accggcaagc tgcccgtgcc ctggcccacc ctcgtgacca     600
ccctgaccta cggcgtgcag tgcttcagcc gctaccccga ccacatgaag cagcacgact     660
tcttcaagtc cgccatgccc gaaggctacg tccaggagcg caccatcttc ttcaaggacg     720
acggcaacta caagacccgc gccgaggtga agttcgaggg cgacaccctg gtgaaccgca     780
tcgagctgaa gggcatcgac ttcaaggagg acggcaacat cctggggcac aagctggagt     840
```

```
acaactacaa cagccacaac gtctatatca tggccgacaa gcagaagaac ggcatcaagg    900
tgaacttcaa gatccgccac aacatcgagg acggcagcgt gcagctcgcc gaccactacc    960
agcagaacac ccccatcggc gacggccccg tgctgctgcc cgacaaccac tacctgagca   1020
cccagtccgc cctgagcaaa gaccccaacg agaagcgcga tcacatggtc ctgctggagt   1080
tcgtgaccgc cgccgggatc actctcggca tggacgagct gtacaagctg ttgaattttg   1140
accttcttaa gcttgcggga gacgtcgagt ccaaccctgg gcccatgcag atcttcgtga   1200
agaccctgac gggcaagacc atcactcttg aggtcgagcc cagtgacacc atcgagaatg   1260
tcaaggccaa gatccaagac aaggaaggca tcccacctga ccagcagagg ctgatattcg   1320
cgggcaaaca gctggaggat ggccgcaccc tgtccgacta caacatccag aaagagtcca   1380
ccttgcacct ggtgctgcgt ctccgcggtg gtatgagcac aaatcctaaa cctcaaagaa   1440
aaaccaaaag aaacaccaac cgtcgcccag aagacgttaa gttcccgggc ggcggccaga   1500
tcgttggcgg agtatacttg ttgccgcgca ggggccccag gttgggtgtg cgcacgacaa   1560
ggaaaacttc ggagcggtcc cagccacgtg ggagacgcca gcccatcccc aaagatcggc   1620
gctccactgg caaggcctgg ggaaaaccag gtcgcccctg gccctatat gggaatgagg    1680
gactcggctg gcaggatgg ctcctgtccc cccgaggctc tcgcccctcc tggggcccca    1740
ctgaccccg gcataggtcg cgcaacgtgg gtaaagtcat cgacaccta acgtgtggct     1800
ttgccgacct catggggtac atccccgtcg taggcgcccc gcttagtggc gccgccagag   1860
ctgtcgcgca cggcgtgaga gtcctggagg acggggttaa ttatgcaaca gggaacctac   1920
ccggtttccc cttttctatc ttcttgctgg ccctgttgtc ctgcatcacc gttccggtct   1980
ctgctgccca ggtgaagaat accagtagca gctacatggt gaccaatgac tgctccaatg   2040
acagcatcac ttggcagctc gaggctgcgg ttctccacgt ccccgggtgc gtcccgtgcg   2100
agagagtggg gaatacgtca cggtgttggg tgccagtctc gccaaacatg gctgtgcggc   2160
agcccggtgc cctcacgcag ggtctgcgga cgcacatcga tatggttgtg atgtccgcca   2220
ccttctgctc tgctctctac gtgggggacc tctgtggcgg ggtgatgctc gcggcccagg   2280
tgttcatcgt ctcgccgcag taccactggt ttgtgcaaga atgcaattgc tccatctacc   2340
ctggcaccat cactggacac cgcatggcat gggacatgat gatgaactgg tcgcccacgg   2400
ccaccatgat cctggcgtac gtgatgcgcg tccccgaggt catcatagac atcgttagcg   2460
gggctcactg gggcgtcatg ttcggcttgg cctacttctc tatgcaggga gcgtgggcga   2520
aggtcattgt catccttctg ctggccgctg gggtggacg gggcaccacc accgttggag   2580
gcgctgttgc acgttccacc aacgtgattg ccggcgtgtt cagccatggc cctcagcaga   2640
acattcagct cattaacacc aacggcagtt ggcacatcaa ccgtactgcc ttgaattgca   2700
atgactcctt gaacaccggc tttctcgcgg ccttgttcta caccaaccgc tttaactcgt   2760
cagggtgtcc agggcgcctg tccgcctgcc gcaacatcga ggctttccgg ataggtgggg   2820
gcaccctaca gtacgaggat aatgtcacca atcagagga tatgaggccg tactgctggc   2880
actacccccc aaagccgtgt ggcgtagtcc ccgcgaggtc tgtgtgtggc ccagtgtact   2940
gtttcacccc cagcccggta gtagtgggca cgaccgacag acgtggagtg cccacctaca   3000
catgggagaa gaatgagaca gatgtcttcc tactgaacag cacccgaccg ccgcagggct   3060
catggttcgg ctgcacgtgg atgaactcca ctggtttcac caagacttgt ggcgcgccac   3120
cttgccgcac cagagctgac ttcaacgcca gcacggactt ggttgtgccct acggattgtt   3180
ttaggaagca tcctgatgcc acttatatta agtgtggttc tgggccctgg ctcacaccaa   3240
```

```
agtgcctggt ccactaccct tacagactct ggcattaccc ctgcacagtc aattttacca    3300
tcttcaagat aagaatgtat gtaggggggg ttgagcacag gctcacggcc gcatgcaact    3360
tcactcgtgg ggatcgctgc gacttggagg acagggacag gagtcagctg tctcctctgt    3420
tgcactctac cacggaatgg gccatcctgc cctgcaccta ctcagactta cccgctttgt    3480
caactggtct tctccacctt caccagaaca tcgtggacgt acaatacatg tatggcctct    3540
cacctgctat cacaaaatac gtcgttcgat gggagtgggt ggtactctta ttcctgctct    3600
tagcggacgc cagagtctgc gcctgcttgt ggatgctcat cttgttgggc caggccgaag    3660
cagcattgga gaagttggtc gtcttgcacg ctgcgagtgc ggctaactgc catggcctcc    3720
tatattttgc catcttcttc gtggcagctt ggcacatcag gggtcgggtg gtccccttga    3780
ccacctattg cctcactggc ctatggccct tctgcctact gctcatggca ctgccccggc    3840
aggcttatgc ctatgacgca cctgtgcacg gacagatagg cgtgggtttg ttgatattga    3900
tcaccctctt cacactcacc ccgggggtata agaccctcct cggccagtgt ctgtggtggt    3960
tgtgctatct cctgaccctg ggggaagcca tgattcagga gtgggtacca cccatgcagg    4020
tgcgcggcgg ccgcgatggc atcgcgtggg ccgtcactat attctgcccg ggtgtggtgt    4080
ttgacattac caaatggctt ttggcgttgc ttgggcctgc ttacctctta agggccgctt    4140
tgacacatgt gccgtacttc gtcagagctc acgtctgat aagggtatgc gctttggtga    4200
agcagctcgc ggggggtagg tatgttcagg tggcgctatt ggcccttggc aggtggactg    4260
gcacctacat ctatgaccac ctcacaccta tgtcggactg ggccgctagc ggcctgcgcg    4320
acttagcggt cgccgtggaa cccatcatct tcagtccgat ggagaagaag gtcatcgtct    4380
ggggagcgga gacggctgca tgtggggaca ttctacatgg acttcccgtg tccgcccgac    4440
tcggccagga gatcctcctc ggcccagctg atggctacac ctccaagggg tggaagctcc    4500
ttgctcccat cactgcttat gcccagcaaa cacgaggcct cctgggcgcc atagtggtga    4560
gtatgacggg gcgtgacagg acagaacagg ccggggaagt ccaaatcctg tccacagtct    4620
ctcagtcctt cctcggaaca accatctcgg gggttttgtg gactgtttac cacgagctg    4680
gcaacaagac tctagccggc ttacggggtc cggtcacgca gatgtactcg agtgctgagg    4740
gggacttggt aggctggccc agccccccctg ggaccaagtc tttggagccg tgcaagtgtg    4800
gagccgtcga cctatatctg gtcacgcgga acgctgatgt catcccggct cggagacgcg    4860
gggacaagcg gggagcattg ctctccccga gacccatttc gaccttgaag gggtcctcgg    4920
gggggccggt gctctgccct aggggccacg tcgttgggct cttccgagca gctgtgtgct    4980
ctcggggcgt ggccaaatcc atcgatttca tccccgttga cactcgac gttgttacaa    5040
ggtctcccac tttcagtgac aacagcacgc caccggctgt gccccagacc tatcaggtcg    5100
ggtacttgca tgctccaact ggcagtggaa agagcaccaa ggtccctgtc gcgtatgccg    5160
cccagggta caaagtacta gtgcttaacc cctcggtagc tgccaccctg ggtttgggg    5220
cgtacctatc caaggcacat ggcatcaatc ccaacattag gactggagtc aggaccgtga    5280
tgaccgggga ggccatcacg tactccacat atggcaaatt tctcgccgat gggggctgcg    5340
ctagcggcgc ctatgacatc atcatatgcg atgaatgcca cgctgtggat gctacctcca    5400
ttctcggcat cggaacggtc cttgatcaag cagagacagc cggggtcaga ctaactgtgc    5460
tggctacggc cacaccccccc gggtcagtga caacccccca tcccgatata aagaggtag    5520
gcctcggcg ggagggtgag atccccttct atggagggc gattccccta tcctgcatca    5580
agggagggag acacctgatt ttctgccact caaagaaaaa gtgtgacgag ctcgcggcgg    5640
```

```
cccttcgggg catgggcttg aatgccgtgg catactatag agggttggac gtctccataa    5700
taccagctca gggagatgtg gtggtcgtcg ccaccgacgc cctcatgacg gggtacactg    5760
gagactttga ctccgtgatc gactgcaatg tagcggtcac ccaagctgtc gacttcagcc    5820
tggaccccac cttcactata accacacaga ctgtcccaca agacgctgtc tcacgcagtc    5880
agcgccgcgg gcgcacaggt agaggaagac agggcactta taggtatgtt tccactggtg    5940
aacgagcctc aggaatgttt gacagtgtag tgctttgtga gtgctacgac gcagggctg     6000 cgtggtacga tctcacacca gcggagacca ccgtcaggct tagagcgtat ttcaacacgc    6060
ccggcctacc cgtgtgtcaa gaccatcttg aattttggga ggcagttttc accggcctca    6120
cacacataga cgcccacttc ctctcccaaa caaagcaagc gggggagaac ttcgcgtacc    6180
tagtagccta ccaagctacg gtgtgcgcca gagccaaggc ccctcccccg tcctgggacg    6240
ccatgtggaa gtgcctggcc cgactcaagc ctacgcttgc gggccccaca cctctcctgt    6300
accgtttggg ccctattacc aatgaggtca ccctcacaca ccctgggacg aagtacatcg    6360
ccacatgcat gcaagctgac cttgaggtca tgaccagcac gtgggtccta gctggaggag    6420
tcctggcagc cgtcgccgca tattgcctgg cgactggatg cgtttccatc atcggccgct    6480
tgcacgtcaa ccagcgagtc gtcgttgcgc cggataagga ggtcctgtat gaggcttttg    6540
atgagatgga ggaatgcgcc tctagggcgg ctctcatcga agaggggcag cggatagccg    6600
agatgttgaa gtccaagatc caaggcttgc tgcagcaggc tctaagcag gcccaggaca     6660 tacaacccgc tatgcaggct tcatggccca aagtggaaca attttgggcc agacacatgt    6720
ggaacttcat tagcggcatc caatacctcg caggattgtc aacactgcca gggaaccccg    6780
cggtggcttc catgatggca ttcagtgccg ccctcaccag tccgttgtcg accagtacca    6840
ccatccttct caacatcatg ggaggctggt tagcgtccca gatcgcacca cccgcggggg    6900
ccaccggctt tgtcgtcagt ggcctggtgg gggctgccgt gggcagcata ggcctgggta    6960
aggtgctggt ggacatcctg gcaggatatg gtgcgggcat ttcgggggcc ctcgtcgcat    7020
tcaagatcat gtctggcgag aagccctcta tggaagatgt catcaatcta ctgcctggga    7080
tcctgtctcc gggagccctg gtggtggggg tcatctgcgc ggccattctg cgccgccacg    7140
tgggaccggg ggagggcgcg gtccaatgga tgaacaggct tattgccttt gcttccagag    7200
gaaaccacgt cgcccctact cactacgtga cggagtcgga tgcgtcgcag cgtgtgaccc    7260
aactacttgg ctctcttact ataaccagcc tactcagaag actccacaat tggataactg    7320
aggactgccc catcccatgc tccggatcct ggctccgcga cgtgtgggac tgggtttgca    7380
ccatcttgac agacttcaaa aattggctga cctctaaatt gttccccaag ctgcccggcc    7440
tccccttcat ctcttgtcaa aagggtacaa agggtgtgtg ggccggcact ggcatcatga    7500
ccacgcgctg cccttgcggc gccaacatct ctggcaatgt ccgcctgggc tctatgagga    7560
tcacagggcc taaaacctgc atgaacacct ggcagggac ctttcctatc aattgctaca     7620
cggagggcca gtgcgcgccg aaaccccca cgaactacaa gaccgccatc tggagggtgg     7680
cggcctcgga gtacgcggag gtgacgcagc atgggtcgta ctcctatgta acaggactga    7740
ccactgacaa tctgaaaatt ccttgccaac taccttctcc agagttttc tcctgggtgg     7800 acggtgtgca gatccatagg tttgcaccca ccaaagcc gttttttccgg gatgaggtct     7860 cgttctgcgt tgggcttaat tcctatgctg tcgggtccca gcttccctgt gaacctgagc    7920
ccgacgcaga cgtattgagg tccatgctaa cagatccgcc ccacatcacg gcggagactg    7980
cggcgcggcg cttggcacgg ggatcacctc catctgaggc gagctcctca gtgagccagc    8040
```

```
tatcagcacc gtcgctgcgg gccacctgca ccacccacag caacacctat gacgtggaca    8100
tggtcgatgc caacctgctc atggagggcg gtgtggctca gacagagcct gagtccaggg    8160
tgcccgttct ggactttctc gagccaatgg ccgaggaaga gagcgacctt gagccctcaa    8220
taccatcgga gtgcatgctc cccaggagcg ggtttccacg ggccttaccg gcttgggcac    8280
ggcctgacta caacccgccg ctcgtggaat cgtggaggag ccagattac caaccgccca     8340
ccgttgctgg ttgtgctctc cccccccca agaaggcccc gacgcctccc ccaaggagac     8400
gccggacagt gggtctgagc gagagcacca tatcagaagc cctccagcaa ctggccatca    8460
agacctttgg ccagcccccc tcgagcggtg atgcaggctc gtccacgggg gcgggcgccg    8520
ccgaatccgg cggtccgacg tcccctggtg agccggcccc ctcagagaca ggttccgcct    8580
cctctatgcc ccccctcgag ggggagcctg agatccggga cctggagtct gatcaggtag    8640
agcttcaacc tcccccccag ggggggggg tagctcccgg ttcgggctcg gggtcttggt     8700
ctacttgctc cgaggaggac gataccaccg tgtgctgctc catgtcatac tcctggaccg    8760
gggctctaat aactccctgt agccccgaag aggaaaagtt gccaatcaac cctttgagta    8820
actcgctgtt gcgataccat aacaaggtgt actgtacaac atcaaagagc gcctcacaga    8880
gggctaaaaa ggtaactttt gacaggacgc aagtgctcga cgcccattat gactcagtct    8940
taaaggacat caagctagcg gcttccaagg tcagcgcaag gctcctcacc ttggaggagg    9000
cgtgccagtt gactccaccc cattctgcaa gatccaagta tggattcggg gccaaggagg    9060
tccgcagctt gtccgggagg gccgttaacc acatcaagtc cgtgtggaag gacctcctgg    9120
aagacccaca acaccaatt cccacaacca tcatggccaa aaatgaggtg ttctgcgtgg     9180
accccgccaa gggggtaag aaaccagctc gcctcatcgt ttaccctgac ctcggcgtcc     9240
gggtctgcga gaaatggcc ctctatgaca ttacacaaaa gcttcctcag gcggtaatgg     9300
gagcttccta tggcttccag tactcccctg cccaacgggt ggagtatctc ttgaaagcat    9360
gggcggaaaa gaaggacccc atgggttttt cgtatgatac ccgatgcttc gactcaaccg    9420
tcactgagag agacatcagg accgaggagt ccatatacca ggcctgctcc ctgcccgagg    9480
aggcccgcac tgccatacac tcgctgactg agagacttta cgtaggaggg cccatgttca    9540
acagcaaggg tcaaacctgc ggttacagac gttgccgcgc cagcggggtg ctaaccacta    9600
gcatgggtaa caccatcaca tgctatgtga agcccctagc ggcctgcaag gctgcgggga    9660
tagttgcgcc cacaatgctg gtatgcgcg atgacctagt agtcatctca gaaagccagg     9720
ggactgagga ggacgagcgg aacctgagag ccttcacgga ggccatgacc aggtactctg    9780
cccctcctgg tgatccccc agaccggaat atgacctgga gctaataaca tcctgttcct     9840
caaatgtgtc tgtggcgttg ggccgcgg gccgccgcag atactacctg accagagacc      9900
caaccactcc actcgcccgg gctgcctggg aaacagttag acactcccct atcaattcat    9960
ggctgggaaa catcatccag tatgctccaa ccatatgggt tcgcatggtc ctaatgacac    10020
acttcttctc cattctcatg gtccaagaca ccctggacca gaacctcaac tttgagatgt    10080
atggatcagt atactccgtg aatccttgg accttccagc cataattgag aggttacacg      10140
ggcttgacgc ctttttctatg cacacatact ctcaccacga actgacgcgg gtggcttcag   10200
ccctcagaaa acttggggcg ccaccccca gggtgtggaa gagtcgggct cgcgcagtca     10260
gggcgtccct catctcccgt ggagggaag cggccgtttg cggccgatat ctcttcaatt     10320
gggcggtgaa gaccaagctc aaactcactc cattgccgga ggcgcgccta ctggactttat   10380
ccagttggtt caccgtcggc gccggcgggg gcgacatttt tcacagcgtg tcgcgcgccc   10440
```

```
gaccccgctc attactcttc ggcctactcc tacttttcgt aggggtaggc ctcttcctac    10500
tccccgctcg gtagagcggc acacactagg tacactccat agctaactgt tcctttttt     10560 ttttttttt  ttttttttt  ttttttttt  ttttttcttt ttttttttt  tccctctttc    10620 ttcccttctc atcttattct actttctttc ttggtggctc catcttagcc ctagtcacgg    10680
ctagctgtga aaggtccgtg agccgcatga ctgcagagag tgccgtaact ggtctctctg    10740
cagatcatgt ctagagtcga cctgcaggca tgcaagcttg gcactggccg tcgttttaca    10800
acgtcgtgac tgggaaaacc ctggcgttac ccaacttaat cgccttgcag cacatccccc    10860
tttcgccagc tggcgtaata gcgaagaggc ccgcaccgat cgcccttccc aacagttgcg    10920
cagcctgaat ggcgaatggc gcctgatgcg gtattttctc cttacgcatc tgtgcggtat    10980
ttcacaccgc atatggtgca ctctcagtac aatctgctct gatgccgcat agttaagcca    11040
gccccgacac ccgccaacac ccgctgacgc gccctgacgg gcttgtctgc tcccggcatc    11100
cgcttacaga caagctgtga ccgtctccgg gagctgcatg tgtcagaggt tttcaccgtc    11160
atcaccgaaa cgcgcgagac gaaagggcct cgtgatacgc ctatttttat aggttaatgt    11220
catgataata atggtttctt agacgtcagg tggcactttt cggggaaatg tgcgcggaac    11280
ccctatttgt ttatttttct aaatacattc aaatatgtat ccgctcatga caataaacc     11340 ctgataaatg cttcaataat attgaaaaag gaagagtatg agtattcaac atttccgtgt    11400
cgcccttatt cccttttttg cggcattttg ccttcctgtt tttgctcacc cagaaacgct    11460
ggtgaaagta aaagatgctg aagatcagtt gggtgcacga gtgggttaca tcgaactgga    11520
tctcaacagc ggtaagatcc ttgagagttt tcgccccgaa gaacgttttc caatgatgag    11580
cacttttaaa gttctgctat gtggcgcggt attatcccgt attgacgccg ggcaagagca    11640
actcggtcgc cgcatacact attctcagaa tgacttggtt gagtactcac cagtcacaga    11700
aaagcatctt acggatggca tgacagtaag agaattatgc agtgctgcca taaccatgag    11760
tgataacact gcggccaact tacttctgac aacgatcgga ggaccgaagg agctaaccgc    11820
ttttttgcac aacatggggg atcatgtaac tcgccttgat cgttgggaac cggagctgaa    11880
tgaagccata ccaaacgacg agcgtgacac cacgatgcct gtagcaatgg caacaacgtt    11940
gcgcaaacta ttaactggcg aactacttac tctagcttcc cggcaacaat taatagactg    12000
gatggaggcg gataaagttg caggaccact tctgcgctcg gcccttccgg ctggctggtt    12060
tattgctgat aaatctggag ccggtgagcg tgggtctcgc ggtatcattg cagcactggg    12120
gccagatggt aagccctccc gtatcgtagt tatctacacg acggggagtc aggcaactat    12180
ggatgaacga aatagacaga tcgctgagat aggtgcctca ctgattaagc attggtaact    12240
gtcagaccaa gtttactcat atatacttta gattgattta aaacttcatt tttaatttaa    12300
aaggatctag gtgaagatcc tttttgataa tctcatgacc aaaatccctt aacgtgagtt    12360
ttcgttccac tgagcgtcag accccgtaga aaagatcaaa ggatcttctt gagatccttt    12420
ttttctgcgc gtaatctgct gcttgcaaac aaaaaaacca ccgctaccag cggtggtttg    12480
tttgccggat caagagctac caactctttt tccgaaggta actggcttca gcagagcgca    12540
gataccaaat actgttcttc tagtgtagcc gtagttaggc caccacttca agaactctgt    12600
agcaccgcct acatacctcg ctctgctaat cctgttacca gtggctgctg ccagtggcga    12660
taagtcgtgt cttaccgggt tggactcaag acgatagtta ccggataagg cgcagcggtc    12720
gggctgaacg gggggttcgt gcacacagcc cagcttggag cgaacgacct acaccgaact    12780
gagataccta cagcgtgagc tatgagaaag cgccacgctt cccgaaggga gaaaggcgga    12840
```

-continued

```
caggtatccg gtaagcggca gggtcggaac aggagagcgc acgagggagc ttccaggggg    12900
aaacgcctgg tatctttata gtcctgtcgg gtttcgccac ctctgacttg agcgtcgatt    12960
tttgtgatgc tcgtcagggg ggcggagcct atggaaaaac gccagcaacg cggccttttt    13020
acggttcctg gccttttgct ggccttttgc tcacatgttc tttcctgcgt tatcccctga    13080
ttctgtggat aaccgtatta ccgcctttga gtgagctgat accgctcgcc gcagccgaac    13140
gaccgagcgc agcgagtcag tgagcgagga agcggaagag cgcccaatac gcaaaccgcc    13200
tctccccgcg cgttggccga ttcattaatg cagctggcac gacaggtttc ccgactggaa    13260
agcgggcagt gagcgcaacg caattaatgt gagttagctc actcattagg caccccaggc    13320
tttacacttt atgcttccgg ctcgtatgtt gtgtggaatt gtgagcggat aacaatttca    13380
cacaggaaac agctatgaca tgattac                                       13407
```

<210> SEQ ID NO 8
<211> LENGTH: 13612
<212> TYPE: DNA
<213> ORGANISM: Artificial Sequence
<220> FEATURE:
<223> OTHER INFORMATION: pRLF2AUbHJ1

<400> SEQUENCE: 8

```
gaattcccaa acgcgttaat acgactcact atagacctgc cctaataggg gcgacactc      60 cgccatgaat cactcccctg tgaggaacta ctgtcttcac gcagaaagcg cctagccatg     120
gcgttagtat gagtgtcgta cagcctccag gccccccccct cccgggagag ccatagtggt    180
ctgcggaacc ggtgagtaca ccggaattgc cgggaagact gggtccttc ttggataaac     240 ccactctatg cccggccatt tgggcgtgcc ccgcaagac tgctagccga gtagcgttgg     300
gttgcgaaag gccttgtggt actgcctgat agggcgcttg cgagtgcccc gggaggtctc    360
gtagaccgtg caccatgagc acaaatccta aacctcaaag aaaaaccaaa atggcttcca    420
aggtgtacga ccccgagcaa cgcaaacgca tgatcactgg gcctcagtgg tgggctcgct    480
gcaagcaaat gaacgtgctg gactccttca tcaactacta tgattccgag aagcacgccg    540
agaacgccgt gattttttctg catggtaacg ctgcctccag ctacctgtgg aggcacgtcg    600
tgcctcacat cgagcccgtg gctagatgca tcatccctga tctgatcgga atgggtaagt    660
ccggcaagag cgggaatggc tcatatcgcc tcctggatca ctacaagtac ctcaccgctt    720
ggttcgagct gctgaacctt ccaaagaaaa tcatctttgt gggccacgac tgggggggctt    780 gtctggcctt tcactactcc tacgagcacc aagacaagat caaggccatc gtccatgctg    840
agagtgtcgt ggacgtgatc gagtcctggg acgagtggcc tgacatcgag gaggatatcg    900
ccctgatcaa gagcgaagag ggcgagaaaa tggtgcttga gaataacttc ttcgtcgaga    960
ccatgctccc aagcaagatc atgcggaaac tggagcctga ggagttcgct gcctacctgg    1020
agccattcaa ggagaagggc gaggttagac ggcctaccct ctcctggcct cgcgagatcc    1080
ctctcgttaa gggaggcaag cccgacgtcg tccagattgt ccgcaactac aacgcctacc    1140
ttcgggccag cgacgatctg cctaagatgt tcatcgagtc cgaccctggg ttctttttcca    1200 acgctattgt cgagggagct aagaagttcc ctaacaccga gttcgtgaag gtgaagggcc    1260
tccacttcag ccaggaggac gctccagatg aaatgggtaa gtacatcaag agcttcgtgg    1320
agcgcgtgct gaagaacgag cagctgttga atttttgacct tcttaagctt gcgggagacg    1380
tcgagtccaa ccctgggccc atgcagatct tcgtgaagac cctgacgggc aagaccatca    1440
ctcttgaggt cgagcccagt gacaccatcg agaatgtcaa ggccaagatc caagacaagg    1500
```

```
aaggcatccc acctgaccag cagaggctga tattcgcggg caaacagctg gaggatggcc  1560
gcaccctgtc cgactacaac atccagaaag agtccacctt gcacctggtg ctgcgtctcc  1620
gcggtggtat gagcacgaat cctaaacctc aaagaaaaac caaacgtaac accaaccgtc  1680
gcccacagga cgtcaagttc ccgggtggcg gtcagatcgt tggtggagtt tacttgttgc  1740
cgcgcagggg ccctagattg ggtgtgcgcg cgacgaggaa gacttccgag cggtcgcaac  1800
ctcgaggtag acgtcagcct atccccaagg cacgtcggcc cgagggcagg acctgggctc  1860
agcccgggta cccttggccc ctctatggca atgagggttg cgggtgggcg ggatggctcc  1920
tgtctccccg tggctctcgg cctagctggg gccccacaga ccccggcgt aggtcgcgca  1980 atttgggtaa ggtcatcgat acccttacgt gcggcttcgc cgacctcatg ggtacatac  2040 cgctcgtcgg cgcccctctt ggaggcgctg ccagggccct ggcgcatggc gtccgggttc  2100
tggaagacgg cgtgaactat gcaacaggga accttcctgg ttgctctttc tctatcttcc  2160
ttctggccct gctctcttgc ctgactgtgc ccgcttcagc ctaccaagtg cgcaattcct  2220 cggggctta ccatgtcacc aatgattgcc ctaactcgag tattgtgtac gaggcggccg  2280
atgccatcct gcacactccg gggtgtgtcc cttgcgttcg cgagggtaac gcctcgaggt  2340
gttgggtggc ggtgaccccc acggtggcca ccagggacgg caaactcccc acaacgcagc  2400
ttcgacgtca tatcgatctg cttgtcggga gcgccaccct ctgctcggcc ctctacgtgg  2460
gggacctgtg cgggtctgtc tttcttgttg gtcaactgtt taccttctct cccaggcgcc  2520 actgacgac gcaagactgc aattgttcta tctatcccgg ccatataacg ggtcatcgca  2580
tggcatggga tatgatgatg aactggtccc ctacggcagc gttggtggta gctcagctgc  2640
tccggatccc acaagccatc atggacatga tcgctggtgc tcactgggga gtcctggcgg  2700
gcatagcgta tttctccatg gtggggaact gggcgaaggt cctggtagtg ctgctgctat  2760
ttgccggcgt cgacgcggaa acccacgtca ccggggggaag tgccggccgc accacggctg  2820
ggcttgttgg tctccttaca ccaggcgcca agcagaacat ccaactgatc aacaccaacg  2880
gcagttggca catcaatagc acggccttga actgcaatga aagccttaac accggctggt  2940
tagcagggct cttctatcag cacaaattca actcttcagg ctgtcctgag aggttggcca  3000
gctgccgacg ccttaccgat tttgcccagg gctggggtcc tatcagttat gccaacggaa  3060
gcggcctcga cgaacgcccc tactgctggc actaccctcc aagaccttgt ggcattgtgc  3120
ccgcaaagag cgtgtgtggc ccggtatatt gcttcactcc cagccccgtg gtggtgggaa  3180
cgaccgacag gtcgggcgcg cctacctaca gctggggtgc aaatgatacg gatgtcttcg  3240
tccttaacaa caccaggcca ccgctgggca attggttcgg ttgtacctgg atgaactcaa  3300
ctggattcac caaagtgtgc ggagcgcccc cttgtgtcat cggaggggtg ggcaacaaca  3360
ccttgctctg ccccactgat tgtttccgca agcatccgga agccacatac tctcggtgcg  3420
gctccggtcc ctggattaca cccaggtgca tggtcgacta cccgtatagg ctttggcact  3480
atccttgtac catcaattac accatattca aagtcaggat gtacgtggga ggggtcgagc  3540
acaggctgga agcggcctgc aactggacgc ggggcgaacg ctgtgatctg gaagacaggg  3600
acaggtccga gctcagccca ttgctgctgt ccaccacaca gtggcaggtc cttccgtgtt  3660 cttcacgac cctgccagcc ttgtccaccg gcctcatcca cctccaccag aacattgtgg  3720
acgtgcagta cttgtacggg gtagggtcaa gcatcgcgtc ctgggccatt aagtgggagt  3780
acgtcgttct cctgttcctc ctgcttgcag acgcgcgcgt ctgctcctgc ttgtggatga  3840
tgttactcat atcccaagcg gaggcggctt tggagaacct cgtaatactc aatgcagcat  3900
```

```
ccctggccgg gacgcacggt cttgtgtcct tcctcgtgtt cttctgcttt gcgtggtatc    3960
tgaagggtag gtgggtgccc ggagcggtct acgccttcta cgggatgtgg cctctcctcc    4020
tgctcctgct ggcgttgcct cagcgggcat acgcactgga cacggaggtg gccgcgtcgt    4080
gtggcggcgt tgttcttgtc gggttaatgg cgctgactct gtcgccatat tacaagcgct    4140
acatcagctg gtgcatgtgg tggcttcagt attttctgac cagagtagaa gcgcaactgc    4200
acgtgtgggt tccccccctc aacgtccggg ggggcgcga tggcatcgcg tgggccgtca    4260
ctatattctg cccgggtgtg gtgtttgaca ttaccaaatg gcttttggcg ttgcttgggc    4320
ctgcttacct cttaagggcc gctttgacac atgtgccgta cttcgtcaga gctcacgctc    4380
tgataagggt atgcgctttg gtgaagcagc tcgcggggg taggtatgtt caggtggcgc     4440
tattggccct tggcaggtgg actggcacct acatctatga ccacctcaca cctatgtcgg    4500
actgggccgc tagcggcctg cgcgacttag cggtcgccgt ggaacccatc atcttcagtc    4560
cgatggagaa gaaggtcatc gtctgggag cggagacggc tgcatgtggg gacattctac     4620
atggacttcc cgtgtccgcc cgactcggcc aggagatcct cctcggccca gctgatggct    4680
acacctccaa ggggtggaag ctccttgctc ccatcactgc ttatgcccag caaacacgag    4740
gcctcctggg cgccatagtg gtgagtatga cggggcgtga caggacagaa caggccgggg    4800
aagtccaaat cctgtccaca gtctctcagt ccttcctcgg aacaaccatc tcggggggttt   4860 tgtggactgt ttaccacgga gctggcaaca agactctagc cggcttacgg ggtccggtca    4920
cgcagatgta ctcgagtgct gagggggact tggtaggctg gcccagcccc cctgggacca    4980
agtctttgga gccgtgcaag tgtggagccg tcgacctata tctggtcacg cggaacgctg    5040
atgtcatccc ggctcggaga cgcggggaca agcggggagc attgctctcc ccgagaccca    5100
tttcgacctt gaaggggtcc tcgggggggc cggtgctctg ccctaggggc cacgtcgttg    5160
ggctcttccg agcagctgtg tgctctcggg gcgtggccaa atccatcgat ttcatccccg    5220
ttgagacact cgacgttgtt acaaggtctc ccactttcag tgacaacagc acgccaccgg    5280
ctgtgcccca gacctatcag gtcgggtact tgcatgctcc aactggcagt ggaaagagca    5340
ccaaggtccc tgtcgcgtat cccgcccagg ggtacaaagt actagtgctt aacccctcgg    5400
tagctgccac cctgggggtt gggcgtacc tatccaaggc acatggcatc aatcccaaca    5460
ttaggactgg agtcaggacc gtgatgaccg gggaggccat cacgtactcc acatatggca    5520
aatttctcgc cgatgggggc tgcgctagcg gcgcctatga catcatcata tgcgatgaat    5580
gccacgctgt ggatgctacc tccattctcg gcatcggaac ggtccttgat caagcagaga    5640
cagccggggt cagactaact gtgctggcta cggccacacc ccccgggtca gtgacaaccc    5700
cccatcccga tatagaagag gtaggcctcg ggcgggaggg tgagatcccc ttctatggga    5760
gggcgattcc cctatcctgc atcaagggag ggagacacct gattttctgc cactcaaaga    5820
aaaagtgtga cgagctcgcg gcggcccttc ggggcatggg cttgaatgcc gtggcatact    5880
atagagggtt ggacgtctcc ataataccag ctcaggaga tgtggtggtc gtcgccaccg     5940
acgccctcat gacggggtac actggagact ttgactccgt gatcgactgc aatgtagcgg    6000
tcacccaagc tgtcgacttc agcctggacc ccaccttcac tataaccaca cagactgtcc    6060
cacaagacgc tgtctcacgc agtcagcgcc gcgggcgcac aggtagagga agacagggca    6120
cttataggta tgtttccact ggtgaacgag cctcaggaat gtttgacagt gtagtgcttt    6180
gtgagtgcta cgacgcaggg gctgcgtggt acgatctcac accagcggag accaccgtca    6240
ggcttagagc gtatttcaac acgcccggcc tacccgtgtg tcaagaccat cttgaattt     6300
```

```
gggaggcagt tttcaccggc ctcacacaca tagacgccca cttcctctcc caaacaaagc   6360
aagcggggga gaacttcgcg tacctagtag cctaccaagc tacggtgtgc gccagagcca   6420
aggcccctcc cccgtcctgg gacgccatgt ggaagtgcct ggcccgactc aagcctacgc   6480
ttgcgggccc cacacctctc ctgtaccgtt tgggccctat taccaatgag gtcaccctca   6540
cacaccctgg gacgaagtac atcgccacat gcatgcaagc tgaccttgag gtcatgacca   6600
gcacgtgggt cctagctgga ggagtcctgg cagccgtcgc cgcatattgc ctggcgactg   6660
gatgcgtttc catcatcggc cgcttgcacg tcaaccagcg agtcgtcgtt gcgccggata   6720
aggaggtcct gtatgaggct tttgatgaga tggaggaatg cgcctctagg gcggctctca   6780
tcgaagaggg gcagcggata gccgagatgt tgaagtccaa gatccaaggc ttgctgcagc   6840
aggcctctaa gcaggcccag gacatacaac ccgctatgca ggcttcatgg cccaaagtgg   6900
aacaattttg ggccagacac atgtggaact tcattagcgg catccaatac ctcgcaggat   6960
tgtcaacact gccagggaac cccgcggtgg cttccatgat ggcattcagt gccgccctca   7020
ccagtccgtt gtcgaccagt accaccatcc ttctcaacat catgggaggc tggttagcgt   7080
cccagatcgc accaccgcg ggggccaccg gctttgtcgt cagtggcctg gtgggggctg   7140
ccgtgggcag cataggcctg ggtaaggtgc tggtggacat cctggcagga tatggtgcgg   7200
gcatttcggg ggccctcgtc gcattcaaga tcatgtctgg cgagaagccc tctatggaag   7260
atgtcatcaa tctactgcct gggatcctgt ctccgggagc cctggtggtg ggggtcatct   7320
gcgcggccat tctgcgccgc cacgtgggac cgggggaggg cgcggtccaa tggatgaaca   7380
ggcttattgc ctttgcttcc agaggaaacc acgtcgcccc tactcactac gtgacggagt   7440
cggatgcgtc gcagcgtgtg acccaactac ttggctctct tactataacc agcctactca   7500
gaagactcca caattggata actgaggact gccccatccc atgctccgga tcctggctcc   7560
gcgacgtgtg ggactgggtt tgcaccatct tgacagactt caaaaattgg ctgacctcta   7620
aattgttccc caagctgccc ggcctcccct tcatctcttg tcaaaagggg tacaagggtg   7680
tgtgggccgg cactggcatc atgaccacgc gctgcccttg cggcgccaac atctctggca   7740
atgtccgcct gggctctatg aggatcacag ggcctaaaac ctgcatgaac acctggcagg   7800
ggacctttcc tatcaattgc tacacggagg ccagtgcgc gccgaaaccc cccacgaact   7860
acaagaccgc catctggagg gtggcggcct cggagtacgc ggaggtgacg cagcatgggt   7920
cgtactccta tgtaacagga ctgaccactg acaatctgaa aattccttgc caactacctt   7980
ctccagagtt tttctcctgg gtggacggtg tgcagatcca taggtttgca cccacaccaa   8040
agccgttttt ccgggatgag gtctcgttct cgcgttgggct taattcctat gctgtcgggt   8100
cccagcttcc ctgtgaacct gagcccgacg cagacgtatt gaggtccatg ctaacagatc   8160
cgccccacat cacggcggag actgcggcgc ggcgcttggc acgggatca cctccatctg   8220 aggcgagctc ctcagtgagc cagctatcag caccgtcgct gcgggccacc tgcaccaccc   8280
acagcaacac ctatgacgtg gacatggtcg atgccaacct gctcatggag ggcggtgtgg   8340
ctcagacaga gcctgagtcc agggtgcccg ttctggactt tctcgagcca atggccgagg   8400
aagagagcga ccttgagccc tcaataccat cggagtgcat gctccccagg agcgggtttc   8460
cacgggcctt accggcttgg gcacggcctg actacaaccc gccgcgtcgtg gaatcgtgga   8520 ggaggccaga ttaccaaccg cccaccgttg ctggttgtgc ctctccccc cccaagaagg   8580 ccccgacgcc tccccaagg agacgccgga cagtgggtct gagcgagagc accatatcag   8640
aagccctcca gcaactggcc atcaagacct ttggccagcc cccctcgagc ggtgatgcag   8700
```

```
gctcgtccac gggggcgggc gccgccgaat ccggcggtcc gacgtcccct ggtgagccgg    8760 cccctcaga  gacaggttcc gcctcctcta tgccccccct cgaggggag  cctggagatc    8820 cggacctgga gtctgatcag gtagagcttc aacctccccc ccaggggggg ggggtagctc    8880
ccggttcggg ctcggggtct tggtctactt gctccgagga ggacgatacc accgtgtgct    8940
gctccatgtc atactcctgg accggggctc taataactcc ctgtagcccc gaagaggaaa    9000
agttgccaat caacccttg  agtaactcgc tgttgcgata ccataacaag gtgtactgta    9060
caacatcaaa gagcgcctca cagagggcta aaaaggtaac ttttgacagg acgcaagtgc    9120
tcgacgccca ttatgactca gtcttaaagg acatcaagct agcggcttcc aaggtcagcg    9180
caaggctcct caccttggag gaggcgtgcc agttgactcc accccattct gcaagatcca    9240
agtatggatt cggggccaag gaggtccgca gcttgtccgg gagggccgtt aaccacatca    9300
agtccgtgtg gaaggacctc ctggaagacc cacaaacacc aattcccaca accatcatgg    9360
ccaaaaatga ggtgttctgc gtggaccccg ccaaggggg  taagaaacca gctcgcctca    9420
tcgtttaccc tgacctcggc gtccgggtct gcgagaaaat ggccctctat gacattacac    9480
aaaagcttcc tcaggcggta atgggagctt cctatggctt ccagtactcc cctgcccaac    9540
gggtggagta tctcttgaaa gcatgggcgg aaaagaagga ccccatgggt ttttcgtatg    9600
atacccgatg cttcgactca accgtcactg agagagacat caggaccgag gagtccatat    9660
accaggcctg ctccctgccc gaggaggccc gcactgccat acactcgctg actgagagac    9720
tttacgtagg agggccatg  ttcaacagca agggtcaaac ctgcggttac agacgttgcc    9780
gcgccagcgg ggtgctaacc actagcatgg gtaacaccat cacatgctat gtgaaagccc    9840
tagcggcctg caaggctgcg gggatagttg cgcccacaat gctggtatgc ggcgatgacc    9900
tagtagtcat ctcagaaagc caggggactg aggaggacga gcggaacctg agagccttca    9960
cggaggccat gaccaggtac tctgcccctc ctggtgatcc cccagaccg  gaatatgacc   10020 tggagctaat aacatcctgt tcctcaaatg tgtctgtggc gttgggcccg cggggccgcc   10080
gcagatacta cctgaccaga gacccaacca ctccactcgc ccgggctgcc tgggaaacag   10140
ttagacactc ccctatcaat tcatggctgg gaaacatcat ccagtatgct ccaaccatat   10200
gggttcgcat ggtcctaatg acacacttct tctccattct catggtccaa gacaccctgg   10260
accagaacct caactttgag atgtatggat cagtatactc cgtgaatcct ttggaccttc   10320
cagccataat tgagaggtta cacgggcttg acgccttttc tatgcacaca tactctcacc   10380
acgaactgac gcgggtggct tcagccctca gaaaacttgg ggcgccaccc ctcagggtgt   10440
ggaagagtcg ggctcgcgca gtcagggcgt ccctcatctc ccgtggaggg aaagcggccg   10500
tttgcggccg atatctcttc aattgggcgg tgaagaccaa gctcaaactc actccattgc   10560
cggaggcgcg cctactggac ttatccagtt ggttcaccgt cggcgccggc gggggcgaca   10620
tttttcacag cgtgtcgcgc gcccgacccc gctcattact cttcggccta ctcctacttt   10680
tcgtaggggt aggcctcttc ctactccccg ctcggtagag cggcacacac taggtacact   10740
ccatagctaa ctgttccttt tttttttttt tttttttttt tttttttttt tttttttttt   10800
cttttttttt ttttccctc  tttcttccct tctcatctta ttctactttc tttcttggtg   10860
gctccatctt agccctagtc acggctagct gtgaaggtc  cgtgagccgc atgactgcag   10920
agagtgccgt aactggtctc tctgcagatc atgtctagag tcgacctgca ggcatgcaag   10980
cttggcactg gccgtcgttt tacaacgtcg tgactgggaa aaccctggcg ttacccaact   11040
taatcgcctt gcagcacatc cccctttcgc cagctggcgt aatagcgaag aggcccgcac   11100
```

```
cgatcgccct tcccaacagt tgcgcagcct gaatggcgaa tggcgcctga tgcggtattt   11160
tctccttacg catctgtgcg gtatttcaca ccgcatatgg tgcactctca gtacaatctg   11220
ctctgatgcc gcatagttaa gccagccccg acacccgcca acacccgctg acgcgccctg   11280
acgggcttgt ctgctcccgg catccgctta cagacaagct gtgaccgtct ccgggagctg   11340
catgtgtcag aggttttcac cgtcatcacc gaaacgcgcg agacgaaagg cctcgtgat    11400 acgcctattt ttataggtta atgtcatgat aataatggtt tcttagacgt caggtggcac   11460
ttttcgggga aatgtgcgcg gaaccsctat ttgtttattt ttctaaatac attcaaatat   11520
gtatccgctc atgagacaat aaccctgata aatgcttcaa taatattgaa aaaggaagag   11580
tatgagtatt caacatttcc gtgtcgccct tattccottt tttgcggcat tttgccttcc   11640
tgtttttgct cacccagaaa cgctggtgaa agtaaaagat gctgaagatc agttgggtgc   11700
acgagtgggt tacatcgaac tggatctcaa cagcggtaag atccttgaga gttttcgccc   11760
cgaagaacgt tttccaatga tgagcacttt taaagttctg ctatgtggcg cggtattatc   11820
ccgtattgac gccgggcaag agcaactcgg tcgccgcata cactattctc agaatgactt   11880
ggttgagtac tcaccagtca cagaaaagca tcttacggat ggcatgacag taagagaatt   11940
atgcagtgct gccataacca tgagtgataa cactgcggcc aacttacttc tgacaacgat   12000
cggaggaccg aaggagctaa ccgcttttt gcacaacatg gggatcatg taactcgcct    12060 tgatcgttgg gaaccggagc tgaatgaagc cataccaaac gacgagcgtg acaccacgat   12120
gcctgtagca atggcaacaa cgttgcgcaa actattaact ggcgaactac ttactctagc   12180
ttcccggcaa caattaatag actggatgga ggcggataaa gttgcaggac cacttctgcg   12240
ctcggccctt ccggctggct ggtttattgc tgataaatct ggagccggtg agcgtgggtc   12300
tcgcggtatc attgcagcac tggggccaga tggtaagccc tcccgtatcg tagttatcta   12360
cacgacgggg agtcaggcaa ctatggatga acgaaataga cagatcgctg agataggtgc   12420
ctcactgatt aagcattggt aactgtcaga ccaagtttac tcatatatac tttagattga   12480
tttaaaactt catttttaat ttaaaaggat ctaggtgaag atcctttttg ataatctcat   12540
gaccaaaatc ccttaacgtg agttttcgtt ccactgagcg tcagaccccg tagaaaagat   12600
caaaggatct tcttgagatc cttttttct gcgcgtaatc tgctgcttgc aaacaaaaaa   12660
accaccgcta ccagcggtgg tttgtttgcc ggatcaagag ctaccaactc ttttccgaa    12720 ggtaactggc ttcagcagag cgcagatacc aaatactgtc cttctagtgt agccgtagtt   12780
aggccaccac ttcaagaact ctgtagcacc gcctacatac ctcgctctgc taatcctgtt   12840
accagtggct gctgccagtg gcgataagtc gtgtcttacc gggttggact caagacgata   12900
gttaccggat aaggcgcagc ggtcgggctg aacggggggt tcgtgcacac agcccagctt   12960
ggagcgaacg acctacaccg aactgagata cctacagcgt gagctatgag aaagcgccac   13020
gcttcccgaa gggagaaagg cggacaggta tccggtaagc ggcagggtcg gaacaggaga   13080
gcgcacgagg gagcttccag ggggaaacgc ctggtatctt tatagtcctg tcgggtttcg   13140
ccacctctga cttgagcgtc gatttttgtg atgctcgtca ggggggcgga gcctatggaa   13200
aaacgccagc aacgcggcct ttttacggtt cctggccttt tgctggcctt ttgctcacat   13260
gttcttccct gcgttatccc ctgattctgt ggataaccgt attaccgcct ttgagtgagc   13320
tgataccgct cgccgcagcc gaacgaccga gcgcagcgag tcagtgagcg aggaagcgga   13380
agagcgccca atacgcaaac cgcctctccc cgcgcgttgg ccgattcatt aatgcagctg   13440
gcacgacagg tttcccgact ggaaagcggg cagtgagcgc aacgcaatta atgtgagtta   13500
```

```
gctcactcat taggcacccc aggctttaca ctttatgctt ccggctcgta tgttgtgtgg    13560
aattgtgagc ggataacaat ttcacacagg aaacagctat gaccatgatt ac           13612

<210> SEQ ID NO 9
<211> LENGTH: 13612
<212> TYPE: DNA
<213> ORGANISM: Artificial Sequence
<220> FEATURE:
<223> OTHER INFORMATION: Synthetic plasmid: pRLF2AUbCJ1

<400> SEQUENCE: 9
gaattcccaa acgcgttaat acgactcact atagacctgc cctaataggg gcgacactc      60 cgccatgaat cactcccctg tgaggaacta ctgtcttcac gcagaaagcg cctagccatg    120
gcgttagtat gagtgtcgta cagcctccag gccccccccct cccgggagag ccatagtggt   180
ctgcggaacc ggtgagtaca ccggaattgc cgggaagact gggtcctttc ttggataaac    240
ccactctatg cccggccatt tgggcgtgcc cccgcaagac tgctagccga gtagcgttgg    300
gttgcgaaag gccttgtggt actgcctgat agggcgcttg cgagtgcccc gggaggtctc    360
gtagaccgtg caccatgagc acaaatccta aacctcaaag aaaaaccaaa atggcttcca    420
aggtgtacga ccccgagcaa cgcaaacgca tgatcactgg gcctcagtgg tgggctcgct    480
gcaagcaaat gaacgtgctg gactccttca tcaactacta tgattccgag aagcacgccg    540
agaacgccgt gattttctg catggtaacg ctgcctccag ctacctgtgg aggcacgtcg     600
tgcctcacat cgagcccgtg gctagatgca tcatccctga tctgatcgga atgggtaagt    660
ccggcaagag cgggaatggc tcatatcgcc tcctggatca ctacaagtac ctcaccgctt    720
ggttcgagct gctgaacctt ccaaagaaaa tcatctttgt gggccacgac tgggggggctt    780 gtctggcctt tcactactcc tacgagcacc aagacaagat caaggccatc gtccatgctg    840
agagtgtcgt ggacgtgatc gagtcctggg acgagtggcc tgacatcgag gaggatatcg    900
ccctgatcaa gagcgaagag ggcgagaaaa tggtgcttga gaataacttc ttcgtcgaga    960
ccatgctccc aagcaagatc atgcggaaac tggagcctga ggagttcgct gcctacctgg   1020
agccattcaa ggagaagggc gaggttagac ggcctacccct ctcctggcct cgcgagatcc   1080
ctctcgttaa gggaggcaag cccgacgtcg tccagattgt ccgcaactac aacgcctacc   1140
ttcgggccag cgacgatctg cctaagatgt tcatcgagtc cgaccctggg ttcttttcca   1200
acgctattgt cgagggagct aagaagttcc ctaacaccga gttcgtgaag gtgaagggcc   1260
tccacttcag ccaggaggac gctccagatg aaatgggtaa gtacatcaag agcttcgtgg   1320
agcgcgtgct gaagaacgag cagctgttga attttgacct tcttaagctt gcgggagacg   1380
tcgagtccaa ccctgggccc atgcagatct tcgtgaagac cctgacgggc aagaccatca   1440
ctcttgaggt cgagcccagt gacaccatcg agaatgtcaa ggccaagatc caagacaagg   1500
aaggcatccc acctgaccag cagaggctga tattcgcggg caaacagctg gaggatggcc   1560
gcaccctgtc cgactacaac atccagaaag agtccacctt gcacctggtg ctgcgtctcc   1620
gcggtggtat gagcacgaat cctaaacctc aaagaaaaac caaacgtaac accaaccgcc   1680
gcccacagga cgtcaagttc ccgggcggtg tcagatcgt cggtggagtt tacctgttgc   1740
cgcgcagggg cccaggttg gtgtgcgcg cgactaggaa gacttccgag cggtcgcaac    1800
ctcgtggaag gcgacaacct atccccaagg ctcgccagcc cgagggtagg gcctgggctc    1860
agcccgggta cccctggccc ctctatgcca atgagggctt ggggtgggca ggatggctcc   1920
tgtcaccccg tggctctcgg cctagttggg gccccacgga ccccggcgt aggtcgcgca    1980
```

```
atttgggtaa ggtcatcgat accctcacgt gcggcttcgc cgatctcatg gggtacattc  2040
cgctcgtcgg cgccccccta gggggcgctg ccagggccct ggcgcatggc gtccgggttc  2100
tggaggacgg cgtgaactat gcaacaggga atctgcccgg ttgctccttt tctatcttcc  2160
ttttggcttt gctgtcctgt ttgaccatcc cagcttccgc ttatgaagtg cgcaacgtat  2220
ccggagtgta ccatgtcacg aacgactgct ccaacgcaag cattgtgtat gaggcagcgg  2280
acatgatcat gcatacccccc gggtgcgtgc cctgcgttcg ggagaacaac tcctcccgct  2340
gctgggtagc gctcactccc acgctcgcgg ccaggaacgc tagcgtcccc actacgacga  2400
tacgacgcca tgtcgatttg ctcgttgggg cggctgctct ctgctccgct atgtacgtgg  2460
gagatctctg cggatctgtt ttcctcgtcg cccagctgtt caccttctcg cctcgccggc  2520
acgagacagt acaggactgc aattgctcaa tatatcccgg ccacgtgaca ggtcaccgta  2580
tggcttggga tatgatgatg aactggtcac ctacagcagc cctagtggta tcgcagttac  2640
tccggatccc acaagctgtc gtggatatgg tggcgggggc ccattgggga gtcctagcgg  2700
gccttgccta ctattccatg gtggggaact gggctaaggt tctgattgtg atgctactct  2760
ttgccggcgt tgacggggga acctatgtga cagggggggac gatggccaaa acaccctcg  2820 ggattacgtc cctctttttca cccgggtcat cccagaaaat ccagcttgta aacaccaacg  2880
gcagctggca catcaacagg actgccctga actgcaatga ctccctcaac actgggttcc  2940
ttgctgcgct gttctacgtg cacaagttca actcatctgg atgcccagag cgcatggcca  3000
gctgcagccc catcgacgcg ttcgctcagg ggtgggggcc catcacttac aatgagtcac  3060
acagctcgga ccagaggcct tattgttggc actacgcacc ccggccgtgc ggtatcgtac  3120
ccgcggcgca ggtgtgtggt ccagtgtact gcttcacccc aagccctgtc gtggtgggga  3180
cgaccgaccg gttcggcgtc cctacgtaca gttgggggga gaatgagacg gacgtgctgc  3240
ttcttaacaa cacgcggccg ccgcaaggca actggtttgg ctgtacatgg atgaatagca  3300
ctgggttcac caagacgtgc ggggggccccc cgtgtaacat cgggggggatc ggcaataaaa  3360 ccttgacctg ccccacggac tgcttccgga agcaccccga ggccacttac accaagtgtg  3420
gttcggggcc ttggttgaca cccagatgct tggtccacta cccatacagg ctttggcact  3480
acccctgcac tgtcaacttt accatcttca aggttaggat gtacgtgggg ggagtggagc  3540
acaggctcga agccgcatgc aattggactc gaggagagcg ttgtaacctg gaggacaggg  3600
acagatcaga gcttagcccg ctgctgctgt ctacaacgga gtggcaggta ttgccctgtt  3660
ccttcaccac cctaccggct ctgtccactg gtttgatcca tctccatcag aacgtcgtgg  3720
acgtacaata cctgtacggt ataggggtcgg cggttgtctc cttttgcaatc aaatgggagt  3780 atgtcctgtt gctcttcctt cttctggcgg acgcgcgcgt ctgtgcctgc ttgtggatga  3840
tgctgctgat agctcaagct gaggccgccc tagagaacct ggtggtcctc aacgcggcat  3900
ccgtggccgg ggcgcatggc attctctcct tcctcgtgtt cttctgtgct gcctggtaca  3960
tcaagggcag gctggtccct ggggcggcat atgccctcta cggcgtatgg ccgctactcc  4020
tgctcctgct ggcgttacca ccacgagcat acgccatgga ccgggagatg gcagcatcgt  4080
gcggaggcgc ggttttcgta ggtctgatac tcttgacctt gtcaccgcac tataagctgt  4140
tcctcgctag gctcatatgg tggttacaat attttatcac cagggccgag gcacacttgc  4200
aagtgtggat ccccccccctc aacgttcggg ggggccgcga tggcatcgcg tgggccgtca  4260
ctatattctg cccgggtgtg gtgtttgaca ttaccaaatg gcttttggcg ttgcttgggc  4320
ctgcttacct cttaagggcc gctttgacac atgtgccgta cttcgtcaga gctcacgctc  4380
```

```
tgataagggt atgcgctttg gtgaagcagc tcgcggggggg taggtatgtt caggtggcgc    4440
tattggccct tggcaggtgg actggcacct acatctatga ccacctcaca cctatgtcgg    4500
actgggccgc tagcggcctg cgcgacttag cggtcgccgt ggaacccatc atcttcagtc    4560
cgatggagaa gaaggtcatc gtctggggag cggagacggc tgcatgtggg gacattctac    4620
atggacttcc cgtgtccgcc cgactcggcc aggagatcct cctcggccca gctgatggct    4680
acacctccaa ggggtggaag ctccttgctc ccatcactgc ttatgcccag caaacacgag    4740
gcctcctggg cgccatagtg gtgagtatga cggggcgtga caggacagaa caggccgggg    4800
aagtccaaat cctgtccaca gtctctcagt ccttcctcgg aacaaccatc tcggggggttt    4860 tgtggactgt ttaccacgga gctggcaaca agactctagc cggcttacgg ggtccggtca    4920
cgcagatgta ctcgagtgct gaggggggact tggtaggctg gcccagcccc cctgggacca    4980
agtctttgga gccgtgcaag tgtggagccg tcgacctata tctggtcacg cggaacgctg    5040
atgtcatccc ggctcggaga cgcggggaca agcggggagc attgctctcc ccgagaccca    5100
tttcgacctt gaaggggtcc tcgggggggc cggtgctctg ccctaggggc cacgtcgttg    5160
ggctcttccg agcagctgtg tgctctcggg gcgtggccaa atccatcgat ttcatccccg    5220
ttgagacact cgacgttgtt acaaggtctc ccactttcag tgacaacagc acgccaccgg    5280
ctgtgcccca gacctatcag gtcgggtact tgcatgctcc aactggcagt ggaaagagca    5340
ccaaggtccc tgtcgcgtat gccgcccagg ggtacaaagt actagtgctt aaccctcgg    5400 tagctgccac cctgggggttt ggggcgtacc tatccaaggc acatggcatc aatcccaaca    5460
ttaggactgg agtcaggacc gtgatgaccg gggaggccat cacgtactcc acatatggca    5520
aatttctcgc cgatgggggc tgcgctagcg gcgcctatga catcatcata tgcgatgaat    5580
gccacgctgt ggatgctacc tccattctcg gcatcggaac ggtccttgat caagcagaga    5640
cagccggggt cagactaact gtgctggcta cggccacacc ccccgggtca gtgacaaccc    5700
cccatcccga tatagaagag gtaggcctcg gcgggaggg tgagatcccc ttctatggga    5760
gggcgattcc cctatcctgc atcaagggag ggagacacct gattttctgc cactcaaaga    5820
aaaagtgtga cgagctcgcg gcggcccttc ggggcatggg cttgaatgcc gtggcatact    5880
atagagggtt ggacgtctcc ataataccag ctcagggaga tgtggtggtc gtcgccaccg    5940
acgccctcat gacggggtac actggagact ttgactccgt gatcgactgc aatgtagcgg    6000
tcacccaagc tgtcgacttc agcctggacc ccaccttcac tataaccaca cagactgtcc    6060
cacaagacgc tgtctcacgc agtcagcgcc gcgggcgcac aggtagagga agacagggca    6120
cttataggta tgtttccact ggtgaacgag cctcaggaat gtttgacagt gtagtgcttt    6180
gtgagtgcta cgacgcaggg gctgcgtggt acgatctcac accagcggag accaccgtca    6240
ggcttagagc gtatttcaac acgcccggcc tacccgtgtg tcaagaccat cttgaatttt    6300
gggaggcagt tttcaccggc ctcacacaca tagacgccca cttcctctcc caaacaaagc    6360 aagcgggggga gaacttcgcg tacctagtag cctaccaagc tacggtgtgc gccagagcca    6420
aggcccctcc cccgtcctgg gacgccatgt ggaagtgcct ggcccgactc aagcctacgc    6480
ttgcgggccc cacacctctc ctgtaccgtt tgggccctat taccaatgag gtcacccctca    6540 cacacccctgg gacgaagtac atcgccacat gcatgcaagc tgaccttgag gtcatgacca    6600
gcacgtgggt cctagctgga ggagtcctgg cagccgtcgc cgcatattgc ctggcgactg    6660
gatgcgtttc catcatcggc cgcttgcacg tcaaccagcg agtcgtcgtt gcgccggata    6720
aggaggtcct gtatgaggct tttgatgaga tggaggaatg cgcctctagg gcggctctca    6780
```

```
tcgaagaggg gcagcggata gccgagatgt tgaagtccaa gatccaaggc ttgctgcagc    6840
aggcctctaa gcaggcccag gacatacaac ccgctatgca ggcttcatgg cccaaagtgg    6900
aacaattttg ggccagacac atgtggaact tcattagcgg catccaatac ctcgcaggat    6960
tgtcaacact gccagggaac cccgcggtgg cttccatgat ggcattcagt gccgccctca    7020
ccagtccgtt gtcgaccagt accaccatcc ttctcaacat catgggaggc tggttagcgt    7080
cccagatcgc accacccgcg ggggccaccg gctttgtcgt cagtggcctg gtggggctg     7140 ccgtgggcag cataggcctg ggtaaggtgc tggtggacat cctggcagga tatggtgcgg    7200
gcatttcggg ggccctcgtc gcattcaaga tcatgtctgg cgagaagccc tctatggaag    7260
atgtcatcaa tctactgcct gggatcctgt ctccgggagc cctggtggtg ggggtcatct    7320
gcgcggccat tctgcgccgc cacgtgggac cgggggaggg cgcggtccaa tggatgaaca    7380
ggcttattgc ctttgcttcc agaggaaacc acgtcgcccc tactcactac gtgacggagt    7440
cggatgcgtc gcagcgtgtg acccaactac ttggctctct tactataacc agcctactca    7500
gaagactcca caattggata actgaggact gccccatccc atgctccgga tcctggctcc    7560
gcgacgtgtg ggactgggtt tgcaccatct tgacagactt caaaaattgg ctgacctcta    7620
aattgttccc caagctgccc ggcctcccct tcatctcttg tcaaaagggg tacaagggtg    7680
tgtgggccgg cactggcatc atgaccacgc gctgcccttg cggcgccaac atctctggca    7740
atgtccgcct gggctctatg aggatcacag ggcctaaaac ctgcatgaac acctggcagg    7800
ggacctttcc tatcaattgc tacacggagg ccagtgcgc gccgaaaccc cccacgaact     7860
acaagaccgc catctggagg gtggcggcct cggagtacgc ggaggtgacg cagcatgggt    7920
cgtactccta tgtaacagga ctgaccactg acaatctgaa aattccttgc caactacctt    7980
ctccagagtt tttctcctgg gtggacggtg tgcagatcca taggtttgca cccacaccaa    8040
agccgttttt ccgggatgag gtctcgttct gcgttgggct taattcctat gctgtcgggt    8100
cccagcttcc ctgtgaacct gagcccgacg cagacgtatt gaggtccatg ctaacagatc    8160
cgccccacat cacggcggag actgcggcgc ggcgcttggc acggggatca cctccatctg    8220
aggcgagctc ctcagtgagc cagctatcag caccgtcgct gcgggccacc tgcaccaccc    8280
acagcaacac ctatgacgtg gacatggtcg atgccaacct gctcatggag ggcggtgtgg    8340
ctcagacaga gcctgagtcc agggtgcccg ttctggactt tctcgagcca atggccgagg    8400
aagagagcga ccttgagccc tcaataccat cggagtgcat gctccccagg agcgggtttc    8460
cacgggcctt accggcttgg gcacggcctg actacaaccc gccgctcgtg gaatcgtgga    8520
ggaggccaga ttaccaaccg cccaccgttg ctggttgtgc tctccccccc cccaagaagg    8580
ccccgacgcc tcccccaagg agacgccgga cagtgggtct gagcgagagc accatatcag    8640
aagccctcca gcaactggcc atcaagacct tggccagcc cccctcgagc ggtgatgcag    8700
gctcgtccac ggggggcggc gccgccgaat ccggcggtcc gacgtcccct ggtgagccgg    8760 cccccctcaga gacaggttcc gcctcctcta tgcccccccct cgaggggag cctggagatc     8820 cggacctgga gtctgatcag gtagagcttc aacctccccc ccaggggggg ggggtagctc    8880
ccggttcggg ctcggggtct tggtctactt gctccgagga ggacgatacc accgtgtgct    8940
gctccatgtc atactcctgg accggggctc taataactcc ctgtagcccc gaagaggaaa    9000
agttgccaat caacccttg agtaactcgc tgttgcgata ccataacaag gtgtactgta    9060
caacatcaaa gagcgcctca cagagggcta aaaggtaac ttttgacagg acgcaagtgc     9120
tcgacgccca ttatgactca gtcttaaagg acatcaagct agcggcttcc aaggtcagcg    9180
```

```
caaggctcct caccttggag gaggcgtgcc agttgactcc accccattct gcaagatcca   9240
agtatggatt cggggccaag gaggtccgca gcttgtccgg gagggccgtt aaccacatca   9300
agtccgtgtg gaaggacctc ctggaagacc cacaaacacc aattcccaca accatcatgg   9360
ccaaaaatga ggtgttctgc gtggaccccg ccaagggggg taagaaacca gctcgcctca   9420
tcgtttaccc tgacctcggc gtccgggtct gcgagaaaat ggccctctat gacattacac   9480
aaaagcttcc tcaggcggta atgggagctt cctatggctt ccagtactcc cctgcccaac   9540
gggtggagta tctcttgaaa gcatgggcgg aaaagaagga ccccatgggt ttttcgtatg   9600
atacccgatg cttcgactca accgtcactg agagagacat caggaccgag gagtccatat   9660
accaggcctg ctccctgccc gaggaggccc gcactgccat acactcgctg actgagagac   9720
tttacgtagg agggcccatg ttcaacagca agggtcaaac ctgcggttac agacgttgcc   9780
gcgccagcgg ggtgctaacc actagcatgg gtaacaccat cacatgctat gtgaaagccc   9840
tagcggcctg caaggctgcg gggatagttg cgcccacaat gctggtatgc ggcgatgacc   9900
tagtagtcat ctcagaaagc caggggactg aggaggacga gcggaacctg agagccttca   9960
cggaggccat gaccaggtac tctgcccctc ctggtgatcc ccccagaccg gaatatgacc  10020
tggagctaat aacatcctgt tcctcaaatg tgtctgtggc gttgggcccg cggggccgcc  10080
gcagatacta cctgaccaga gacccaacca ctccactcgc ccgggctgcc tgggaaacag  10140
ttagacactc ccctatcaat tcatggctgg gaaacatcat ccagtatgct ccaaccatat  10200
gggttcgcat ggtcctaatg acacacttct tctccattct catggtccaa gacaccctgg  10260
accagaacct caactttgag atgtatggat cagtatactc cgtgaatcct ttggaccttc  10320
cagccataat tgagaggtta cacgggcttg acgccttttc tatgcacaca tactctcacc  10380
acgaactgac gcgggtggct tcagccctca gaaaacttgg ggcgccaccc ctcagggtgt  10440
ggaagagtcg ggctcgcgca gtcagggcgt ccctcatctc ccgtggaggg aaagcggccg  10500
tttgcggccg atatctcttc aattgggcgg tgaagaccaa gctcaaactc actccattgc  10560
cggaggcgcg cctactggac ttatccagtt ggttcaccgt cggcgccggc ggggcgaca  10620
ttttcacag cgtgtcgcgc gcccgacccc gctcattact cttcggccta ctcctacttt  10680
tcgtaggggt aggcctcttc ctactccccg ctcggtagag cggcacacac taggtacact  10740
ccatagctaa ctgttccttt tttttttttt tttttttttt tttttttttt tttttttttt  10800
cttttttttt tttttccctc tttcttccct tctcatctta ttctactttc tttcttggtg  10860
gctccatctt agccctagtc acggctagct gtgaaaggtc cgtgagccgc atgactgcag  10920
agagtgccgt aactggtctc tctgcagatc atgtctagag tcgacctgca ggcatgcaag  10980
cttggcactg gccgtcgttt tacaacgtcg tgactgggaa aaccctggcg ttacccaact  11040
taatcgcctt gcagcacatc cccctttcgc cagctggcgt aatagcgaag aggcccgcac  11100
cgatcgccct tcccaacagt tgcgcagcct gaatggcgaa tggcgcctga tgcggtattt  11160
tctccttacg catctgtgcg gtatttcaca ccgcatatgg tgcactctca gtacaatctg  11220
ctctgatgcc gcatagttaa gccagccccg acacccgcca cacccgctg acgcgccctg  11280
acgggcttgt ctgctcccgg catccgctta cagacaagct gtgaccgtct ccgggagctg  11340
catgtgtcag aggttttcac cgtcatcacc gaaacgcgcg agacgaaagg gcctcgtgat  11400
acgcctattt ttataggtta atgtcatgat aataatggtt tcttagacgt caggtggcac  11460
ttttcgggga aatgtgcgcg gaaccccctat ttgtttattt ttctaaatac attcaaatat  11520
gtatccgctc atgagacaat aaccctgata aatgcttcaa taatattgaa aaaggaagag  11580
```

```
tatgagtatt caacatttcc gtgtcgccct tattcccttt tttgcggcat tttgccttcc    11640 tgttttgct  cacccagaaa cgctggtgaa agtaaaagat gctgaagatc agttgggtgc    11700
acgagtgggt tacatcgaac tggatctcaa cagcggtaag atccttgaga gttttcgccc    11760
cgaagaacgt tttccaatga tgagcacttt taaagttctg ctatgtggcg cggtattatc    11820
ccgtattgac gccgggcaag agcaactcgg tcgccgcata cactattctc agaatgactt    11880
ggttgagtac tcaccagtca cagaaaagca tcttacggat ggcatgacag taagagaatt    11940
atgcagtgct gccataacca tgagtgataa cactgcggcc aacttacttc tgacaacgat    12000
cggaggaccg aaggagctaa ccgcttttt  gcacaacatg ggggatcatg taactcgcct    12060
tgatcgttgg gaaccggagc tgaatgaagc cataccaaac gacgagcgtg acaccacgat    12120
gcctgtagca atggcaacaa cgttgcgcaa actattaact ggcgaactac ttactctagc    12180
ttcccggcaa caattaatag actggatgga ggcggataaa gttgcaggac cacttctgcg    12240
ctcggccctt ccggctggct ggtttattgc tgataaatct ggagccggtg agcgtgggtc    12300
tcgcggtatc attgcagcac tggggccaga tggtaagccc tcccgtatcg tagttatcta    12360
cacgacgggg agtcaggcaa ctatggatga acgaaataga cagatcgctg agataggtgc    12420
ctcactgatt aagcattggt aactgtcaga ccaagtttac tcatatatac tttagattga    12480
tttaaaactt cattttaat  ttaaaaggat ctaggtgaag atcctttttg ataatctcat    12540
gaccaaaatc ccttaacgtg agttttcgtt ccactgagcg tcagaccccg tagaaaagat    12600
caaaggatct tcttgagatc ctttttttct gcgcgtaatc tgctgcttgc aaacaaaaaa    12660
accaccgcta ccagcggtgg tttgtttgcc ggatcaagag ctaccaactc tttttccgaa    12720
ggtaactggc ttcagcagag cgcagatacc aaatactgtc cttctagtgt agccgtagtt    12780
aggccaccac ttcaagaact ctgtagcacc gcctacatac ctcgctctgc taatcctgtt    12840
accagtggct gctgccagtg gcgataagtc gtgtcttacc gggttggact caagacgata    12900
gttaccggat aaggcgcagc ggtcgggctg aacggggggt tcgtgcacac agcccagctt    12960
ggagcgaacg acctacaccg aactgagata cctacagcgt gagctatgag aaagcgccac    13020
gcttcccgaa gggagaaagg cggacaggta tccggtaagc ggcagggtcg aacaggaga    13080 gcgcacgagg gagcttccag ggggaaacgc ctggtatctt tatagtcctg tcgggtttcg    13140
ccacctctga cttgagcgtc gatttttgtg atgctcgtca ggggggcgga gcctatggaa    13200
aaacgccagc aacgcggcct ttttacggtt cctggccttt tgctggcctt ttgctcacat    13260
gttctttcct gcgttatccc ctgattctgt ggataaccgt attaccgcct tgagtgagc    13320 tgataccgct cgccgcagcc gaacgaccga gcgcagcgag tcagtgagcg aggaagcgga    13380
agagcgccca atacgcaaac cgcctctccc cgcgcgttgg ccgattcatt aatgcagctg    13440
gcacgacagg tttcccgact ggaaagcggg cagtgagcgc aacgcaatta atgtgagtta    13500
gctcactcat taggcacccc aggctttaca ctttatgctt ccggctcgta tgttgtgtgg    13560
aattgtgagc ggataacaat ttcacacagg aaacagctat gaccatgatt ac            13612
```

<210> SEQ ID NO 10
<211> LENGTH: 13630
<212> TYPE: DNA
<213> ORGANISM: Artificial Sequence
<220> FEATURE:
<223> OTHER INFORMATION: Synthetic plasmid: pRLF2AUbNJ1

<400> SEQUENCE: 10

```
gaattcccaa acgcgttaat acgactcact atagacctgc ccctaatagg ggcgacactc       60
```

```
cgccatgaat cactcccctg tgaggaacta ctgtcttcac gcagaaagcg cctagccatg    120
gcgttagtat gagtgtcgta cagcctccag gcccccccct cccgggagag ccatagtggt    180
ctgcggaacc ggtgagtaca ccggaattgc cgggaagact gggtcctttc ttggataaac    240
ccactctatg cccggccatt tgggcgtgcc cccgcaagac tgctagccga gtagcgttgg    300
gttgcgaaag gccttgtggt actgcctgat agggcgcttg cgagtgcccc ggaggtctc     360 gtagaccgtg caccatgagc acaaatccta aacctcaaag aaaaaccaaa atggcttcca    420
aggtgtacga ccccgagcaa cgcaaacgca tgatcactgg gcctcagtgg tgggctcgct    480
gcaagcaaat gaacgtgctg gactccttca tcaactacta tgattccgag aagcacgccg    540
agaacgccgt gattttctg catggtaacg ctgcctccag ctacctgtgg aggcacgtcg     600
tgcctcacat cgagcccgtg gctagatgca tcatccctga tctgatcgga atgggtaagt    660
ccggcaagag cgggaatggc tcatatcgcc tcctggatca ctacaagtac ctcaccgctt    720
ggttcgagct gctgaacctt ccaaagaaaa tcatctttgt gggccacgac tggggggctt    780
gtctggcctt tcactactcc tacgagcacc aagacaagat caaggccatc gtccatgctg    840
agagtgtcgt ggacgtgatc gagtcctggg acgagtggcc tgacatcgag gaggatatcg    900
ccctgatcaa gagcgaagag ggcgagaaaa tggtgcttga gaataacttc ttcgtcgaga    960
ccatgctccc aagcaagatc atgcggaaac tggagcctga ggagttcgct gcctacctgg    1020
agccattcaa ggagaagggc gaggttagac ggcctaccct ctcctggcct cgcgagatcc    1080
ctctcgttaa gggaggcaag cccgacgtcg tccagattgt ccgcaactac aacgcctacc    1140
ttcgggccag cgacgatctg cctaagatgt tcatcgagtc cgaccctggg ttcttttcca    1200
acgctattgt cgagggagct aagaagttcc ctaacaccga gttcgtgaag gtgaagggcc    1260
tccacttcag ccaggaggac gctccagatg aaatgggtaa gtacatcaag agcttcgtgg    1320
agcgcgtgct gaagaacgag cagctgttga attttgacct tcttaagctt gcgggagacg    1380
tcgagtccaa ccctgggccc atgcagatct tcgtgaagac cctgacgggc aagaccatca    1440
ctcttgaggt cgagcccagt gacaccatcg agaatgtcaa ggccaagatc caagacaagg    1500
aaggcatccc acctgaccag cagaggctga tattcgcggg caaacagctg gaggatggcc    1560
gcaccctgtc cgactacaac atccagaaag agtccacctt gcacctggtg ctgcgtctcc    1620
gcggtggtat gagcacactt cctaaacctc aaagaaaaac caaagaaac accatccgtc     1680 gcccacagga cgtcaagttc ccgggtggcg gacagatcgt tggtggagta tacgtgttgc    1740
cgcgcagggg cccacgattg ggtgtgcgcg cgacgcgtaa aacttctgaa cggtcacagc    1800
ctcgcggacg acgacagcct atccccaagg cgcgtcggag cgaaggccgg tcctgggctc    1860
agcccgggta cccttggccc ctctatggta acgagggctg cgggtgggca gggtggctcc    1920
tgtccccacg cggctcccgt ccatcctggg gcccaaatga ccccggcgg aggtcccgca     1980 atttgggtaa agtcatcgat accctaacgt gcggattcgc cgacctcatg gggtacatcc    2040
cgctcgtcgg cgctcctgta ggaggcgtcg caagagccct cgcgcatggc gtgagggccc    2100
ttgaagacgg gataaatttc gcaacaggga acttgcccgg ttgctccttt tctatcttcc    2160
ttcttgctct gttctcttgc ttaattcatc cagcagccag tcttgagtgg cggaatacgt    2220
ctggcctcta cgtccttacc aacgactgtt ccaatagcag tattgtgtat gaggccgatg    2280
atgtcattct gcacacaccc ggctgtgtac cttgtgtcca ggacggcaat acatctacgt    2340
gctgaccccc agtgacacct acagtggcag tcaggtacgt cggagcaact actgcttcga    2400
tacgcagtca tgtggaccta ttagtaggcg cggccacgat gtgctctgcg ctctacgtgg    2460
```

```
gtgatatgtg tggggctgtc tttctcgtgg gacaagcctt cacgttcaga cctcgacgcc   2520
atcaaacggt ccagacctgt aactgctcgc tgtacccagg ccatctttca ggacatcgaa   2580
tggcttggga tatgatgatg aattggtccc ccgctgtggg tatggtggtg gcgcatgtcc   2640
tgcgtttacc ccagaccttg ttcgacataa tggccggggc ccattggggc atcttggcgg   2700
gcctggccta ttactccatg cagggcaact gggccaaggt cgcaatcatc atggttatgt   2760
tctcaggggt cgatgcccac acatatacca ccggtggcac tgcatctcgt catacccaag   2820
cgtttgctgg tcttttttgac ataggccccc aacagaaact gcagctggtc aacaccaatg   2880
gctcgtggca catcaacagt actgccctaa attgcaatga gtccataaac accgggttta   2940
tagctgggtt gttttattac cataagttca actctactgg atgtcctcaa aggctcagca   3000
gctgcaagcc catcactttc ttcaggcagg gatgggccc cttaacagat gctaacatca   3060
ccggtccttc tgatgacaga ccatactgct ggcactacgc acctagacct tgtgacattg   3120
tcccggcatc aagtgtctgc ggccctgtgt actgcttcac accatcgcca gtggtcgtag   3180
gcactactga tgccaggggc gtgccaacct acacctgggg tgagaatgag aaagatgtgt   3240
tcctgctgaa gtcccagcgg cctcccagtg gtcggtggtt tgggtgctcg tggatgaact   3300
ccacggggtt tctcaagacg tgcggagctc cccctgtaa catctatggg ggcgagggga   3360
atccccacaa tgaatcagat cttttctgcc ccactgactg cttcaggaaa catcccgaga   3420
ccacgtacag ccggtgtggt gcagggccct ggttgacacc tcgttgcatg gttgactacc   3480
cataccggct ttggcattac ccatgtacag tcgatttcag attgttcaag gtgaggatgt   3540
ttgtgggtgg gtttgaacat cgatttaccg ccgcttgcaa ctggaccagg ggggagcgct   3600
gcgatatcga ggatcgtgac cgcagtgagc aacatccgct gctgcattca acaactgagc   3660
ttgctatact gccttgctct ttcacgccca tgcctgcgct gtcaacaggt ctgatacacc   3720
tccaccaaaa catcgtggat gtccaatacc tttatggcgt tggatctggc atggtgggat   3780
gggcgctgaa atgggagttc gtcatcctcg ttttcctcct tctggcggac gcacgcgtgt   3840
gcgttgccct ttggctgatg ctgatgatat cacagacaga agcagccttg gagaacctgg   3900
tcacgctgaa cgccgtcgct gctgctggga cacatggtat cggctggtac ctggtagctt   3960
tttgcgcggc gtggtacgtg cggggtaaac tcgtcccgct ggtgacctac agcctgacgg   4020
gtctttggtc cctagcattg ctcgtcctct tgctccccca acgtgcgtat gcttggtcgg   4080
gtgaagacag cgccactctt ggcgctgggg tcttggtcct cttcggcttc tttaccttgt   4140
caccctggta taagcattgg atcggccgcc tcatgtggtg gaaccagtac accatatgca   4200
gatgcgagtc cgcccttcac gtgtgggttc ccccccttact cgcacgcggg agtagggatg   4260
gcatcgcgtg ggccgtcact atattctgcc cgggtgtggt gtttgacatt accaaatggc   4320
ttttggcgtt gcttgggcct gcttacctct taagggccgc tttgacacat gtgccgtact   4380
tcgtcagagc tcacgctctg ataagggtat gcgctttggt gaagcagctc gcgggggta   4440 ggtatgttca ggtggcgcta ttggcccttg gcaggtggac tggcacctac atctatgacc   4500
acctcacacc tatgtcggac tgggccgcta gcggcctgcg cgacttagcg gtcgccgtgg   4560
aacccatcat cttcagtccg atggagaaga aggtcatcgt ctggggagcg gagacggctg   4620
catgtgggga cattctacat ggacttcccg tgtccgcccg actcggccag gagatcctcc   4680
tcggcccagc tgatggctac acctccaagg ggtggaagct ccttgctccc atcactgctt   4740
atgcccagca aacacgaggc ctcctgggcg ccatagtggt gagtatgacg gggcgtgaca   4800
ggacagaaca ggccggggaa gtccaaatcc tgtccacagt ctctcagtcc ttcctcggaa   4860
```

```
caaccatctc gggggttttg tggactgttt accacggagc tggcaacaag actctagccg    4920
gcttacgggg tccggtcacg cagatgtact cgagtgctga gggggacttg gtaggctggc    4980 ccagccccc  tggaccaag  tctttggagc cgtgcaagtg tggagccgtc gacctatatc    5040
tggtcacgcg gaacgctgat gtcatcccgg ctcggagacg cggggacaag cggggagcat    5100
tgctctcccc gagacccatt tcgaccttga aggggtcctc gggggggccg gtgctctgcc    5160
ctagggccca cgtcgttggg ctcttccgag cagctgtgtg ctctcggggc gtggccaaat    5220
ccatcgattt catccccgtt gagacactcg acgttgttac aaggtctccc actttcagtg    5280
acaacagcac gccaccggct gtgcccagaa cctatcaggt cgggtacttg catgctccaa    5340
ctggcagtgg aaagagcacc aaggtccctg tcgcgtatgc cgcccagggg tacaaagtac    5400
tagtgcttaa cccctcggta gctgccaccc tgggtttgg  ggcgtaccta tccaaggcac    5460
atggcatcaa tcccaacatt aggactggag tcaggaccgt gatgaccggg gaggccatca    5520
cgtactccac atatggcaaa tttctcgccg atggggctg  cgctagcggc gcctatgaca    5580
tcatcatatg cgatgaatgc cacgctgtgg atgctacctc cattctcggc atcggaacgg    5640
tccttgatca agcagagaca gccggggtca gactaactgt gctggctacg ccacaccccc    5700
ccgggtcagt gacaaccccc catcccgata tagaagaggt aggcctcggg cgggagggtg    5760 agatccccctt ctatgggagg gcgattcccc tatcctgcat caaggaggg  agacacctga    5820 ttttctgcca ctcaaagaaa agtgtgacg  agctcgcggc ggcccttcgg ggcatgggct    5880
tgaatgccgt ggcatactat agaggggttgg acgtctccat aataccagct cagggagatg    5940
tggtggtcgt cgccaccgac gccctcatga cggggtacac tggagacttt gactccgtga    6000
tcgactgcaa tgtagcggtc acccaagctg tcgacttcag cctggaccccc accttcacta    6060 taaccacaca gactgtccca caagacgctg tctcacgcag tcagcgccgc gggcgcacag    6120
gtagaggaag acagggcact tataggtatg tttccactgg tgaacgagcc tcaggaatgt    6180
ttgacagtgt agtgctttgt gagtgctacg acgcaggggc tgcgtggtac gatctcacac    6240
cagcggagac caccgtcagg cttagagcgt atttcaacac gcccggccta cccgtgtgtc    6300
aagaccatct tgaattttgg gaggcagttt tcaccggcct cacacacata gacgcccact    6360
tcctctccca aacaaagcaa gcgggggaga acttcgcgta cctagtagcc taccaagcta    6420
cggtgtgcgc cagagccaag gcccctcccc cgtcctggga cgccatgtgg aagtgcctgg    6480
cccgactcaa gcctacgctt gcgggcccca caccctctcct gtaccgtttg ggccctatta    6540
ccaatgaggt caccctcaca cacctggga  cgaagtacat cgccacatgc atgcaagctg    6600
accttgaggt catgaccagc acgtgggtcc tagctggagg agtcctggca gccgtcgccg    6660
catattgcct ggcgactgga tgcgtttcca tcatcggccg cttgcacgtc aaccagcgag    6720
tcgtcgttgc gccggataag gaggtcctgt atgaggcttt tgatgagatg gaggaatgcg    6780
cctctagggc ggctctcatc gaagagggc  agcggatagc cgagatgttg aagtccaaga    6840
tccaaggctt gctgcagcag gcctctaagc aggcccagga catacaaccc gctatgcagg    6900
cttcatggcc caaagtggaa caattttggg ccagacacat gtggaacttc attagcggca    6960
tccaatacct cgcaggattg tcaacactgc cagggaaccc cgcggtggct tccatgatgg    7020
cattcagtgc cgccctcacc agtccgttgt cgaccagtac caccatcctt ctcaacatca    7080
tgggaggctg gttagcgtcc cagatcgcac cacccgcggg ggccaccggc tttgtcgtca    7140
gtggcctggt gggggctgcc gtgggcagca taggcctggg taaggtgctg gtggacatcc    7200
tggcaggata tggtgcgggc atttcggggg ccctcgtcgc attcaagatc atgtctggcg    7260
```

```
agaagccctc tatggaagat gtcatcaatc tactgcctgg gatcctgtct ccgggagccc    7320
tggtggtggg ggtcatctgc gcggccattc tgcgccgcca cgtgggaccg ggggagggcg    7380
cggtccaatg gatgaacagg cttattgcct ttgcttccag aggaaaccac gtcgcccta    7440 ctcactacgt gacggagtcg gatgcgtcgc agcgtgtgac ccaactactt ggctctctta    7500
ctataaccag cctactcaga agactccaca attggataac tgaggactgc ccatcccat    7560 gctccggatc ctggctccgc gacgtgtggg actgggtttg caccatcttg acagacttca    7620
aaaattggct gacctctaaa ttgttcccca agctgcccgg cctccccttc atctcttgtc    7680
aaaaggggta caagggtgtg tgggccggca ctggcatcat gaccacgcgc tgcccttgcg    7740
gcgccaacat ctctggcaat gtccgcctgg gctctatgag gatcacaggg cctaaaacct    7800
gcatgaacac ctggcagggg accttttccta tcaattgcta cacggagggc cagtgcgcgc    7860
cgaaaccccc cacgaactac aagaccgcca tctggagggt ggcggcctcg gagtacgcgg    7920
aggtgacgca gcatgggtcg tactcctatg taacaggact gaccactgac aatctgaaaa    7980
ttccttgcca actaccttct ccagagtttt tctcctgggt ggacggtgtg cagatccata    8040
ggtttgcacc cacaccaaag ccgttttttcc gggatgaggt ctcgttctgc gttgggctta    8100
attcctatgc tgtcgggtcc cagcttccct gtgaacctga gcccgacgca gacgtattga    8160
ggtccatgct aacagatccg ccccacatca cggcggagac tgcggcgcgg cgcttggcac    8220
ggggatcacc tccatctgag gcgagctcct cagtgagcca gctatcagca ccgtcgctgc    8280
gggccacctg caccacccac agcaacacct atgacgtgga catggtcgat gccaacctgc    8340
tcatggaggg cggtgtggct cagacagagc ctgagtccag ggtgcccgtt ctggactttc    8400
tcgagccaat ggccgaggaa gagagcgacc ttgagccctc aataccatcg gagtgcatgc    8460
tccccaggag cgggtttcca cgggccttac cggcttgggc acggcctgac tacaacccgc    8520
cgctcgtgga atcgtggagg aggccagatt accaaccgcc caccgttgct ggttgtgctc    8580 tcccccccc caagaaggcc ccgacgcctc ccccaaggag acgccggaca gtgggtctga    8640
gcgagagcac catatcagaa gccctccagc aactggccat caagaccttt ggccagcccc    8700
cctcgagcgg tgatgcaggc tcgtccacgg gggcgggcgc cgccgaatcc ggcggtccga    8760
cgtcccctgg tgagccggcc ccctcagaga caggttccgc ctcctctatg cccccctcg    8820 aggggggagcc tggagatccg gacctggagt ctgatcaggt agagcttcaa cctccccccc    8880 agggggggg ggtagctccc ggttcgggct cggggtcttg gtctacttgc tccgaggagg    8940
acgataccac cgtgtgctgc tccatgtcat actcctggac cggggctcta ataactccct    9000
gtagccccga agaggaaaag ttgccaatca accctttgag taactcgctg ttgcgatacc    9060
ataacaaggt gtactgtaca acatcaaaga gcgcctcaca gagggctaaa aaggtaactt    9120
ttgacaggac gcaagtgctc gacgcccatt atgactcagt cttaaaggac atcaagctag    9180
cggcttccaa ggtcagcgca aggctcctca ccttggagga ggcgtgccag ttgactccac    9240
cccattctgc aagatccaag tatgattcg gggccaagga ggtccgcagc ttgtccggga    9300
gggccgttaa ccacatcaag tccgtgtgga aggacctcct ggaagaccca caaacaccaa    9360 ttccacacaac catcatggcc aaaaatgagg tgttctgcgt ggaccccgcc aagggggta    9420 agaaaccagc tcgcctcatc gtttaccctg acctcggcgt ccgggtctgc gagaaaatgg    9480
ccctctatga cattacacaa aagcttcctc aggcggtaat gggagcttcc tatggcttcc    9540
agtactcccc tgcccaacgg gtggagtatc tcttgaaagc atgggcggaa aagaaggacc    9600
ccatgggttt ttcgtatgat acccgatgct tcgactcaac cgtcactgag agagacatca    9660
```

```
ggaccgagga gtccatatac caggcctgct ccctgcccga ggaggcccgc actgccatac    9720
actcgctgac tgagagactt tacgtaggag ggcccatgtt caacagcaag ggtcaaacct    9780
gcggttacag acgttgccgc gccagcgggg tgctaaccac tagcatgggt aacaccatca    9840
catgctatgt gaaagcccta gcggcctgca aggctgcggg gatagttgcg cccacaatgc    9900
tggtatgcgg cgatgaccta gtagtcatct cagaaagcca ggggactgag gaggacgagc    9960
ggaacctgag agccttcacg gaggccatga ccaggtactc tgcccctcct ggtgatcccc   10020
ccagaccgga atatgacctg gagctaataa catcctgttc ctcaaatgtg tctgtggcgt   10080
tgggcccgcg gggccgccgc agatactacc tgaccagaga cccaaccact ccactcgccc   10140
gggctgcctg ggaaacagtt agacactccc ctatcaattc atggctggga aacatcatcc   10200
agtatgctcc aaccatatgg gttcgcatgg tcctaatgac acacttcttc tccattctca   10260
tggtccaaga caccctggac cagaacctca actttgagat gtatggatca gtatactccg   10320
tgaatccttt ggaccttcca gccataattg agaggttaca cgggcttgac gccttttcta   10380
tgcacacata ctctcaccac gaactgacgc gggtggcttc agccctcaga aaacttgggg   10440
cgccacccct caggggtgtgg aagagtcggg ctcgcgcagt cagggcgtcc ctcatctccc   10500
gtggagggaa agcggccgtt tgcggccgat atctcttcaa ttgggcggtg aagaccaagc   10560
tcaaactcac tccattgccg gaggcgcgcc tactggactt atccagttgg ttcaccgtcg   10620
gcgccggcgg gggcgacatt tttcacagcg tgtcgcgcgc ccgacccgc tcattactct   10680
tcggcctact cctactttc gtaggggtag gcctcttcct actccccgct cggtagagcg   10740
gcacacacta ggtacactcc atagctaact gttccttttt tttttttttt tttttttttt   10800
tttttttttt tttttttttct ttttttttttt tttccctctt tcttcccttc tcatcttatt   10860
ctactttctt tcttggtggc tccatcttag ccctagtcac ggctagctgt gaaaggtccg   10920
tgagccgcat gactgcagag agtgccgtaa ctggtctctc tgcagatcat gtctagagtc   10980
gacctgcagg catgcaagct tggcactggc cgtcgtttta caacgtcgtg actgggaaaa   11040
ccctggcgtt acccaactta atcgccttgc agcacatccc cctttcgcca gctggcgtaa   11100
tagcgaagag gcccgcaccg atcgcccttc ccaacagttg cgcagcctga atggcgaatg   11160
gcgcctgatg cggtattttc tccttacgca tctgtgcggt atttcacacc gcatatggtg   11220
cactctcagt acaatctgct ctgatgccgc atagttaagc cagccccgac acccgccaac   11280
acccgctgac gcgccctgac gggcttgtct gctcccggca tccgcttaca gacaagctgt   11340
gaccgtctcc gggagctgca tgtgtcagag gttttcaccg tcatcaccga aacgcgcgag   11400
acgaaagggc ctcgtgatac gcctattttt ataggttaat gtcatgataa taatggtttc   11460
ttagacgtca ggtggcactt ttcggggaaa tgtgcgcgga acccctattt gtttattttt   11520
ctaaatacat tcaaatatgt atccgctcat gagacaataa ccctgataaa tgcttcaata   11580
atattgaaaa aggaagagta tgagtattca acatttccgt gtcgccctta ttcccttttt   11640
tgcggcattt tgccttcctg tttttgctca cccagaaacg ctggtgaaag taaaagatgc   11700
tgaagatcag ttgggtgcac gagtgggtta catcgaactg gatctcaaca gcggtaagat   11760
ccttgagagt tttcgccccg aagaacgttt tccaatgatg agcacttta aagttctgct   11820
atgtggcgcg gtattatccc gtattgacgc cgggcaagag caactcggtc gccgcataca   11880
ctattctcag aatgacttgg ttgagtactc accagtcaca gaaaagcatc ttacggatgg   11940
catgacagta agagaattat gcagtgctgc cataaccatg agtgataaca ctgcggccaa   12000
cttacttctg acaacgatcg gaggaccgaa ggagctaacc gcttttttgc acaacatggg   12060
```

```
ggatcatgta actcgccttg atcgttggga accggagctg aatgaagcca taccaaacga    12120
cgagcgtgac accacgatgc ctgtagcaat ggcaacaacg ttgcgcaaac tattaactgg    12180
cgaactactt actctagctt cccggcaaca attaatagac tggatggagg cggataaagt    12240
tgcaggacca cttctgcgct cggcccttcc ggctggctgg tttattgctg ataaatctgg    12300
agccggtgag cgtgggtctc gcggtatcat tgcagcactg gggccagatg gtaagccctc    12360
ccgtatcgta gttatctaca cgacggggag tcaggcaact atggatgaac gaaatagaca    12420
gatcgctgag ataggtgcct cactgattaa gcattggtaa ctgtcagacc aagtttactc    12480
atatatactt tagattgatt taaaacttca tttttaattt aaaaggatct aggtgaagat    12540
cctttttgat aatctcatga ccaaaatccc ttaacgtgag ttttcgttcc actgagcgtc    12600
agaccccgta gaaaagatca aaggatcttc ttgagatcct ttttttctgc gcgtaatctg    12660
ctgcttgcaa acaaaaaaac caccgctacc agcggtggtt tgtttgccgg atcaagagct    12720
accaactctt tttccgaagg taactggctt cagcagagcg cagataccaa atactgtcct    12780
tctagtgtag ccgtagttag gccaccactt caagaactct gtagcaccgc ctacatacct    12840
cgctctgcta atcctgttac cagtggctgc tgccagtggc gataagtcgt gtcttaccgg    12900
gttggactca agacgatagt taccggataa ggcgcagcgg tcgggctgaa cggggggttc    12960
gtgcacacag cccagcttgg agcgaacgac ctacaccgaa ctgagatacc tacagcgtga    13020
gctatgagaa agcgccacgc ttcccgaagg gagaaaggcg gacaggtatc cggtaagcgg    13080
cagggtcgga acaggagagc gcacgaggga gcttccaggg ggaaacgcct ggtatcttta    13140
tagtcctgtc gggtttcgcc acctctgact tgagcgtcga ttttgtgat gctcgtcagg    13200 ggggcggagc ctatggaaaa acgccagcaa cgcggccttt ttacggttcc tggccttttg    13260
ctggcctttt gctcacatgt tctttcctgc gttatcccct gattctgtgg ataaccgtat    13320
taccgccttt gagtgagctg ataccgctcg ccgcagccga acgaccgagc gcagcgagtc    13380
agtgagcgag gaagcggaag agcgcccaat acgcaaaccg cctctccccg cgcgttggcc    13440
gattcattaa tgcagctggc acgacaggtt cccgactgg aaagcgggca gtgagcgcaa    13500
cgcaattaat gtgagttagc tcactcatta ggcaccccag gctttacact ttatgcttcc    13560
ggctcgtatg ttgtgtggaa ttgtgagcgg ataacaattt cacacaggaa acagctatga    13620
ccatgattac                                                         13630

<210> SEQ ID NO 11
<211> LENGTH: 6979
<212> TYPE: DNA
<213> ORGANISM: Artificial Sequence
<220> FEATURE:
<223> OTHER INFORMATION: Synthetic plasmid: pCMVIII_NS1

<400> SEQUENCE: 11
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg    120 ttggcgggtg tcgggctgg cttaactatg cggcatcaga gcagattgta ctgagagtgc    180
accatatgaa gctttttgca aaagcctagg cctccaaaaa agcctcctca ctacttctgg    240
aatagctcag aggccgaggc ggcctcggcc tctgcataaa taaaaaaaat tagtcagcca    300
tggggcggag aatgggcgga actgggcggg agggaatta ttggctattg gccattgcat    360
acgttgtatc tatatcataa tatgtacatt tatattggct catgtccaat atgaccgcca    420
tgttgacatt gattattgac tagttattaa tagtaatcaa ttacggggtc attagttcat    480
```

```
agcccatata tggagttccg cgttacataa cttacggtaa atgggcccgcc tggctgaccg    540
cccaacgacc cccgcccatt gacgtcaata atgacgtatg ttcccatagt aacgccaata    600
gggactttcc attgacgtca atgggtggag tatttacggt aaactgccca cttggcagta    660
catcaagtgt atcatatgcc aagtccgccc cctattgacg tcaatgacgg taaatggccc    720
gcctggcatt atgcccagta catgacctta cgggactttc ctacttggca gtacatctac    780
gtattagtca tcgctattac catggtgatg cggttttggc agtacaccaa tgggcgtgga    840
tagcggtttg actcacgggg atttccaagt ctccacccca ttgacgtcaa tgggagtttg    900
ttttggcacc aaaatcaacg ggactttcca aaatgtcgta ataaccccgc cccgttgacg    960
caaatgggcg gtaggcgtgt acggtgggag gtctatataa gcagagctcg tttagtgaac   1020
cgtcagatcg cctggagacg ccatccacgc tgttttgacc tccatagaag acaccgggac   1080
cgatccagcc tccgcggccg ggaacggtgc attggaacgc ggattccccg tgccaagagt   1140
gacgtaagta ccgcctatag actctatagg cacaccccett tggctcttat gcatgctata   1200
ctgttttgg cttggggcct atacaccccc gctccttatg ctataggtga tggtatagct   1260
tagcctatag gtgtgggtta ttgaccatta ttgaccactc ccctattggt gacgatactt   1320
tccattacta atccataaca tggctctttg ccacaactat ctctattggc tatatgccaa   1380
tactctgtcc ttcagagact gacacggact ctgtattttt acaggatggg gtccatttat   1440
tatttacaaa ttcacatata caacaacgcc gtcccccgtg cccgcagttt ttattaaaca   1500
tagcgtggga tctccgacat ctcgggtacg tgttccggac atgggctctt ctccggtagc   1560
ggcggagctt ccacatccga gccctggtcc catccgtcca gcggctcatg gtcgctcggc   1620
agctccttgc tcctaacagt ggaggccaga cttaggcaca gcacaatgcc caccaccacc   1680
agtgtgccgc acaaggccgt ggcggtaggg tatgtgtctg aaaatgagct cggagattgg   1740
gctcgcacct ggacgcagat ggaagactta aggcagcggc agaagaagat gcaggcagct   1800
gagttgttgt attctgataa gagtcagagg taactcccgt tgcggtgctg ttaacggtgg   1860
agggcagtgt agtctgagca gtactcgttg ctgccgcgcg cgccaccaga cataatagct   1920
gacagactaa cagactgttc cttttccatgg gtctttttctg cagtcaccgt cgtcgaccgg   1980
tcgcgaattc gtacgatatc ggcgcgcctc gaggtcgaag gcgcgccgcc accatggatc   2040
ctaacactgt gagctccttt caagtggact gctttctttg gcatgtacgg aagcgcgtcg   2100
ccgaccaaga actgggagac gcccccttc tggatcggct gcgacgggac caaaaatcct   2160
tgagaggtcg gggctctacg ctgggcctcg atatcgaaac cgctaccagg gcagggaagc   2220
aaattgtgga gaggattctg aaagaagagt ccgatgaggc acttaaaatg accatggcat   2280
ccgtgccagc ctcacgatac ctgaccgata tgacattgga agaaatgtca agagaatggt   2340
caatgctgat cccaaagcag aaagtcgctg gtccactgtg tatccgaatg gatcaggcta   2400
tcatggacaa aaatattata ttgaaggcaa atttcagcgt gatcttcgac cggttggaga   2460
cacttatact gctgagggcc ttcaccgagg aaggtgccat cgtcggtgag atttcccctc   2520
tgccgagcct gccaggacat accgccgaag acgtgaaaaa tgcagtaggc gttttgatcg   2580
ggggactgga atggaacgac aataccgtta gagtgagcga gacactgcaa cgctttgcct   2640
ggcggagttc taacgaaaat ggacggccgc ccttgacccc aaaacaaaag agagagatgg   2700
ccggcaccat ccggtctgag gtataggcgg ccgcatcgat agatctcccg ggtctagagg   2760
gagaccacac cggtttccct ctagcgggat caattccgcc cccccccta acgttactgg   2820
ccgaagccgc ttggaataag gccggtgtgc gtttgtctat atgttatttt ccaccatatt   2880
```

```
gccgtctttt ggcaatgtga gggcccggaa acctggccct gtcttcttga cgagcattcc    2940 tagggtctt tcccctctcg ccaaaggaat gcaaggtctg ttgaatgtcg tgaaggaagc     3000
agttcctctg gaagcttctt gaagacaaac aacgtctgta gcgacccttt gcaggcagcg    3060 gaaccccca cctggcgaca ggtgcctctg cggccaaaag ccacgtgtat aagatacacc     3120
tgcaaaggcg gcacaacccc agtgccacgt tgtgagttgg atagttgtgg aaagagtcaa    3180
atggctctcc tcaagcgtat tcaacaaggg gctgaaggat gcccagaagg taccccattg    3240
tatgggatct gatctggggc ctcggtgcac atgctttaca tgtgtttagt cgaggttaaa    3300
aaacgtctag gccccccgaa ccacggggac gtggttttcc tttgaaaaac acgataatac    3360
catggttcga ccattgaact gcatcgtcgc cgtgtcccaa aatatgggga ttggcaagaa    3420
cggagaccta ccctggcctc cgctcaggaa cgagttcaag tacttccaaa gaatgaccac    3480
aacctcttca gtggaaggta aacagaatct ggtgattatg ggtaggaaaa cctggttctc    3540
cattcctgag aagaatcgac ctttaaagga cagaattaat atagttctca gtagagaact    3600
caaagaacca ccacgaggag ctcatttttct tgccaaaagt ttggatgatg ccttaagact    3660
tattgaacaa ccggaattgg caagtaaagt agacatggtt tggatagtcg gaggcagttc    3720
tgtttaccag gaagccatga atcaaccagg ccacctcaga ctctttgtga caaggatcat    3780
gcaggaattt gaaagtgaca cgttttttccc agaaattgat ttggggaaat ataaacttct    3840
cccagaatac ccaggcgtcc tctctgaggt ccaggaggaa aaaggcatca agtataagtt    3900
tgaagtctac gagaagaaag acggaggagg atccatgatt gaacaagatg gattgcacgc    3960
aggttctccg gccgcttggg tggagaggct attcggctat gactgggcac aacagacaat    4020
cggctgctct gatgccgccg tgttccggct gtcagcgcag gggcgcccgg ttcttttttgt    4080 caagaccgac ctgtccggtg ccctgaatga actgcaggac gaggcagcgc ggctatcgtg    4140
gctggccacg acgggcgttc cttgcgcagc tgtgctcgac gttgtcactg aagcgggaag    4200
ggactggctg ctattgggcg aagtgccggg gcaggatctc ctgtcatctc accttgctcc    4260
tgccgagaaa gtatccatca tggctgatgc aatgcggcgg ctgcatacgc ttgatccggc    4320
tacctgccca ttcgaccacc aagcgaaaca tcgcatcgag cgagcacgta ctcggatgga    4380
agccggtctt gtcgatcagg atgatctgga cgaagagcat caggggctcg cgccagccga    4440
actgttcgcc aggctcaagg cgcgcatgcc cgacggcgag gatctcgtcg tgacccatgg    4500
cgatgcctgc ttgccgaata tcatggtgga aaatggccgc ttttctggat tcatcgactg    4560
tggccggctg ggtgtggcgg accgctatca ggacatagcg ttggctaccc gtgatattgc    4620
tgaagagctt ggcggcgaat gggctgaccg cttcctcgtg ctttacggta tcgccgctcc    4680
cgattcgcag cgcatcgcct tctatcgcct tcttgacgag ttcttctgag atccactac     4740 gcgttagagc tcgctgatca gcctcgactg tgccttctag ttgccagcca tctgttgttt    4800
gcccctcccc cgtgccttcc ttgaccctgg aaggtgccac tcccactgtc ctttcctaat    4860
aaaatgagga aattgcatcg cattgtctga gtaggtgtca ttctattctg ggggtgggg    4920 tggggcagga cagcaagggg gaggattggg aagacaatag caggcatgct ggggagctct    4980
tccgcttcct cgctcactga ctcgctgcgc tcggtcgttc ggctgcggcg agcggtatca    5040
gctcactcaa aggcggtaat acggttatcc acagaatcag gggataacgc aggaaagaac    5100
atgtgagcaa aaggccagca aaaggccagg aaccgtaaaa aggccgcgtt gctggcgttt    5160
ttccataggc tccgcccccc tgacgagcat cacaaaaatc gacgctcaag tcagaggtgg    5220
cgaaacccga caggactata aagataccag gcgtttcccc ctggaagctc cctcgtgcgc    5280
```

-continued

```
tctcctgttc cgaccctgcc gcttaccgga tacctgtccg cctttctccc ttcgggaagc    5340
gtggcgcttt ctcaatgctc acgctgtagg tatctcagtt cggtgtaggt cgttcgctcc    5400
aagctgggct gtgtgcacga accccccgtt cagcccgacc gctgcgcctt atccggtaac    5460
tatcgtcttg agtccaaccc ggtaagacac gacttatcgc cactggcagc agccactggt    5520
aacaggatta gcagagcgag gtatgtaggc ggtgctacag agttcttgaa gtggtggcct    5580
aactacggct acactagaag gacagtattt ggtatctgcg ctctgctgaa gccagttacc    5640
ttcggaaaaa gagttggtag ctcttgatcc ggcaaacaaa ccaccgctgg tagcggtggt    5700
ttttttgttt gcaagcagca gattacgcgc agaaaaaaag gatctcaaga agatcctttg    5760
atcttttcta cggggtctga cgctcagtgg aacgaaaact cacgttaagg gattttggtc    5820
atgagattat caaaaaggat cttcacctag atccttttaa attaaaaatg aagttttaaa    5880
tcaatctaaa gtatatatga gtaaacttgg tctgacagtt accaatgctt aatcagtgag    5940
gcacctatct cagcgatctg tctatttcgt tcatccatag ttgcctgact ccccgtcgtg    6000
tagataacta cgatacggga gggcttacca tctggcccca gtgctgcaat gataccgcga    6060
gacccacgct caccggctcc agatttatca gcaataaacc agccagccgg aagggccgag    6120
cgcagaagtg gtcctgcaac tttatccgcc tccatccagt ctattaattg ttgccgggaa    6180
gctagagtaa gtagttcgcc agttaatagt ttgcgcaacg ttgttgccat tgctacaggc    6240
atcgtggtgt cacgctcgtc gtttggtatg gcttcattca gctccggttc ccaacgatca    6300
aggcgagtta catgatcccc catgttgtgc aaaaaagcgg ttagctcctt cggtcctccg    6360
atcgttgtca gaagtaagtt ggccgcagtg ttatcactca tggttatggc agcactgcat    6420
aattctctta ctgtcatgcc atccgtaaga tgcttttctg tgactggtga gtactcaacc    6480
aagtcattct gagaatagtg tatgcggcga ccgagttgct cttgcccggc gtcaatacgg    6540 gataatacc g cgccacatag cagaacttta aaagtgctca tcattggaaa acgttcttcg    6600
gggcgaaaac tctcaaggat cttaccgctg ttgagatcca gttcgatgta acccactcgt    6660
gcacccaact gatcttcagc atcttttact ttcaccagcg tttctgggtg agcaaaaaca    6720
ggaaggcaaa atgccgcaaa aaagggaata agggcgacac ggaaatgttg aatactcata    6780
ctcttccttt ttcaatatta ttgaagcatt tatcagggtt attgtctcat gagcggatac    6840
atatttgaat gtatttagaa aaataaacaa ataggggttc cgcgcacatt tccccgaaaa    6900
gtgccacctg acgtctaaga aaccattatt atcatgacat taacctataa aaataggcgt    6960
atcacgaggc cctttcgtc                                                  6979
```

<210> SEQ ID NO 12
<211> LENGTH: 6535
<212> TYPE: DNA
<213> ORGANISM: Artificial Sequence
<220> FEATURE:
<223> OTHER INFORMATION: Synthetic plasmid: pCMVIII_NS82

<400> SEQUENCE: 12

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgaa gctttttgca aaagcctagg cctccaaaaa agcctcctca ctacttctgg    240
aatagctcag aggccgaggc ggcctcggcc tctgcataaa taaaaaaaat tagtcagcca    300
tggggcggag aatgggcgga actgggcggg agggaattat ttggctattg ccattgcat    360
```

```
acgttgtatc tatatcataa tatgtacatt tatattggct catgtccaat atgaccgcca    420
tgttgacatt gattattgac tagttattaa tagtaatcaa ttacggggtc attagttcat    480
agcccatata tggagttccg cgttacataa cttacggtaa atggcccgcc tggctgaccg    540
cccaacgacc cccgcccatt gacgtcaata atgacgtatg ttcccatagt aacgccaata    600
gggactttcc attgacgtca atgggtggag tatttacggt aaactgccca cttggcagta    660
catcaagtgt atcatatgcc aagtccgccc cctattgacg tcaatgacgg taaatggccc    720
gcctggcatt atgcccagta catgacctta cgggactttc ctacttggca gtacatctac    780
gtattagtca tcgctattac catggtgatg cggttttggc agtacaccaa tgggcgtgga    840
tagcggtttg actcacgggg atttccaagt ctccacccca ttgacgtcaa tgggagtttg    900
ttttggcacc aaaatcaacg ggactttcca aaatgtcgta ataaccccgc ccgttgacg     960
caaatgggcg gtaggcgtgt acggtggag gtctatataa gcagagctcg tttagtgaac   1020
cgtcagatcg cctggagacg ccatccacgc tgttttgacc tccatagaag acaccgggac   1080
cgatccagcc tccgcggccg ggaacggtgc attggaacgc ggattccccg tgccaagagt   1140
gacgtaagta ccgcctatag actctatagg cacaccccct tggctcttat gcatgctata   1200
ctgtttttgg cttggggcct atacaccccc gctccttatg ctataggtga tggtatagct   1260
tagcctatag gtgtgggtta ttgaccatta ttgaccactc ccctattggt gacgatactt   1320
tccattacta atccataaca tggctctttg ccacaactat ctctattggc tatatgccaa   1380
tactctgtcc ttcagagact gacacggact ctgtattttt acaggatggg gtccatttat   1440
tatttacaaa ttcacatata caacaacgcc gtccccgtg cccgcagttt ttattaaaca   1500
tagcgtggga tctccgacat ctcgggtacg tgttccggac atgggctctt ctccggtagc   1560
ggcggagctt ccacatccga gccctggtcc catccgtcca gcggctcatg gtcgctcggc   1620
agctccttgc tcctaacagt ggaggccaga cttaggcaca gcacaatgcc caccaccacc   1680
agtgtgccgc acaaggccgt ggcggtaggg tatgtgtctg aaaatgagct cggagattgg   1740
gctcgcacct ggacgcagat ggaagactta aggcagcggc agaagaagat gcaggcagct   1800
gagttgttgt attctgataa gagtcagagg taactcccgt tgcggtgctg ttaacggtgg   1860
agggcagtgt agtctgagca gtactcgttg ctgccgcgcg cgccaccaga cataatagct   1920
gacagactaa cagactgttc cttttccatgg gtcttttctg cagtcaccgt cgtcgaccgg   1980
tcgcgaattc gtacgatatc ggcgcgcctc gaggtcgaag gcgcgccgcc accatggatc   2040
ctaacactgt gagctccttt caagtggact gctttctttg gcatgtacgg aagcgcgtcg   2100
ccgaccaaga actgggagac gcccccttc tggatcggct gcgacgggac caaaaatcct   2160
tgagaggtcg gggctctacg ctgggcctcg atatcgaaac cgctaccagg gcagggaagc   2220
aaattgtgga gaggattctg aaagaagagt ccgatgaggc acttaaaatg accatggcat   2280
aggcggccgc atcgatagat ctcccgggtc tagagggaga ccacaacggt ttccctctag   2340
cgggatcaat tccgcccccc cccctaacgt tactggccga agccgcttgg aataaggccg   2400
gtgtgcgttt gtctatatgt tatttccac catattgccg tcttttggca atgtgagggc   2460
ccggaaacct ggccctgtct tcttgacgag cattcctagg gtctttccc ctctcgccaa   2520
aggaatgcaa ggtctgttga atgtcgtgaa ggaagcagtt cctctggaag cttcttgaag   2580
acaaacaacg tctgtagcga ccctttgcag gcagcggaac cccccacctg gcgacaggtg   2640
cctctgcggc caaaagccac gtgtataaga tacacctgca aaggcggcac aaccccagtg   2700
ccacgttgtg agttggatag ttgtggaaag agtcaaatgg ctctcctcaa gcgtattcaa   2760
```

```
caaggggctg aaggatgccc agaaggtacc ccattgtatg ggatctgatc tggggcctcg   2820
gtgcacatgc tttacatgtg tttagtcgag gttaaaaaac gtctaggccc cccgaaccac   2880
ggggacgtgg ttttcctttg aaaaacacga taataccatg gttcgaccat tgaactgcat   2940
cgtcgccgtg tcccaaaata tggggattgg caagaacgga gacctaccct ggcctccgct   3000
caggaacgag ttcaagtact tccaaagaat gaccacaacc tcttcagtgg aaggtaaaca   3060
gaatctggtg attatgggta ggaaaacctg gttctccatt cctgagaaga atcgaccttt   3120
aaaggacaga attaatatag ttctcagtag agaactcaaa gaaccaccac gaggagctca   3180
ttttcttgcc aaaagtttgg atgatgcctt aagacttatt gaacaaccgg aattggcaag   3240
taaagtagac atggtttgga tagtcggagg cagttctgtt taccaggaag ccatgaatca   3300
accaggccac ctcagactct ttgtgacaag gatcatgcag gaatttgaaa gtgacacgtt   3360
tttcccagaa attgatttgg ggaaatataa acttctccca gaatacccag gcgtcctctc   3420
tgaggtccag gaggaaaaag gcatcaagta taagtttgaa gtctacgaga agaaagacgg   3480
aggaggatcc atgattgaac aagatggatt gcacgcaggt tctccggccg cttgggtgga   3540
gaggctattc ggctatgact gggcacaaca gacaatcggc tgctctgatg ccgccgtgtt   3600
ccggctgtca gcgcaggggc gcccggttct ttttgtcaag accgacctgt ccggtgccct   3660
gaatgaactg caggacgagg cagcgcggct atcgtggctg gccacgacgg gcgttccttg   3720
cgcagctgtg ctcgacgttg tcactgaagc gggaagggac tggctgctat gggcgaagt    3780 gccggggcag gatctcctgt catctcacct tgctcctgcc gagaaagtat ccatcatggc   3840
tgatgcaatg cggcggctgc atacgcttga tccggctacc tgcccattcg accaccaagc   3900
gaaacatcgc atcgagcgag cacgtactcg gatggaagcc ggtcttgtcg atcaggatga   3960
tctggacgaa gagcatcagg ggctcgcgcc agccgaactg ttcgccaggc tcaaggcgcg   4020
catgcccgac ggcgaggatc tcgtcgtgac ccatggcgat gcctgcttgc cgaatatcat   4080
ggtggaaaat ggccgctttt ctggattcat cgactgtggc cggctgggtg tggcggaccg   4140
ctatcaggac atagcgttgg ctacccgtga tattgctgaa gagcttggcg gcgaatgggc   4200
tgaccgcttc ctcgtgcttt acggtatcgc cgctcccgat tcgcagcgca tcgccttcta   4260
tcgccttctt gacgagttct tctgaggatc cactacgcgt tagagctcgc tgatcagcct   4320
cgactgtgcc ttctagttgc cagccatctg ttgtttgccc ctcccccgtg ccttccttga   4380
ccctggaagg tgccactccc actgtccttt cctaataaaa tgaggaaatt gcatcgcatt   4440
gtctgagtag gtgtcattct attctggggg gtggggtggg gcaggacagc aaggggagg   4500 attgggaaga caatagcagg catgctgggg agctcttccg cttcctcgct cactgactcg   4560
ctgcgctcgg tcgttcggct gcggcgagcg gtatcagctc actcaaaggc ggtaatacgg   4620
ttatccacag aatcagggga taacgcagga agaacatgt gagcaaaagg ccagcaaaag   4680
gccaggaacc gtaaaaaggc cgcgttgctg gcgtttttcc ataggctccg cccccctgac   4740
gagcatcaca aaaatcgacg ctcaagtcag aggtggcgaa acccgacagg actataaaga   4800
taccaggcgt ttccccctgg aagctccctc gtgcgctctc ctgttccgac cctgccgctt   4860
accggatacc tgtccgcctt tctcccttcg ggaagcgtgg cgctttctca atgctcacgc   4920
tgtaggtatc tcagttcggt gtaggtcgtt cgctccaagc tgggctgtgt gcacgaaccc   4980
cccgttcagc ccgaccgctg cgccttatcc ggtaactatc gtcttgagtc aacccggta    5040 agacacgact tatcgccact ggcagcagcc actggtaaca ggattagcag agcgaggtat   5100
gtaggcggtg ctacagagtt cttgaagtgg tggcctaact acggctacac tagaaggaca   5160
```

```
gtatttggta tctgcgctct gctgaagcca gttaccttcg gaaaaagagt tggtagctct    5220
tgatccggca aacaaaccac cgctggtagc ggtggttttt ttgtttgcaa gcagcagatt    5280
acgcgcagaa aaaaggatc tcaagaagat cctttgatct tttctacggg gtctgacgct     5340
cagtggaacg aaaactcacg ttaagggatt ttggtcatga gattatcaaa aaggatcttc    5400
acctagatcc ttttaaatta aaaatgaagt tttaaatcaa tctaaagtat atatgagtaa    5460
acttggtctg acagttacca atgcttaatc agtgaggcac ctatctcagc gatctgtcta    5520
tttcgttcat ccatagttgc ctgactcccc gtcgtgtaga taactacgat acgggagggc    5580
ttaccatctg gccccagtgc tgcaatgata ccgcgagacc cacgctcacc ggctccagat    5640
ttatcagcaa taaaccagcc agccggaagg gccgagcgca gaagtggtcc tgcaacttta    5700
tccgcctcca tccagtctat taattgttgc cgggaagcta gagtaagtag ttcgccagtt    5760
aatagtttgc gcaacgttgt tgccattgct acaggcatcg tggtgtcacg ctcgtcgttt    5820
ggtatggctt cattcagctc cggttcccaa cgatcaaggc gagttacatg atccccccatg   5880 ttgtgcaaaa aagcggttag ctccttcggt cctccgatcg ttgtcagaag taagttggcc    5940
gcagtgttat cactcatggt tatggcagca ctgcataatt ctcttactgt catgccatcc    6000
gtaagatgct tttctgtgac tggtgagtac tcaaccaagt cattctgaga atagtgtatg    6060
cggcgaccga gttgctcttg cccggcgtca atacggata taccgcgcc acatagcaga     6120 actttaaaag tgctcatcat tggaaaacgt tcttcggggc gaaaactctc aaggatctta    6180
ccgctgttga tccagttc gatgtaaccc actcgtgcac ccaactgatc ttcagcatct      6240
tttactttca ccagcgtttc tgggtgagca aaaacaggaa ggcaaaatgc cgcaaaaaag    6300
ggaataaggg cgacacggaa atgttgaata ctcatactct tcctttttca atattattga    6360
agcatttatc agggttattg tctcatgagc ggatacatat ttgaatgtat ttagaaaaat    6420
aaacaaatag gggttccgcg cacatttccc cgaaaagtgc cacctgacgt ctaagaaacc    6480
attattatca tgacattaac ctataaaaat aggcgtatca cgaggccctt tcgtc         6535
```

<210> SEQ ID NO 13
<211> LENGTH: 6829
<212> TYPE: DNA
<213> ORGANISM: Artificial Sequence
<220> FEATURE:
<223> OTHER INFORMATION: Synthetic plasmid: pCMVIII_NS180

<400> SEQUENCE: 13

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgaa gctttttgca aaagcctagg cctccaaaaa agcctcctca ctacttctgg    240
aatagctcag aggccgaggc ggcctcggcc tctgcataaa taaaaaaaat tagtcagcca    300
tggggcggag aatgggcgga actgggcggg agggaatta ttggctattg gccattgcat     360
acgttgtatc tatatcataa tatgtacatt tatattggct catgtccaat atgaccgcca    420
tgttgacatt gattattgac tagttattaa tagtaatcaa ttacggggtc attagttcat    480
agcccatata tggagttccg cgttacataa cttacggtaa atggcccgcc tggctgaccg    540
cccaacgacc cccgcccatt gacgtcaata atgacgtatg ttcccatagt aacgccaata    600
gggactttcc attgacgtca atgggtggag tatttacggt aaactgccca cttggcagta    660
catcaagtgt atcatatgcc aagtccgccc cctattgacg tcaatgacgg taaatggccc    720
```

```
gcctggcatt atgcccagta catgacctta cgggactttc ctacttggca gtacatctac    780
gtattagtca tcgctattac catggtgatg cggttttggc agtacaccaa tgggcgtgga    840
tagcggtttg actcacgggg atttccaagt ctccacccca ttgacgtcaa tgggagtttg    900
ttttggcacc aaaatcaacg ggactttcca aatgtcgta ataaccccgc cccgttgacg     960
caaatgggcg gtaggcgtgt acggtgggag gtctatataa gcagagctcg tttagtgaac   1020
cgtcagatcg cctggagacg ccatccacgc tgttttgacc tccatagaag acaccgggac   1080
cgatccagcc tccgcggccg ggaacggtgc attggaacgc ggattccccg tgccaagagt   1140
gacgtaagta ccgcctatag actctatagg cacaccccct tggctcttat gcatgctata   1200
ctgttttgg cttggggcct atacaccccc gctccttatg ctataggtga tggtatagct    1260
tagcctatag gtgtgggtta ttgaccatta ttgaccactc ccctattggt gacgatactt   1320
tccattacta atccataaca tggctctttg ccacaactat ctctattggc tatatgccaa   1380
tactctgtcc ttcagagact gacacggact ctgtattttt acaggatggg gtccatttat   1440
tatttacaaa ttcacatata caacaacgcc gtccccccgtg cccgcagttt ttattaaaca   1500
tagcgtggga tctccgacat ctcgggtacg tgttccggac atgggctctt ctccggtagc   1560
ggcggagctt ccacatccga gccctggtcc catccgtcca gcggctcatg gtcgctcggc   1620
agctccttgc tcctaacagt ggaggccaga cttaggcaca gcacaatgcc caccaccacc   1680
agtgtgccgc acaaggccgt ggcggtaggg tatgtgtctg aaaatgagct cggagattgg   1740
gctcgcacct ggacgcagat ggaagactta aggcagcggc agaagaagat gcaggcagct   1800
gagttgttgt attctgataa gagtcagagg taactcccgt tgcggtgctg ttaacggtgg   1860
agggcagtgt agtctgagca gtactcgttg ctgccgcgcg cgccaccaga cataatagct   1920
gacagactaa cagactgttc cttttccatgg gtcttttctg cagtcaccgt cgtcgaccgg   1980
tcgcgaattc gtacgatatc ggcgcgcctc gaggtcgaag gcgcgccgcc accatggatc   2040
ctaacactgt gagctccttt caagtggact gctttctttg gcatgtacgg aagcgcgtcg   2100
ccgaccaaga actgggagac gccccctttc tggatcggct gcgacgggac caaaaatcct   2160
tgagaggtcg gggctctacg ctgggcctcg atatcgaaac cgctaccagg gcagggaagc   2220
aaattgtgga gaggattctg aaagaagagt ccgatgaggc acttaaaatg accatggcat   2280
ccgtgccagc ctcacgatac ctgaccgata tgacattgga agaaatgtca agagaatggt   2340
caatgctgat cccaaagcag aaagtcgctg gtccactgtg tatccgaatg gatcaggcta   2400
tcatggacaa aaatattata ttgaaggcaa atttcagcgt gatcttcgac cggttggaga   2460
cacttatact gctgagggcc ttcaccgagg aaggtgccat cgtcggtgag atttccctc    2520
tgccgagcct gccaggacat accgccgaag acgtgaaaaa tgcagtaggc gtttaggcgg   2580
ccgcatcgat agatctcccg ggtctagagg gagaccacaa cggtttccct ctagcgggat   2640
caattccgcc cccccccta acgttactgg ccgaagccgc ttggaataag gccggtgtgc    2700
gtttgtctat atgttatttt ccaccatatt gccgtctttt ggcaatgtga gggcccggaa   2760
acctggccct gtcttcttga cgagcattcc tagggtctt tcccctctcg ccaaaggaat    2820
gcaaggtctg ttgaatgtcg tgaaggaagc agttcctctg gaagcttctt gaagacaaac   2880
aacgtctgta gcgaccctt gcaggcagcg gaaccccca cctggcgaca ggtgcctctg     2940
cggccaaaag ccacgtgtat aagatacacc tgcaaaggcg gcacaacccc agtgccacgt   3000
tgtgagttgg atagttgtgg aaagagtcaa atggctctcc tcaagcgtat tcaacaaggg   3060
gctgaaggat gcccagaagg tacccccattg tatgggatct gatctggggc ctcggtgcac   3120
```

```
atgctttaca tgtgtttagt cgaggttaaa aaacgtctag gccccccgaa ccacggggac   3180
gtggttttcc tttgaaaaac acgataatac catggttcga ccattgaact gcatcgtcgc   3240
cgtgtcccaa aatatgggga ttggcaagaa cggagaccta ccctggcctc cgctcaggaa   3300
cgagttcaag tacttccaaa gaatgaccac aacctcttca gtggaaggta aacagaatct   3360
ggtgattatg ggtaggaaaa cctggttctc cattcctgag aagaatcgac ctttaaagga   3420
cagaattaat atagttctca gtagagaact caaagaacca ccacgaggag ctcattttct   3480
tgccaaaagt ttggatgatg ccttaagact tattgaacaa ccggaattgg caagtaaagt   3540
agacatggtt tggatagtcg gaggcagttc tgtttaccag gaagccatga atcaaccagg   3600
ccacctcaga ctctttgtga caaggatcat gcaggaattt gaaagtgaca cgttttttccc   3660 agaaattgat ttggggaaat ataaacttct cccagaatac ccaggcgtcc tctctgaggt   3720
ccaggaggaa aaaggcatca agtataagtt tgaagtctac gagaagaaag acggaggagg   3780
atccatgatt gaacaagatg gattgcacgc aggttctccg ccgcttgggt ggagaggct   3840 attcggctat gactgggcac aacagacaat cggctgctct gatgccgccg tgttccggct   3900
gtcagcgcag gggcgcccgg ttcttttttgt caagaccgac ctgtccggtg ccctgaatga   3960
actgcaggac gaggcagcgc ggctatcgtg gctggccacg acgggcgttc cttgcgcagc   4020
tgtgctcgac gttgtcactg aagcgggaag ggactggctg ctattgggcg aagtgccggg   4080
gcaggatctc ctgtcatctc accttgctcc tgccgagaaa gtatccatca tggctgatgc   4140
aatgcggcgg ctgcatacgc ttgatccggc tacctgccca ttcgaccacc aagcgaaaca   4200
tcgcatcgag cgagcacgta ctcggatgga agccggtctt gtcgatcagg atgatctgga   4260
cgaagagcat caggggctcg cgccagccga actgttcgcc aggctcaagg cgcgcatgcc   4320
cgacggcgag gatctcgtcg tgacccatgg cgatgcctgc ttgccgaata tcatggtgga   4380
aaatggccgc ttttctggat tcatcgactg tggccggctg ggtgtggcgg accgctatca   4440
ggacatagcg ttggctaccc gtgatattgc tgaagagctt ggcggcgaat gggctgaccg   4500
cttcctcgtg ctttacggta tcgccgctcc cgattcgcag cgcatcgcct ctatcgcct   4560 tcttgacgag ttcttctgag gatccactac gcgttagagc tcgctgatca gcctcgactg   4620
tgccttctag ttgccagcca tctgttgttt gcccctcccc cgtgccttcc ttgaccctgg   4680
aaggtgccac tcccactgtc ctttcctaat aaaatgagga aattgcatcg cattgtctga   4740
gtaggtgtca ttctattctg gggggtgggg tggggcagga cagcaagggg gaggattggg   4800
aagacaatag caggcatgct ggggagctct tccgcttcct cgctcactga ctcgctgcgc   4860
tcggtcgttc ggctgcggcg agcggtatca gctcactcaa aggcggtaat acggttatcc   4920
acagaatcag gggataacgc aggaaagaac atgtgagcaa aaggccagca aaaggccagg   4980
aaccgtaaaa aggccgcgtt gctggcgttt ttccataggc tccgcccccc tgacgagcat   5040
cacaaaaatc gacgctcaag tcagaggtgg cgaaacccga caggactata aagataccag   5100
gcgtttcccc ctggaagctc cctcgtgcgc tctcctgttc cgaccctgcc gcttaccgga   5160
tacctgtccg cctttctccc ttcgggaagc gtggcgcttt ctcaatgctc acgctgtagg   5220
tatctcagtt cggtgtaggt cgttcgctcc aagctgggct gtgtgcacga accccccgtt   5280
cagcccgacc gctgcgcctt atccggtaac tatcgtcttg agtccaaccc ggtaagacac   5340
gacttatcgc cactggcagc agccactggt aacaggatta gcagagcgag gtatgtaggc   5400
ggtgctacag agttcttgaa gtggtggcct aactacggct acactagaag gacagtattt   5460
ggtatctgcg ctctgctgaa gccagttacc ttcggaaaaa gagttggtag ctcttgatcc   5520
```

```
ggcaaacaaa ccaccgctgg tagcggtggt ttttttgttt gcaagcagca gattacgcgc   5580
agaaaaaaag gatctcaaga agatcctttg atctttttcta cggggtctga cgctcagtgg   5640
aacgaaaact cacgttaagg gattttggtc atgagattat caaaaaggat cttcacctag   5700
atccttttaa attaaaaatg aagttttaaa tcaatctaaa gtatatatga gtaaacttgg   5760
tctgacagtt accaatgctt aatcagtgag gcacctatct cagcgatctg tctatttcgt   5820
tcatccatag ttgcctgact ccccgtcgtg tagataacta cgatacggga gggcttacca   5880
tctggcccca gtgctgcaat gataccgcga gacccacgct caccggctcc agatttatca   5940
gcaataaacc agccagccgg aagggccgag cgcagaagtg gtcctgcaac tttatccgcc   6000
tccatccagt ctattaattg ttgccgggaa gctagagtaa gtagttcgcc agttaatagt   6060
ttgcgcaacg ttgttgccat tgctacaggc atcgtggtgt cacgctcgtc gtttggtatg   6120
gcttcattca gctccggttc ccaacgatca aggcgagtta catgatcccc catgttgtgc   6180
aaaaaagcgg ttagctcctt cggtcctccg atcgttgtca gaagtaagtt ggccgcagtg   6240
ttatcactca tggttatggc agcactgcat aattctctta ctgtcatgcc atccgtaaga   6300
tgcttttctg tgactggtga gtactcaacc aagtcattct gagaatagtg tatgcggcga   6360
ccgagttgct cttgcccggc gtcaatacgg gataataccg cgccacatag cagaacttta   6420
aaagtgctca tcattggaaa acgttcttcg ggcgaaaac tctcaaggat cttaccgctg   6480
ttgagatcca gttcgatgta acccactcgt gcacccaact gatcttcagc atctttttact   6540 ttcaccagcg tttctgggtg agcaaaaaca ggaaggcaaa atgccgcaaa aaagggaata   6600
agggcgacac ggaaatgttg aatactcata ctcttccttt ttcaatatta ttgaagcatt   6660
tatcagggtt attgtctcat gagcggatac atatttgaat gtatttagaa aaataaacaa   6720
ataggggttc cgcgcacatt tccccgaaaa gtgccacctg acgtctaaga aaccattatt   6780
atcatgacat taacctataa aaataggcgt atcacgaggc cctttcgtc   6829
```

<210> SEQ ID NO 14
<211> LENGTH: 6874
<212> TYPE: DNA
<213> ORGANISM: Artificial Sequence
<220> FEATURE:
<223> OTHER INFORMATION: Synthetic plasmid: pCMVIII_NSdel50-84

<400> SEQUENCE: 14

```
tcgcgcgttt cggtgatgac ggtgaaaacc tctgacacat gcagctcccg gagacggtca     60
cagcttgtct gtaagcggat gccggagcca gacaagcccg tcagggcgcg tcagcgggtg    120
ttggcgggtg tcggggctgg cttaactatg cggcatcaga gcagattgta ctgagagtgc    180
accatatgaa gcttttttgca aaagcctagg cctccaaaaa agcctcctca ctacttctgg    240
aatagctcag aggccgaggc ggcctcggcc tctgcataaa taaaaaaaat tagtcagcca    300
tggggcggag aatgggcgga actgggcggg agggaatta ttgctattg gccattgcat    360 acgttgtatc tatatcataa tatgtacatt tatattggct catgtccaat atgaccgcca    420
tgttgacatt gattattgac tagttattaa tagtaatcaa ttacggggtc attagttcat    480
agcccatata tggagttccg cgttacataa cttacggtaa atggcccgcc tggctgaccg    540
cccaacgacc cccgcccatt gacgtcaata atgacgtatg ttcccatagt aacgccaata    600
gggactttcc attgacgtca atgggtggag tatttacggt aaactgccca cttggcagta    660
catcaagtgt atcatatgcc aagtccgccc cctattgacg tcaatgacgg taaatggccc    720
gcctggcatt atgcccagta catgacctta cgggactttc ctacttggca gtacatctac    780
```

```
gtattagtca tcgctattac catggtgatg cggttttggc agtacaccaa tgggcgtgga    840
tagcggtttg actcacgggg atttccaagt ctccacccca ttgacgtcaa tgggagtttg    900
ttttggcacc aaaatcaacg ggactttcca aaatgtcgta ataacccgc cccgttgacg     960 caaatgggcg gtaggcgtgt acggtgggag gtctatataa gcagagctcg tttagtgaac   1020
cgtcagatcg cctggagacg ccatccacgc tgttttgacc tccatagaag acaccgggac   1080
cgatccagcc tccgcggccg ggaacggtgc attggaacgc ggattccccg tgccaagagt   1140
gacgtaagta ccgcctatag actctatagg cacacccctt tggctcttat gcatgctata   1200
ctgttttggg cttgggcct atacacccc gctccttatg ctataggtga tggtatagct    1260
tagcctatag gtgtgggtta ttgaccatta ttgaccactc ccctattggt gacgatactt   1320
tccattacta atccataaca tggctctttg ccacaactat ctctattggc tatatgccaa   1380
tactctgtcc ttcagagact gacacggact ctgtatttt acaggatggg gtccatttat    1440
tatttacaaa ttcacatata caacaacgcc gtccccgtg cccgcagttt ttattaaaca    1500
tagcgtggga tctccgacat ctcgggtacg tgttccggac atgggctctt ctccggtagc   1560
ggcggagctt ccacatccga gccctggtcc catccgtcca gcggctcatg gtcgctcggc   1620
agctccttgc tcctaacagt ggaggccaga cttaggcaca gcacaatgcc caccaccacc   1680
agtgtgccgc acaaggccgt ggcggtaggg tatgtgtctg aaaatgagct cggagattgg   1740
gctcgcacct ggacgcagat ggaagactta aggcagcggc agaagaagat gcaggcagct   1800
gagttgttgt attctgataa gagtcagagg taactcccgt tgcggtgctg ttaacggtgg   1860
agggcagtgt agtctgagca gtactcgttg ctgccgcgcg cgccaccaga cataatagct   1920
gacagactaa cagactgttc cttccatgg gtcttttctg cagtcaccgt cgtcgaccgg    1980
tcgcgaattc gtacgatatc ggcgcgcctc gaggtcgaag gcgcgccgcc accatggatc   2040
ctaacactgt gagctccttt caagtggact gctttctttg gcatgtacgg aagcgcgtcg   2100
ccgaccaaga actgggagac gccccctttc tggatcggct gcgacgggac caaaaatcct   2160
tgagaggtcg gggctctacg ccagcctcac gatacctgac cgatatgaca ttggaagaaa   2220
tgtcaagaga atggtcaatg ctgatcccaa agcagaaagt cgctggtcca ctgtgtatcc   2280
gaatggatca ggctatcatg gacaaaaata ttatattgaa ggcaaatttc agcgtgatct   2340
tcgaccggtt ggagacactt atactgctga gggccttcac cgaggaaggt gccatcgtcg   2400
gtgagatttc ccctctgccg agcctgccag gacataccgc cgaagacgtg aaaaatgcag   2460
taggcgtttt gatcggggga ctggaatgga acgacaatac cgttagagtg agcgagacac   2520
tgcaacgctt tgcctggcgg agttctaacg aaaatggacg gccgcccttg accccaaaac   2580
aaaagagaga gatggccggc accatccggt ctgaggtata ggcggccgca tcgatagatc   2640
tcccgggtct agagggagac cacaacggtt tccctctagc gggatcaatt ccgcccccc    2700 ccctaacgtt actggccgaa gccgcttgga ataaggccgg tgtgcgtttg tctatatgtt   2760
attttccacc atattgccgt cttttggcaa tgtgagggcc cggaaacctg gccctgtctt   2820
cttgacgagc attcctaggg gtctttcccc tctcgccaaa ggaatgcaag gtctgttgaa   2880
tgtcgtgaag gaagcagttc ctctggaagc ttcttgaaga caacaacgt ctgtagcgac    2940 cctttgcagg cagcggaacc cccacctgg cgacaggtgc ctctgcggcc aaaagccacg    3000
tgtataagat acacctgcaa aggcggcaca accccagtgc cacgttgtga gttggatagt   3060
tgtggaaaga gtcaaatggc tctcctcaag cgtattcaac aaggggctga aggatgccca   3120
gaaggtaccc cattgtatgg gatctgatct ggggcctcgg tgcacatgct ttacatgtgt   3180
```

```
ttagtcgagg ttaaaaaacg tctaggcccc ccgaaccacg gggacgtggt tttcctttga   3240
aaaacacgat aataccatgg ttcgaccatt gaactgcatc gtcgccgtgt cccaaaatat   3300
ggggattggc aagaacggag acctaccctg gcctccgctc aggaacgagt tcaagtactt   3360
ccaaagaatg accacaacct cttcagtgga aggtaaacag aatctggtga ttatgggtag   3420
gaaaacctgg ttctccattc ctgagaagaa tcgacccttta aaggacagaa ttaatatagt   3480
tctcagtaga gaactcaaag aaccaccacg aggagctcat tttcttgcca aaagtttgga   3540
tgatgcctta agacttattg aacaaccgga attggcaagt aaagtagaca tggtttggat   3600
agtcggaggc agttctgttt accaggaagc catgaatcaa ccaggccacc tcagactctt   3660
tgtgacaagg atcatgcagg aatttgaaag tgacacgttt ttcccagaaa ttgatttggg   3720
gaaatataaa cttctcccag aatacccagg cgtcctctct gaggtccagg aggaaaaagg   3780
catcaagtat aagtttgaag tctacgaaga gaaagacgga ggaggatcca tgattgaaca   3840
agatggattg cacgcaggtt ctccggccgc ttgggtggag aggctattcg gctatgactg   3900
ggcacaacag acaatcggct gctctgatgc cgccgtgttc cggctgtcag cgcaggggcg   3960
cccggttctt tttgtcaaga ccgacctgtc cggtgccctg aatgaactgc aggacgaggc   4020
agcgcggcta tcgtggctgg ccacgacggg cgttccttgc gcagctgtgc tcgacgttgt   4080
cactgaagcg ggaagggact ggctgctatt gggcgaagtg ccggggcagg atctcctgtc   4140
atctcacctt gctcctgccg agaaagtatc catcatggct gatgcaatgc ggcggctgca   4200
tacgcttgat ccggctacct gcccattcga ccaccaagcg aaacatcgca tcgagcgagc   4260
acgtactcgg atggaagccg gtcttgtcga tcaggatgat ctggacgaag agcatcaggg   4320
gctcgcgcca gccgaactgt tcgccaggct caaggcgcgc atgcccgacg gcgaggatct   4380
cgtcgtgacc catggcgatg cctgcttgcc gaatatcatg gtggaaaatg gccgcttttc   4440
tggattcatc gactgtggcc ggctgggtgt ggcggaccgc tatcaggaca tagcgttggc   4500
tacccgtgat attgctgaag agcttggcgg cgaatgggct gaccgcttcc tcgtgcttta   4560
cggtatcgcc gctcccgatt cgcagcgcat cgccttctat cgccttcttg acgagttctt   4620
ctgaggatcc actacgcgtt agagctcgct gatcagcctc gactgtgcct tctagttgcc   4680
agccatctgt tgtttgcccc tcccccgtgc cttccttgac cctggaaggt gccactccca   4740
ctgtcctttc ctaataaaat gaggaaattg catcgcattg tctgagtagg tgtcattcta   4800
ttctgggggg tggggtgggg caggacagca agggggagga ttgggaagac aatagcaggc   4860
atgctgggga gctcttccgc ttcctcgctc actgactcgc tgcgctcggt cgttcggctg   4920
cggcgagcgg tatcagctca ctcaaaggcg gtaatacggt tatccacaga atcaggggat   4980
aacgcaggaa agaacatgtg agcaaaaggc cagcaaaagg ccaggaaccg taaaaaggcc   5040
gcgttgctgg cgttttttcca taggctccgc ccccctgacg agcatcacaa aaatcgacgc   5100
tcaagtcaga ggtggcgaaa cccgacagga ctataaagat accaggcgtt tccccctgga   5160
agctccctcg tgcgctctcc tgttccgacc ctgccgctta ccggatacct gtccgccttt   5220
ctcccttcgg gaagcgtggc gctttctcaa tgctcacgct gtaggtatct cagttcggtg   5280
taggtcgttc gctccaagct gggctgtgtg cacgaacccc ccgttcagcc cgaccgctgc   5340
gccttatccg gtaactatcg tcttgagtcc aacccggtaa gacacgactt atcgccactg   5400
gcagcagcca ctggtaacag gattagcaga gcgaggtatg taggcggtgc tacagagttc   5460
ttgaagtggt ggcctaacta cggctacact agaaggacag tatttggtat ctgcgctctg   5520
ctgaagccag ttaccttcgg aaaaagagtt ggtagctctt gatccggcaa acaaaccacc   5580
```

```
gctggtagcg gtggtttttt tgtttgcaag cagcagatta cgcgcagaaa aaaaggatct    5640
caagaagatc ctttgatctt ttctacgggg tctgacgctc agtggaacga aaactcacgt    5700
taagggattt tggtcatgag attatcaaaa aggatcttca cctagatcct tttaaattaa    5760
aaatgaagtt ttaaatcaat ctaaagtata tatgagtaaa cttggtctga cagttaccaa    5820
tgcttaatca gtgaggcacc tatctcagcg atctgtctat ttcgttcatc catagttgcc    5880
tgactccccg tcgtgtagat aactacgata cgggagggct taccatctgg ccccagtgct    5940
gcaatgatac cgcgagaccc acgctcaccg gctccagatt tatcagcaat aaaccagcca    6000
gccggaaggg ccgagcgcag aagtggtcct gcaactttat ccgcctccat ccagtctatt    6060
aattgttgcc gggaagctag agtaagtagt tcgccagtta atagtttgcg caacgttgtt    6120
gccattgcta caggcatcgt ggtgtcacgc tcgtcgtttg gtatggcttc attcagctcc    6180
ggttcccaac gatcaaggcg agttacatga tcccccatgt tgtgcaaaaa agcggttagc    6240
tccttcggtc ctccgatcgt tgtcagaagt aagttggccg cagtgttatc actcatggtt    6300
atggcagcac tgcataattc tcttactgtc atgccatccg taagatgctt ttctgtgact    6360
ggtgagtact caaccaagtc attctgagaa tagtgtatgc ggcgaccgag ttgctcttgc    6420
ccggcgtcaa tacgggataa taccgcgcca catagcagaa ctttaaaagt gctcatcatt    6480
ggaaaacgtt cttcggggcg aaaactctca aggatcttac cgctgttgag atccagttcg    6540
atgtaaccca ctcgtgcacc caactgatct tcagcatctt ttactttcac cagcgtttct    6600
gggtgagcaa aaacaggaag gcaaaatgcc gcaaaaaagg gaataagggc gacacggaaa    6660
tgttgaatac tcatactctt ccttttcaa tattattgaa gcatttatca gggttattgt    6720
ctcatgagcg gatacatatt tgaatgtatt tagaaaaata aacaaatagg ggttccgcgc    6780
acatttcccc gaaaagtgcc acctgacgtc taagaaacca ttattatcat gacattaacc    6840
tataaaaata ggcgtatcac gaggcccttt cgtc                               6874
```

<210> SEQ ID NO 15
<211> LENGTH: 230
<212> TYPE: PRT
<213> ORGANISM: Influenza A virus

<400> SEQUENCE: 15

```
Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Glu Trp Ser Met Leu Ile Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140
```

```
Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Asp Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val
225                 230

<210> SEQ ID NO 16
<211> LENGTH: 12376
<212> TYPE: DNA
<213> ORGANISM: Artificial Sequence
<220> FEATURE:
<223> OTHER INFORMATION: Synthetic plasmid: pRLF2AUb452JFH1

<400> SEQUENCE: 16
```

| | | | | | |
|---|---|---|---|---|---|
| gaattcccaa | acgcgttaat | acgactcact | atagacctgc | ccctaatagg | ggcgacactc | 60 |
| cgccatgaat | cactcccctg | tgaggaacta | ctgtcttcac | gcagaaagcg | cctagccatg | 120 |
| gcgttagtat | gagtgtcgta | cagcctccag | gcccccccct | cccgggagag | ccatagtggt | 180 |
| ctgcggaacc | ggtgagtaca | ccggaattgc | cgggaagact | gggtcctttc | ttggataaac | 240 |
| ccactctatg | cccggccatt | gggcgtgccc | ccgcaagac | tgctagccga | gtagcgttgg | 300 |
| gttgcgaaag | gccttgtggt | actgcctgat | agggcgcttg | cgagtgcccc | gggaggtctc | 360 |
| gtagaccgtg | caccatgagc | acacttccta | aacctcaaag | aaaaaccaaa | agaaacacca | 420 |
| tccgtcgccc | acaggacgtc | aagttcccgg | gtggcggaca | gatcgttggt | ggagtatacg | 480 |
| tgttgccgcg | caggggccca | cgattgggtg | tgtgcgcgac | gcgtaaaact | tctgaacggt | 540 |
| cacagcctcg | cggacggcga | cagcctatcc | ccaaggcgcg | tcggagcgaa | ggccggtcct | 600 |
| gggctcagcc | cgggtacccc | tggccctct | atggtaacga | gggctgcggg | tgggcagggt | 660 |
| ggctcctgtc | cccacgcggc | tcccgtccat | cttggggccc | aaatgacccc | cggcggaggt | 720 |
| cccgcaattt | gggtaaagtc | atcgataccc | tcacgtgcgg | attcgccgat | ctcatggggt | 780 |
| acatcccgct | cgtcggcgcc | ccgtaggag | gcgtcgcaag | agccctcgcg | catggcgtga | 840 |
| gggcccttga | agacgggata | aatttcgcaa | caggggaactt | gcctggttgc | tcttttttcta | 900 |
| tcttccttct | tgctctgttc | tcttgcttag | ttcatccagc | agctagttta | gagtggcgga | 960 |
| atacgtctgg | cctctacgtc | cttaccaacg | actgtcccaa | tagcagtatt | gtgtatgagg | 1020 |
| ccgatgacgt | cattctgcac | acgcctggct | gtataccttg | tgtccaggac | ggcaataaat | 1080 |
| ccacgtgctg | gacttcagtg | acacctacag | tggcagtcaa | gtacgtcgga | gcaaccaccg | 1140 |
| cttcgatacg | cagtcatgta | gacctgctag | tgggcgcggc | cacgatgtgc | tctgcgctct | 1200 |
| acgtgggtga | tatgtgtggg | gccgtcttcc | tcgtgggaca | agccttcacg | ttcagacctc | 1260 |
| gtcgccatca | aacggtccag | acctgtaact | gctcgctgta | tccaggccat | ctctcaggtc | 1320 |
| atcgaatggc | ttgggatatg | atgatgaatt | ggtccccgc | tgtgggtatg | gtggtagcgc | 1380 |
| acgtcctgcg | tctgccccag | accttgttcg | acataatagc | cggggcccat | tggggcattt | 1440 |
| tggcgggcct | agcctattac | tccatgcagg | gcaactgggc | caaggtcgct | atcatcatgg | 1500 |
| ttatgttttc | aggagtcgat | gccaccacat | ataccaccgg | tggcaatgca | gcccgtggtg | 1560 |

```
ccagcgggat tgttagtctt tttactccgg gcgccaaaca gaacctgcag ctggtcaaca    1620
ccaatggctc gtggcacatt aacaggactg ccctgaactg caatgattcc ataaacacag    1680
ggtttatagc cgggttgatt tattatcata agttcaactc tactggatgt cctcaaaggc    1740
tcagcagctg caagcccatt accttcttca ggcaggggtg gggctccctg acggatgcta    1800
acatcaccgg tccctctgat gacaaaccgt actgctggca ctacccacct aggccttgtg    1860
atactatccg ggcatcaagt gtctgcggtc cggtgtactg cttcacacca tcgccagtgg    1920
ttgtaggcac tactgatgct aagggcgccc aacctacaa ctggggcgcg aatgagacag     1980
acatgtttct gctgcagtcc ctgccggcctc ccagtggtcg gtggttcggg tgcacgtgga   2040
tgaactccac agggtttacc aagacgtgcg gagctccccc ttgtaacatc tatggggtg    2100 gggggaatct caacaatgag tcagacctct tctgccccac cgactgcttc aggaaacatc    2160
ctgaggccac ttacagccgg tgtggcgcgg ggccttggtt aacacctcga tgcttggtcg    2220
actatccgta ccggctttgg cattacccctt gtacagtcaa ttttacattg ttccggatga   2280
ggacgtttgt gggtgggttt gagcaccggt ttactgctgc ttgcaattgg accagagggg    2340
agcgctgcaa tatcgaggat cgtgaccgca gcgagcaaca tccgctgctg cattcaacaa    2400
ctgagcttgc tatactgcct tgctccttca cgcccatgcc tgcattgtca acaggtctga    2460
tacacctcca ccaaaacatt gtggatgtcc aatacccttta tggcattgga tctggtgtgg    2520
tgggatgggc gttgaaatgg gagttcgtta tcctcgtgtt cctcctccta gcagacgcac    2580
gcgtgtgcgt tgctctttgg ctgatgctga tgatatcaca agcagaagca gccttggaga    2640
acctcgtcac gctgaacgcc gttgctgttg ccgggacaca tggtataggc tggtacctgg    2700
tagccttttg cgcggcgtgg cacgtgcggg gcaaacttgt cccgctggtg acctacagcc    2760
tgacgggtct ttggtcccta gcattgctcg tcctcttgct cccccaacgg gcgtatgctt    2820
ggtcgggtga agacagcgct actctcggcg ctgggatctt ggtcctcttc ggcttcttta    2880
ccttatcacc ttggtataag cattggatca gccgcctcat gtggtggaac cagtacacca    2940
tatgcagatg cgaggccacc ttcaagtgt gggtccctcc cttacttgct cgcgggagta     3000
gggacggtgt catcctgcta acaagcctgc tttatccatc tttaattttt gacatcacta    3060
agctgctgat agcaatattg ggcccattat acttaataca ggccgccatc actaccaccc    3120
cctactttgt gcgtgcacat gtactggtcc gcctttgcat gctcgtgcgc tccgtgatgg    3180
ggggaaaata cttccagatg ccatactga gcgttggcag atggtttaac acctacctat    3240
acgatcacct agcgccaatg caacattggg ccgcagccgg cctcaaagac ctagcagttg    3300
ccactgaacc tataatattt agtcccatgg aaatcaaggt tatcacctgg ggcgcggata    3360
cagcagcttg cggagatatt ctttgcggc tgcccgtctc tgcgcgatta ggccgtgagg     3420
tgctgttggg acctgctgat gactatcggg agatggggtt gcgcctgttg gctcccatca    3480
ctgcttatgc ccagcaaaca cgaggcctcc tgggcgccat agtggtgagt atgacggggc    3540
gtgacaggac agaacaggcc ggggaagtcc aaatcctgtc cacagtctct cagtccttcc    3600
tcggaacaac catctcgggg gttttgtgga ctgtttacca cggagctggc aacaagactc    3660
tagccggctt acggggtccg gtcacgcaga tgtactcgag tgctgagggg acttggtag     3720 gctgcccag ccccctggg accaagtctt tggagccgtg caagtgtgga gccgtcgacc     3780
tatatctggt cacgcggaac gctgatgtca tcccggctcg gagacgcggg gacaagcggg    3840
gagcattgct ctccccgaga cccatttcga ccttgaaggg gtcctcgggg gggccggtgc    3900
tctgccctag gggccacgtc gttgggctct tccgagcagc tgtgtgctct cggggcgtgg    3960
```

```
ccaaatccat cgatttcatc cccgttgaga cactcgacgt tgttacaagg tctcccactt   4020
tcagtgacaa cagcacgcca ccggctgtgc cccagaccta tcaggtcggg tacttgcatg   4080
ctccaactgg cagtggaaag agcaccaagg tccctgtcgc gtatgccgcc cagggggtaca  4140 aagtactagt gcttaacccc tcggtagctg ccacccctggg gttgggggcg tacctatcca  4200
aggcacatgg catcaatccc aacattagga ctggagtcag gaccgtgatg accggggagg   4260
ccatcacgta ctccacatat ggcaaatttc tcgccgatgg gggctgcgct agcggcgcct   4320
atgacatcat catatgcgat gaatgccacg ctgtggatgc tacctccatt ctcggcatcg   4380
gaacggtcct tgatcaagca gagacagccg gggtcagact aactgtgctg gctacggcca   4440
caccccccgg gtcagtgaca accccccatc ccgatataga agaggtaggc ctcgggcggg   4500
agggtgagat ccccttctat gggagggcga ttccccctatc ctgcatcaag ggagggagac   4560
acctgatttt ctgccactca aagaaaaagt gtgacgagct cgcggcggcc cttcggggca   4620
tgggcttgaa tgccgtggca tactatagag ggttggacgt ctccataata ccagctcagg   4680
gagatgtggt ggtcgtcgcc accgacgccc tcatgacggg gtacactgga gactttgact   4740
ccgtgatcga ctgcaatgta gcggtcaccc aagctgtcga cttcagcctg gaccccacct   4800
tcactataac cacacagact gtcccacaag acgctgtctc acgcagtcag cgccgcgggc   4860
gcacaggtag aggaagacag ggcacttata ggtatgtttc cactggtgaa cgagcctcag   4920
gaatgtttga cagtgtagtg ctttgtgagt gctacgacgc aggggctgcg tggtacgatc   4980
tcacaccagc ggagaccacc gtcaggctta gagcgtattt caacacgccc ggcctacccg   5040
tgtgtcaaga ccatcttgaa ttttgggagg cagttttcac cggcctcaca cacatagacg   5100
cccacttcct ctcccaaaca aagcaagcgg gggagaactt cgcgtaccta gtagcctacc   5160
aagctacggt gtgcgccaga gccaaggccc ctcccccgtc ctgggacgcc atgtggaagt   5220
gcctggcccg actcaagcct acgcttgcgg gccccacacc tctcctgtac cgtttgggcc   5280
ctattaccaa tgaggtcacc ctcacacacc ctggacgaa gtacatcgcc acatgcatgc   5340
aagctgacct tgaggtcatg accagcacgt gggtcctagc tggaggagtc ctggcagccg   5400
tcgccgcata ttgcctggcg actggatgcg ttttccatcat cggccgcttg cacgtcaacc   5460
agcgagtcgt cgttgcgccg gataaggagg tcctgtatga ggcttttgat gagatggagg   5520
aatgcgcctc tagggcggct ctcatcgaag aggggcagcg gatagccgag atgttgaagt   5580
ccaagatcca aggcttgctg cagcaggcct ctaagcaggc ccaggacata caacccgcta   5640
tgcaggcttc atggcccaaa gtggaacaat tttgggccag acacatgtgg aacttcatta   5700
gcggcatcca ataccctcgca ggattgtcaa cactgccagg gaaccccgcg gtggcttcca   5760
tgatggcatt cagtgccgcc ctcaccagtc gttgtcgac cagtaccacc atccttctca   5820
acatcatggg aggctggtta gcgtcccaga tcgcaccacc gcgggggcc accggctttg   5880 tcgtcagtgg cctggtgggg gctgccgtgg cagcatagg cctgggtaag gtgctggtgg   5940
acatcctggc aggatatggt gcgggcattt cgggggccct cgtcgcattc aagatcatgt   6000
ctggcgagaa gcctctatg gaagatgtca tcaatctact gcctgggatc ctgtctccgg   6060
gagccctggt ggtgggggtc atctgcgcgg ccattctgcg ccgccacgtg gaccggggg   6120 agggcgcggt ccaatggatg aacaggctta ttgcctttgc ttccagagga aaccacgtcg   6180
cccctactca ctacgtgacg gagtcggatg cgtcgcagcg tgtgacccaa ctacttggct   6240
ctcttactat aaccagccta ctcagaagac tccacaattg gataactgag gactgcccca   6300
tcccatgctc cggatcctgg ctccgcgacg tgtgggactg ggtttgcacc atcttgacag   6360
```

```
acttcaaaaa ttggctgacc tctaaattgt tccccaagct gcccggcctc cccttcatct   6420
cttgtcaaaa ggggtacaag ggtgtgtggg ccggcactgg catcatgacc acgcgctgcc   6480
cttgcggcgc caacatctct ggcaatgtcc gcctgggctc tatgaggatc acagggccta   6540
aaacctgcat gaacacctgg caggggacct ttcctatcaa ttgctacacg gagggccagt   6600
gcgcgccgaa accccccacg aactacaaga ccgccatctg gagggtggcg gcctcggagt   6660
acgcggaggt gacgcagcat gggtcgtact cctatgtaac aggactgacc actgacaatc   6720
tgaaaattcc ttgccaacta ccttctccag agttttttctc ctgggtggac ggtgtgcaga   6780
tccataggtt tgcacccaca ccaaagccgt ttttccggga tgaggtctcg ttctgcgttg   6840
ggcttaattc ctatgctgtc gggtcccagc ttccctgtga acctgagccc gacgcagacg   6900
tattgaggtc catgctaaca gatccgcccc acatcacggc ggagactgcg gcgcggcgct   6960
tggcacgggg atcacctcca tctgaggcga gctcctcagt gagccagcta tcagcaccgt   7020
cgctgcgggc cacctgcacc acccacagca acacctatga cgtggacatg gtcgatgcca   7080
acctgctcat ggagggcggt gtggctcaga cagagcctga gtccagggtg cccgttctgg   7140
actttctcga gccaatggcc gaggaagaga gcgaccttga gccctcaata ccatcggagt   7200
gcatgctccc caggagcggg tttccacggg ccttaccggc ttgggcacgg cctgactaca   7260
acccgccgct cgtggaatcg tggaggaggc cagattacca accgccacc gttgctggtt    7320
gtgctctccc ccccccaag aaggccccga cgcctccccc aaggagacgc cggacagtgg    7380
gtctgagcga gagcaccata tcagaagccc tccagcaact ggccatcaag acctttggcc   7440
agccccctc gagcggtgat gcaggctcgt ccacgggggc gggcgccgcc gaatccggcg    7500
gtccgacgtc ccctggtgag ccggcccct cagagacagg ttccgcctcc tctatgcccc    7560
ccctcgaggg ggagcctgga gatccggacc tggagtctga tcaggtagag cttcaacctc   7620
cccccaggg gggggggta gctcccggtt cgggctcggg gtcttggtct acttgctccg    7680
aggaggacga taccaccgtg tgctgctcca tgtcatactc ctggacccgg gctctaataa   7740
ctccctgtag ccccgaagag gaaaagttgc caatcaaccc tttgagtaac tcgctgttgc   7800
gataccataa caaggtgtac tgtacaacat caaagagcgc ctcacagagg gctaaaaagg   7860
taacttttga caggacgcaa gtgctcgacg cccattatga ctcagtctta aaggacatca   7920
agctagcggc ttcaaggtc agcgcaaggc tcctcacctt ggaggaggcg tgccagttga   7980
ctccacccca ttctgcaaga tccaagtatg gattcggggc caaggaggtc cgcagcttgt   8040
ccgggagggc cgttaaccac atcaagtccg tgtggaagga cctcctggaa gacccacaaa   8100
caccaattcc cacaaccatc atggccaaaa atgaggtgtt ctgcgtggac cccgccaagg   8160
ggggtaagaa accagctcgc ctcatcgttt accctgacct cggcgtccgg gtctgcgaga   8220
aaatggccct ctatgacatt acacaaaagc ttcctcaggc ggtaatggga gcttcctatg   8280
gcttccagta ctcccctgcc caacgggtgg agtatctctt gaaagcatgg gcggaaaaga   8340
aggacccat gggttttttcg tatgataccc gatgcttcga ctcaaccgtc actgagagag   8400
acatcaggac cgaggagtcc atataccagg cctgctccct gcccgaggag gcccgcactg   8460
ccatacactc gctgactgag agactttacg taggagggcc catgttcaac agcaagggtc   8520
aaacctgcgg ttacagacgt tgccgcgcca gcggggtgct aaccactagc atgggtaaca   8580
ccatcacatg ctatgtgaaa gccctagcgg cctgcaaggc tgcggggata gttgcgccca   8640
caatgctggt atgcggcgat gacctagtag tcatctcaga aagccagggg actgaggagg   8700
acgagcggaa cctgagagcc ttcacggagg ccatgaccag gtactctgcc cctcctggtg   8760
```

```
atccccccag accggaatat gacctggagc taataacatc ctgttcctca aatgtgtctg    8820
tggcgttggg cccgcggggc cgccgcagat actacctgac cagagaccca accactccac    8880
tcgcccgggc tgcctgggaa acagttagac actccctat caattcatgg ctgggaaaca     8940
tcatccagta tgctccaacc atatgggttc gcatggtcct aatgacacac ttcttctcca    9000
ttctcatggt ccaagacacc ctggaccaga acctcaactt tgagatgtat ggatcagtat    9060
actccgtgaa tcctttggac cttccagcca taattgagag gttacacggg cttgacgcct    9120
tttctatgca cacatactct caccacgaac tgacgcgggt ggcttcagcc ctcagaaaac    9180
ttggggcgcc acccctcagg gtgtggaaga gtcgggctcg cgcagtcagg gcgtccctca    9240
tctcccgtgg agggaaagcg gccgtttgcg gccgatatct cttcaattgg gcggtgaaga    9300
ccaagctcaa actcactcca ttgccggagg cgcgcctact ggacttatcc agttggttca    9360
ccgtcggcgc cggcggggc gacattttc acagcgtgtc gcgcgcccga ccccgctcat     9420
tactcttcgg cctactccta ctttcgtag gggtaggcct cttcctactc cccgctcggt     9480
agagcggcac acactaggta cactccatag ctaactgttc ctttttttt ttttttttt     9540
ttttttttt ttttttttt ttttcttttt ttttttttc cctctttctt cccttctcat       9600
cttattctac tttctttctt ggtggctcca tcttagccct agtcacggct agctgtgaaa    9660
ggtccgtgag ccgcatgact gcagagagtg ccgtaactgg tctctctgca gatcatgtct    9720
agagtcgacc tgcaggcatg caagcttggc actggccgtc gttttacaac gtcgtgactg    9780
ggaaaaccct ggcgttaccc aacttaatcg ccttgcagca catccccctt cgccagctg     9840
gcgtaatagc gaagaggccc gcaccgatcg cccttcccaa cagttgcgca gcctgaatgg    9900
cgaatgcgc ctgatgcggt attttctcct tacgcatctg tgcggtattt cacaccgcat     9960
atggtgcact ctcagtacaa tctgctctga tgccgcatag ttaagccagc ccgacaccc    10020
gccaacaccc gctgacgcgc cctgacgggc ttgtctgctc ccggcatccg cttacagaca   10080
agctgtgacc gtctccggga gctgcatgtg tcagaggttt tcaccgtcat caccgaaacg   10140
cgcgagacga aagggcctcg tgatacgcct atttttatag gttaatgtca tgataataat   10200
ggtttcttag acgtcaggtg gcacttttcg gggaaatgtg cgcggaaccc ctatttgttt   10260
attttctaa atacattcaa atatgtatcc gctcatgaga caataaccct gataaatgct   10320
tcaataatat tgaaaaagga agagtatgag tattcaacat ttccgtgtcg cccttattcc   10380
ctttttgcg gcattttgcc ttcctgtttt tgctcaccca gaaacgctgg tgaaagtaaa   10440
agatgctgaa gatcagttgg gtgcacgagt gggttacatc gaactggatc tcaacagcgg   10500
taagatcctt gagagttttc gccccgaaga acgttttcca atgatgagca cttttaaagt   10560
tctgctatgt ggcgcggtat tatcccgtat tgacgccggg caagagcaac tcggtcgccg   10620
catacactat tctcagaatg acttggttga gtactcacca gtcacagaaa agcatcttac   10680
ggatggcatg acagtaagag aattatgcag tgctgccata accatgagtg ataacactgc   10740
ggccaactta cttctgacaa cgatcggagg accgaaggag ctaaccgctt ttttgcacaa   10800
catgggggat catgtaactc gccttgatcg ttgggaaccg gagctgaatg aagccatacc   10860
aaacgacgag cgtgacacca cgatgcctgt agcaatggca acaacgttgc gcaaactatt   10920
aactggcgaa ctacttactc tagcttcccg gcaacaatta atagactgga tggaggcgga   10980
taaagttgca ggaccacttc tgcgctcggc ccttccggct ggctggttta ttgctgataa   11040
atctggagcc ggtgagcgtg ggtctcgcgg tatcattgca gcactggggc cagatggtaa   11100
gccctcccgt atcgtagtta tctacacgac ggggagtcag gcaactatgg atgaacgaaa   11160
```

-continued

```
tagacagatc gctgagatag gtgcctcact gattaagcat tggtaactgt cagaccaagt    11220
ttactcatat atactttaga ttgatttaaa acttcatttt taatttaaaa ggatctaggt    11280
gaagatcctt tttgataatc tcatgaccaa aatcccttaa cgtgagtttt cgttccactg    11340
agcgtcagac cccgtagaaa agatcaaagg atcttcttga gatccttttt ttctgcgcgt    11400
aatctgctgc ttgcaaacaa aaaaaccacc gctaccagcg gtggtttgtt tgccggatca    11460
agagctacca actcttttc cgaaggtaac tggcttcagc agagcgcaga taccaaatac    11520
tgtccttcta gtgtagccgt agttaggcca ccacttcaag aactctgtag caccgcctac    11580
atacctcgct ctgctaatcc tgttaccagt ggctgctgcc agtggcgata agtcgtgtct    11640 taccggttg gactcaagac gatagttacc ggataaggcg cagcggtcgg gctgaacggg    11700
gggttcgtgc acacagccca gcttggagcg aacgacctac accgaactga gatacctaca    11760
gcgtgagcta tgagaaagcg ccacgcttcc cgaagggaga aaggcggaca ggtatccggt    11820
aagcggcagg gtcggaacag gagagcgcac gagggagctt ccaggggaa acgcctggta    11880 tctttatagt cctgtcgggt ttcgccacct ctgacttgag cgtcgatttt tgtgatgctc    11940 gtcaggggg cggagcctat ggaaaaacgc cagcaacgcg gcctttttac ggttcctggc    12000
cttttgctgg ccttttgctc acatgttctt tcctgcgtta tcccctgatt ctgtggataa    12060
ccgtattacc gcctttgagt gagctgatac cgctcgccgc agccgaacga ccgagcgcag    12120
cgagtcagtg agcgaggaag cggaagagcg cccaatacgc aaaccgcctc tccccgcgcg    12180
ttggccgatt cattaatgca gctggcacga caggtttccc gactggaaag cgggcagtga    12240
gcgcaacgca attaatgtga gttagctcac tcattaggca ccccaggctt tacactttat    12300
gcttccggct cgtatgttgt gtggaattgt gagcggataa caatttcaca caggaaacag    12360
ctatgaccat gattac                                                    12376
```